US012797466B2

(12) United States Patent
Lu et al.

(10) Patent No.: US 12,797,466 B2
(45) Date of Patent: Nov. 17, 2026

(54) ENGINEERED iPSC AND ARMED IMMUNE EFFECTOR CELLS

(71) Applicant: Fate Therapeutics, Inc., San Diego, CA (US)

(72) Inventors: Dan Lu, San Diego, CA (US); Bahram Valamehr, San Diego, CA (US); Eigen Peralta, San Diego, CA (US); Tom Lee, San Diego, CA (US); Alec Witty, San Diego, CA (US)

(73) Assignee: Fate Therapeutics, Inc., San Diego, CA (US)

(*) Notice: Subject to any disclaimer, the term of this patent is extended or adjusted under 35 U.S.C. 154(b) by 734 days.

(21) Appl. No.: 18/028,457

(22) PCT Filed: Oct. 8, 2021

(86) PCT No.: PCT/US2021/054302

§ 371 (c)(1),
(2) Date: Mar. 24, 2023

(87) PCT Pub. No.: WO2022/076910

PCT Pub. Date: Apr. 14, 2022

(65) Prior Publication Data

US 2024/0033355 A1 Feb. 1, 2024

Related U.S. Application Data

(60) Provisional application No. 63/172,383, filed on Apr. 8, 2021, provisional application No. 63/090,113, filed on Oct. 9, 2020.

(51) Int. Cl.

| | |
|---|---|
| ***A61K 40/31*** | (2025.01) |
| ***A61K 40/11*** | (2025.01) |
| ***A61K 40/33*** | (2025.01) |
| ***A61K 40/42*** | (2025.01) |
| ***A61P 35/00*** | (2006.01) |
| ***C12N 5/078*** | (2010.01) |
| ***C12N 5/0783*** | (2010.01) |

(52) U.S. Cl.

CPC .............. *A61K 40/31* (2025.01); *A61K 40/11* (2025.01); *A61K 40/33* (2025.01); *A61K 40/4211* (2025.01); *A61K 40/4254* (2025.01); *A61P 35/00* (2018.01); *C12N 5/0634* (2013.01); *C12N 5/0636* (2013.01); *C12N 5/0646* (2013.01); *C07K 2317/31* (2013.01); *C07K 2317/75* (2013.01); *C07K 2319/03* (2013.01); *C12N 2506/45* (2013.01); *C12N 2510/00* (2013.01)

(58) Field of Classification Search

None

See application file for complete search history.

(56) References Cited

U.S. PATENT DOCUMENTS

| | | | |
|---|---|---|---|
| 6,140,081 | A | 10/2000 | Barbas |
| 6,352,694 | B1 | 3/2002 | June et al. |
| 6,453,242 | B1 | 9/2002 | Eisenberg et al. |
| 6,534,261 | B1 | 3/2003 | Cox, III et al. |
| 7,888,121 | B2 | 2/2011 | Urnov et al. |
| 7,972,854 | B2 | 7/2011 | Miller et al. |
| 8,409,577 | B2 | 4/2013 | Thompson et al. |
| 9,447,194 | B2 | 9/2016 | Jensen |
| 9,587,020 | B2 | 3/2017 | Wu et al. |
| 2004/0101519 | A1 | 5/2004 | June et al. |
| 2006/0034810 | A1 | 2/2006 | Riley et al. |
| 2011/0145940 | A1 | 6/2011 | Voytas et al. |
| 2014/0134142 | A1 | 5/2014 | Smith et al. |
| 2014/0219975 | A1 | 8/2014 | June et al. |
| 2015/0140665 | A1 | 5/2015 | Calos et al. |
| 2016/0046700 | A1 | 2/2016 | Foster et al. |
| 2016/0058857 | A1 | 3/2016 | Spencer et al. |
| 2017/0166877 | A1 | 6/2017 | Bayle et al. |
| 2017/0183407 | A1 | 6/2017 | Cooper et al. |
| 2018/0282386 | A1 | 10/2018 | Vallera et al. |
| 2019/0328784 | A1 | 10/2019 | Ostertag et al. |

FOREIGN PATENT DOCUMENTS

| | | | |
|---|---|---|---|
| WO | WO 1998/053058 | A1 | 11/1998 |
| WO | WO 1998/053059 | A1 | 11/1998 |
| WO | WO 1998/053060 | A1 | 11/1998 |
| WO | WO 2002/016536 | A1 | 2/2002 |
| WO | WO 2003/016496 | A2 | 2/2003 |
| WO | WO 2011/159726 | A2 | 12/2011 |
| WO | WO 2015/134652 | A1 | 9/2015 |
| WO | WO 2015/148926 | A1 | 10/2015 |

(Continued)

OTHER PUBLICATIONS

Cao et al (Frontiers in Oncology, 2019, 9:767, internet pp. 1-11).*
Mihara et al (British Journal of Hematology, 2010, 151:37-46).*
Casneuf et al., "Effects of daratumumab on natural killer cells and impact on clinical outcomes in relapsed or refractory multiple myeloma," *Blood Adv.*, 1(23):2105-2114 (2017).
Clarke et al., "Generation of off-the-shelf TCR-less CAR-targeted cytotoxic T cells from renewable pluripotent cells for cancer immunotherapy," *Cancer Research*, Proceedings: AACR Annual Meeting, Abstract LB-108, pp. 1-2 (2018).

(Continued)

*Primary Examiner* — Laura B Goddard
(74) *Attorney, Agent, or Firm* — Greenberg Traurig LLP

(57) ABSTRACT

Provided are methods and compositions for obtaining functionally enhanced derivative effector cells obtained from directed differentiation of genomically engineered iPSCs. The iPSC-derived cells provided herein have stable and functional genome editing that delivers improved or enhanced therapeutic effects. Also provided are therapeutic compositions and the use thereof comprising the functionally enhanced derivative effector cells alone, or with antibodies or checkpoint inhibitors in combination therapies.

23 Claims, 23 Drawing Sheets

Specification includes a Sequence Listing.

(56) References Cited

FOREIGN PATENT DOCUMENTS

| | | | | | |
|---|---|---|---|---|---|
| WO | WO 2016/054520 | A2 | | 4/2016 | |
| WO | WO 2017/027392 | A1 | | 2/2017 | |
| WO | WO 2017/066634 | A1 | | 4/2017 | |
| WO | WO 2017/078807 | A1 | | 5/2017 | |
| WO | WO 2019/075057 | A1 | | 4/2019 | |
| WO | WO 2019/097305 | A2 | | 5/2019 | |
| WO | WO 2019/112899 | A2 | | 6/2019 | |
| WO | WO-2019126748 | A1 | * | 6/2019 | ........... C12N 15/907 |
| WO | WO-2020193506 | A1 | * | 10/2020 | ......... A61K 40/4211 |
| WO | WO 2021/048724 | A1 | | 3/2021 | |

OTHER PUBLICATIONS

Donnelly et al., "The 'cleavage' activities of foot-and-mouth disease virus 2A site-directed mutants and naturally occurring '2A-like' sequences," *J. Gen. Virol.*, 82:1027-1041 (2001).

Dragomir et al., "Key questions about the checkpoint blockade-are microRNAs an answer?," *Cancer Biol. Med.*, 15(2):103-115 (2018).

Hegde et al., "Tandem CAR T cells targeting HER2 and IL13Rα2 mitigate tumor antigen escape," *J. Clin. Invest.*, 126(8):3036-3052 (2016).

Krenciute et al., "Characterization and functional analysis of scFv-based chimeric antigen receptors to redirect T cells to IL13Rα2-positive glioma," *Molecular Therapy*, 24(2);354-363 (2016).

Peralta et al., "Chimeric fusion receptors provide a CD3-mediated activation signal to off-the-shelf iPSC-derived TCR-less CAR-T cells for enhanced efficacy," *Cancer Research*, Proceedings: AACR Annual Meeting, Abstract 332, pp. 1-2 (2021).

Ryan et al., "Cleavage of foot-and-mouth disease virus polyprotein is mediated by residues located within a 19 amino acid sequence," *J. Gen. Virol.*, 72:2727-2732 (1991).

Zhao, J. et al., "Universal CARs, universal T cells, and universal Car T cells," *J Hematol Oncol*, 11(132):1-9 (2018).

* cited by examiner

Non-binding TCR (nb-rTCR)

Defined TCR (d-rTCR)

Pre-TCRα
(+ non-binding TCRβ)

(p-rTCR)

CD3 anchored to non-binding TCR (nb-rTCR-CD3)

CD3 Chimeric Chain (ccCD3)

FIG. 2C

| | 1 | 2 | 3 | 4 | 5 |
|---|---|---|---|---|---|
| | **Non-binding TCR**<br><br>**(nb-rTCR)** | **Defined TCR**<br><br>**(d-rTCR)** | **Pre-TCRα**<br>**(+ non-binding TCRβ)**<br><br>**(p-rTCR)** | **CD3 anchored to non-binding TCR**<br><br>**(nb-rTCR-CD3)** | **CD3 Chimeric Chain**<br><br>**(ccCD3)** |
| Endogenous TCR KO | TCR(α or β) KO (+the other optional) | TCRα KO+ TCRβ KO | TCRα KO<br>(+ TCRβ KO) | TCRα KO+ TCRβ KO | TCRα KO |
| Transgenic/modified protein expression | tgTRAC (+tgTRBC); or tgTRBC (+tgTRAC) | Defined tgTCRα+tgTCRβ | tgpTCRα<br>(+ tgTRBC);<br>or<br>upregulating (down-reg prevention) endogenous pre-TCRα | tgCD3(ε-δ)-TRAC fusion and/or tgCD3(ε-γ)-TRBC fusion | tgCD3(ε- γ/δ)-(28/BB)ζ |
| Locus/promoter | TCRα (+ TCRβ) or constitutive | TCRα + TCRβ or constitutive | Constitutive | TCRα + TCRβ or constitutive | Constitutive |
| Peptide-MHC binding | No binding | Defined/No binding | No binding | No binding | No binding |
| Signaling | Canonical TCR/CD3 | Canonical TCR/CD3 | Canonical TCR/CD3 | CDζ only | z/28z/BBz specific |

FIG. 13A
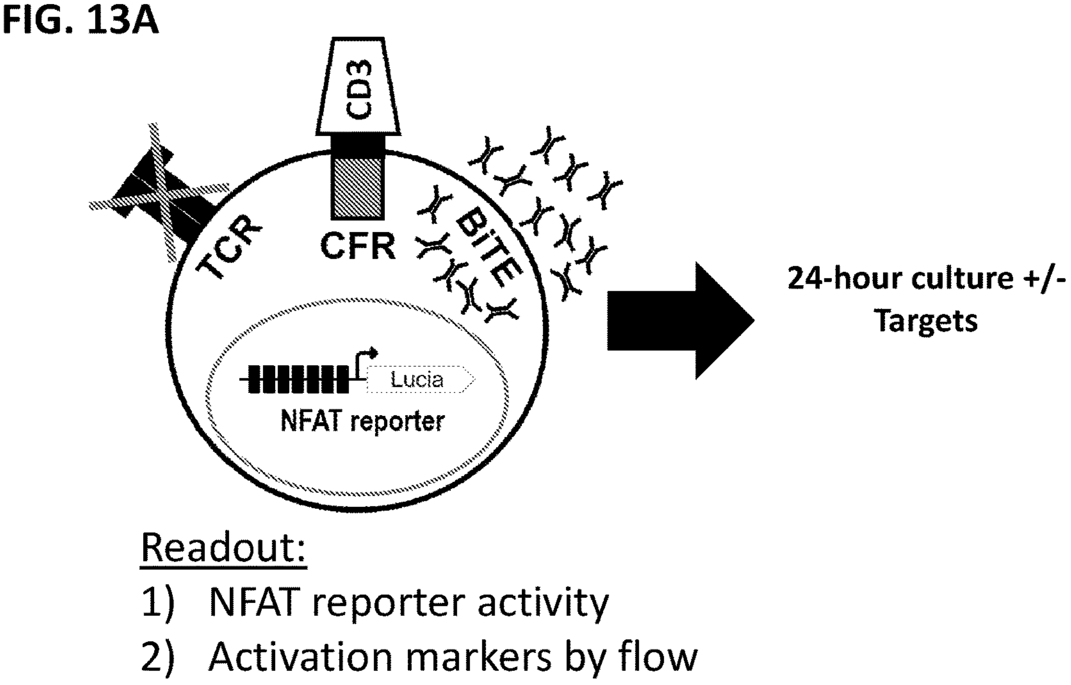
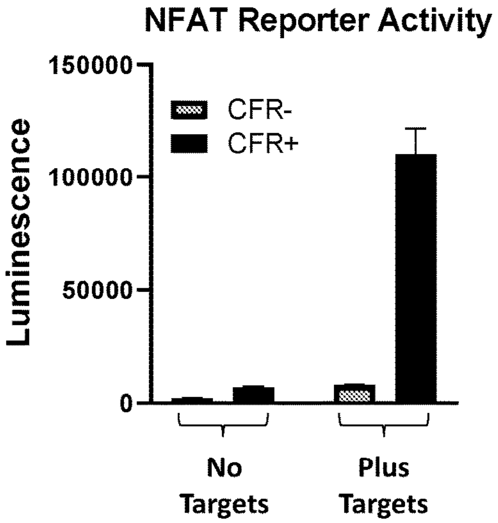
FIG. 13B
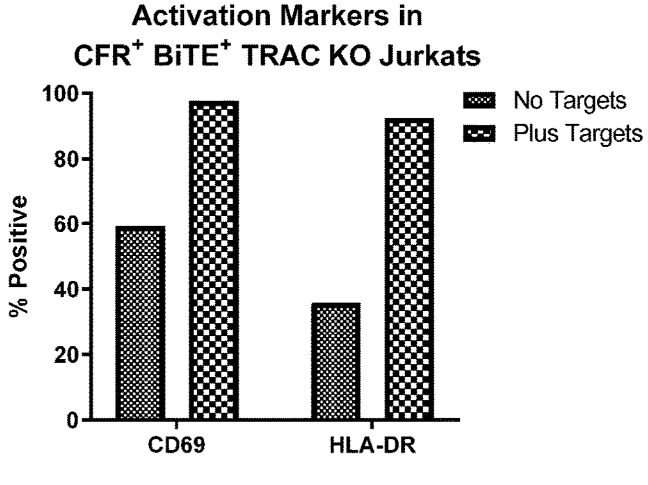
FIG. 13C

SEQUENCE LISTING

```
<160> NUMBER OF SEQ ID NOS: 59

<210> SEQ ID NO 1
<211> LENGTH: 140
<212> TYPE: PRT
<213> ORGANISM: Artificial Sequence
<220> FEATURE:
<223> OTHER INFORMATION: a construct comprising constant region of
      TCR-beta (TRBC)

<400> SEQUENCE: 1

Ile Gln Asn Pro Asp Pro Ala Val Tyr Gln Leu Arg Asp Ser Lys Ser
1               5                   10                  15

Ser Asp Lys Ser Val Cys Leu Phe Thr Asp Phe Asp Ser Gln Thr Asn
            20                  25                  30

Val Ser Gln Ser Lys Asp Ser Asp Val Tyr Ile Thr Asp Lys Thr Val
        35                  40                  45

Leu Asp Met Arg Ser Met Asp Phe Lys Ser Asn Ser Ala Val Ala Trp
    50                  55                  60

Ser Asn Lys Ser Asp Phe Ala Cys Ala Asn Ala Phe Asn Asn Ser Ile
65                  70                  75                  80

Ile Pro Glu Asp Thr Phe Phe Pro Ser Pro Glu Ser Ser Cys Asp Val
                85                  90                  95

Lys Leu Val Glu Lys Ser Phe Glu Thr Asp Thr Asn Leu Asn Phe Gln
            100                 105                 110
```

```
Asn Leu Ser Val Ile Gly Phe Arg Ile Leu Leu Leu Lys Val Ala Gly
        115                 120                 125

Phe Asn Leu Leu Met Thr Leu Arg Leu Trp Ser Ser
    130                 135                 140


<210> SEQ ID NO 2
<211> LENGTH: 176
<212> TYPE: PRT
<213> ORGANISM: Artificial Sequence
<220> FEATURE:
<223> OTHER INFORMATION: a construct comprising constant region of
      TCR-beta(TRBC1)

<400> SEQUENCE: 2

Asp Leu Asn Lys Val Phe Pro Pro Glu Val Ala Val Phe Glu Pro Ser
1               5                   10                  15

Glu Ala Glu Ile Ser His Thr Gln Lys Ala Thr Leu Val Cys Leu Ala
            20                  25                  30

Thr Gly Phe Phe Pro Asp His Val Glu Leu Ser Trp Trp Val Asn Gly
        35                  40                  45

Lys Glu Val His Ser Gly Val Ser Thr Asp Pro Gln Pro Leu Lys Glu
    50                  55                  60

Gln Pro Ala Leu Asn Asp Ser Arg Tyr Cys Leu Ser Ser Arg Leu Arg
65                  70                  75                  80

Asn His Phe Arg Cys Arg Val Ser Ala Thr Phe Trp Gln Asn Pro Gln
                85                  90                  95

Val Gln Phe Tyr Gly Leu Ser Glu Asn Asp Glu Trp Thr Gln Asp Arg
            100                 105                 110

Ala Lys Pro Val Thr Gln Ile Val Ser Ala Glu Ala Trp Gly Arg Ala
        115                 120                 125

Asp Cys Gly Phe Thr Ser Val Ser Tyr Gln Gln Gly Val Leu Ser Ala
    130                 135                 140

Thr Ile Leu Tyr Glu Ile Leu Leu Gly Lys Ala Thr Leu Tyr Ala Val
145                 150                 155                 160

Leu Val Ser Ala Leu Val Leu Met Ala Met Val Lys Arg Lys Asp Phe
                165                 170                 175


<210> SEQ ID NO 3
<211> LENGTH: 178
<212> TYPE: PRT
<213> ORGANISM: Artificial Sequence
<220> FEATURE:
<223> OTHER INFORMATION: TRBC2

<400> SEQUENCE: 3

Asp Leu Lys Asn Val Phe Pro Pro Lys Val Ala Val Phe Glu Pro Ser
1               5                   10                  15

Glu Ala Glu Ile Ser His Thr Gln Lys Ala Thr Leu Val Cys Leu Ala
            20                  25                  30

Thr Gly Phe Tyr Pro Asp His Val Glu Leu Ser Trp Trp Val Asn Gly
        35                  40                  45

Lys Glu Val His Ser Gly Val Ser Thr Asp Pro Gln Pro Leu Lys Glu
    50                  55                  60

Gln Pro Ala Leu Asn Asp Ser Arg Tyr Cys Leu Ser Ser Arg Leu Arg
65                  70                  75                  80

Val Ser Ala Thr Phe Trp Gln Asn Pro Arg Asn His Phe Arg Cys Gln
                85                  90                  95

Val Gln Phe Tyr Gly Leu Ser Glu Asn Asp Glu Trp Thr Gln Asp Arg
```

```
            100                 105                 110

Ala Lys Pro Val Thr Gln Ile Val Ser Ala Glu Ala Trp Gly Arg Ala
        115                 120                 125

Asp Cys Gly Phe Thr Ser Glu Ser Tyr Gln Gln Gly Val Leu Ser Ala
    130                 135                 140

Thr Ile Leu Tyr Glu Ile Leu Leu Gly Lys Ala Thr Leu Tyr Ala Val
145                 150                 155                 160

Leu Val Ser Ala Leu Val Leu Met Ala Met Val Lys Arg Lys Asp Ser
                165                 170                 175

Arg Gly


<210> SEQ ID NO 4
<211> LENGTH: 18
<212> TYPE: PRT
<213> ORGANISM: Artificial Sequence
<220> FEATURE:
<223> OTHER INFORMATION: Exemplary signal peptide for the construct
      comprising TCR-beta constant region (tgTRBC) - CD8asp

<400> SEQUENCE: 4

Met Ala Leu Pro Val Thr Ala Leu Leu Leu Pro Leu Ala Leu Leu Leu
1               5                   10                  15

His Ala


<210> SEQ ID NO 5
<211> LENGTH: 21
<212> TYPE: PRT
<213> ORGANISM: Artificial Sequence
<220> FEATURE:
<223> OTHER INFORMATION: Exemplary signal peptide for the construct
      comprising TCR-beta constant region (tgTRBC) - IgKsp

<400> SEQUENCE: 5

Met Asp Phe Gln Val Gln Ile Phe Ser Phe Leu Leu Ile Ser Ala Ser
1               5                   10                  15

Val Ile Met Ser Arg
            20


<210> SEQ ID NO 6
<211> LENGTH: 8
<212> TYPE: PRT
<213> ORGANISM: Artificial Sequence
<220> FEATURE:
<223> OTHER INFORMATION: Exemplary linker peptide for the construct
      comprising TCR-beta constant region (tgTRBC) - FLAG

<400> SEQUENCE: 6

Asp Tyr Lys Asp Asp Asp Asp Lys
1               5


<210> SEQ ID NO 7
<211> LENGTH: 340
<212> TYPE: PRT
<213> ORGANISM: Artificial Sequence
<220> FEATURE:
<223> OTHER INFORMATION: 340 a.a. CD64 domain-based construction

<400> SEQUENCE: 7

Met Trp Phe Leu Thr Thr Leu Leu Leu Trp Val Pro Val Asp Gly Gln
1               5                   10                  15

Val Asp Thr Thr Lys Ala Val Ile Thr Leu Gln Pro Pro Trp Val Ser
            20                  25                  30
```

```
Val Phe Gln Glu Glu Thr Val Thr Leu His Cys Glu Val Leu His Leu
        35                  40                  45

Pro Gly Ser Ser Ser Thr Gln Trp Phe Leu Asn Gly Thr Ala Thr Gln
    50                  55                  60

Thr Ser Thr Pro Ser Tyr Arg Ile Thr Ser Ala Ser Val Asn Asp Ser
65                  70                  75                  80

Gly Glu Tyr Arg Cys Gln Arg Gly Leu Ser Gly Arg Ser Asp Pro Ile
                85                  90                  95

Gln Leu Glu Ile His Arg Gly Trp Leu Leu Leu Gln Val Ser Ser Arg
            100                 105                 110

Val Phe Thr Glu Gly Glu Pro Leu Ala Leu Arg Cys His Ala Trp Lys
        115                 120                 125

Asp Lys Leu Val Tyr Asn Val Leu Tyr Tyr Arg Asn Gly Lys Ala Phe
    130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                165                 170                 175

Thr Ser Ala Gly Ile Ser Val Thr Val Lys Glu Leu Phe Pro Ala Pro
            180                 185                 190

Val Leu Asn Ala Ser Val Thr Ser Pro Leu Leu Glu Gly Asn Leu Val
        195                 200                 205

Thr Leu Ser Cys Glu Thr Lys Leu Leu Leu Gln Arg Pro Gly Leu Gln
    210                 215                 220

Leu Tyr Phe Ser Phe Tyr Met Gly Ser Lys Thr Leu Arg Gly Arg Asn
225                 230                 235                 240

Thr Ser Ser Glu Tyr Gln Ile Leu Thr Ala Arg Arg Glu Asp Ser Gly
                245                 250                 255

Leu Tyr Trp Cys Glu Ala Ala Thr Glu Asp Gly Asn Val Leu Lys Arg
            260                 265                 270

Ser Pro Glu Leu Glu Leu Gln Val Leu Gly Leu Gln Leu Pro Thr Pro
        275                 280                 285

Val Trp Phe His Tyr Gln Val Ser Phe Cys Leu Val Met Val Leu Leu
    290                 295                 300

Phe Ala Val Asp Thr Gly Leu Tyr Phe Ser Val Lys Thr Asn Ile Arg
305                 310                 315                 320

Ser Ser Thr Arg Asp Trp Lys Asp His Lys Phe Lys Trp Arg Lys Asp
                325                 330                 335

Pro Gln Asp Lys
            340


<210> SEQ ID NO 8
<211> LENGTH: 336
<212> TYPE: PRT
<213> ORGANISM: Artificial Sequence
<220> FEATURE:
<223> OTHER INFORMATION: 336 a.a. CD64 exon-based construction

<400> SEQUENCE: 8

Met Trp Phe Leu Thr Thr Leu Leu Leu Trp Val Pro Val Asp Gly Gln
1               5                   10                  15

Val Asp Thr Thr Lys Ala Val Ile Thr Leu Gln Pro Pro Trp Val Ser
            20                  25                  30

Val Phe Gln Glu Glu Thr Val Thr Leu His Cys Glu Val Leu His Leu
        35                  40                  45
```

Pro Gly Ser Ser Ser Thr Gln Trp Phe Leu Asn Gly Thr Ala Thr Gln
50 55 60

Thr Ser Thr Pro Ser Tyr Arg Ile Thr Ser Ala Ser Val Asn Asp Ser
65 70 75 80

Gly Glu Tyr Arg Cys Gln Arg Gly Leu Ser Gly Arg Ser Asp Pro Ile
85 90 95

Gln Leu Glu Ile His Arg Gly Trp Leu Leu Leu Gln Val Ser Ser Arg
100 105 110

Val Phe Thr Glu Gly Glu Pro Leu Ala Leu Arg Cys His Ala Trp Lys
115 120 125

Asp Lys Leu Val Tyr Asn Val Leu Tyr Tyr Arg Asn Gly Lys Ala Phe
130 135 140

Lys Phe Phe His Trp Asn Ser Asn Leu Thr Ile Leu Lys Thr Asn Ile
145 150 155 160

Ser His Asn Gly Thr Tyr His Cys Ser Gly Met Gly Lys His Arg Tyr
165 170 175

Thr Ser Ala Gly Ile Ser Val Thr Val Lys Glu Leu Phe Pro Ala Pro
180 185 190

Val Leu Asn Ala Ser Val Thr Ser Pro Leu Leu Glu Gly Asn Leu Val
195 200 205

Thr Leu Ser Cys Glu Thr Lys Leu Leu Leu Gln Arg Pro Gly Leu Gln
210 215 220

Leu Tyr Phe Ser Phe Tyr Met Gly Ser Lys Thr Leu Arg Gly Arg Asn
225 230 235 240

Thr Ser Ser Glu Tyr Gln Ile Leu Thr Ala Arg Arg Glu Asp Ser Gly
245 250 255

Leu Tyr Trp Cys Glu Ala Ala Thr Glu Asp Gly Asn Val Leu Lys Arg
260 265 270

Ser Pro Glu Leu Glu Leu Gln Val Leu Gly Leu Phe Phe Pro Pro Gly
275 280 285

Tyr Gln Val Ser Phe Cys Leu Val Met Val Leu Leu Phe Ala Val Asp
290 295 300

Thr Gly Leu Tyr Phe Ser Val Lys Thr Asn Ile Arg Ser Ser Thr Arg
305 310 315 320

Asp Trp Lys Asp His Lys Phe Lys Trp Arg Lys Asp Pro Gln Asp Lys
325 330 335

<210> SEQ ID NO 9
<211> LENGTH: 335
<212> TYPE: PRT
<213> ORGANISM: Artificial Sequence
<220> FEATURE:
<223> OTHER INFORMATION: 335 a.a. CD64 exon-based construction

<400> SEQUENCE: 9

Met Trp Phe Leu Thr Thr Leu Leu Leu Trp Val Pro Val Asp Gly Gln
1 5 10 15

Val Asp Thr Thr Lys Ala Val Ile Thr Leu Gln Pro Pro Trp Val Ser
20 25 30

Val Phe Gln Glu Glu Thr Val Thr Leu His Cys Glu Val Leu His Leu
35 40 45

Pro Gly Ser Ser Ser Thr Gln Trp Phe Leu Asn Gly Thr Ala Thr Gln
50 55 60

Thr Ser Thr Pro Ser Tyr Arg Ile Thr Ser Ala Ser Val Asn Asp Ser
65 70 75 80

```
Gly Glu Tyr Arg Cys Gln Arg Gly Leu Ser Gly Arg Ser Asp Pro Ile
                85                  90                  95

Gln Leu Glu Ile His Arg Gly Trp Leu Leu Gln Val Ser Ser Arg
            100                 105                 110

Val Phe Thr Glu Gly Glu Pro Leu Ala Leu Arg Cys His Ala Trp Lys
        115                 120                 125

Asp Lys Leu Val Tyr Asn Val Leu Tyr Tyr Arg Asn Gly Lys Ala Phe
    130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                165                 170                 175

Thr Ser Ala Gly Ile Ser Val Thr Val Lys Glu Leu Phe Pro Ala Pro
            180                 185                 190

Val Leu Asn Ala Ser Val Thr Ser Pro Leu Leu Glu Gly Asn Leu Val
        195                 200                 205

Thr Leu Ser Cys Glu Thr Lys Leu Leu Leu Gln Arg Pro Gly Leu Gln
    210                 215                 220

Leu Tyr Phe Ser Phe Tyr Met Gly Ser Lys Thr Leu Arg Gly Arg Asn
225                 230                 235                 240

Thr Ser Ser Glu Tyr Gln Ile Leu Thr Ala Arg Arg Glu Asp Ser Gly
                245                 250                 255

Leu Tyr Trp Cys Glu Ala Ala Thr Glu Asp Gly Asn Val Leu Lys Arg
            260                 265                 270

Ser Pro Glu Leu Glu Leu Gln Val Leu Gly Phe Phe Pro Pro Gly Tyr
        275                 280                 285

Gln Val Ser Phe Cys Leu Val Met Val Leu Leu Phe Ala Val Asp Thr
    290                 295                 300

Gly Leu Tyr Phe Ser Val Lys Thr Asn Ile Arg Ser Ser Thr Arg Asp
305                 310                 315                 320

Trp Lys Asp His Lys Phe Lys Trp Arg Lys Asp Pro Gln Asp Lys
                325                 330                 335
```

<210> SEQ ID NO 10
<211> LENGTH: 1032
<212> TYPE: DNA
<213> ORGANISM: Artificial Sequence
<220> FEATURE:
<223> OTHER INFORMATION: exemplifying sequence encoding 340 a.a. CD64
      domain-based construction

<400> SEQUENCE: 10

```
cttggagaca acatgtggtt cttgacaact ctgctccttt gggttccagt tgatgggcaa     60

gtggacacca caaaggcagt gatcactttg cagcctccat gggtcagcgt gttccaagag    120

gaaaccgtaa ccttgcattg tgaggtgctc catctgcctg ggagcagctc tacacagtgg    180

tttctcaatg gcacagccac tcagacctcg acccccagct acagaatcac ctctgccagt    240

gtcaatgaca gtggtgaata caggtgccag agaggtctct cagggcgaag tgaccccata    300

cagctggaaa tccacagagg ctggctacta ctgcaggtct ccagcagagt cttcacggaa    360

ggagaacctc tggccttgag gtgtcatgcg tggaaggata agctggtgta caatgtgctt    420

tactatcgaa atggcaaagc ctttaagttt ttccactgga attctaacct caccattctg    480

aaaaccaaca taagtcacaa tggcacctac cattgctcag gcatgggaaa gcatcgctac    540

acatcagcag gaatatctgt cactgtgaaa gagctatttc cagctccagt gctgaatgca    600
```

```
tctgtgacat ccccactcct ggaggggaat ctggtcaccc tgagctgtga aacaaagttg    660

ctcttgcaga ggcctggttt gcagctttac ttctccttct acatgggcag caagaccctg    720

cgaggcagga acacatcctc tgaataccaa atactaactg ctagaagaga agactctggg    780

ttatactggt gcgaggctgc cacagaggat ggaaatgtcc ttaagcgcag ccctgagttg    840

gagcttcaag tgcttggcct ccagttacca actcctgtct ggtttcatta ccaagtctct    900

ttctgcttgg tgatggtact cctttttgca gtggacacag gactatattt ctctgtgaag    960

acaaacattc gaagctcaac aagagactgg aaggaccata aatttaaatg gagaaaggac   1020

cctcaagaca aa                                                       1032
```

```
<210> SEQ ID NO 11
<211> LENGTH: 1020
<212> TYPE: DNA
<213> ORGANISM: Artificial Sequence
<220> FEATURE:
<223> OTHER INFORMATION: exemplifying sequence encoding 336 a.a. CD64
      exon-based construction

<400> SEQUENCE: 11

cttggagaca acatgtggtt cttgacaact ctgctccttt gggttccagt tgatgggcaa     60

gtggacacca caaaggcagt gatcactttg cagcctccat gggtcagcgt gttccaagag    120

gaaaccgtaa ccttgcattg tgaggtgctc catctgcctg ggagcagctc tacacagtgg    180

tttctcaatg gcacagccac tcagacctcg acccccagct acagaatcac ctctgccagt    240

gtcaatgaca gtggtgaata caggtgccag agaggtctct cagggcgaag tgaccccata    300

cagctggaaa tccacagagg ctggctacta ctgcaggtct ccagcagagt cttcacggaa    360

ggagaacctc tggccttgag gtgtcatgcg tggaaggata agctggtgta caatgtgctt    420

tactatcgaa atggcaaagc ctttaagttt ttccactgga attctaacct caccattctg    480

aaaaccaaca taagtcacaa tggcacctac cattgctcag gcatgggaaa gcatcgctac    540

acatcagcag gaatatctgt cactgtgaaa gagctatttc cagctccagt gctgaatgca    600

tctgtgacat ccccactcct ggaggggaat ctggtcaccc tgagctgtga aacaaagttg    660

ctcttgcaga ggcctggttt gcagctttac ttctccttct acatgggcag caagaccctg    720

cgaggcagga acacatcctc tgaataccaa atactaactg ctagaagaga agactctggg    780

ttatactggt gcgaggctgc cacagaggat ggaaatgtcc ttaagcgcag ccctgagttg    840

gagcttcaag tgcttggttt gttctttcca cctgggtacc aagtctcttt ctgcttggtg    900

atggtactcc tttttgcagt ggacacagga ctatatttct ctgtgaagac aaacattcga    960

agctcaacaa gagactggaa ggaccataaa tttaaatgga gaaaggaccc tcaagacaaa   1020
```

```
<210> SEQ ID NO 12
<211> LENGTH: 1005
<212> TYPE: DNA
<213> ORGANISM: Artificial Sequence
<220> FEATURE:
<223> OTHER INFORMATION: exemplifying sequence encoding 335 a.a. CD64
      exon-based construction

<400> SEQUENCE: 12

atgtggttct tgacaactct gctcctttgg gttccagttg atgggcaagt ggacaccaca     60

aaggcagtga tcactttgca gcctccatgg gtcagcgtgt tccaagagga aaccgtaacc    120

ttgcactgtg aggtgctcca tctgcctggg agcagctcta cacagtggtt tctcaatggc    180

acagccactc agacctcgac ccccagctac agaatcacct ctgccagtgt caatgacagt    240
```

```
ggtgaataca ggtgccagag aggtctctca gggcgaagtg accccataca gctggaaatc    300

cacagaggct ggctactact gcaggtctcc agcagagtct tcacggaagg agaacctctg    360

gccttgaggt gtcatgcgtg gaaggataag ctggtgtaca atgtgcttta ctatcgaaat    420

ggcaaagcct ttaagttttt ccactggaac tctaacctca ccattctgaa aaccaacata    480

agtcacaatg gcacctacca ttgctcaggc atgggaaagc atcgctacac atcagcagga    540

atatctgtca ctgtgaaaga gctatttcca gctccagtgc tgaatgcatc tgtgacatcc    600

ccactcctgg aggggaatct ggtcaccctg agctgtgaaa caaagttgct cttgcagagg    660

cctggtttgc agctttactt ctccttctac atgggcagca agaccctgcg aggcaggaac    720

acatcctctg aataccaaat actaactgct agaagagaag actctgggtt atactggtgc    780

gaggctgcca cagaggatgg aaatgtcctt aagcgcagcc ctgagttgga gcttcaagtg    840

cttggcttct ttccacctgg gtaccaagtc tctttctgct tggtgatggt actccttttt    900

gcagtggaca caggactata tttctctgtg aagacaaaca ttcgaagctc aacaagagac    960

tggaaggacc ataaatttaa atggagaaag gaccctcaag acaaa                  1005
```

<210> SEQ ID NO 13
<211> LENGTH: 153
<212> TYPE: PRT
<213> ORGANISM: Artificial Sequence
<220> FEATURE:
<223> OTHER INFORMATION: 153 a.a. CD28 co-stim + CD3-zeta-ITAM

<400> SEQUENCE: 13

```
Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser Arg Val Lys Phe Ser Arg Ser
        35                  40                  45

Ala Asp Ala Pro Ala Tyr Gln Gln Gly Gln Asn Gln Leu Tyr Asn Glu
    50                  55                  60

Leu Asn Leu Gly Arg Arg Glu Glu Tyr Asp Val Leu Asp Lys Arg Arg
65                  70                  75                  80

Gly Arg Asp Pro Glu Met Gly Gly Lys Pro Arg Arg Lys Asn Pro Gln
                85                  90                  95

Glu Gly Leu Phe Asn Glu Leu Gln Lys Asp Lys Met Ala Glu Ala Phe
            100                 105                 110

Ser Glu Ile Gly Met Lys Gly Glu Arg Arg Arg Gly Lys Gly His Asp
        115                 120                 125

Gly Leu Phe Gln Gly Leu Ser Thr Ala Thr Lys Asp Thr Phe Asp Ala
    130                 135                 140

Leu His Met Gln Ala Leu Pro Pro Arg
145                 150
```

<210> SEQ ID NO 14
<211> LENGTH: 219
<212> TYPE: PRT
<213> ORGANISM: Artificial Sequence
<220> FEATURE:
<223> OTHER INFORMATION: 219 a.a. CD28 hinge + CD28 TM + CD28 co-stim +
CD3-zeta-ITAM

<400> SEQUENCE: 14

```
Ile Glu Val Met Tyr Pro Pro Pro Tyr Leu Asp Asn Glu Lys Ser Asn
```

```
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60

Trp Val Arg Ser Lys Arg Ser Arg Leu Leu His Ser Asp Tyr Met Asn
65                  70                  75                  80

Met Thr Pro Arg Arg Pro Gly Pro Thr Arg Lys His Tyr Gln Pro Tyr
                85                  90                  95

Ala Pro Pro Arg Asp Phe Ala Ala Tyr Arg Ser Arg Val Lys Phe Ser
            100                 105                 110

Arg Ser Ala Asp Ala Pro Ala Tyr Gln Gln Gly Gln Asn Gln Leu Tyr
        115                 120                 125

Asn Glu Leu Asn Leu Gly Arg Arg Glu Glu Tyr Asp Val Leu Asp Lys
    130                 135                 140

Arg Arg Gly Arg Asp Pro Glu Met Gly Gly Lys Pro Arg Arg Lys Asn
145                 150                 155                 160

Pro Gln Glu Gly Leu Phe Asn Glu Leu Gln Lys Asp Lys Met Ala Glu
                165                 170                 175

Ala Phe Ser Glu Ile Gly Met Lys Gly Glu Arg Arg Arg Gly Lys Gly
            180                 185                 190

His Asp Gly Leu Phe Gln Gly Leu Ser Thr Ala Thr Lys Asp Thr Phe
        195                 200                 205

Asp Ala Leu His Met Gln Ala Leu Pro Pro Arg
    210                 215


<210> SEQ ID NO 15
<211> LENGTH: 263
<212> TYPE: PRT
<213> ORGANISM: Artificial Sequence
<220> FEATURE:
<223> OTHER INFORMATION: 263 a.a NKG2D TM + 2B4 + CD3-zeta

<400> SEQUENCE: 15

Ser Asn Leu Phe Val Ala Ser Trp Ile Ala Val Met Ile Ile Phe Arg
1               5                   10                  15

Ile Gly Met Ala Val Ala Ile Phe Cys Cys Phe Phe Phe Pro Ser Trp
            20                  25                  30

Arg Arg Lys Arg Lys Glu Lys Gln Ser Glu Thr Ser Pro Lys Glu Phe
        35                  40                  45

Leu Thr Ile Tyr Glu Asp Val Lys Asp Leu Lys Thr Arg Arg Asn His
    50                  55                  60

Glu Gln Glu Gln Thr Phe Pro Gly Gly Gly Ser Thr Ile Tyr Ser Met
65                  70                  75                  80

Ile Gln Ser Gln Ser Ser Ala Pro Thr Ser Gln Glu Pro Ala Tyr Thr
                85                  90                  95

Leu Tyr Ser Leu Ile Gln Pro Ser Arg Lys Ser Gly Ser Arg Lys Arg
            100                 105                 110

Asn His Ser Pro Ser Phe Asn Ser Thr Ile Tyr Glu Val Ile Gly Lys
        115                 120                 125

Ser Gln Pro Lys Ala Gln Asn Pro Ala Arg Leu Ser Arg Lys Glu Leu
    130                 135                 140

Glu Asn Phe Asp Val Tyr Ser Arg Val Lys Phe Ser Arg Ser Ala Asp
```

```
145                 150                 155                 160

Ala Pro Ala Tyr Lys Gln Gly Gln Asn Gln Leu Tyr Asn Glu Leu Asn
                165                 170                 175

Leu Gly Arg Arg Glu Glu Tyr Asp Val Leu Asp Lys Arg Arg Gly Arg
            180                 185                 190

Asp Pro Glu Met Gly Gly Lys Pro Arg Arg Lys Asn Pro Gln Glu Gly
        195                 200                 205

Leu Tyr Asn Glu Leu Gln Lys Asp Lys Met Ala Glu Ala Tyr Ser Glu
    210                 215                 220

Ile Gly Met Lys Gly Glu Arg Arg Arg Gly Lys Gly His Asp Gly Leu
225                 230                 235                 240

Tyr Gln Gly Leu Ser Thr Ala Thr Lys Asp Thr Tyr Asp Ala Leu His
                245                 250                 255

Met Gln Ala Leu Pro Pro Arg
            260


<210> SEQ ID NO 16
<211> LENGTH: 308
<212> TYPE: PRT
<213> ORGANISM: Artificial Sequence
<220> FEATURE:
<223> OTHER INFORMATION: 308 a.a CD8 hinge + NKG2D TM + 2B4 + CD3-zeta

<400> SEQUENCE: 16

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ser Asn Leu
        35                  40                  45

Phe Val Ala Ser Trp Ile Ala Val Met Ile Ile Phe Arg Ile Gly Met
    50                  55                  60

Ala Val Ala Ile Phe Cys Cys Phe Phe Phe Pro Ser Trp Arg Arg Lys
65                  70                  75                  80

Arg Lys Glu Lys Gln Ser Glu Thr Ser Pro Lys Glu Phe Leu Thr Ile
                85                  90                  95

Tyr Glu Asp Val Lys Asp Leu Lys Thr Arg Arg Asn His Glu Gln Glu
            100                 105                 110

Gln Thr Phe Pro Gly Gly Gly Ser Thr Ile Tyr Ser Met Ile Gln Ser
        115                 120                 125

Gln Ser Ser Ala Pro Thr Ser Gln Glu Pro Ala Tyr Thr Leu Tyr Ser
    130                 135                 140

Leu Ile Gln Pro Ser Arg Lys Ser Gly Ser Arg Lys Arg Asn His Ser
145                 150                 155                 160

Pro Ser Phe Asn Ser Thr Ile Tyr Glu Val Ile Gly Lys Ser Gln Pro
                165                 170                 175

Lys Ala Gln Asn Pro Ala Arg Leu Ser Arg Lys Glu Leu Glu Asn Phe
            180                 185                 190

Asp Val Tyr Ser Arg Val Lys Phe Ser Arg Ser Ala Asp Ala Pro Ala
        195                 200                 205

Tyr Lys Gln Gly Gln Asn Gln Leu Tyr Asn Glu Leu Asn Leu Gly Arg
    210                 215                 220

Arg Glu Glu Tyr Asp Val Leu Asp Lys Arg Arg Gly Arg Asp Pro Glu
225                 230                 235                 240

Met Gly Gly Lys Pro Arg Arg Lys Asn Pro Gln Glu Gly Leu Tyr Asn
```

```
                245                 250                 255

Glu Leu Gln Lys Asp Lys Met Ala Glu Ala Tyr Ser Glu Ile Gly Met
            260                 265                 270

Lys Gly Glu Arg Arg Arg Gly Lys Gly His Asp Gly Leu Tyr Gln Gly
        275                 280                 285

Leu Ser Thr Ala Thr Lys Asp Thr Tyr Asp Ala Leu His Met Gln Ala
    290                 295                 300

Leu Pro Pro Arg
305


<210> SEQ ID NO 17
<211> LENGTH: 379
<212> TYPE: PRT
<213> ORGANISM: Artificial Sequence
<220> FEATURE:
<223> OTHER INFORMATION: construct mimicking trans-presentation of IL15
      (design 3)

<400> SEQUENCE: 17

Met Asp Trp Thr Trp Ile Leu Phe Leu Val Ala Ala Ala Thr Arg Val
1               5                   10                  15

His Ser Gly Ile His Val Phe Ile Leu Gly Cys Phe Ser Ala Gly Leu
            20                  25                  30

Pro Lys Thr Glu Ala Asn Trp Val Asn Val Ile Ser Asp Leu Lys Lys
        35                  40                  45

Ile Glu Asp Leu Ile Gln Ser Met His Ile Asp Ala Thr Leu Tyr Thr
    50                  55                  60

Glu Ser Asp Val His Pro Ser Cys Lys Val Thr Ala Met Lys Cys Phe
65                  70                  75                  80

Leu Leu Glu Leu Gln Val Ile Ser Leu Glu Ser Gly Asp Ala Ser Ile
                85                  90                  95

His Asp Thr Val Glu Asn Leu Ile Ile Leu Ala Asn Asn Ser Leu Ser
            100                 105                 110

Ser Asn Gly Asn Val Thr Glu Ser Gly Cys Lys Glu Cys Glu Glu Leu
        115                 120                 125

Glu Glu Lys Asn Ile Lys Glu Phe Leu Gln Ser Phe Val His Ile Val
    130                 135                 140

Gln Met Phe Ile Asn Thr Ser Ser Gly Gly Gly Ser Gly Gly Gly Gly
145                 150                 155                 160

Ser Gly Gly Gly Gly Ser Gly Gly Gly Gly Ser Gly Gly Gly Ser Leu
                165                 170                 175

Gln Ile Thr Cys Pro Pro Pro Met Ser Val Glu His Ala Asp Ile Trp
            180                 185                 190

Val Lys Ser Tyr Ser Leu Tyr Ser Arg Glu Arg Tyr Ile Cys Asn Ser
        195                 200                 205

Gly Phe Lys Arg Lys Ala Gly Thr Ser Ser Leu Thr Glu Cys Val Leu
    210                 215                 220

Asn Lys Ala Thr Asn Val Ala His Trp Thr Thr Pro Ser Leu Lys Cys
225                 230                 235                 240

Ile Arg Asp Pro Ala Leu Val His Gln Arg Pro Ala Pro Pro Ser Thr
                245                 250                 255

Val Thr Thr Ala Gly Val Thr Pro Gln Pro Glu Ser Leu Ser Pro Ser
            260                 265                 270

Gly Lys Glu Pro Ala Ala Ser Ser Pro Ser Ser Asn Asn Thr Ala Ala
        275                 280                 285
```

-continued

Thr Thr Ala Ala Ile Val Pro Gly Ser Gln Leu Met Pro Ser Lys Ser
290 295 300

Pro Ser Thr Gly Thr Thr Glu Ile Ser Ser His Glu Ser Ser His Gly
305 310 315 320

Thr Pro Ser Gln Thr Thr Ala Lys Asn Trp Glu Leu Thr Ala Ser Ala
325 330 335

Ser His Gln Pro Pro Gly Val Tyr Pro Gln Gly His Ser Asp Thr Thr
340 345 350

Val Ala Ile Ser Thr Ser Thr Val Leu Leu Cys Gly Leu Ser Ala Val
355 360 365

Ser Leu Leu Ala Cys Tyr Leu Lys Ser Arg Gln
370 375

<210> SEQ ID NO 18
<211> LENGTH: 1140
<212> TYPE: DNA
<213> ORGANISM: Artificial Sequence
<220> FEATURE:
<223> OTHER INFORMATION: an exemplary nucleic acid sequence encoding construct mimicking trans-presentation of IL15 (design 3)

<400> SEQUENCE: 18
atggactgga cctggattct gttcctggtc gcggctgcaa cgcgagtcca tagcggtatc 60
catgttttta ttcttgggtg tttttctgct gggctgccta agaccgaggc caactgggta 120
aatgtcatca gtgacctcaa gaaaatagaa gaccttatac aaagcatgca cattgatgct 180
actctctaca ctgagtcaga tgtacatccc tcatgcaaag tgacggccat gaaatgtttc 240
ctcctcgaac ttcaagtcat atctctggaa agtggcgacg cgtccatcca cgacacggtc 300
gaaaacctga taatactcgc taataatagt ctctcttcaa atggtaacgt aaccgagtca 360
ggttgcaaag agtgcgaaga gttggaagaa aaaaacataa aggagttcct gcaaagtttc 420
gtgcacattg tgcagatgtt cattaatacc tctagcggcg gaggatcagg tggcggtgga 480
agcggaggtg gaggctccgg tggaggaggt agtggcggag gttctcttca aataacttgt 540
cctccaccga tgtccgtaga acatgcggat atttgggtaa aatcctatag cttgtacagc 600
cgagagcggt atatctgcaa cagcggcttc aagcggaagg ccggcacaag cagcctgacc 660
gagtgcgtgc tgaacaaggc caccaacgtg gcccactgga ccacccctag cctgaagtgc 720
atcagagatc ccgccctggt gcatcagcgg cctgcccctc caagcacagt gacaacagct 780
ggcgtgaccc cccagcctga gagcctgagc ccttctggaa aagagcctgc cgccagcagc 840
cccagcagca acaatactgc cgccaccaca gccgccatcg tgcctggatc tcagctgatg 900
cccagcaaga gccctagcac cggcaccacc gagatcagca gccacgagtc tagccacggc 960
accccatctc agaccaccgc caagaactgg gagctgacag ccagcgcctc tcaccagcct 1020
ccaggcgtgt accctcaggg ccacagcgat accacagtgg ccatcagcac ctccaccgtg 1080
ctgctgtgtg gactgagcgc cgtgtcactg ctggcctgct acctgaagtc cagacagtga 1140

<210> SEQ ID NO 19
<211> LENGTH: 242
<212> TYPE: PRT
<213> ORGANISM: Artificial Sequence
<220> FEATURE:
<223> OTHER INFORMATION: fused IL15/mb-Sushi construct (design 4)

<400> SEQUENCE: 19

Met Asp Trp Thr Trp Ile Leu Phe Leu Val Ala Ala Ala Thr Arg Val
1 5 10 15

```
His Ser Gly Ile His Val Phe Ile Leu Gly Cys Phe Ser Ala Gly Leu
            20                  25                  30

Pro Lys Thr Glu Ala Asn Trp Val Asn Val Ile Ser Asp Leu Lys Lys
        35                  40                  45

Ile Glu Asp Leu Ile Gln Ser Met His Ile Asp Ala Thr Leu Tyr Thr
    50                  55                  60

Glu Ser Asp Val His Pro Ser Cys Lys Val Thr Ala Met Lys Cys Phe
65                  70                  75                  80

Leu Leu Glu Leu Gln Val Ile Ser Leu Glu Ser Gly Asp Ala Ser Ile
                85                  90                  95

His Asp Thr Val Glu Asn Leu Ile Ile Leu Ala Asn Asn Ser Leu Ser
            100                 105                 110

Ser Asn Gly Asn Val Thr Glu Ser Gly Cys Lys Glu Cys Glu Glu Leu
        115                 120                 125

Glu Glu Lys Asn Ile Lys Glu Phe Leu Gln Ser Phe Val His Ile Val
    130                 135                 140

Gln Met Phe Ile Asn Thr Ser Ser Gly Gly Gly Ser Gly Gly Gly Gly
145                 150                 155                 160

Ser Gly Gly Gly Gly Ser Gly Gly Gly Gly Ser Gly Gly Gly Ser Leu
                165                 170                 175

Gln Ile Thr Cys Pro Pro Pro Met Ser Val Glu His Ala Asp Ile Trp
            180                 185                 190

Val Lys Ser Tyr Ser Leu Tyr Ser Arg Glu Arg Tyr Ile Cys Asn Ser
        195                 200                 205

Gly Phe Lys Arg Lys Ala Gly Thr Ser Ser Leu Thr Glu Cys Val Leu
    210                 215                 220

Asn Lys Ala Thr Asn Val Ala His Trp Thr Thr Pro Ser Leu Lys Cys
225                 230                 235                 240

Ile Arg
```

<210> SEQ ID NO 20
<211> LENGTH: 726
<212> TYPE: DNA
<213> ORGANISM: Artificial Sequence
<220> FEATURE:
<223> OTHER INFORMATION: an exemplary nucleic acid sequence encoding fused IL15/mb-Sushi construct (design 4)

<400> SEQUENCE: 20

```
atggactgga cctggattct gttcctggtc gcggctgcaa cgcgagtcca tagcggtatc     60

catgttttta ttcttgggtg tttttctgct gggctgccta agaccgaggc caactgggta    120

aatgtcatca gtgacctcaa gaaaatagaa gaccttatac aaagcatgca cattgatgct    180

actctctaca ctgagtcaga tgtacatccc tcatgcaaag tgacggccat gaaatgtttc    240

ctcctcgaac ttcaagtcat atctctggaa agtggcgacg cgtccatcca cgacacggtc    300

gaaaacctga taatactcgc taataatagt ctctcttcaa atggtaacgt aaccgagtca    360

ggttgcaaag agtgcgaaga gttggaagaa aaaaacataa aggagttcct gcaaagtttc    420

gtgcacattg tgcagatgtt cattaatacc tctagcggcg gaggatcagg tggcggtgga    480

agcggaggtg gaggctccgg tggaggaggt agtggcggag gttctcttca aataacttgt    540

cctccaccga tgtccgtaga acatgcggat atttgggtaa aatcctatag cttgtacagc    600

cgagagcggt atatctgcaa cagcggcttc aagcggaagg ccggcacaag cagcctgacc    660

gagtgcgtgc tgaacaaggc caccaacgtg gcccactgga ccacccctag cctgaagtgc    720
```

atcaga 726

<210> SEQ ID NO 21
<211> LENGTH: 375
<212> TYPE: PRT
<213> ORGANISM: Artificial Sequence
<220> FEATURE:
<223> OTHER INFORMATION: protein construct further modified from SEQ ID NO. 17

<400> SEQUENCE: 21

Met Asp Trp Thr Trp Ile Leu Phe Leu Val Ala Ala Ala Thr Arg Val
1 5 10 15

His Ser Gly Ile His Val Phe Ile Leu Gly Cys Phe Ser Ala Gly Leu
20 25 30

Pro Lys Thr Glu Ala Asn Trp Val Asn Val Ile Ser Asp Leu Lys Lys
35 40 45

Ile Glu Asp Leu Ile Gln Ser Met His Ile Asp Ala Thr Leu Tyr Thr
50 55 60

Glu Ser Asp Val His Pro Ser Cys Lys Val Thr Ala Met Lys Cys Phe
65 70 75 80

Leu Leu Glu Leu Gln Val Ile Ser Leu Glu Ser Gly Asp Ala Ser Ile
85 90 95

His Asp Thr Val Glu Asn Leu Ile Ile Leu Ala Asn Asn Ser Leu Ser
100 105 110

Ser Asn Gly Asn Val Thr Glu Ser Gly Cys Lys Glu Cys Glu Glu Leu
115 120 125

Glu Glu Lys Asn Ile Lys Glu Phe Leu Gln Ser Phe Val His Ile Val
130 135 140

Gln Met Phe Ile Asn Thr Ser Ser Gly Gly Gly Ser Gly Gly Gly Gly
145 150 155 160

Ser Gly Gly Gly Gly Ser Gly Gly Gly Gly Ser Gly Gly Gly Ser Leu
165 170 175

Gln Ile Thr Cys Pro Pro Pro Met Ser Val Glu His Ala Asp Ile Trp
180 185 190

Val Lys Ser Tyr Ser Leu Tyr Ser Arg Glu Arg Tyr Ile Cys Asn Ser
195 200 205

Gly Phe Lys Arg Lys Ala Gly Thr Ser Ser Leu Thr Glu Cys Val Leu
210 215 220

Asn Lys Ala Thr Asn Val Ala His Trp Thr Thr Pro Ser Leu Lys Cys
225 230 235 240

Ile Arg Asp Pro Ala Leu Val His Gln Arg Pro Ala Pro Pro Ser Thr
245 250 255

Val Thr Thr Ala Gly Val Thr Pro Gln Pro Glu Ser Leu Ser Pro Ser
260 265 270

Gly Lys Glu Pro Ala Ala Ser Ser Pro Ser Ser Asn Asn Thr Ala Ala
275 280 285

Thr Thr Ala Ala Ile Val Pro Gly Ser Gln Leu Met Pro Ser Lys Ser
290 295 300

Pro Ser Thr Gly Thr Thr Glu Ile Ser Ser His Glu Ser Ser His Gly
305 310 315 320

Thr Pro Ser Gln Thr Thr Ala Lys Asn Trp Glu Leu Thr Ala Ser Ala
325 330 335

Ser His Gln Pro Pro Gly Val Tyr Pro Gln Gly His Ser Asp Thr Thr
340 345 350

Val Ala Ile Ser Thr Ser Thr Val Leu Leu Cys Gly Leu Ser Ala Val
355 360 365

Ser Leu Leu Ala Cys Tyr Leu
370 375

<210> SEQ ID NO 22
<211> LENGTH: 23
<212> TYPE: PRT
<213> ORGANISM: Artificial Sequence
<220> FEATURE:
<223> OTHER INFORMATION: non-limiting exemplary signal peptide for the construct comprising tgpTCR-alpha

<400> SEQUENCE: 22

Met Ala Gly Thr Trp Leu Leu Leu Leu Leu Ala Leu Gly Cys Pro Ala
1 5 10 15

Leu Pro Thr Gly Val Gly Gly
20

<210> SEQ ID NO 23
<211> LENGTH: 273
<212> TYPE: PRT
<213> ORGANISM: Artificial Sequence
<220> FEATURE:
<223> OTHER INFORMATION: exemplary sequence of a construct comprising tgpTCR-alpha (tgpTCR-alpha with TM)

<400> SEQUENCE: 23

Thr Pro Phe Pro Ser Leu Ala Pro Pro Ile Met Leu Leu Val Asp Gly
1 5 10 15

Lys Gln Gln Met Val Val Val Cys Leu Val Leu Asp Val Ala Pro Pro
20 25 30

Gly Leu Asp Ser Pro Ile Trp Phe Ser Ala Gly Asn Gly Ser Ala Leu
35 40 45

Asp Ala Phe Thr Tyr Gly Pro Ser Pro Ala Thr Asp Gly Thr Trp Thr
50 55 60

Asn Leu Ala His Leu Ser Leu Pro Ser Glu Glu Leu Ala Ser Trp Glu
65 70 75 80

Pro Leu Val Cys His Thr Gly Pro Gly Ala Glu Gly His Ser Arg Ser
85 90 95

Thr Gln Pro Met His Leu Ser Gly Glu Ala Ser Thr Ala Arg Thr Cys
100 105 110

Pro Gln Glu Pro Leu Arg Gly Gly Cys Gly Leu Leu Arg Ala Pro Glu
115 120 125

Arg Phe Leu Leu Ala Gly Thr Pro Gly Gly Ala Leu Trp Leu Gly Val
130 135 140

Leu Arg Leu Leu Leu Phe Lys Leu Leu Leu Phe Asp Leu Leu Leu Thr
145 150 155 160

Cys Ser Cys Leu Cys Asp Pro Ala Gly Pro Leu Pro Ser Pro Ala Thr
165 170 175

Thr Thr Arg Leu Arg Ala Leu Gly Ser His Arg Leu His Pro Ala Thr
180 185 190

Glu Thr Gly Gly Arg Glu Ala Thr Ser Ser Pro Arg Pro Gln Pro Arg
195 200 205

Asp Arg Arg Trp Gly Asp Thr Pro Pro Gly Arg Lys Pro Gly Ser Pro
210 215 220

Val Trp Gly Glu Gly Ser Tyr Leu Ser Ser Tyr Pro Thr Cys Pro Ala
225 230 235 240

```
Gln Ala Trp Cys Ser Arg Ser Ala Leu Arg Ala Pro Ser Ser Ser Leu
                245                 250                 255

Gly Ala Phe Phe Ala Gly Asp Leu Pro Pro Pro Leu Gln Ala Gly Ala
            260                 265                 270

Ala


<210> SEQ ID NO 24
<211> LENGTH: 225
<212> TYPE: PRT
<213> ORGANISM: Artificial Sequence
<220> FEATURE:
<223> OTHER INFORMATION: partial length of a construct comprising
      tgpTCR-alpha (Truncated tgpTCR-alpha with TM)

<400> SEQUENCE: 24

Thr Pro Phe Pro Ser Leu Ala Pro Pro Ile Met Leu Leu Val Asp Gly
1               5                   10                  15

Lys Gln Gln Met Val Val Val Cys Leu Val Leu Asp Val Ala Pro Pro
            20                  25                  30

Gly Leu Asp Ser Pro Ile Trp Phe Ser Ala Gly Asn Gly Ser Ala Leu
        35                  40                  45

Asp Ala Phe Thr Tyr Gly Pro Ser Pro Ala Thr Asp Gly Thr Trp Thr
    50                  55                  60

Asn Leu Ala His Leu Ser Leu Pro Ser Glu Glu Leu Ala Ser Trp Glu
65                  70                  75                  80

Pro Leu Val Cys His Thr Gly Pro Gly Ala Glu Gly His Ser Arg Ser
                85                  90                  95

Thr Gln Pro Met His Leu Ser Gly Glu Ala Ser Thr Ala Arg Thr Cys
            100                 105                 110

Pro Gln Glu Pro Leu Arg Gly Gly Cys Gly Leu Leu Arg Ala Pro Glu
        115                 120                 125

Arg Phe Leu Leu Ala Gly Thr Pro Gly Gly Ala Leu Trp Leu Gly Val
    130                 135                 140

Leu Arg Leu Leu Leu Phe Lys Leu Leu Leu Phe Asp Leu Leu Leu Thr
145                 150                 155                 160

Cys Ser Cys Leu Cys Asp Pro Ala Gly Pro Leu Pro Ser Pro Ala Thr
                165                 170                 175

Thr Thr Arg Leu Arg Ala Leu Gly Ser His Arg Leu His Pro Ala Thr
            180                 185                 190

Glu Thr Gly Gly Arg Glu Ala Thr Ser Ser Pro Arg Pro Gln Pro Arg
        195                 200                 205

Asp Arg Arg Trp Gly Asp Thr Pro Pro Gly Arg Lys Pro Gly Ser Pro
    210                 215                 220

Val
225


<210> SEQ ID NO 25
<211> LENGTH: 104
<212> TYPE: PRT
<213> ORGANISM: Artificial Sequence
<220> FEATURE:
<223> OTHER INFORMATION: exemplary sequence of a construct comprising a
      full or partial length of CD3-epsilon ectodomain

<400> SEQUENCE: 25

Asp Gly Asn Glu Glu Met Gly Gly Ile Thr Gln Thr Pro Tyr Lys Val
1               5                   10                  15
```

-continued

```
Ser Ile Ser Gly Thr Thr Val Ile Leu Thr Cys Pro Gln Tyr Pro Gly
            20                  25                  30

Ser Glu Ile Leu Trp Gln His Asn Asp Lys Asn Ile Gly Gly Asp Glu
        35                  40                  45

Asp Asp Lys Asn Ile Gly Ser Asp Glu Asp His Leu Ser Leu Lys Glu
    50                  55                  60

Phe Ser Glu Leu Glu Gln Ser Gly Tyr Tyr Val Cys Tyr Pro Arg Gly
65                  70                  75                  80

Ser Lys Pro Glu Asp Ala Asn Phe Tyr Leu Tyr Leu Arg Ala Arg Val
                85                  90                  95

Cys Glu Asn Cys Met Glu Met Asp
            100


<210> SEQ ID NO 26
<211> LENGTH: 84
<212> TYPE: PRT
<213> ORGANISM: Artificial Sequence
<220> FEATURE:
<223> OTHER INFORMATION: exemplary sequence of a construct comprising a
      full or partial length of CD3-delta ectodomain

<400> SEQUENCE: 26

Phe Lys Ile Pro Ile Glu Glu Leu Glu Asp Arg Val Phe Val Asn Cys
1               5                   10                  15

Asn Thr Ser Ile Thr Trp Val Glu Gly Thr Val Gly Thr Leu Leu Ser
            20                  25                  30

Asp Ile Thr Arg Leu Asp Leu Gly Lys Arg Ile Leu Asp Pro Arg Gly
        35                  40                  45

Ile Tyr Arg Cys Asn Gly Thr Asp Ile Tyr Lys Asp Lys Glu Ser Thr
    50                  55                  60

Val Gln Val His Tyr Arg Met Cys Gln Ser Cys Val Glu Leu Asp Pro
65                  70                  75                  80

Ala Thr Val Ala


<210> SEQ ID NO 27
<211> LENGTH: 94
<212> TYPE: PRT
<213> ORGANISM: Artificial Sequence
<220> FEATURE:
<223> OTHER INFORMATION: exemplary sequence of a construct comprising
      a full or partial length of CD3-gamma ectodomain

<400> SEQUENCE: 27

Gln Ser Ile Lys Gly Asn His Leu Val Lys Val Tyr Asp Tyr Gln Glu
1               5                   10                  15

Asp Gly Ser Val Leu Leu Thr Cys Asp Ala Glu Ala Lys Asn Ile Thr
            20                  25                  30

Trp Phe Lys Asp Gly Lys Met Ile Gly Phe Leu Thr Glu Asp Lys Lys
        35                  40                  45

Lys Trp Asn Leu Gly Ser Asn Ala Lys Asp Pro Arg Gly Met Tyr Gln
    50                  55                  60

Cys Lys Gly Ser Gln Asn Lys Ser Lys Pro Leu Gln Val Tyr Tyr Arg
65                  70                  75                  80

Met Cys Gln Asn Cys Ile Glu Leu Asn Ala Ala Thr Ile Ser
                85                  90


<210> SEQ ID NO 28
<211> LENGTH: 22
<212> TYPE: PRT
```

<213> ORGANISM: Artificial Sequence
<220> FEATURE:
<223> OTHER INFORMATION: signal peptide for a construct comprising a full or partial length of CD3-epsilon ectodomain

<400> SEQUENCE: 28

Met Gln Ser Gly Thr His Trp Arg Val Leu Gly Leu Cys Leu Leu Ser
1 5 10 15

Val Gly Val Trp Gly Gln
20

<210> SEQ ID NO 29
<211> LENGTH: 21
<212> TYPE: PRT
<213> ORGANISM: Artificial Sequence
<220> FEATURE:
<223> OTHER INFORMATION: signal peptide for a construct comprising a full or partial length of CD3-delta ectodomain

<400> SEQUENCE: 29

Met Glu His Ser Thr Phe Leu Ser Gly Leu Val Leu Ala Thr Leu Leu
1 5 10 15

Ser Gln Val Ser Pro
20

<210> SEQ ID NO 30
<211> LENGTH: 22
<212> TYPE: PRT
<213> ORGANISM: Artificial Sequence
<220> FEATURE:
<223> OTHER INFORMATION: signal peptide for a construct comprising a full or partial length of CD3-gamma ectodomain

<400> SEQUENCE: 30

Met Glu Gln Gly Lys Gly Leu Ala Val Leu Ile Leu Ala Ile Ile Leu
1 5 10 15

Leu Gln Gly Thr Leu Ala
20

<210> SEQ ID NO 31
<211> LENGTH: 348
<212> TYPE: PRT
<213> ORGANISM: Artificial Sequence
<220> FEATURE:
<223> OTHER INFORMATION: exemplary sequence comprising tgCD3(epsilon-delta)-TRAC fusion protein

<400> SEQUENCE: 31

Asp Gly Asn Glu Glu Met Gly Gly Ile Thr Gln Thr Pro Tyr Lys Val
1 5 10 15

Ser Ile Ser Gly Thr Thr Val Ile Leu Thr Cys Pro Gln Tyr Pro Gly
20 25 30

Ser Glu Ile Leu Trp Gln His Asn Asp Lys Asn Ile Gly Gly Asp Glu
35 40 45

Asp Asp Lys Asn Ile Gly Ser Asp Glu Asp His Leu Ser Leu Lys Glu
50 55 60

Phe Ser Glu Leu Glu Gln Ser Gly Tyr Tyr Val Cys Tyr Pro Arg Gly
65 70 75 80

Ser Lys Pro Glu Asp Ala Asn Phe Tyr Leu Tyr Leu Arg Ala Arg Val
85 90 95

Gly Ser Ala Asp Asp Ala Lys Lys Asp Ala Ala Lys Lys Asp Asp Ala
100 105 110

```
Lys Lys Asp Asp Ala Lys Lys Asp Gly Ser Phe Lys Ile Pro Ile Glu
        115                 120                 125

Glu Leu Glu Asp Arg Val Phe Val Asn Cys Asn Thr Ser Ile Thr Trp
    130                 135                 140

Val Glu Gly Thr Val Gly Thr Leu Leu Ser Asp Ile Thr Arg Leu Asp
145                 150                 155                 160

Leu Gly Lys Arg Ile Leu Asp Pro Arg Gly Ile Tyr Arg Cys Asn Gly
                165                 170                 175

Thr Asp Ile Tyr Lys Asp Lys Glu Ser Thr Val Gln Val His Tyr Arg
            180                 185                 190

Met Gly Gly Gly Gly Ser Gly Gly Gly Gly Ser Gly Gly Gly Gly Ser
        195                 200                 205

Ile Gln Asn Pro Asp Pro Ala Val Tyr Gln Leu Arg Asp Ser Lys Ser
    210                 215                 220

Ser Asp Lys Ser Val Cys Leu Phe Thr Asp Phe Asp Ser Gln Thr Asn
225                 230                 235                 240

Val Ser Gln Ser Lys Asp Ser Asp Val Tyr Ile Thr Asp Lys Thr Val
                245                 250                 255

Leu Asp Met Arg Ser Met Asp Phe Lys Ser Asn Ser Ala Val Ala Trp
            260                 265                 270

Ser Asn Lys Ser Asp Phe Ala Cys Ala Asn Ala Phe Asn Asn Ser Ile
        275                 280                 285

Ile Pro Glu Asp Thr Phe Phe Pro Ser Pro Glu Ser Ser Cys Asp Val
    290                 295                 300

Lys Leu Val Glu Lys Ser Phe Glu Thr Asp Thr Asn Leu Asn Phe Gln
305                 310                 315                 320

Asn Leu Ser Val Ile Gly Phe Arg Ile Leu Leu Leu Lys Val Ala Gly
                325                 330                 335

Phe Asn Leu Leu Met Thr Leu Arg Leu Trp Ser Ser
            340                 345
```

<210> SEQ ID NO 32
<211> LENGTH: 394
<212> TYPE: PRT
<213> ORGANISM: Artificial Sequence
<220> FEATURE:
<223> OTHER INFORMATION: exemplary sequence comprising tgCD3(epsilon-delta)-TRAC fusion protein

<400> SEQUENCE: 32

```
Asp Gly Asn Glu Glu Met Gly Gly Ile Thr Gln Thr Pro Tyr Lys Val
1               5                   10                  15

Ser Ile Ser Gly Thr Thr Val Ile Leu Thr Cys Pro Gln Tyr Pro Gly
            20                  25                  30

Ser Glu Ile Leu Trp Gln His Asn Asp Lys Asn Ile Gly Gly Asp Glu
        35                  40                  45

Asp Asp Lys Asn Ile Gly Ser Asp Glu Asp His Leu Ser Leu Lys Glu
    50                  55                  60

Phe Ser Glu Leu Glu Gln Ser Gly Tyr Tyr Val Cys Tyr Pro Arg Gly
65                  70                  75                  80

Ser Lys Pro Glu Asp Ala Asn Phe Tyr Leu Tyr Leu Arg Ala Arg Val
                85                  90                  95

Gly Ser Ala Asp Asp Ala Lys Lys Asp Ala Ala Lys Lys Asp Asp Ala
            100                 105                 110

Lys Lys Asp Asp Ala Lys Lys Asp Gly Ser Gln Ser Ile Lys Gly Asn
        115                 120                 125
```

His Leu Val Lys Val Tyr Asp Tyr Gln Glu Asp Gly Ser Val Leu Leu
    130                 135                 140

Thr Cys Asp Ala Glu Ala Lys Asn Ile Thr Trp Phe Lys Asp Gly Lys
145                 150                 155                 160

Met Ile Gly Phe Leu Thr Glu Asp Lys Lys Lys Trp Asn Leu Gly Ser
                165                 170                 175

Asn Ala Lys Asp Pro Arg Gly Met Tyr Gln Cys Lys Gly Ser Gln Asn
            180                 185                 190

Lys Ser Lys Pro Leu Gln Val Tyr Tyr Arg Met Gly Gly Gly Gly Ser
        195                 200                 205

Gly Gly Gly Gly Ser Gly Gly Gly Gly Ser Asp Leu Asn Lys Val Phe
    210                 215                 220

Pro Pro Glu Val Ala Val Phe Glu Pro Ser Glu Ala Glu Ile Ser His
225                 230                 235                 240

Thr Gln Lys Ala Thr Leu Val Cys Leu Ala Thr Gly Phe Phe Pro Asp
                245                 250                 255

His Val Glu Leu Ser Trp Trp Val Asn Gly Lys Glu Val His Ser Gly
            260                 265                 270

Val Ser Thr Asp Pro Gln Pro Leu Lys Glu Gln Pro Ala Leu Asn Asp
        275                 280                 285

Ser Arg Tyr Cys Leu Ser Ser Arg Leu Arg Val Ser Ala Thr Phe Trp
    290                 295                 300

Gln Asn Pro Arg Asn His Phe Arg Cys Gln Val Gln Phe Tyr Gly Leu
305                 310                 315                 320

Ser Glu Asn Asp Glu Trp Thr Gln Asp Arg Ala Lys Pro Val Thr Gln
                325                 330                 335

Ile Val Ser Ala Glu Ala Trp Gly Arg Ala Asp Cys Gly Phe Thr Ser
            340                 345                 350

Val Ser Tyr Gln Gln Gly Val Leu Ser Ala Thr Ile Leu Tyr Glu Ile
        355                 360                 365

Leu Leu Gly Lys Ala Thr Leu Tyr Ala Val Leu Val Ser Ala Leu Val
    370                 375                 380

Leu Met Ala Met Val Lys Arg Lys Asp Phe
385                 390

<210> SEQ ID NO 33
<211> LENGTH: 26
<212> TYPE: PRT
<213> ORGANISM: Artificial Sequence
<220> FEATURE:
<223> OTHER INFORMATION: linker sequence to the sequence comprising
      tgCD3(epsilon-delta)-TRAC fusion protein (G4S linker)

<400> SEQUENCE: 33

Gly Ser Ala Asp Asp Ala Lys Lys Asp Ala Ala Lys Lys Asp Asp Ala
1               5                   10                  15

Lys Lys Asp Asp Ala Lys Lys Asp Gly Ser
            20                  25

<210> SEQ ID NO 34
<211> LENGTH: 15
<212> TYPE: PRT
<213> ORGANISM: Artificial Sequence
<220> FEATURE:
<223> OTHER INFORMATION: linker sequence to the sequence comprising
      tgCD3(epsilon-delta)-TRAC fusion protein (G4S linker)

<400> SEQUENCE: 34

Gly Gly Gly Gly Ser Gly Gly Gly Gly Ser Gly Gly Gly Gly Ser
1 5 10 15

<210> SEQ ID NO 35
<211> LENGTH: 163
<212> TYPE: PRT
<213> ORGANISM: Artificial Sequence
<220> FEATURE:
<223> OTHER INFORMATION: exemplary sequence comprising a full or partial length of CD3-zeta endodomain

<400> SEQUENCE: 35

Met Lys Trp Lys Ala Leu Phe Thr Ala Ala Ile Leu Gln Ala Gln Leu
1 5 10 15

Pro Ile Thr Glu Ala Gln Ser Phe Gly Leu Leu Asp Pro Lys Leu Cys
20 25 30

Tyr Leu Leu Asp Gly Ile Leu Phe Ile Tyr Gly Val Ile Leu Thr Ala
35 40 45

Leu Phe Leu Arg Val Lys Phe Ser Arg Ser Ala Asp Ala Pro Ala Tyr
50 55 60

Gln Gln Gly Gln Asn Gln Leu Tyr Asn Glu Leu Asn Leu Gly Arg Arg
65 70 75 80

Glu Glu Tyr Asp Val Leu Asp Lys Arg Arg Gly Arg Asp Pro Glu Met
85 90 95

Gly Gly Lys Pro Arg Arg Lys Asn Pro Gln Glu Gly Leu Tyr Asn Glu
100 105 110

Leu Gln Lys Asp Lys Met Ala Glu Ala Tyr Ser Glu Ile Gly Met Lys
115 120 125

Gly Glu Arg Arg Arg Gly Lys Gly His Asp Gly Leu Tyr Gln Gly Leu
130 135 140

Ser Thr Ala Thr Lys Asp Thr Tyr Asp Ala Leu His Met Gln Ala Leu
145 150 155 160

Pro Pro Arg

<210> SEQ ID NO 36
<211> LENGTH: 29
<212> TYPE: PRT
<213> ORGANISM: Artificial Sequence
<220> FEATURE:
<223> OTHER INFORMATION: ITAM1 sequence

<400> SEQUENCE: 36

Ala Pro Ala Tyr Gln Gln Gly Gln Asn Gln Leu Tyr Asn Glu Leu Asn
1 5 10 15

Leu Gly Arg Arg Glu Glu Tyr Asp Val Leu Asp Lys Arg
20 25

<210> SEQ ID NO 37
<211> LENGTH: 28
<212> TYPE: PRT
<213> ORGANISM: Artificial Sequence
<220> FEATURE:
<223> OTHER INFORMATION: ITAM2 sequence

<400> SEQUENCE: 37

Pro Arg Arg Lys Asn Pro Gln Glu Gly Leu Tyr Asn Glu Leu Gln Lys
1 5 10 15

Asp Lys Met Ala Glu Ala Tyr Ser Glu Ile Gly Met
20 25

```
<210> SEQ ID NO 38
<211> LENGTH: 29
<212> TYPE: PRT
<213> ORGANISM: Artificial Sequence
<220> FEATURE:
<223> OTHER INFORMATION: ITAM3 sequence

<400> SEQUENCE: 38

Glu Arg Arg Arg Gly Lys Gly His Asp Gly Leu Tyr Gln Gly Leu Ser
1               5                   10                  15

Thr Ala Thr Lys Asp Thr Tyr Asp Ala Leu His Met Gln
            20                  25


<210> SEQ ID NO 39
<211> LENGTH: 153
<212> TYPE: PRT
<213> ORGANISM: Artificial Sequence
<220> FEATURE:
<223> OTHER INFORMATION: exemplary sequence from which any one or two
      CD3-zeta ITAMs may be removed

<400> SEQUENCE: 39

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser Arg Val Lys Phe Ser Arg Ser
        35                  40                  45

Ala Asp Ala Pro Ala Tyr Gln Gln Gly Gln Asn Gln Leu Tyr Asn Glu
    50                  55                  60

Leu Asn Leu Gly Arg Arg Glu Glu Tyr Asp Val Leu Asp Lys Arg Arg
65                  70                  75                  80

Gly Arg Asp Pro Glu Met Gly Gly Lys Pro Arg Arg Lys Asn Pro Gln
                85                  90                  95

Glu Gly Leu Tyr Asn Glu Leu Gln Lys Asp Lys Met Ala Glu Ala Tyr
            100                 105                 110

Ser Glu Ile Gly Met Lys Gly Glu Arg Arg Arg Gly Lys Gly His Asp
        115                 120                 125

Gly Leu Tyr Gln Gly Leu Ser Thr Ala Thr Lys Asp Thr Tyr Asp Ala
    130                 135                 140

Leu His Met Gln Ala Leu Pro Pro Arg
145                 150


<210> SEQ ID NO 40
<211> LENGTH: 154
<212> TYPE: PRT
<213> ORGANISM: Artificial Sequence
<220> FEATURE:
<223> OTHER INFORMATION: exemplary sequence CD3 chimeric chain with 41BB
      signaling domain from which any one or two CD3-zeta ITAMs may be
      removed

<400> SEQUENCE: 40

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu Arg Val Lys Phe Ser Arg
        35                  40                  45

Ser Ala Asp Ala Pro Ala Tyr Gln Gln Gly Gln Asn Gln Leu Tyr Asn
```

```
    50                  55                  60

Glu Leu Asn Leu Gly Arg Arg Glu Glu Tyr Asp Val Leu Asp Lys Arg
65                  70                  75                  80

Arg Gly Arg Asp Pro Glu Met Gly Gly Lys Pro Arg Arg Lys Asn Pro
                85                  90                  95

Gln Glu Gly Leu Tyr Asn Glu Leu Gln Lys Asp Lys Met Ala Glu Ala
            100                 105                 110

Tyr Ser Glu Ile Gly Met Lys Gly Glu Arg Arg Arg Gly Lys Gly His
        115                 120                 125

Asp Gly Leu Tyr Gln Gly Leu Ser Thr Ala Thr Lys Asp Thr Tyr Asp
    130                 135                 140

Ala Leu His Met Gln Ala Leu Pro Pro Arg
145                 150


<210> SEQ ID NO 41
<211> LENGTH: 195
<212> TYPE: PRT
<213> ORGANISM: Artificial Sequence
<220> FEATURE:
<223> OTHER INFORMATION: exemplary sequence comprising a full or partial
      length of 28BB-zeta endodomain

<400> SEQUENCE: 41

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser Lys Arg Gly Arg Lys Lys Leu
        35                  40                  45

Leu Tyr Ile Phe Lys Gln Pro Phe Met Arg Pro Val Gln Thr Thr Gln
    50                  55                  60

Glu Glu Asp Gly Cys Ser Cys Arg Phe Pro Glu Glu Glu Glu Gly Gly
65                  70                  75                  80

Cys Glu Leu Arg Val Lys Phe Ser Arg Ser Ala Asp Ala Pro Ala Tyr
                85                  90                  95

Gln Gln Gly Gln Asn Gln Leu Tyr Asn Glu Leu Asn Leu Gly Arg Arg
            100                 105                 110

Glu Glu Tyr Asp Val Leu Asp Lys Arg Arg Gly Arg Asp Pro Glu Met
        115                 120                 125

Gly Gly Lys Pro Arg Arg Lys Asn Pro Gln Glu Gly Leu Tyr Asn Glu
    130                 135                 140

Leu Gln Lys Asp Lys Met Ala Glu Ala Tyr Ser Glu Ile Gly Met Lys
145                 150                 155                 160

Gly Glu Arg Arg Arg Gly Lys Gly His Asp Gly Leu Tyr Gln Gly Leu
                165                 170                 175

Ser Thr Ala Thr Lys Asp Thr Tyr Asp Ala Leu His Met Gln Ala Leu
            180                 185                 190

Pro Pro Arg
        195


<210> SEQ ID NO 42
<211> LENGTH: 426
<212> TYPE: PRT
<213> ORGANISM: Artificial Sequence
<220> FEATURE:
<223> OTHER INFORMATION: exemplary sequence comprising a full or partial
      length of 28BB-zeta endodomain
```

<400> SEQUENCE: 42

Asp Gly Asn Glu Glu Met Gly Gly Ile Thr Gln Thr Pro Tyr Lys Val
1 5 10 15

Ser Ile Ser Gly Thr Thr Val Ile Leu Thr Cys Pro Gln Tyr Pro Gly
20 25 30

Ser Glu Ile Leu Trp Gln His Asn Asp Lys Asn Ile Gly Gly Asp Glu
35 40 45

Asp Asp Lys Asn Ile Gly Ser Asp Glu Asp His Leu Ser Leu Lys Glu
50 55 60

Phe Ser Glu Leu Glu Gln Ser Gly Tyr Tyr Val Cys Tyr Pro Arg Gly
65 70 75 80

Ser Lys Pro Glu Asp Ala Asn Phe Tyr Leu Tyr Leu Arg Ala Arg Val
85 90 95

Gly Ser Ala Asp Asp Ala Lys Lys Asp Ala Ala Lys Lys Asp Asp Ala
100 105 110

Lys Lys Asp Asp Ala Lys Lys Asp Gly Ser Gln Ser Ile Lys Gly Asn
115 120 125

His Leu Val Lys Val Tyr Asp Tyr Gln Glu Asp Gly Ser Val Leu Leu
130 135 140

Thr Cys Asp Ala Glu Ala Lys Asn Ile Thr Trp Phe Lys Asp Gly Lys
145 150 155 160

Met Ile Gly Phe Leu Thr Glu Asp Lys Lys Lys Trp Asn Leu Gly Ser
165 170 175

Asn Ala Lys Asp Pro Arg Gly Met Tyr Gln Cys Lys Gly Ser Gln Asn
180 185 190

Lys Ser Lys Pro Leu Gln Val Tyr Tyr Arg Met Arg Ala Ala Ala Ile
195 200 205

Glu Val Met Tyr Pro Pro Pro Tyr Leu Asp Asn Glu Lys Ser Asn Gly
210 215 220

Thr Ile Ile His Val Lys Gly Lys His Leu Cys Pro Ser Pro Leu Phe
225 230 235 240

Pro Gly Pro Ser Lys Pro Phe Trp Val Leu Val Val Val Gly Gly Val
245 250 255

Leu Ala Cys Tyr Ser Leu Leu Val Thr Val Ala Phe Ile Ile Phe Trp
260 265 270

Val Arg Ser Lys Arg Ser Arg Leu Leu His Ser Asp Tyr Met Asn Met
275 280 285

Thr Pro Arg Arg Pro Gly Pro Thr Arg Lys His Tyr Gln Pro Tyr Ala
290 295 300

Pro Pro Arg Asp Phe Ala Ala Tyr Arg Ser Arg Val Lys Phe Ser Arg
305 310 315 320

Ser Ala Asp Ala Pro Ala Tyr Gln Gln Gly Gln Asn Gln Leu Tyr Asn
325 330 335

Glu Leu Asn Leu Gly Arg Arg Glu Glu Tyr Asp Val Leu Asp Lys Arg
340 345 350

Arg Gly Arg Asp Pro Glu Met Gly Gly Lys Pro Arg Arg Lys Asn Pro
355 360 365

Gln Glu Gly Leu Tyr Asn Glu Leu Gln Lys Asp Lys Met Ala Glu Ala
370 375 380

Tyr Ser Glu Ile Gly Met Lys Gly Glu Arg Arg Arg Gly Lys Gly His
385 390 395 400

Asp Gly Leu Tyr Gln Gly Leu Ser Thr Ala Thr Lys Asp Thr Tyr Asp
405 410 415

Ala Leu His Met Gln Ala Leu Pro Pro Arg
420 425

<210> SEQ ID NO 43
<211> LENGTH: 416
<212> TYPE: PRT
<213> ORGANISM: Artificial Sequence
<220> FEATURE:
<223> OTHER INFORMATION: polypeptide comprising construct tgCD3(epsilon-delta)-(28/BB)-zeta

<400> SEQUENCE: 43

Asp Gly Asn Glu Glu Met Gly Gly Ile Thr Gln Thr Pro Tyr Lys Val
1 5 10 15

Ser Ile Ser Gly Thr Thr Val Ile Leu Thr Cys Pro Gln Tyr Pro Gly
20 25 30

Ser Glu Ile Leu Trp Gln His Asn Asp Lys Asn Ile Gly Gly Asp Glu
35 40 45

Asp Asp Lys Asn Ile Gly Ser Asp Glu Asp His Leu Ser Leu Lys Glu
50 55 60

Phe Ser Glu Leu Glu Gln Ser Gly Tyr Tyr Val Cys Tyr Pro Arg Gly
65 70 75 80

Ser Lys Pro Glu Asp Ala Asn Phe Tyr Leu Tyr Leu Arg Ala Arg Val
85 90 95

Gly Ser Ala Asp Asp Ala Lys Lys Asp Ala Ala Lys Lys Asp Asp Ala
100 105 110

Lys Lys Asp Asp Ala Lys Lys Asp Gly Ser Phe Lys Ile Pro Ile Glu
115 120 125

Glu Leu Glu Asp Arg Val Phe Val Asn Cys Asn Thr Ser Ile Thr Trp
130 135 140

Val Glu Gly Thr Val Gly Thr Leu Leu Ser Asp Ile Thr Arg Leu Asp
145 150 155 160

Leu Gly Lys Arg Ile Leu Asp Pro Arg Gly Ile Tyr Arg Cys Asn Gly
165 170 175

Thr Asp Ile Tyr Lys Asp Lys Glu Ser Thr Val Gln Val His Tyr Arg
180 185 190

Met Arg Ala Ala Ala Ile Glu Val Met Tyr Pro Pro Pro Tyr Leu Asp
195 200 205

Asn Glu Lys Ser Asn Gly Thr Ile Ile His Val Lys Gly Lys His Leu
210 215 220

Cys Pro Ser Pro Leu Phe Pro Gly Pro Ser Lys Pro Phe Trp Val Leu
225 230 235 240

Val Val Val Gly Gly Val Leu Ala Cys Tyr Ser Leu Leu Val Thr Val
245 250 255

Ala Phe Ile Ile Phe Trp Val Arg Ser Lys Arg Ser Arg Leu Leu His
260 265 270

Ser Asp Tyr Met Asn Met Thr Pro Arg Arg Pro Gly Pro Thr Arg Lys
275 280 285

His Tyr Gln Pro Tyr Ala Pro Pro Arg Asp Phe Ala Ala Tyr Arg Ser
290 295 300

Arg Val Lys Phe Ser Arg Ser Ala Asp Ala Pro Ala Tyr Gln Gln Gly
305 310 315 320

Gln Asn Gln Leu Tyr Asn Glu Leu Asn Leu Gly Arg Arg Glu Glu Tyr
325 330 335

Asp Val Leu Asp Lys Arg Arg Gly Arg Asp Pro Glu Met Gly Gly Lys

```
            340                 345                 350

Pro Arg Arg Lys Asn Pro Gln Glu Gly Leu Tyr Asn Glu Leu Gln Lys
        355                 360                 365

Asp Lys Met Ala Glu Ala Tyr Ser Glu Ile Gly Met Lys Gly Glu Arg
    370                 375                 380

Arg Arg Gly Lys Gly His Asp Gly Leu Tyr Gln Gly Leu Ser Thr Ala
385                 390                 395                 400

Thr Lys Asp Thr Tyr Asp Ala Leu His Met Gln Ala Leu Pro Pro Arg
                405                 410                 415


<210> SEQ ID NO 44
<211> LENGTH: 276
<212> TYPE: PRT
<213> ORGANISM: Homo sapiens

<400> SEQUENCE: 44

Met Lys Lys His Leu Thr Thr Phe Leu Val Ile Leu Trp Leu Tyr Phe
1               5                   10                  15

Tyr Arg Gly Asn Gly Lys Asn Gln Val Glu Gln Ser Pro Gln Ser Leu
            20                  25                  30

Ile Ile Leu Glu Gly Lys Asn Cys Thr Leu Gln Cys Asn Tyr Thr Val
        35                  40                  45

Ser Pro Phe Ser Asn Leu Arg Trp Tyr Lys Gln Asp Thr Gly Arg Gly
    50                  55                  60

Pro Val Ser Leu Thr Ile Met Thr Phe Ser Glu Asn Thr Lys Ser Asn
65                  70                  75                  80

Gly Arg Tyr Thr Ala Thr Leu Asp Ala Asp Thr Lys Gln Ser Ser Leu
                85                  90                  95

His Ile Thr Ala Ser Gln Leu Ser Asp Ser Ala Ser Tyr Ile Cys Val
            100                 105                 110

Val Ser Asp Arg Gly Ser Thr Leu Gly Arg Leu Tyr Phe Gly Arg Gly
        115                 120                 125

Thr Gln Leu Thr Val Trp Pro Asp Ile Gln Asn Pro Asp Pro Ala Val
    130                 135                 140

Tyr Gln Leu Arg Asp Ser Lys Ser Ser Asp Lys Ser Val Cys Leu Phe
145                 150                 155                 160

Thr Asp Phe Asp Ser Gln Thr Asn Val Ser Gln Ser Lys Asp Ser Asp
                165                 170                 175

Val Tyr Ile Thr Asp Lys Thr Val Leu Asp Met Arg Ser Met Asp Phe
            180                 185                 190

Lys Ser Asn Ser Ala Val Ala Trp Ser Asn Lys Ser Asp Phe Ala Cys
        195                 200                 205

Ala Asn Ala Phe Asn Asn Ser Ile Ile Pro Glu Asp Thr Phe Phe Pro
    210                 215                 220

Ser Pro Glu Ser Ser Cys Asp Val Lys Leu Val Glu Lys Ser Phe Glu
225                 230                 235                 240

Thr Asp Thr Asn Leu Asn Phe Gln Asn Leu Ser Val Ile Gly Phe Arg
                245                 250                 255

Ile Leu Leu Leu Lys Val Ala Gly Phe Asn Leu Leu Met Thr Leu Arg
            260                 265                 270

Leu Trp Ser Ser
        275


<210> SEQ ID NO 45
<211> LENGTH: 289
```

<212> TYPE: PRT
<213> ORGANISM: Homo sapiens

<400> SEQUENCE: 45

Met Thr Ile Arg Leu Leu Cys Tyr Met Gly Phe Tyr Phe Leu Gly Ala
1 5 10 15

Gly Leu Met Glu Ala Asp Ile Tyr Gln Thr Pro Arg Tyr Leu Val Ile
20 25 30

Gly Thr Gly Lys Lys Ile Thr Leu Glu Cys Ser Gln Thr Met Gly His
35 40 45

Asp Lys Met Tyr Trp Tyr Gln Gln Asp Pro Gly Met Glu Leu His Leu
50 55 60

Ile His Tyr Ser Tyr Gly Val Asn Ser Thr Glu Lys Gly Asp Leu Ser
65 70 75 80

Ser Glu Ser Thr Val Ser Arg Ile Arg Thr Glu His Phe Pro Leu Thr
85 90 95

Leu Glu Ser Ala Arg Pro Ser His Thr Ser Gln Tyr Leu Cys Ala Ser
100 105 110

Glu Asp Leu Asn Lys Val Phe Pro Pro Glu Val Ala Val Phe Glu Pro
115 120 125

Ser Glu Ala Glu Ile Ser His Thr Gln Lys Ala Thr Leu Val Cys Leu
130 135 140

Ala Thr Gly Phe Phe Pro Asp His Val Glu Leu Ser Trp Trp Val Asn
145 150 155 160

Gly Lys Glu Val His Ser Gly Val Ser Thr Asp Pro Gln Pro Leu Lys
165 170 175

Glu Gln Pro Ala Leu Asn Asp Ser Arg Tyr Cys Leu Ser Ser Arg Leu
180 185 190

Arg Val Ser Ala Thr Phe Trp Gln Asn Pro Arg Asn His Phe Arg Cys
195 200 205

Gln Val Gln Phe Tyr Gly Leu Ser Glu Asn Asp Glu Trp Thr Gln Asp
210 215 220

Arg Ala Lys Pro Val Thr Gln Ile Val Ser Ala Glu Ala Trp Gly Arg
225 230 235 240

Ala Asp Cys Gly Phe Thr Ser Val Ser Tyr Gln Gln Gly Val Leu Ser
245 250 255

Ala Thr Ile Leu Tyr Glu Ile Leu Leu Gly Lys Ala Thr Leu Tyr Ala
260 265 270

Val Leu Val Ser Ala Leu Val Leu Met Ala Met Val Lys Arg Lys Asp
275 280 285

Phe

<210> SEQ ID NO 46
<211> LENGTH: 134
<212> TYPE: PRT
<213> ORGANISM: Artificial Sequence
<220> FEATURE:
<223> OTHER INFORMATION: Synthetic construct

<400> SEQUENCE: 46

Asn Lys Ile Leu Val Lys Gln Ser Pro Met Leu Val Ala Tyr Asp Asn
1 5 10 15

Ala Val Asn Leu Ser Cys Lys Tyr Ser Tyr Asn Leu Phe Ser Arg Glu
20 25 30

Phe Arg Ala Ser Leu His Lys Gly Leu Asp Ser Ala Val Glu Val Cys
35 40 45

Val Val Tyr Gly Asn Tyr Ser Gln Gln Leu Gln Val Tyr Ser Lys Thr
50 55 60

Gly Phe Asn Cys Asp Gly Lys Leu Gly Asn Glu Ser Val Thr Phe Tyr
65 70 75 80

Leu Gln Asn Leu Tyr Val Asn Gln Thr Asp Ile Tyr Phe Cys Lys Ile
85 90 95

Glu Val Met Tyr Pro Pro Pro Tyr Leu Asp Asn Glu Lys Ser Asn Gly
100 105 110

Thr Ile Ile His Val Lys Gly Lys His Leu Cys Pro Ser Pro Leu Phe
115 120 125

Pro Gly Pro Ser Lys Pro
130

<210> SEQ ID NO 47
<211> LENGTH: 27
<212> TYPE: PRT
<213> ORGANISM: Artificial Sequence
<220> FEATURE:
<223> OTHER INFORMATION: Synthetic construct

<400> SEQUENCE: 47

Phe Trp Val Leu Val Val Val Gly Gly Val Leu Ala Cys Tyr Ser Leu
1 5 10 15

Leu Val Thr Val Ala Phe Ile Ile Phe Trp Val
20 25

<210> SEQ ID NO 48
<211> LENGTH: 21
<212> TYPE: PRT
<213> ORGANISM: Artificial Sequence
<220> FEATURE:
<223> OTHER INFORMATION: Synthetic construct

<400> SEQUENCE: 48

Ile Tyr Ile Trp Ala Pro Leu Ala Gly Thr Cys Gly Val Leu Leu Leu
1 5 10 15

Ser Leu Val Ile Thr
20

<210> SEQ ID NO 49
<211> LENGTH: 22
<212> TYPE: PRT
<213> ORGANISM: Artificial Sequence
<220> FEATURE:
<223> OTHER INFORMATION: Synthetic construct

<400> SEQUENCE: 49

Met Ala Leu Ile Val Leu Gly Gly Val Ala Gly Leu Leu Leu Phe Ile
1 5 10 15

Gly Leu Gly Ile Phe Phe
20

<210> SEQ ID NO 50
<211> LENGTH: 55
<212> TYPE: PRT
<213> ORGANISM: Artificial Sequence
<220> FEATURE:
<223> OTHER INFORMATION: Synthetic construct

<400> SEQUENCE: 50

Lys Asn Arg Lys Ala Lys Ala Lys Pro Val Thr Arg Gly Ala Gly Ala
1 5 10 15

```
Gly Gly Arg Gln Arg Gly Gln Asn Lys Glu Arg Pro Pro Pro Val Pro
            20                  25                  30

Asn Pro Asp Tyr Glu Pro Ile Arg Lys Gly Gln Arg Asp Leu Tyr Ser
        35                  40                  45

Gly Leu Asn Gln Arg Arg Ile
    50                  55


<210> SEQ ID NO 51
<211> LENGTH: 55
<212> TYPE: PRT
<213> ORGANISM: Artificial Sequence
<220> FEATURE:
<223> OTHER INFORMATION: Synthetic construct

<400> SEQUENCE: 51

Lys Asn Arg Lys Ala Lys Ala Lys Pro Val Thr Arg Gly Ala Gly Ala
1               5                   10                  15

Gly Gly Arg Gln Arg Gly Gln Asn Lys Glu Arg Pro Pro Pro Val Pro
            20                  25                  30

Asn Pro Asp Tyr Glu Pro Ile Arg Lys Gly Gln Arg Asp Leu Tyr Ser
        35                  40                  45

Gly Leu Asn Gln Ser Arg Ile
    50                  55


<210> SEQ ID NO 52
<211> LENGTH: 45
<212> TYPE: PRT
<213> ORGANISM: Artificial Sequence
<220> FEATURE:
<223> OTHER INFORMATION: Synthetic construct

<400> SEQUENCE: 52

Gly His Glu Thr Gly Arg Leu Ser Gly Ala Ala Asp Thr Gln Ala Leu
1               5                   10                  15

Leu Arg Asn Asp Gln Val Tyr Gln Pro Leu Arg Asp Arg Asp Asp Ala
            20                  25                  30

Gln Tyr Ser His Leu Gly Gly Asn Trp Ala Arg Asn Lys
        35                  40                  45


<210> SEQ ID NO 53
<211> LENGTH: 45
<212> TYPE: PRT
<213> ORGANISM: Artificial Sequence
<220> FEATURE:
<223> OTHER INFORMATION: Synthetic construct

<400> SEQUENCE: 53

Gly His Glu Thr Gly Arg Leu Ser Gly Ala Ala Asp Thr Gln Ala Ala
1               5                   10                  15

Leu Arg Asn Asp Gln Val Tyr Gln Pro Leu Arg Asp Arg Asp Asp Ala
            20                  25                  30

Gln Tyr Ser His Leu Gly Gly Asn Trp Ala Ala Asn Lys
        35                  40                  45


<210> SEQ ID NO 54
<211> LENGTH: 45
<212> TYPE: PRT
<213> ORGANISM: Artificial Sequence
<220> FEATURE:
<223> OTHER INFORMATION: Synthetic construct

<400> SEQUENCE: 54
```

Gly Gln Asp Gly Val Arg Gln Ser Arg Ala Ser Asp Lys Gln Thr Leu
1 5 10 15

Leu Pro Asn Asp Gln Leu Tyr Gln Pro Leu Lys Asp Arg Glu Asp Asp
20 25 30

Gln Tyr Ser His Leu Gln Gly Asn Gln Leu Arg Arg Asn
35 40 45

<210> SEQ ID NO 55
<211> LENGTH: 45
<212> TYPE: PRT
<213> ORGANISM: Artificial Sequence
<220> FEATURE:
<223> OTHER INFORMATION: Synthetic construct

<400> SEQUENCE: 55

Gly Gln Asp Gly Val Arg Gln Ser Arg Ala Ser Asp Lys Gln Thr Ala
1 5 10 15

Leu Pro Asn Asp Gln Leu Tyr Gln Pro Leu Lys Asp Arg Glu Asp Asp
20 25 30

Gln Tyr Ser His Leu Gln Gly Asn Gln Leu Ala Arg Asn
35 40 45

<210> SEQ ID NO 56
<211> LENGTH: 41
<212> TYPE: PRT
<213> ORGANISM: Artificial Sequence
<220> FEATURE:
<223> OTHER INFORMATION: Synthetic construct

<400> SEQUENCE: 56

Arg Ser Lys Arg Ser Arg Leu Leu His Ser Asp Tyr Met Asn Met Thr
1 5 10 15

Pro Arg Arg Pro Gly Pro Thr Arg Lys His Tyr Gln Pro Tyr Ala Pro
20 25 30

Pro Arg Asp Phe Ala Ala Tyr Arg Ser
35 40

<210> SEQ ID NO 57
<211> LENGTH: 17
<212> TYPE: PRT
<213> ORGANISM: Artificial Sequence
<220> FEATURE:
<223> OTHER INFORMATION: Synthetic construct

<400> SEQUENCE: 57

Met Leu Arg Leu Leu Leu Ala Leu Asn Leu Phe Pro Ser Ile Gln Val
1 5 10 15

Thr

<210> SEQ ID NO 58
<211> LENGTH: 214
<212> TYPE: PRT
<213> ORGANISM: Artificial Sequence
<220> FEATURE:
<223> OTHER INFORMATION: Synthetic construct

<400> SEQUENCE: 58

Asp Gly Asn Glu Glu Met Gly Gly Ile Thr Gln Thr Pro Tyr Lys Val
1 5 10 15

Ser Ile Ser Gly Thr Thr Val Ile Leu Thr Cys Pro Gln Tyr Pro Gly
20 25 30

Ser Glu Ile Leu Trp Gln His Asn Asp Lys Asn Ile Gly Gly Asp Glu
35 40 45

Asp Asp Lys Asn Ile Gly Ser Asp Glu Asp His Leu Ser Leu Lys Glu
50 55 60

Phe Ser Glu Leu Glu Gln Ser Gly Tyr Tyr Val Cys Tyr Pro Arg Gly
65 70 75 80

Ser Lys Pro Glu Asp Ala Asn Phe Tyr Leu Tyr Leu Arg Ala Arg Val
85 90 95

Cys Glu Asn Cys Met Glu Met Asp Gly Ser Ala Asp Asp Ala Lys Lys
100 105 110

Asp Ala Ala Lys Lys Asp Asp Ala Lys Lys Asp Asp Ala Lys Lys Asp
115 120 125

Gly Ser Phe Lys Ile Pro Ile Glu Glu Leu Glu Asp Arg Val Phe Val
130 135 140

Asn Cys Asn Thr Ser Ile Thr Trp Val Glu Gly Thr Val Gly Thr Leu
145 150 155 160

Leu Ser Asp Ile Thr Arg Leu Asp Leu Gly Lys Arg Ile Leu Asp Pro
165 170 175

Arg Gly Ile Tyr Arg Cys Asn Gly Thr Asp Ile Tyr Lys Asp Lys Glu
180 185 190

Ser Thr Val Gln Val His Tyr Arg Met Cys Gln Ser Cys Val Glu Leu
195 200 205

Asp Pro Ala Thr Val Ala
210

<210> SEQ ID NO 59
<211> LENGTH: 224
<212> TYPE: PRT
<213> ORGANISM: Artificial Sequence
<220> FEATURE:
<223> OTHER INFORMATION: Synthetic construct

<400> SEQUENCE: 59

Asp Gly Asn Glu Glu Met Gly Gly Ile Thr Gln Thr Pro Tyr Lys Val
1 5 10 15

Ser Ile Ser Gly Thr Thr Val Ile Leu Thr Cys Pro Gln Tyr Pro Gly
20 25 30

Ser Glu Ile Leu Trp Gln His Asn Asp Lys Asn Ile Gly Gly Asp Glu
35 40 45

Asp Asp Lys Asn Ile Gly Ser Asp Glu Asp His Leu Ser Leu Lys Glu
50 55 60

Phe Ser Glu Leu Glu Gln Ser Gly Tyr Tyr Val Cys Tyr Pro Arg Gly
65 70 75 80

Ser Lys Pro Glu Asp Ala Asn Phe Tyr Leu Tyr Leu Arg Ala Arg Val
85 90 95

Cys Glu Asn Cys Met Glu Met Asp Gly Ser Ala Asp Asp Ala Lys Lys
100 105 110

Asp Ala Ala Lys Lys Asp Asp Ala Lys Lys Asp Asp Ala Lys Lys Asp
115 120 125

Gly Ser Gln Ser Ile Lys Gly Asn His Leu Val Lys Val Tyr Asp Tyr
130 135 140

Gln Glu Asp Gly Ser Val Leu Leu Thr Cys Asp Ala Glu Ala Lys Asn
145 150 155 160

Ile Thr Trp Phe Lys Asp Gly Lys Met Ile Gly Phe Leu Thr Glu Asp
165 170 175

-continued

```
Lys Lys Lys Trp Asn Leu Gly Ser Asn Ala Lys Asp Pro Arg Gly Met
            180                 185                 190

Tyr Gln Cys Lys Gly Ser Gln Asn Lys Ser Lys Pro Leu Gln Val Tyr
        195                 200                 205

Tyr Arg Met Cys Gln Asn Cys Ile Glu Leu Asn Ala Ala Thr Ile Ser
    210                 215                 220
```

ENGINEERED iPSC AND ARMED IMMUNE EFFECTOR CELLS

RELATED APPLICATIONS

This application claims priority to U.S. Provisional Application Ser. No. 63/090,113, filed Oct. 9, 2020, and to U.S. Provisional Application Ser. No. 63/172,383, filed Apr. 8, 2021, the disclosure of each of which is hereby incorporated by reference in their entireties.

REFERENCE TO SEQUENCE LISTING SUBMITTED ELECTRONICALLY

This application incorporates by reference a Computer Readable Form (CRF) of a Sequence Listing in ASCII text format submitted with this application, entitled 184143-629601_SEQUENCE_LISTING_ST25.TXT, which was created on Oct. 7, 2021, and is 86,415 bytes in size.

FIELD OF THE INVENTION

The present disclosure is broadly concerned with the field of off-the-shelf immunocellular products. More particularly, the present disclosure is concerned with the strategies for developing multifunctional effector cells capable of delivering therapeutically relevant properties in vivo. The cell products developed under embodiments according to the present disclosure address critical limitations of patient-sourced cell therapies.

BACKGROUND OF THE INVENTION

The field of adoptive cell therapy is currently focused on using patient- and donor-sourced cells, which makes it particularly difficult to achieve consistent manufacturing of cancer immunotherapies and to deliver therapies to all patients who may benefit. There is also the need to improve the efficacy and persistence of adoptively transferred lymphocytes to promote favorable patient outcome. Lymphocytes such as T cells and natural killer (NK) cells are potent anti-tumor effectors that play an important role in innate and adaptive immunity. However, the use of these immune cells for adoptive cell therapies remains challenging and has unmet needs for improvement. Therefore, significant opportunities remain to harness the full potential of T and NK cells, or other immune effector cells in adoptive immunotherapy.

SUMMARY OF THE INVENTION

There is a need for functionally improved effector cells that address issues ranging from response rate, cell exhaustion, loss of transfused cells (survival and/or persistence), tumor escape through target loss or lineage switch, tumor targeting precision, off-target toxicity, off-tumor effect, to efficacy against solid tumors, i.e., tumor microenvironment and related immune suppression, recruiting, trafficking and infiltration.

It is an object of the present invention to provide methods and compositions to generate derivative non-pluripotent cells differentiated from a single cell derived iPSC (induced pluripotent stem cell) clonal line, which iPSC comprises one or several genetic modifications in its genome. Said one or several genetic modifications include DNA insertion, deletion, and substitution, and which modifications are retained and remain functional in subsequently derived cells after differentiation, expansion, passaging and/or transplantation.

In some embodiments, the iPSC-derived non-pluripotent cells of the present application include, but are not limited to, CD34 cells, hemogenic endothelium cells, HSCs (hematopoietic stem and progenitor cells), hematopoietic multipotent progenitor cells, T cell progenitors, NK cell progenitors, T cells, NKT cells, NK cells, B cells, and immune effector cells having one or more functional features that are not present in a primary NK, T, and/or NKT cell. The iPSC-derived non-pluripotent cells according to some embodiments of the present application comprise one or several genetic modifications in their genome through differentiation from an iPSC comprising the same genetic modifications. In some embodiments, the engineered clonal iPSC differentiation strategy for obtaining genetically engineered derivative cells requires that the developmental potential of the iPSC in differentiation is not adversely impacted by the engineered modality in the iPSC, and also that the engineered modality functions as intended in the derivative cell. Further, this strategy overcomes the present barrier in engineering primary lymphocytes, such as T cells or NK cells obtained from peripheral blood, as such cells are difficult to engineer, with engineering of such cells often lacking reproducibility and uniformity, resulting in cells exhibiting poor cell persistence with high cell death and low cell expansion. Moreover, this strategy avoids production of a heterogenous effector cell population otherwise obtained using primary cell sources which are heterogenous to start with.

Some aspects of the present invention provide genome-engineered iPSCs obtained using a method comprising (I), (II) or (III), reflecting a strategy of genomic engineering subsequently to, simultaneously with, and prior to the reprogramming process, respectively:

(I): genetically engineering iPSCs by one or both of (i) and (ii), in any order: (i) introducing into iPSCs one or more construct(s) to allow targeted integration at selected site(s); (ii) (a) introducing into iPSCs one or more double stranded break(s) at selected site(s) using one or more endonuclease capable of selected site recognition; and (b) culturing the iPSCs of step (I)(ii)(a) to allow endogenous DNA repair to generate targeted in/dels at the selected site(s), simultaneously or sequentially; thereby obtaining genome-engineered iPSCs capable of differentiation into partially or fully differentiated cells.

(II): genetically engineering reprogramming non-pluripotent cells to obtain the genome-engineered iPSCs comprising: (i) contacting non-pluripotent cells with one or more reprogramming factors, and optionally a small molecule composition comprising a TGFβ receptor/ALK inhibitor, a MEK inhibitor, a GSK3 inhibitor and/or a ROCK inhibitor to initiate reprogramming of the non-pluripotent cells; and (ii) introducing into the reprogramming non-pluripotent cells of step (II)(i) one or both of (a) and (b), in any order: (a) one or more construct(s) to allow targeted integration at selected site(s); (b) one or more double stranded break(s) at a selected site using at least one endonuclease capable of selected site recognition, then the cells of step (II)(ii)(b) are cultured to allow endogenous DNA repair to generate targeted in/dels at the selected site(s); as such the obtained genome-engineered iPSCs comprise at least one functional targeted genomic edit, and said genome-engineered iPSCs are capable of differentiation into partially or fully differentiated cells.

(III): genetically engineering non-pluripotent cells for reprogramming to obtain genome-engineered iPSCs comprising (i) and (ii): (i) introducing into non-pluripotent cells one or both of (a) and (b), in any order: (a) one or more construct(s) to allow targeted integration at selected site(s); (b) one or more double stranded break(s) at a selected site using at least one endonuclease capable of selected site recognition, wherein the cells of step (III)(i)(b) are cultured to allow endogenous DNA repair to generate targeted in/dels at the selected sites; and (ii) contacting the cells of step (III)(i) with one or more reprogramming factors, and optionally a small molecule composition comprising a TGFβ receptor/ALK inhibitor, a MEK inhibitor, a GSK3 inhibitor and/or a ROCK inhibitor, to obtain genome-engineered iPSCs comprising targeted editing at selected sites; thereby obtaining genome-engineered iPSCs comprising at least one functional targeted genomic edit, and said genome-engineered iPSCs are capable of being differentiated into partially differentiated cells or fully-differentiated cells.

In one embodiment of the above method, the at least one targeted genomic edit at one or more selected sites comprises insertion of one or more exogenous polynucleotides encoding safety switch proteins, targeting modalities, receptors, signaling molecules, transcription factors, pharmaceutically active proteins and peptides, drug target candidates, or proteins promoting engraftment, trafficking, homing, viability, self-renewal, persistence, and/or survival of the genome-engineered iPSCs or derivative cells therefrom. In some embodiments, the exogenous polynucleotides for insertion are operatively linked to (1) one or more exogenous promoters comprising CMV, EF1α, PGK, CAG, UBC, or other constitutive, inducible, temporal-, tissue-, or cell type-specific promoters; or (2) one or more endogenous promoters comprised in the selected sites comprising AAVS1, CCR5, ROSA26, collagen, HTRP, H11, beta-2 microglobulin, CD38, GAPDH, TCR or RUNX1, or other locus meeting the criteria of a genome safe harbor. In some embodiments, the genome-engineered iPSCs generated using the above method comprise one or more different exogenous polynucleotides encoding protein(s) comprising caspase, thymidine kinase, cytosine deaminase, modified EGFR, or B-cell CD20, wherein when the genome-engineered iPSCs comprise two or more suicide genes, the suicide genes are integrated in different safe harbor locus comprising AAVS1, CCR5, ROSA26, collagen, HTRP, H11, beta-2 microglobulin, CD38, GAPDH, TCR or RUNX1. In one embodiment, the exogenous polynucleotide encodes a partial or full length peptide of IL2, IL4, IL6, IL7, IL9, IL10, IL11, IL12, IL15, IL18, IL21, and/or respective receptors thereof. In some embodiments, the partial or full peptide of IL2, IL4, IL6, IL7, IL9, IL10, IL11, IL12, IL15, IL18, IL21, and/or respective receptors thereof encoded by the exogenous polynucleotide is in a form of fusion protein.

In some other embodiments, the genome-engineered iPSCs generated using the method provided herein comprise in/del at one or more endogenous genes associated with targeting modality, receptors, signaling molecules, transcription factors, drug target candidates, immune response regulation and modulation, or proteins suppressing engraftment, trafficking, homing, viability, self-renewal, persistence, and/or survival of the iPSCs or derivative cells therefrom. In some embodiments, the endogenous gene for disruption comprises at least one of CD38, B2M, TAP1, TAP2, Tapasin, NLRC5, PD1, LAGS, TIM3, RFXANK, CIITA, RFX5, RFXAP, RAG1, and any gene in the chromosome 6p21 region.

In yet some other embodiments, the genome-engineered iPSCs generated using the method provided herein comprise a caspase encoding exogenous polynucleotide at AAVS1 locus, and a thymidine kinase encoding exogenous polynucleotide at H11 locus.

In still some other embodiments, approach (I), (II) and/or (III) further comprises: contacting the genome-engineered iPSCs with a small molecule composition comprising a MEK inhibitor, a GSK3 inhibitor and a ROCK inhibitor, to maintain the pluripotency of the genomic-engineered iPSCs. In one embodiment, the obtained genome engineered iPSCs comprising at least one targeted genomic edit are functional, are differentiation potent, and are capable of differentiating into non-pluripotent cells comprising the same functional genomic edit.

Accordingly, in one aspect, the present invention provides a chimeric fusion receptor (CFR), wherein the CFR comprises an ectodomain, a transmembrane domain, and an endodomain, and wherein the ectodomain, the transmembrane domain and the endodomain do not comprise any endoplasmic reticulum (ER) retention signals or endocytosis signals. In some embodiments, the ectodomain is not an scFv (single-chain variable fragment) of an antibody; the ectodomain initiates signal transduction upon binding to a selected agonist; the endodomain comprises at least one signaling domain that activates a selected signaling pathway for enhancing cell therapeutic properties; the CFR is cell surface presented when expressed; and the CFR has reduced internalization and surface downregulation. In some embodiments, the endodomain and the ectodomain are modular; or wherein for a given endodomain of the CFR, the ectodomain is switchable depending on binding specificity of a selected agonist; or wherein for a given ectodomain, the endodomain is switchable depending on a selected signaling pathway for regulation. In particular embodiments, the ectodomain comprises a full or partial length of an extracellular portion of a signaling protein comprising at least one of CD3ε, CD3γ, CD3δ, CD28, CD5, CD16, CD64, CD32, CD33, CD89, NKG2C, NKG2D, any functional variants, and a combination or a chimera thereof.

In some embodiments, the ectodomain comprises a full or partial length of an extracellular portion of: (a) CD3ε, CD3γ, CD3δ, any functional variants, or combinational or chimeric forms thereof; (b) a heterodimer of CD3ε and CD3γ; or (c) a heterodimer of CD3ε and CD3δ; and the agonist has a binding specificity to the ectodomain of CD3; or wherein the agonist comprises at least one of CD3×CD19, CD3×CD20, CD3×CD33, blinatumomab, catumaxomab, ertumaxomab, RO6958688, AFM11, MT110/AMG 110, MT111/AMG211/MEDI-565, AMG330, MT112/BAY2010112, MOR209/ES414, MGD006/S80880, MGD007, and FBTA05. In other embodiments, the ectodomain comprises a full or partial length of an extracellular portion of NKG2C, or any functional variants thereof; and the agonist has a binding specificity to the ectodomain of NKG2C; or wherein the agonist comprises at least one of an NKG2C-IL15-CD33 TriKE, an NKG2C-IL15-CD19 TriKE, and an NKG2C-IL15-CD20 TriKE. In still other embodiments, the ectodomain comprises a full or partial length of an extracellular portion of CD28, or any functional variants thereof; and the agonist has a binding specificity to the ectodomain of CD28; or the agonist comprises at least one of 15E8, CD28.2, CD28.6, YTH913.12, 37.51, 9D7 (TGN1412), 5.11A1, ANC28.1/5D10, and 37407. In still other embodiments, the ectodomain comprises a full or partial length of an extracellular portion of CD16, CD64, or any functional variants or combined/chimeric forms thereof; the agonist has a binding specificity to the ectodomain of CD16 or CD64; or the agonist comprises at least one of IgG antibody, CD16×

CD30, CD64×CD30, CD16×BCMA, CD64×BCMA, CD16-IL-EPCAM or CD64-IL-EPCAM, CD16-IL-CD33 and CD64-IL-CD33; and IL comprises all or a portion of at least one cytokine comprising IL2, IL4, IL6, IL7, IL9, IL10, IL11, IL12, IL15, IL18, IL21, or any functional variants or chimeric forms thereof.

In those embodiments where the ectodomain initiates signal transduction upon binding to a selected ligand, the selected ligand may be (i) an antibody or a functional variant or fragment thereof; or (ii) an engager; and the selected agonist may comprise at least a binding domain specific to an epitope comprised in the ectodomain of the CFR. In some embodiments, the selected ligand is a selected agonist. In some embodiments, the selected agonist comprises at least a binding domain that is specific to an extracellular portion of CD3ε, CD3γ, CD3δ, CD28, CD5, CD16, CD64, CD32, CD33, CD89, NKG2C, NKG2D, or any functional variants thereof; or wherein the engager further comprises a binding domain specific to at least one tumor antigen comprising B7H3, BCMA, CD10, CD19, CD20, CD22, CD24, CD30, CD33, CD34, CD38, CD44, CD79a, CD79b, CD123, CD138, CD179b, CEA, CLEC12A, CS-1, DLL3, EGFR, EGFRvIII, EPCAM, FLT-3, FOLR1, FOLR3, GD2, gpA33, HER2, HM1.24, LGR5, MSLN, MCSP, MICA/B, PSMA, PAMA, P-cadherin, or ROR1.

In various embodiments of the CFR, the transmembrane domain of the CFR: (i) has no ER retention or endocytosis signals, or has ER retention and endocytosis signals removed by engineering; and (ii) comprises all or a part of a transmembrane domain of: (a) a transmembrane protein or a membrane protein; (b) a protein comprising CD3ε, CD3γ, CD3δ, CD3ζ, CD4, CD8, CD8a, CD8b, CD27, CD28, CD40, CD84, CD137, CD166, FcεRIγ, 4-1BB, OX40, ICOS, ICAM-1, CTLA-4, PD-1, LAG-3, 2B4, BTLA, CD16, IL7, IL12, IL15, KIR2DL4, KIR2DS1, NKp30, NKp44, NKp46, NKG2C, NKG2D, a T cell receptor, a nicotinic acetylcholine receptor, a GABA receptor, or a combination thereof; or (c) CD28, CD8, CD3ε, or CD4.

In various embodiments of the CFR, the endodomain comprises at least a cytotoxicity domain, and optionally one or more of a co-stimulatory domain, a persistency signaling domain, a death-inducing signaling domain, a tumor cell control signaling domain, and any combinations thereof. In some embodiments, the endodomain comprises a cytotoxicity domain comprising at least a full length or a portion of CD3ζ, 2B4, DAP10, DAP12, DNAM1, CD137 (4-1BB), IL21, IL7, IL12, IL15, NKp30, NKp44, NKp46, NKG2C, or NKG2D polypeptide; and optionally wherein the endodomain further comprises one or more of: (i) a co-stimulatory domain comprising a full length or a portion of CD2, CD27, CD28, CD40L, 4-1BB, OX40, ICOS, PD-1, LAG-3, 2B4, BTLA, DAP10, DAP12, CTLA-4, or NKG2D polypeptide, or any combination thereof; (ii) a co-stimulatory domain comprising a full length or a portion of CD28, 4-1BB, CD27, CD40L, ICOS, CD2, or any combination thereof; (iii) a persistency signaling domain comprising a full length or a portion of an endodomain of a cytokine receptor comprising IL2R, IL7R, IL15R, IL18R, IL12R, IL23R, or any combination thereof; and/or (iv) a full or a partial intracellular portion of a receptor tyrosine kinase (RTK), a tumor necrosis factor receptor (TNFR), an EGFR or a FAS receptor.

In another aspect, the invention provides a cell or a population thereof, wherein the cell comprises a polynucleotide encoding the chimeric fusion receptor (CFR) described herein, wherein the cell is an eukaryotic cell, an animal cell, a human cell, an immune cell, a feeder cell, an induced pluripotent stem cell (iPSC), a clonal iPSC or a derivative effector cell thereof. In some embodiments, the effector cell further comprises one or more of: (i) a CAR having a targeting specificity; (ii) a CD16 or a variant thereof; (iii) CD38 knockout; (iv) a partial or full peptide of a cell surface expressed exogenous cytokine and/or a receptor thereof; (v) HLA-I deficiency, and optionally HLA-II deficiency; (vi) introduction of HLA-G or non-cleavable HLA-G, or knockout of one or both of CD58 and CD54; (vii) at least one of the genotypes listed in Table 1; (viii) deletion or disruption of at least one of TAP1, TAP2, Tapasin, NLRC5, CIITA, RFXANK, RFX5, RFXAP, TCR, NKG2A, NKG2D, CD25, CD69, CD44, CD56, CIS, CBL-B, SOCS2, PD1, CTLA4, LAG3, TIM3, and TIGIT; or (ix) introduction of at least one of HLA-E, 4-1BBL, CD3, CD4, CD8, CD16, CD47, CD113, CD131, CD137, CD80, PDL1, $A_{2A}R$, antigen-specific TCR, Fc receptor, an antibody or functional variant or fragment thereof, a checkpoint inhibitor, an engager, and surface triggering receptor for coupling with an agonist.

In some embodiments, the cell has therapeutic properties comprising one or more of: (i) increased cytotoxicity; (ii) improved persistency and/or survival; (iii) enhanced migrating, and/or activating or recruiting bystander immune cells, to tumor sites; (iv) improved tumor penetration; (v) enhanced ability to reduce tumor immunosuppression; (vi) improved ability in rescuing tumor antigen escape; (vii) controlled apoptosis; (viii) enhanced or acquired ADCC; and (ix) ability to avoid fratricide, in comparison to its counterpart primary cell obtained from peripheral blood, umbilical cord blood, or any other donor tissues. In those embodiments where the effector cell comprises a CD16 or variant thereof, the CD16 or a variant thereof may comprise at least one of: (a) a high affinity non-cleavable CD16 (hnCD16); (b) F176V and S197P in ectodomain domain of CD16; (c) a full or partial ectodomain originated from CD64; (d) a non-native (or non-CD16) transmembrane domain; (e) a non-native (or non-CD16) intracellular domain; (f) a non-native (or non-CD16) signaling domain; (g) a non-native stimulatory domain; and (h) transmembrane, signaling, and stimulatory domains that are not originated from CD16, and are originated from a same or different polypeptide. In those embodiments where the effector cell comprises a CAR having target specificity, the CAR may be: (i) T cell specific or NK cell specific; (ii) a bi-specific antigen binding CAR; (iii) a switchable CAR; (iv) a dimerized CAR; (v) a split CAR; (vi) a multi-chain CAR; (vii) an inducible CAR; (viii) co-expressed with a partial or full peptide of a cell surface expressed exogenous cytokine and/or a receptor thereof, optionally in separate constructs or in a bi-cistronic construct; (xi) co-expressed with a checkpoint inhibitor, optionally in separate constructs or in a bi-cistronic construct; (x) specific to at least one of CD19, BCMA, CD20, CD22, CD38, CD123, HER2, CD52, EGFR, GD2, MICA/B, MSLN, VEGF-R2, PSMA and PDL1; and/or (xi) specific to any one of ADGRE2, carbonic anhydrase IX (CAIX), CCR1, CCR4, carcinoembryonic antigen (CEA), CD3, CD5, CD7, CD8, CD10, CD20, CD22, CD30, CD33, CD34, CD38, CD41, CD44, CD44V6, CD49f, CD56, CD70, CD74, CD99, CD123, CD133, CD138, CDS, CLEC12A, an antigen of a cytomegalovirus (CMV) infected cell, epithelial glycoprotein-2 (EGP-2), epithelial glycoprotein-40 (EGP-40), epithelial cell adhesion molecule (EpCAM), EGFRvIII, receptor tyrosine-protein kinases erb-B2,3,4, EGFIR, EGFR-VIII, ERBB folate-binding protein (FBP), fetal acetylcholine receptor (AChR), folate receptor-α, Ganglioside G2 (GD2), Ganglioside G3 (GD3), human Epidermal Growth Factor Receptor 2 (HER2), human telomerase reverse transcriptase (hTERT), ICAM-1, Integrin B7, Interleukin-13 receptor subunit alpha-2 (IL-13Rα2), κ-light chain, kinase insert domain receptor (KDR), Lewis A (CA19.9), Lewis Y (LeY), L1 cell adhesion molecule (L1-CAM), LILRB2, melanoma antigen family A 1 (MAGE-A1), MICA/B, Mucin 1 (Muc-1), Mucin 16 (Muc-16), Mesothelin (MSLN), NKCSI, NKG2D ligands, c-Met, cancer-testis antigen NY-ESO-1, oncofetal antigen (h5T4), PRAME, prostate stem cell antigen (PSCA), PRAME prostate-specific membrane antigen (PSMA), tumor-associated glycoprotein 72 (TAG-72), TIM-3, TRBC1, TRBC2, vascular endothelial growth factor R2 (VEGF-R2), Wilms tumor protein (WT-1), and a pathogen antigen; and optionally, wherein the CAR of any one of (i) to (xi) is inserted at a TCR locus, and/or is driven by an endogenous promoter of TCR, and/or the TCR is knocked out by the CAR insertion.

In some embodiments, the cell comprises a partial or full peptide of a cell surface expressed exogenous cytokine and/or a receptor thereof, and wherein the exogenous cytokine or receptor thereof: (a) comprises at least one of IL2, IL4, IL6, IL7, IL9, IL10, IL11, IL12, IL15, IL18, IL21, and its respective receptor(s); or (b) comprises at least one of: (i) co-expression of IL15 and IL15Rα by using a self-cleaving peptide; (ii) a fusion protein of IL15 and IL15Rα; (iii) an IL15/IL15Rα fusion protein with intracellular domain of IL15Rα truncated or eliminated; (iv) a fusion protein of IL15 and membrane bound Sushi domain of IL15Rα; (v) a fusion protein of IL15 and IL15Rβ; (vi) a fusion protein of IL15 and common receptor γC, wherein the common receptor γC is native or modified; and (vii) a homodimer of IL1510, wherein any one of (i)-(vii) can be co-expressed with a CAR in separate constructs or in a bi-cistronic construct; and optionally, (c) is transiently expressed.

In those embodiments where the effector cell comprises introduction of a checkpoint inhibitor, the checkpoint inhibitor may be an antagonist to one or more checkpoint molecules comprising PD-1, PDL-1, TIM-3, TIGIT, LAG-3, CTLA-4, 2B4, 4-1BB, 4-1BBL, $A_{2A}R$, BATE, BTLA, CD39, CD47, CD73, CD94, CD96, CD160, CD200, CD200R, CD274, CEACAM1, CSF-1R, Foxpl, GARP, HVEM, IDO, EDO, TDO, LAIR-1, MICA/B, NR4A2, MAFB, OCT-2, Rara (retinoic acid receptor alpha), TLR3, VISTA, NKG2A/HLA-E, and inhibitory KIR; or the engager may comprise a bi-specific T cell engager (BiTE) or a tri-specific killer cell engager (TriKE).

In various embodiments, the derivative effector cell is capable of recruiting, and/or migrating T cells to tumor sites, and wherein the derivative effector cell is capable of reducing tumor immunosuppression in the presence of one or more checkpoint inhibitors. In various embodiments, the cell comprises: (i) one or more exogenous polynucleotides integrated in a safe harbor locus or a selected gene locus; or (ii) more than two exogenous polynucleotides integrated in different safe harbor loci or two or more selected gene loci. In particular embodiments, the safe harbor locus comprises at least one of AAVS1, CCR5, ROSA26, collagen, HTRP, H11, GAPDH, or RUNX1; and wherein the selected gene locus is one of B2M, TAP1, TAP2, Tapasin, NLRC5, CIITA, RFXANK, RFX5, RFXAP, TCR, NKG2A, NKG2D, CD38, CD25, CD69, CD44, CD58, CD54, CD56, CIS, CBL-B, SOCS2, PD1, CTLA4, LAG3, TIM3, or TIGIT; and/or wherein the integration of the exogenous polynucleotides knocks out expression of the gene in the locus. In some embodiments, the TCR locus may be a constant region of TCR alpha and/or TCR beta. In various embodiments, the derivative cell comprises a derivative CD34 cell, a derivative hematopoietic stem and progenitor cell, a derivative hematopoietic multipotent progenitor cell, a derivative T cell progenitor, a derivative NK cell progenitor, a derivative T lineage cell, a derivative NKT lineage cell, a derivative NK lineage cell, a derivative B lineage cell, or a derivative immune effector cell having one or more functional features that are not present in a counterpart primary T, NK, NKT, and/or B cell.

In another aspect, the invention provides a composition comprising the cell or population thereof as described herein. Also provided is a master cell bank (MCB) comprising the clonal iPSC as described herein.

In yet another aspect, the invention provides a composition for therapeutic use comprising the cell or population thereof as described herein, and one or more therapeutic agents. In some embodiments, the therapeutic agents comprise a peptide, a cytokine, a checkpoint inhibitor, an antibody or functional variant or fragment thereof, an engager, a mitogen, a growth factor, a small RNA, a dsRNA (double stranded RNA), mononuclear blood cells, feeder cells, feeder cell components or replacement factors thereof, a vector comprising one or more polynucleic acids of interest, a chemotherapeutic agent or a radioactive moiety, and/or an immunomodulatory drug (IMiD). In those embodiments of the composition where the therapeutic agent comprises a checkpoint inhibitor, the checkpoint inhibitor may comprise: (i) one or more antagonist checkpoint molecules comprising PD-1, PDL-1, TIM-3, TIGIT, LAG-3, CTLA-4, 2B4, 4-1BB, 4-1BBL, $A_{2A}R$, BATE, BTLA, CD39, CD47, CD73, CD94, CD96, CD160, CD200, CD200R, CD274, CEACAM1, CSF-1R, Foxpl, GARP, HVEM, IDO, EDO, TDO, LAIR-1, MICA/B, NR4A2, MAFB, OCT-2, Rara (retinoic acid receptor alpha), TLR3, VISTA, NKG2A/HLA-E, or inhibitory KIR; (ii) one or more of atezolizumab, avelumab, durvalumab, ipilimumab, IPH4102, IPH43, IPH33, lirilumab, monalizumab, nivolumab, pembrolizumab, and their derivatives or functional equivalents; or (iii) at least one of atezolizumab, nivolumab, and pembrolizumab. In some embodiments, the engager comprises a bi-specific T cell engager (BiTE) or a tri-specific killer cell engager (TriKE). In particular embodiments, the therapeutic agents comprise one or more of venetoclax, azacitidine, and pomalidomide.

In those embodiments of the composition where the therapeutic agent comprises an antibody, or functional variant or fragment thereof, the antibody, or functional variant or fragment thereof may comprise: (a) anti-CD20, anti-CD22, anti-HER2, anti-CD52, anti-EGFR, anti-CD123, anti-GD2, anti-PDL1, and/or anti-CD38 antibody; (b) one or more of rituximab, veltuzumab, ofatumumab, ublituximab, ocaratuzumab, obinutuzumab, ibritumomab, ocrelizumab, inotuzumab, moxetumomab, epratuzumab, trastuzumab, pertuzumab, alemtuzumab, cetuximab, dinutuximab, avelumab, daratumumab, isatuximab, MOR202, 7G3, CSL362, elotuzumab, and their humanized or Fc modified variants or fragments and their functional equivalents and biosimilars; or (c) daratumumab, and wherein the derivative effector cell comprises a CD38 knockout, and optionally an expression of CD16 or a variant thereof.

In yet another aspect, the invention provides for therapeutic use of the composition described herein, by introducing the composition to a subject suitable for adoptive cell therapy, wherein the subject has an autoimmune disorder, a hematological malignancy, a solid tumor, cancer, or a viral infection.

In yet another aspect, the invention provides a method of manufacturing a derivative effector cell comprising the CFR as described herein, wherein the method comprises differentiating a genetically engineered iPSC, wherein the iPSC comprises a polynucleotide encoding the CFR, and optionally one or more edits resulting in: (i) CD38 knockout; (ii) HLA-I deficiency, and optionally HLA-II deficiency; (iii) introduction of HLA-G or non-cleavable HLA-G, or knockout of one or both of CD58 and CD54; (iv) a CD16 or a variant thereof; (v) a CAR having a targeting specificity; (vi) a partial or full peptide of a cell surface expressed exogenous cytokine and/or a receptor thereof; (vii) at least one of the genotypes listed in Table 1; (viii) deletion or disruption of at least one of TAP1, TAP2, Tapasin, NLRC5, CIITA, RFXANK, RFX5, RFXAP, TCR, NKG2A, NKG2D, CD25, CD69, CD44, CD56, CIS, CBL-B, SOCS2, PD1, CTLA4, LAG3, TIM3, and TIGIT; or (ix) introduction of at least one of HLA-E, 4-1BBL, CD3, CD4, CD8, CD16, CD47, CD113, CD131, CD137, CD80, PDL1, $A_{2A}R$, antigen-specific TCR, Fc receptor, an antibody or functional variant or fragment thereof, a checkpoint inhibitor, an engager, and surface triggering receptor for coupling with an agonist. In some embodiments, the method further comprises genomically engineering a clonal iPSC to knock in a polynucleotide encoding the CFR; and optionally: (i) to knock out CD38, (ii) to knock out B2M and CIITA, (iii) to knock out one or both CD58 and CD54, and/or (iv) to introduce HLA-G or non-cleavable HLA-G, a high affinity non-cleavable CD16 or a variant thereof, a CAR, and/or a partial or full peptide of a cell surface expressed exogenous cytokine and/or a receptor thereof. In various embodiments, the genomic engineering comprises targeted editing. In some embodiments, the targeted editing comprises deletion, insertion, or in/del, and wherein the targeted editing is carried out by CRISPR, ZFN, TALEN, homing nuclease, homology recombination, or any other functional variation of these methods.

In yet another aspect, the invention provides CRISPR mediated editing of clonal iPSCs, wherein the editing comprises a knock-in of a polynucleotide encoding the CFR as described herein. In some embodiments, the editing of clonal iPSCs further comprises knocking out TCR, or the CFR is inserted at one of the gene loci comprising: B2M, TAP1, TAP2, Tapasin, NLRC5, CIITA, RFXANK, RFX5, RFXAP, TCR, NKG2A, NKG2D, CD38, CD25, CD69, CD44, CD58, CD54, CD56, CIS, CBL-B, SOCS2, PD1, CTLA4, LAG3, TIM3, or TIGIT; and wherein the insertion knocks out expression of the gene in the locus.

In yet another aspect, the invention provides a method of treating a disease or a condition comprising administering to a subject in need thereof cells comprising the CFR as described herein and an agonist specific to the CFR. In some embodiments, the cells may express an antibody or functional variant or fragment thereof, or an engager that is specific to the CFR. In some embodiments, the cells are iPSC-derived effector cells further comprising one or more of: (i) a CD38 knockout; (ii) $TCR^{neg}$; (iii) an exogenous CD16 or a variant thereof; (iv) HLA-I and/or HLA-II deficiency; (v) introduction of HLA-G or non-cleavable HLA-G, or knockout of one or both of CD58 and CD54; (vi) introduction of a CAR; and/or (vii) a partial or full peptide of a cell surface expressed exogenous cytokine and/or a receptor thereof. In some embodiments, administration of the cells results in one or more of: (i) increased cytotoxicity; (ii) improved persistency and/or survival; (iii) enhanced ability in migrating, and/or activating or recruiting bystander immune cells, to tumor sites; (iv) improved tumor penetration; (v) enhanced ability to reduce tumor immunosuppression; (vi) improved ability in rescuing tumor antigen escape; (vii) controlled apoptosis; (viii) enhanced or acquired ADCC; and (ix) ability to avoid fratricide, in comparison to their counterpart primary cells obtained from peripheral blood, umbilical cord blood, or any other donor tissues.

Various objects and advantages of the compositions and methods as provided herein will become apparent from the following description taken in conjunction with the accompanying drawings wherein are set forth, by way of illustration and example, certain embodiments of this invention.

BRIEF DESCRIPTION OF THE DRAWINGS

FIGS. 2A-2C show exemplary illustrative designs for generating a cell surface presented CD3 complex, or a subunit or a subdomain thereof (cs-CD3) associated with recombinant TCR complex, or subunits thereof upon disruption of endogenous TCR in a cell: (1) nb-rTCR (non-binding recombinant TCR); (2) d-rTCR (defined recombinant TCR); (3) p-rTCR (recombinant pre-TCRα, with optional non-binding TCRβ); (4) nb-rTCR-CD3 (non-binding recombinant TCR anchored CD3); and (5) ccCD3 (CD3 chimeric chain).

(FIG. 6A) Illustration of NFAT-luciferase reporter assay; (FIG. 6B) Cell surface CD3 and TCRαβ expression in Jurkat-NFAT WT (left) and TRAC KO cells (right); (FIG. 6C) NFAT luciferase activity in Jurkat WT and TRAC KO cells with anti-CD3 antibody stimulation for 24 hours; (FIG. 6D) NFAT luciferase activity in various CFR-engineered Jurkat-TRAC KO cells stimulated with either SP34 or OKT3 antibody for 24 hours.

(FIG. 7A) Illustration of BiTE's binding on target cell and CFR of effector cells with the NFAT reporter transgene for NFAT-luciferase assay; (FIG. 7B) NFAT luciferase activity in Jurkat WT and TRAC KO cells expressing CFR 3ε-28-3ε* alone, or in combination with 3γ-28-3γ* or 3δ-28-3δ*.

(FIG. 8A) CFR designs with switchable ecto and endo domains; (FIGS. 8B and 8C) NFAT reporter activity in Jurkat TRAC KO cells expressing CFRs that share the same endodomain with different ectodomains, or CFRs that share the same ectodomain but different endodomains.

(FIG. 9A) cytotoxicity measurement in CAR-iT cells transduced with CFR of 3ε-28-3ε* together with 3δ-28-3δ* or 3γ-28-3γ* in the presence of anti-CD3; (FIG. 9B) cytotoxicity measurement in CAR-iT cells transduced with CFR of 28-28-28z alone in the presence of anti-CD28. Untransduced CAR-iT cells are included to show baseline cytotoxicity in each experiment.

FIG. 10A shows $CFR^+$ (3ε-28-3ε*) and $CFR^-$ (untransduced; UNTR) iT phenotype with selective T cell surface markers. xCELLigence assay results shows comparable CAR-dependent cytolysis between $CFR^+$ (3ε-28-3ε*) and $CFR^-$ (UNTR) iTs at E:T ratio of 3:1 (FIG. 10B) or 1:1 (FIG. 10C) against $Antigen^+$ target cells.

FIG. 11A shows an illustration of spiking BiTE supernatant collected from 293 cultures into CAR-iT cells; FIGS. 11B and 11C show CFR-dependent cytolysis of CAR-iTs against $Antigen^-$ targets at E:T ratio of 3:1 (FIG. 11B) or 1:1 (FIG. 11C) with or without BiTE supernatant; $CFR^+$ CAR-iTs show enhanced cytolysis against $Antigen^+$/$Antigen^-$ mixed targets at E:T ratio of 1:1 with BiTE supernatant (FIG. 11D); and FIG. 11E shows end-of-assay phenotyping of mixed $Antigen^+$/$Antigen^-$ target cells.

(FIG. 12B) CFR-expressing effector cell or feeder cell having an inducible apoptosis mechanism.

FIGS. 13A-13C show that CFR-armed T cells expressing a BiTE exhibit target-dependent signaling and activation. FIG. 13A shows a schematic representation of a Jurkat TRAC KO cell expressing a CD3-based CFR and a BiTE cultured with and without target cells for 24 hours, and tested for NFAT reporter activity (FIG. 13B) and activation marker expression by flow cytometry (FIG. 13C).

FIG. 14A illustrates an exemplary BiTE self-secretion model by introducing a polynucleotide encoding BiTE into CAR-iT cells; FIG. 14B shows expression of CFR (staining for CD3e and mCherry), BiTE (staining for Thy1.1) and CAR in iT cells; FIG. 14C shows CFR-dependent BiTE-inducible cytolysis against $Antigen^-$ targets at E:T ratio of 3:1; FIG. 14D shows that $CFR^-$/$CAR^+$ iT cells have enhanced cytolysis against $Antigen^+$/$Antigen^-$ mixed targets at an E:T ratio of 1:1 with self-secreting BiTEs.

FIG. 16A shows a schematic representation of an agonistic anti-CD28 antibody binding and activating a CFR with the IL-2 receptor beta endodomain, allowing signal transduction and phosphorylation of STAT5. FIG. 16B shows flow cytometry data showing expression of CD28-based CFRs in TRAC KO Jurkats. FIG. 16C shows flow-based detection of phosphorylated STAT5 in Untransduced or CFR-transduced cells in the presence or absence of agonistic antibody.

DETAILED DESCRIPTION OF THE INVENTION

Figure 1:
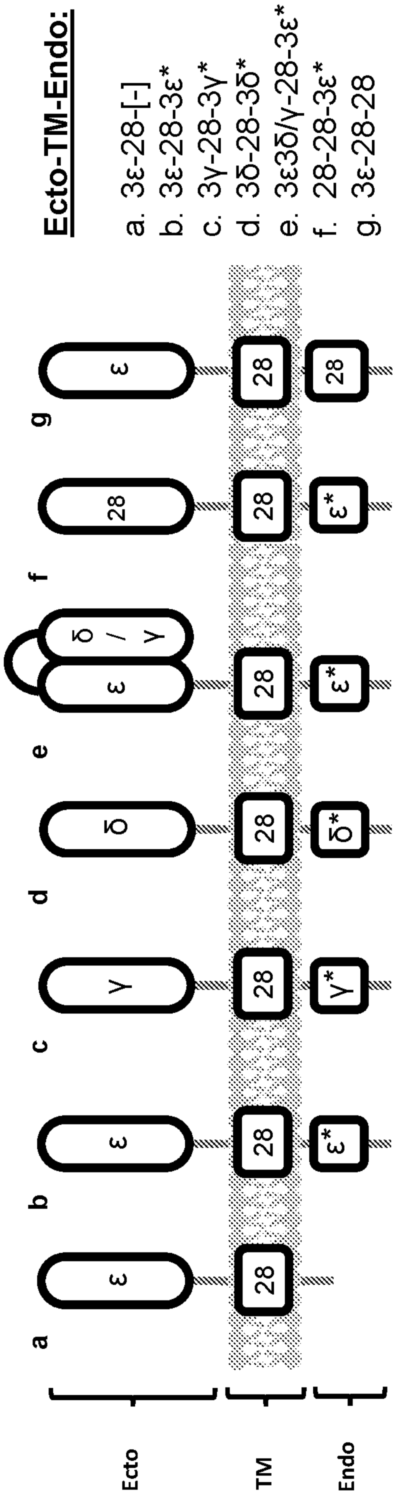
FIG. 1 shows exemplary CD3- and CD28-based CFR designs comprising an ectodomain, a transmembrane domain, and an endodomain having at least an activation/cytotoxicity signal, and the CFR does not have ER retention and endocytosis motifs.

Genomic modification of iPSCs (induced pluripotent stem cells) includes polynucleotide insertion, deletion and substitution. Exogenous gene expression in genome-engineered iPSCs often encounters problems such as gene silencing or reduced gene expression after prolonged clonal expansion of the original genome-engineered iPSCs, after cell differentiation, and in dedifferentiated cell types from the cells derived from the genome-engineered iPSCs. On the other hand, direct engineering of primary immune cells such as T or NK cells is challenging, and presents a hurdle to the preparation and delivery of engineered immune cells for adoptive cell therapy. In some embodiments, the present invention provides an efficient, reliable, and targeted approach for stably integrating one or more exogenous genes, including suicide genes and other functional modalities, which provide improved therapeutic properties relating to engraftment, trafficking, homing, migration, cytotoxicity, viability, maintenance, expansion, longevity, self-renewal, persistence, and/or survival, into iPSC derivative cells, including but not limited to HSCs (hematopoietic stem and progenitor cell), T cell progenitor cells, NK cell progenitor cells, T lineage cells, NKT lineage cells, NK lineage cells, and immune effector cells having one or more functional features that are not present in primary NK, T, and/or NKT cells.

Definitions

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein, the articles “a,” “an,” and “the” are used herein to refer to one or to more than one (i.e., to at least one) of the grammatical object of the article. By way of example, “an element” means one element or more than one element.

The use of the alternative (e.g., “or”) should be understood to mean either one, both, or any combination thereof of the alternatives.

The term “and/or” should be understood to mean either one, or both of the alternatives.

As used herein, the term “about” or “approximately” refers to a quantity, level, value, number, frequency, percentage, dimension, size, amount, weight or length that varies by as much as 15%, 10%, 9%, 8%, 7%, 6%, 5%, 4%, 3%, 2% or 1% compared to a reference quantity, level, value, number, frequency, percentage, dimension, size, amount, weight or length. In one embodiment, the term “about” or “approximately” refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

As used herein, the term "substantially" or "essentially" refers to a quantity, level, value, number, frequency, percentage, dimension, size, amount, weight or length that is about 90%, 91%, 92%, 93%, 94%, 95%, 96%, 97%, 98%, or 99% or higher compared to a reference quantity, level, value, number, frequency, percentage, dimension, size, amount, weight or length. In one embodiment, the terms "essentially the same" or "substantially the same" refer a range of quantity, level, value, number, frequency, percentage, dimension, size, amount, weight or length that is about the same as a reference quantity, level, value, number, frequency, percentage, dimension, size, amount, weight or length.

As used herein, the terms "substantially free of" and "essentially free of" are used interchangeably, and when used to describe a composition, such as a cell population or culture media, refer to a composition that is free of a specified substance or its source thereof, such as, 95% free, 96% free, 97% free, 98% free, 99% free of the specified substance or its source thereof, or is undetectable as measured by conventional means. The term "free of" or "essentially free of" a certain ingredient or substance in a composition also means that no such ingredient or substance is (1) included in the composition at any concentration, or (2) included in the composition functionally inert, but at a low concentration. Similar meaning can be applied to the term "absence of," where referring to the absence of a particular substance or its source thereof of a composition.

Throughout this specification, unless the context requires otherwise, the words "comprise," "comprises" and "comprising" will be understood to imply the inclusion of a stated step or element or group of steps or elements but not the exclusion of any other step or element or group of steps or elements. In particular embodiments, the terms "include," "has," "contains," and "comprise" are used synonymously.

By "consisting of" is meant including, and limited to, whatever follows the phrase "consisting of" Thus, the phrase "consisting of" indicates that the listed elements are required or mandatory, and that no other elements may be present.

By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments.

The term "ex vivo" refers generally to activities that take place outside an organism, such as experimentation or measurements done in or on living tissue in an artificial environment outside the organism, preferably with minimum alteration of the natural conditions. In particular embodiments, "ex vivo" procedures involve living cells or tissues taken from an organism and cultured in a laboratory apparatus, usually under sterile conditions, and typically for a few hours or up to about 24 hours, but including up to 48 or 72 hours or longer, depending on the circumstances. In certain embodiments, such tissues or cells can be collected and frozen, and later thawed for ex vivo treatment. Tissue culture experiments or procedures lasting longer than a few days using living cells or tissue are typically considered to be "in vitro," though in certain embodiments, this term can be used interchangeably with ex vivo.

The term "in vivo" refers generally to activities that take place inside an organism.

As used herein, the terms "reprogramming" or "dedifferentiation" or "increasing cell potency" or "increasing developmental potency" refers to a method of increasing the potency of a cell or dedifferentiating the cell to a less differentiated state. For example, a cell that has an increased cell potency has more developmental plasticity (i.e., can differentiate into more cell types) compared to the same cell in the non-reprogrammed state. In other words, a reprogrammed cell is one that is in a less differentiated state than the same cell in a non-reprogrammed state.

As used herein, the term "differentiation" is the process by which an unspecialized ("uncommitted") or less specialized cell acquires the features of a specialized cell such as, for example, a blood cell or a muscle cell. A differentiated or differentiation-induced cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. As used herein, the term "pluripotent" refers to the ability of a cell to form all lineages of the body or soma (i.e., the embryo proper). For example, embryonic stem cells are a type of pluripotent stem cells that are able to form cells from each of the three germs layers: the ectoderm, the mesoderm, and the endoderm. Pluripotency is a continuum of developmental potencies ranging from the incompletely or partially pluripotent cell (e.g., an epiblast stem cell or EpiSC), which is unable to give rise to a complete organism to the more primitive, more pluripotent cell, which is able to give rise to a complete organism (e.g., an embryonic stem cell).

As used herein, the term "induced pluripotent stem cells" or "iPSCs", means that the stem cells are produced in vitro, using reprogramming factor and/or small molecule chemical driven methods, from differentiated adult, neonatal or fetal cells that have been induced or changed, i.e., reprogrammed into cells capable of differentiating into tissues of all three germ or dermal layers: mesoderm, endoderm, and ectoderm. The iPSCs produced do not refer to cells as they are found in nature.

As used herein, the term "embryonic stem cell" refers to naturally occurring pluripotent stem cells of the inner cell mass of the embryonic blastocyst. Embryonic stem cells are pluripotent and give rise during development to all derivatives of the three primary germ layers: ectoderm, endoderm and mesoderm. They do not contribute to the extra-embryonic membranes or the placenta, i.e., are not totipotent.

As used herein, the term “multipotent stem cell” refers to a cell that has the developmental potential to differentiate into cells of one or more germ layers (ectoderm, mesoderm and endoderm), but not all three. Thus, a multipotent cell can also be termed a “partially differentiated cell.” Multipotent cells are well known in the art, and examples of multipotent cells include adult stem cells, such as for example, hematopoietic stem cells and neural stem cells. “Multipotent” indicates that a cell may form many types of cells in a given lineage, but not cells of other lineages. For example, a multipotent hematopoietic cell can form the many different types of blood cells (red, white, platelets, etc.), but it cannot form neurons. Accordingly, the term “multipotency” refers to a state of a cell with a degree of developmental potential that is less than totipotent and pluripotent.

Pluripotency can be determined, in part, by assessing pluripotency characteristics of the cells. Pluripotency characteristics include, but are not limited to: (i) pluripotent stem cell morphology; (ii) the potential for unlimited self-renewal; (iii) expression of pluripotent stem cell markers including, but not limited to SSEA1 (mouse only), SSEA3/4, SSEA5, TRA1-60/81, TRA1-85, TRA2-54, GCTM-2, TG343, TG30, CD9, CD29, CD133/prominin, CD140a, CD56, CD73, CD90, CD105, OCT4, NANOG, SOX2, CD30 and/or CD50; (iv) ability to differentiate to all three somatic lineages (ectoderm, mesoderm and endoderm); (v) teratoma formation consisting of the three somatic lineages; and (vi) formation of embryoid bodies consisting of cells from the three somatic lineages.

Two types of pluripotency have previously been described: the “primed” or “metastable” state of pluripotency akin to the epiblast stem cells (EpiSC) of the late blastocyst, and the “Naïve” or “Ground” state of pluripotency akin to the inner cell mass of the early/preimplantation blastocyst. While both pluripotent states exhibit the characteristics as described above, the naïve or ground state further exhibits: (i) pre-inactivation or reactivation of the X-chromosome in female cells; (ii) improved clonality and survival during single-cell culturing; (iii) global reduction in DNA methylation; (iv) reduction of H3K27me3 repressive chromatin mark deposition on developmental regulatory gene promoters; and (v) reduced expression of differentiation markers relative to primed state pluripotent cells. Standard methodologies of cellular reprogramming in which exogenous pluripotency genes are introduced to a somatic cell, expressed, and then either silenced or removed from the resulting pluripotent cells are generally seen to have characteristics of the primed-state of pluripotency. Under standard pluripotent cell culture conditions such cells remain in the primed state unless the exogenous transgene expression is maintained, wherein characteristics of the ground-state are observed.

As used herein, the term “pluripotent stem cell morphology” refers to the classical morphological features of an embryonic stem cell. Normal embryonic stem cell morphology is characterized by being round and small in shape, with a high nucleus-to-cytoplasm ratio, the notable presence of nucleoli, and typical inter-cell spacing.

As used herein, the term “subject” refers to any animal, preferably a human patient, livestock, or other domesticated animal.

A “pluripotency factor,” or “reprogramming factor,” refers to an agent capable of increasing the developmental potency of a cell, either alone or in combination with other agents. Pluripotency factors include, without limitation, polynucleotides, polypeptides, and small molecules capable of increasing the developmental potency of a cell. Exemplary pluripotency factors include, for example, transcription factors and small molecule reprogramming agents.

“Culture” or “cell culture” refers to the maintenance, growth and/or differentiation of cells in an in vitro environment. “Cell culture media,” “culture media” (singular “medium” in each case), “supplement” and “media supplement” refer to nutritive compositions that cultivate cell cultures.

“Cultivate” or “maintain” refers to the sustaining, propagating (growing) and/or differentiating of cells outside of tissue or the body, for example in a sterile plastic (or coated plastic) cell culture dish or flask. “Cultivating” or “maintaining” may utilize a culture medium as a source of nutrients, hormones and/or other factors helpful to propagate and/or sustain the cells.

As used herein, the term “mesoderm” refers to one of the three germinal layers that appears during early embryogenesis and which gives rise to various specialized cell types including blood cells of the circulatory system, muscles, the heart, the dermis, skeleton, and other supportive and connective tissues.

As used herein, the term “definitive hemogenic endothelium” (HE) or “pluripotent stem cell-derived definitive hemogenic endothelium” (iHE) refers to a subset of endothelial cells that give rise to hematopoietic stem and progenitor cells in a process called endothelial-to-hematopoietic transition. The development of hematopoietic cells in the embryo proceeds sequentially from lateral plate mesoderm through the hemangioblast to the definitive hemogenic endothelium and hematopoietic progenitors.

The term “hematopoietic stem and progenitor cells,” “hematopoietic stem cells,” “hematopoietic progenitor cells,” or “hematopoietic precursor cells” refers to cells which are committed to a hematopoietic lineage but are capable of further hematopoietic differentiation and include, multipotent hematopoietic stem cells (hematoblasts), myeloid progenitors, megakaryocyte progenitors, erythrocyte progenitors, and lymphoid progenitors. Hematopoietic stem and progenitor cells (HSCs) are multipotent stem cells that give rise to all the blood cell types including myeloid (monocytes and macrophages, neutrophils, basophils, eosinophils, erythrocytes, megakaryocytes/platelets, dendritic cells), and lymphoid lineages (T cells, B cells, NK cells). The term “definitive hematopoietic stem cell” as used herein, refers to $CD34^+$ hematopoietic cells capable of giving rise to both mature myeloid and lymphoid cell types including T lineage cells, NK lineage cells and B lineage cells. Hematopoietic cells also include various subsets of primitive hematopoietic cells that give rise to primitive erythrocytes, megakaryocytes and macrophages.

As used herein, the terms “T lymphocyte” and “T cell” are used interchangeably and refer to a principal type of white blood cell that completes maturation in the thymus and that has various roles in the immune system, including the identification of specific foreign antigens in the body and the activation and deactivation of other immune cells in an MHC class I-restricted manner. A T cell can be any T cell, such as a cultured T cell, e.g., a primary T cell, or a T cell from a cultured T cell line, e.g., Jurkat, SupT1, etc., or a T cell obtained from a mammal. The T cell can be $CD3^+$ cells. The T cell can be any type of T cell and can be of any developmental stage, including but not limited to, $CD4^+$/$CD8^+$ double positive T cells, $CD4^+$ helper T cells (e.g., Th1 and Th2 cells), $CD8^+$ T cells (e.g., cytotoxic T cells), peripheral blood mononuclear cells (PBMCs), peripheral blood leukocytes (PBLs), tumor infiltrating lymphocytes (TILs), memory T cells, naïve T cells, regulator T cells, gamma delta T cells (γδ T cells), and the like. Additional types of helper T cells include cells such as Th3 (Treg), Th17, Th9, or Tfh cells. Additional types of memory T cells include cells such as central memory T cells (Tcm cells), effector memory T cells (Tem cells and TEMRA cells). The T cell can also refer to a genetically engineered T cell, such as a T cell modified to express a T cell receptor (TCR) or a chimeric antigen receptor (CAR). A T cell, or a T cell like effector cell, can also be differentiated from a stem cell or progenitor cell. A T cell like derivative effector cell may have a T cell lineage in some respects, but at the same time has one or more functional features that are not present in a primary T cell.

"$CD4^+$ T cells" refers to a subset of T cells that express CD4 on their surface and are associated with cell-mediated immune response. They are characterized by the secretion profiles following stimulation, which may include secretion of cytokines such as IFN-gamma, TNF-alpha, IL2, IL4 and IL10. "CD4" are 55-kD glycoproteins originally defined as differentiation antigens on T-lymphocytes, but also found on other cells including monocytes/macrophages. CD4 antigens are members of the immunoglobulin supergene family and are implicated as associative recognition elements in MEW (major histocompatibility complex) class II-restricted immune responses. On T-lymphocytes they define the helper/inducer subset.

"$CD8^+$ T cells" refers to a subset of T cells which express CD8 on their surface, are MHC class I-restricted, and function as cytotoxic T cells. "CD8" molecules are differentiation antigens found on thymocytes and on cytotoxic and suppressor T-lymphocytes. CD8 antigens are members of the immunoglobulin supergene family and are associative recognition elements in major histocompatibility complex class I-restricted interactions.

As used herein, the term "NK cell" or "Natural Killer cell" refers to a subset of peripheral blood lymphocytes defined by the expression of CD56 or CD16 and the absence of the T cell receptor (CD3). As used herein, the terms "adaptive NK cell" and "memory NK cell" are interchangeable and refer to a subset of NK cells that are phenotypically $CD3^-$ and $CD56^+$, expressing at least one of NKG2C and CD57, and optionally, CD16, but lack expression of one or more of the following: PLZF, SYK, FceRγ, and EAT-2. In some embodiments, isolated subpopulations of $CD56^+$ NK cells comprise expression of CD16, NKG2C, CD57, NKG2D, NCR ligands, NKp30, NKp40, NKp46, activating and inhibitory KIRs, NKG2A and/or DNAM-1. $CD56^+$ can be dim or bright expression. An NK cell, or an NK cell like effector cell may be differentiated from a stem cell or progenitor cell. An NK cell like derivative effector cell may have an NK cell lineage in some respects, but at the same time has one or more functional features that are not present in a primary NK cell.

As used herein, the term "NKT cells" or "natural killer T cells" refers to CD1d-restricted T cells, which express a T cell receptor (TCR). Unlike conventional T cells that detect peptide antigens presented by conventional major histocompatibility (MHC) molecules, NKT cells recognize lipid antigens presented by CD1d, a non-classical MHC molecule. Two types of NKT cells are recognized. Invariant or type I NKT cells express a very limited TCR repertoire—a canonical α-chain (Vα24-Jα18 in humans) associated with a limited spectrum of β chains (Vβ11 in humans). The second population of NKT cells, called non-classical or non-invariant type II NKT cells, display a more heterogeneous TCRαβ usage. Type I NKT cells are considered suitable for immunotherapy. Adaptive or invariant (type I) NKT cells can be identified with the expression of at least one or more of the following markers, TCR Va24-Ja18, Vb11, CD1d, CD3, CD4, CD8, aGalCer, CD161 and CD56.

As used herein, the term "isolated" or the like refers to a cell, or a population of cells, which has been separated from its original environment, i.e., the environment of the isolated cells is substantially free of at least one component as found in the environment in which the "un-isolated" reference cells exist. The term includes a cell that is removed from some or all components as it is found in its natural environment, for example, isolated from a tissue or biopsy sample. The term also includes a cell that is removed from at least one, some or all components as the cell is found in non-naturally occurring environments, for example, isolated from a cell culture or cell suspension. Therefore, an isolated cell is partly or completely separated from at least one component, including other substances, cells or cell populations, as it is found in nature or as it is grown, stored or subsisted in non-naturally occurring environments. Specific examples of isolated cells include partially pure cell compositions, substantially pure cell compositions and cells cultured in a medium that is non-naturally occurring. Isolated cells may be obtained by separating the desired cells, or populations thereof, from other substances or cells in the environment, or by removing one or more other cell populations or subpopulations from the environment.

As used herein, the term "purify" or the like refers to increasing purity. For example, the purity can be increased to at least 50%, 60%, 70%, 80%, 90%, 95%, 99%, or 100%.

As used herein, the term "encoding" refers to the inherent property of specific sequences of nucleotides in a polynucleotide, such as a gene, a cDNA, or a mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

A "construct" refers to a macromolecule or complex of molecules comprising a polynucleotide to be delivered to a host cell, either in vitro or in vivo. A "vector," as used herein refers to any nucleic acid construct capable of directing the delivery or transfer of a foreign genetic material to target cells, where it can be replicated and/or expressed. The term "vector" as used herein comprises the construct to be delivered. A vector can be a linear or a circular molecule. A vector can be integrating or non-integrating. The major types of vectors include, but are not limited to, plasmids, episomal vector, viral vectors, cosmids, and artificial chromosomes. Viral vectors include, but are not limited to, adenovirus vector, adeno-associated virus vector, retrovirus vector, lentivirus vector, Sendai virus vector, and the like.

By "integration" it is meant that one or more nucleotides of a construct is stably inserted into the cellular genome, i.e., covalently linked to the nucleic acid sequence within the cell's chromosomal DNA. By "targeted integration" it is meant that the nucleotide(s) of a construct is inserted into the cell's chromosomal or mitochondrial DNA at a pre-selected site or "integration site". The term "integration" as used herein further refers to a process involving insertion of one or more exogenous sequences or nucleotides of the construct, with or without deletion of an endogenous sequence or nucleotide at the integration site. In the case, where there is a deletion at the insertion site, "integration" may further comprise replacement of the endogenous sequence or a nucleotide that is deleted with the one or more inserted nucleotides.

As used herein, the term "exogenous" is intended to mean that the referenced molecule or the referenced activity is introduced into, or is non-native to, the host cell. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the cell. The term "endogenous" refers to a referenced molecule or activity that is present in the host cell. Similarly, the term when used in reference to expression of an encoding nucleic acid refers to expression of an encoding nucleic acid contained within the cell and not exogenously introduced.

As used herein, a "gene of interest" or "a polynucleotide sequence of interest" is a DNA sequence that is transcribed into RNA and in some instances translated into a polypeptide in vivo when placed under the control of appropriate regulatory sequences. A gene or polynucleotide of interest can include, but is not limited to, prokaryotic sequences, cDNA from eukaryotic mRNA, genomic DNA sequences from eukaryotic (e.g., mammalian) DNA, and synthetic DNA sequences. For example, a gene of interest may encode an miRNA, an shRNA, a native polypeptide (i.e., a polypeptide found in nature) or fragment thereof; a variant polypeptide (i.e., a mutant of the native polypeptide having less than 100% sequence identity with the native polypeptide) or fragment thereof; an engineered polypeptide or peptide fragment, a therapeutic peptide or polypeptide, an imaging marker, a selectable marker, and the like.

As used herein, the term "polynucleotide" refers to a polymeric form of nucleotides of any length, either deoxyribonucleotides or ribonucleotides or analogs thereof. The sequence of a polynucleotide is composed of four nucleotide bases: adenine (A); cytosine (C); guanine (G); thymine (T); and uracil (U) for thymine when the polynucleotide is RNA. A polynucleotide can include a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. Polynucleotide also refers to both double- and single-stranded molecules.

As used herein, the term "peptide," "polypeptide," and "protein" are used interchangeably and refer to a molecule having amino acid residues covalently linked by peptide bonds. A polypeptide must contain at least two amino acids, and no limitation is placed on the maximum number of amino acids of a polypeptide. As used herein, the terms refer to both short chains, which are also commonly referred to in the art as peptides, oligopeptides and oligomers, for example, and to longer chains, which generally are referred to in the art as polypeptides or proteins. "Polypeptides" include, for example, biologically active fragments, substantially homologous polypeptides, oligopeptides, homodimers, heterodimers, variants of polypeptides, modified polypeptides, derivatives, analogs, and fusion proteins, among others. The polypeptides include natural polypeptides, recombinant polypeptides, synthetic polypeptides, or a combination thereof.

As used herein, the term "subunit" refers to each separate polypeptide chain of a protein complex, where each separate polypeptide chain can form a stable folded structure by itself. Many protein molecules are composed of more than one subunit, where the amino acid sequences can either be identical for each subunit, or similar, or completely different. For example, the CD3 complex is composed of CD3α, CD3ε, CD3δ, CD3γ, and CD3ζ subunits, which form the CD3ε/CD3γ, CD3ε/CD3δ, and CD3ζ/CD3ζ dimers. Within a single subunit, contiguous portions of the polypeptide chain frequently fold into compact, local, semi-independent units that are called "domains". Many protein domains may further comprise independent "structural subunits", also called subdomains, contributing to a common function of the domain. As such, the term "subdomain" as used herein refers to a protein domain inside of a larger domain, for example, a binding domain within an ectodomain of a cell surface receptor; or a stimulatory domain or a signaling domain of an endodomain of a cell surface receptor.

"Operably linked" or "operatively linked," interchangeable with "operably connected" or "operatively connected," refers to the association of nucleic acid sequences on a single nucleic acid fragment so that the function or operation of one is affected by the other. For example, a promoter is operably-linked with a coding sequence or functional RNA when it is capable of affecting the expression of that coding sequence or functional RNA (i.e., the coding sequence or functional RNA is under the transcriptional control of the promoter). Coding sequences can be operably linked to regulatory sequences in sense or antisense orientation.

"Fusion proteins" or "chimeric proteins", as used herein, are proteins created through genetic engineering to join two or more partial or whole polynucleotide coding sequences encoding separate proteins, and the expression of these joined polynucleotides results in a single peptide or multiple polypeptides with functional properties derived from each of the original proteins or fragments thereof. Between two neighboring polypeptides of different sources in the fusion protein, a linker (or spacer) peptide can be added. The chimeric fusion receptors (CFRs) described herein are fusion, or chimeric, proteins.

As used herein, the term "genetic imprint" refers to genetic or epigenetic information that contributes to preferential therapeutic attributes in a source cell or an iPSC, and is retainable in the source cell derived iPSCs, and/or the iPSC-derived hematopoietic lineage cells. As used herein, "a source cell" is a non-pluripotent cell that may be used for generating iPSCs through reprogramming, and the source cell derived iPSCs may be further differentiated to specific cell types including any hematopoietic lineage cells. The source cell derived iPSCs, and differentiated cells therefrom are sometimes collectively called "derived" or "derivative" cells depending on the context. For example, derivative effector cells, or derivative NK lineage cells or derivative T lineage cells, as used throughout this application are cells differentiated from an iPSC, as compared to their counterpart primary cells obtained from natural/native sources such as peripheral blood, umbilical cord blood, or other donor tissues. As used herein, the genetic imprint(s) conferring a preferential therapeutic attribute is incorporated into the iPSCs either through reprogramming a selected source cell that is donor-, disease-, or treatment response-specific, or through introducing genetically modified modalities to the iPSC using genomic editing. In the aspect of a source cell obtained from a specifically selected donor, disease or treatment context, the genetic imprint contributing to preferential therapeutic attributes may include any context specific genetic or epigenetic modifications which manifest a retainable phenotype, i.e., a preferential therapeutic attribute, that is passed on to iPSC-derived cells of the selected source cell, irrespective of the underlying molecular events being identified or not. Donor-, disease-, or treatment response-specific source cells may comprise genetic imprints that are retainable in iPSCs and derived hematopoietic lineage cells, which genetic imprints include, but are not limited to, prearranged monospecific TCR, for example, from a viral specific T cell or invariant natural killer T (iNKT) cell; trackable and desirable genetic polymorphisms, for example, homozygous for a point mutation that encodes for the high-affinity CD16 receptor in selected donors; and predetermined HLA requirements, i.e., selected HLA-matched donor cells exhibiting a haplotype with increased population. As used herein, preferential therapeutic attributes include improved engraftment, trafficking, homing, viability, self-renewal, persistence, immune response regulation and modulation, survival, and cytotoxicity of a derived cell. A preferential therapeutic attribute may also relate to antigen targeting receptor expression; HLA presentation or lack thereof; resistance to tumor microenvironment; induction of bystander immune cells and immune modulations; improved on-target specificity with reduced off-tumor effect; and/or resistance to treatment such as chemotherapy.

The term "enhanced therapeutic property" as used herein, refers to a therapeutic property of a cell that is enhanced as compared to a typical immune cell of the same general cell type. For example, an NK cell with an "enhanced therapeutic property" will possess an enhanced, improved, and/or augmented therapeutic property as compared to a typical, unmodified, and/or naturally occurring NK cell. Therapeutic properties of an immune cell may include, but are not limited to, cell engraftment, trafficking, homing, viability, self-renewal, persistence, immune response regulation and modulation, survival, and cytotoxicity. Therapeutic properties of an immune cell are also manifested by antigen targeting receptor expression; HLA presentation or lack thereof; resistance to tumor microenvironment; induction of bystander immune cells and immune modulations; improved on-target specificity with reduced off-tumor effect; and/or resistance to treatment such as chemotherapy.

As used herein, the term "engager" refers to a molecule, e.g., a fusion polypeptide, which is capable of forming a link between an immune cell (e.g., a T cell, a NK cell, a NKT cell, a B cell, a macrophage, or a neutrophil), and a tumor cell; and activating the immune cell. Examples of engagers include, but are not limited to, bi-specific T cell engagers (BiTEs), bi-specific killer cell engagers (BiKEs), tri-specific killer cell engagers (TriKEs), or multi-specific killer cell engagers, and universal engagers compatible with multiple immune cell types.

As used herein, the term "surface triggering receptor" refers to a receptor capable of triggering or initiating an immune response, e.g., a cytotoxic response. Surface triggering receptors may be engineered, and may be expressed on effector cells, e.g., a T cell, a NK cell, a NKT cell, a B cell, a macrophage, a neutrophil. In some embodiments, the surface triggering receptor facilitates bi- or multi-specific antibody engagement between the effector cells and specific target cell (e.g., a tumor cell) independent of the effector cell's natural receptors and cell types. Using this approach, one may generate iPSCs comprising a universal surface triggering receptor, and then differentiate such iPSCs into populations of various effector cell types that express the universal surface triggering receptor. By "universal", it is meant that the surface triggering receptor can be expressed in, and activate, any effector cells irrespective of the cell type, and all effector cells expressing the universal receptor can be coupled or linked to the engagers recognizable by the surface triggering receptor, regardless of the engager's tumor binding specificities. In some embodiments, engagers having the same tumor targeting specificity are used to couple with the universal surface triggering receptor. In some embodiments, engagers having different tumor targeting specificity are used to couple with the universal surface triggering receptor. As such, one or multiple effector cell types can be engaged to kill one specific type of tumor cell in some cases, and to kill two or more types of tumors in some other cases. A surface triggering receptor generally comprises a co-stimulatory domain for effector cell activation and an epitope that is specific to the epitope binding region of an engager. A bi-specific engager is specific to the epitope of a surface triggering receptor on one end, and is specific to a tumor antigen on the other end.

As used herein, the term "safety switch protein" refers to an engineered protein designed to prevent potential toxicity or otherwise adverse effects of a cell therapy. In some instances, the safety switch protein expression is conditionally controlled to address safety concerns for transplanted engineered cells that have permanently incorporated the gene encoding the safety switch protein into its genome. This conditional regulation could be variable and might include control through a small molecule-mediated post-translational activation and tissue-specific and/or temporal transcriptional regulation. The safety switch could mediate induction of apoptosis, inhibition of protein synthesis, DNA replication, growth arrest, transcriptional and post-transcriptional genetic regulation and/or antibody-mediated depletion. In some instances, the safety switch protein is activated by an exogenous molecule, e.g., a prodrug, that when activated, triggers apoptosis and/or cell death of a therapeutic cell. Examples of safety switch proteins, include, but are not limited to suicide genes such as caspase 9 (or caspase 3 or 7), thymidine kinase, cytosine deaminase, B-cell CD20, modified EGFR, and any combination thereof. In this strategy, a prodrug that is administered in the event of an adverse event is activated by the suicide-gene product and kills the transduced cell.

As used herein, the term "pharmaceutically active proteins or peptides" refer to proteins or peptides that are capable of achieving a biological and/or pharmaceutical effect on an organism. A pharmaceutically active protein has healing, curative or palliative properties against a disease and may be administered to ameliorate relieve, alleviate, reverse or lessen the severity of a disease. A pharmaceutically active protein also has prophylactic properties and is used to prevent the onset of a disease or to lessen the severity of such disease or pathological condition when it does emerge. Pharmaceutically active proteins include an entire protein or peptide or pharmaceutically active fragments thereof. It also includes pharmaceutically active analogs of the protein or peptide or analogs of fragments of the protein or peptide. The term pharmaceutically active protein also refers to a plurality of proteins or peptides that act cooperatively or synergistically to provide a therapeutic benefit. Examples of pharmaceutically active proteins or peptides include, but are not limited to, receptors, binding proteins, transcription and translation factors, tumor growth suppressing proteins, antibodies or fragments thereof, growth factors, and/or cytokines.

As used herein, the term "signaling molecule" refers to any molecule that modulates, participates in, inhibits, activates, reduces, or increases, the cellular signal transduction. "Signal transduction" refers to the transmission of a molecular signal in the form of chemical modification by recruitment of protein complexes along a pathway that ultimately triggers a biochemical event in the cell. Signal transduction pathways are well known in the art, and include, but are not limited to, G protein coupled receptor signaling, tyrosine kinase receptor signaling, integrin signaling, toll gate signaling, ligand-gated ion channel signaling, ERK/MAPK signaling pathway, Wnt signaling pathway, cAMP-dependent pathway, and IP3/DAG signaling pathway.

As used herein, the term "targeting modality" refers to a molecule, e.g., a polypeptide, that is genetically incorporated into a cell to promote antigen and/or epitope specificity that includes, but is not limited to i) antigen specificity as it relates to a unique chimeric antigen receptor (CAR) or T cell receptor (TCR), ii) engager specificity as it relates to monoclonal antibodies or bispecific engager, iii) targeting of a transformed cell, iv) targeting of a cancer stem cell, and v) other targeting strategies in the absence of a specific antigen or surface molecule.

As used herein, the term "specific" or "specificity" can be used to refer to the ability of a molecule, e.g., a receptor or an engager, to selectively bind to a target molecule, in contrast to non-specific or non-selective binding.

The term "adoptive cell therapy" as used herein refers to a cell-based immunotherapy that, as used herein, relates to the transfusion of autologous or allogenic lymphocytes, identified as T or B cells, genetically modified or not, that have been expanded ex vivo prior to said transfusion.

A "therapeutically sufficient amount", as used herein, includes within its meaning a non-toxic but sufficient and/or effective amount of the particular therapeutic and/or pharmaceutical composition to which it is referring to provide a desired therapeutic effect. The exact amount required will vary from subject to subject depending on factors such as the patient's general health, the patient's age and the stage and severity of the condition. In particular embodiments, a therapeutically sufficient amount is sufficient and/or effective to ameliorate, reduce, and/or improve at least one symptom associated with a disease or condition of the subject being treated.

Differentiation of pluripotent stem cells requires a change in the culture system, such as changing the stimuli agents in the culture medium or the physical state of the cells. The most conventional strategy utilizes the formation of embryoid bodies (EBs) as a common and critical intermediate to initiate the lineage-specific differentiation. "Embryoid bodies" are three-dimensional clusters that have been shown to mimic embryo development as they give rise to numerous lineages within their three-dimensional area. Through the differentiation process, typically a few hours to days, simple EBs (for example, aggregated pluripotent stem cells elicited to differentiate) continue maturation and develop into a cystic EB at which time, typically days to a few weeks, they are further processed to continue differentiation. EB formation is initiated by bringing pluripotent stem cells into close proximity with one another in three-dimensional multilayered clusters of cells, typically this is achieved by one of several methods including allowing pluripotent cells to sediment in liquid droplets, sedimenting cells into "U" bottomed well-plates or by mechanical agitation. To promote EB development, the pluripotent stem cell aggregates require further differentiation cues, as aggregates maintained in pluripotent culture maintenance medium do not form proper EBs. As such, the pluripotent stem cell aggregates need to be transferred to a differentiation medium that provides eliciting cues towards the lineage of choice. EB-based culture of pluripotent stem cells typically results in generation of differentiated cell populations (ectoderm, mesoderm and endoderm germ layers) with modest proliferation within the EB cell cluster. Although proven to facilitate cell differentiation, EBs, however, give rise to heterogeneous cells in a variable differentiation state because of the inconsistent exposure of the cells in the three-dimensional structure to differentiation cues from the environment. In addition, EBs are laborious to create and maintain. Moreover, cell differentiation through EB formation is accompanied with modest cell expansion, which also contributes to low differentiation efficiency.

In comparison, "aggregate formation," as distinct from "EB formation," can be used to expand the populations of pluripotent stem cell derived cells. For example, during aggregate-based pluripotent stem cell expansion, culture media are selected to maintain proliferation and pluripotency. Cell proliferation generally increases the size of the aggregates forming larger aggregates, and these aggregates can be routinely mechanically or enzymatically dissociated into smaller aggregates to maintain cell proliferation within the culture and increase numbers of cells. As distinct from EB culture, cells cultured within aggregates in maintenance culture maintain markers of pluripotency. The pluripotent stem cell aggregates require further differentiation cues to induce differentiation.

As used herein, "monolayer differentiation" is a term referring to a differentiation method distinct from differentiation through three-dimensional multilayered clusters of cells, i.e., "EB formation." Monolayer differentiation, among other advantages disclosed herein, avoids the need for EB formation for differentiation initiation. Because monolayer culturing does not mimic embryo development such as EB formation, differentiation towards specific lineages is deemed as minimal as compared to all three germ layer differentiation in EB.

As used herein, a "dissociated" cell refers to a cell that has been substantially separated or purified away from other cells or from a surface (e.g., a culture plate surface). For example, cells can be dissociated from an animal or tissue by mechanical or enzymatic methods. Alternatively, cells that aggregate in vitro can be dissociated from each other, such as by dissociation into a suspension of clusters, single cells or a mixture of single cells and clusters, enzymatically or mechanically. In yet another alternative embodiment, adherent cells are dissociated from a culture plate or other surface. Dissociation thus can involve breaking cell interactions with extracellular matrix (ECM) and substrates (e.g., culture surfaces), or breaking the ECM between cells.

As used herein, "feeder cells" or "feeders" are terms describing cells of one type that are co-cultured with cells of a second type to provide an environment in which the cells of the second type can grow, expand, or differentiate, as the feeder cells provide stimulation, growth factors and nutrients for the support of the second cell type. The feeder cells are optionally from a different species as the cells they are supporting. For example, certain types of human cells, including stem cells, can be supported by primary cultures of mouse embryonic fibroblasts, or immortalized mouse embryonic fibroblasts. In another example, peripheral blood derived cells or transformed leukemia cells support the expansion and maturation of natural killer cells. The feeder cells may typically be inactivated when being co-cultured with other cells by irradiation or treatment with an antagonistic mitotic agent such as mitomycin to prevent them from outgrowing the cells they are supporting. Feeder cells may include endothelial cells, stromal cells (for example, epithelial cells or fibroblasts), and leukemic cells. Without limiting the foregoing, one specific feeder cell type may be a human feeder, such as a human skin fibroblast. Another feeder cell type may be mouse embryonic fibroblasts (MEF). In general, various feeder cells can be used in part to maintain pluripotency, direct differentiation towards a certain lineage, enhance proliferation capacity and promote maturation to a specialized cell type, such as an effector cell.

As used herein, a “feeder-free” (FF) environment refers to an environment such as a culture condition, cell culture or culture media which is essentially free of feeder or stromal cells, and/or which has not been pre-conditioned by the cultivation of feeder cells. “Pre-conditioned” medium refers to a medium harvested after feeder cells have been cultivated within the medium for a period of time, such as for at least one day. Pre-conditioned medium contains many mediator substances, including growth factors and cytokines secreted by the feeder cells cultivated in the medium. In some embodiments, a feeder-free environment is free of both feeder or stromal cells and is also not pre-conditioned by the cultivation of feeder cells.

“Functional” as used in the context of genomic editing or modification of iPSC, and derived non-pluripotent cells differentiated therefrom, or genomic editing or modification of non-pluripotent cells and derived iPSCs reprogrammed therefrom, refers to (1) at the gene level—successful knocked-in, knocked-out, knocked-down gene expression, transgenic or controlled gene expression such as inducible or temporal expression at a desired cell development stage, which is achieved through direct genomic editing or modification, or through “passing-on” via differentiation from or reprogramming of a starting cell that is initially genomically engineered; or (2) at the cell level—successfully removing, adding, or altering a cell function/characteristic via (i) gene expression modification obtained in said cell through direct genomic editing, (ii) gene expression modification maintained in said cell through “passing-on” via differentiation from or reprogramming of a starting cell that is initially genomically engineered; (iii) downstream gene regulation in said cell as a result of gene expression modification that only appears in an earlier development stage of said cell, or only appears in the starting cell that gives rise to said cell via differentiation or reprogramming; or (iv) enhanced or newly attained cellular function or attribute displayed within the mature cellular product, initially derived from the genomic editing or modification conducted at the iPSC, progenitor or dedifferentiated cellular origin.

“HLA deficient”, including HLA class I deficient, or HLA class II deficient, or both, refers to cells that either lack, or no longer maintain, or have a reduced level of surface expression of a complete MHC complex comprising a HLA class I protein heterodimer and/or a HLA class II heterodimer, such that the diminished or reduced level is less than the level naturally detectable by other cells or by synthetic methods.

“Modified HLA deficient iPSC,” as used herein, refers to an HLA deficient iPSC that is further modified by introducing genes expressing proteins related but not limited to improved differentiation potential, antigen targeting, antigen presentation, antibody recognition, persistence, immune evasion, resistance to suppression, proliferation, co-stimulation, cytokine stimulation, cytokine production (autocrine or paracrine), chemotaxis, and cellular cytotoxicity, such as non-classical HLA class I proteins (e.g., HLA-E and HLA-G), chimeric antigen receptor (CAR), T cell receptor (TCR), CD16 Fc Receptor, BCL11b, NOTCH, RUNX1, IL15, 4-1BB, DAP10, DAP12, CD24, CD3ζ, 4-1BBL, CD47, CD113, and PDL1. The cells that are “modified HLA deficient” also include cells other than iPSCs.

The term “ligand” refers to a substance that forms a complex with a target molecule to produce a signal by binding to a site on the target. The ligand may be a natural or artificial substance capable of specific binding to the target. The ligand may be in the form of a protein, a peptide, an antibody, an antibody complex, a conjugate, a nucleic acid, a lipid, a polysaccharide, a monosaccharide, a small molecule, a nanoparticle, an ion, a neurotransmitter, or any other molecular entity capable of specific binding to a target. The target to which the ligand binds, may be a protein, a nucleic acid, an antigen, a receptor, a protein complex, or a cell. A ligand that binds to and alters the function of the target and triggers a response is called “agonistic” or “an agonist”. A ligand that binds to a target but fails to produce a response is “antagonistic” or “an antagonist.”

The term “antibody” is used herein in the broadest sense and refers generally to a molecule that contains at least one binding site that specifically binds to a particular target of interest, wherein the target may be an antigen, or a receptor that is capable of interacting with certain antibodies. For example, an NK cell can be activated by the binding of an antibody or the Fc region of an antibody to its Fc-gamma receptors (FcγR), thereby triggering the ADCC (antibody-dependent cellular cytotoxicity) mediated effector cell activation. A specific piece or portion of an antigen or receptor, or a target in general, to which an antibody binds is known as an epitope or an antigenic determinant. The term “antibody” includes, but is not limited to, native antibodies and variants thereof, fragments of native antibodies and variants thereof, peptibodies and variants thereof, and antibody mimetics that mimic the structure and/or function of an antibody or a specified fragment or portion thereof, including single chain antibodies and fragments thereof. An antibody may be a murine antibody, a human antibody, a humanized antibody, a camel IgG, single variable new antigen receptor (VNAR), shark heavy-chain antibody (Ig-NAR), a chimeric antibody, a recombinant antibody, a single-domain antibody (dAb), an anti-idiotype antibody, a bispecific-, multi-specific- or multimeric-antibody, or antibody fragment thereof. Anti-idiotype antibodies are specific for binding to an idiotope of another antibody, wherein the idiotope is an antigenic determinant of an antibody. A bi-specific antibody may be a BiTE (bi-specific T cell engager) or a BiKE (bi-specific killer cell engager), and a multi-specific antibody may be a TriKE (tri-specific Killer cell engager). Non-limiting examples of antibody fragments include Fab, Fab', F(ab')2, F(ab')3, Fv, Fabc, pFc, Fd, single chain fragment variable (scFv), tandem scFv (scFv)2, single chain Fab (scFab), disulfide stabilized Fv (dsFv), minibody, diabody, triabody, tetrabody, single-domain antigen binding fragments (sdAb), camelid heavy-chain IgG and Nanobody® fragments, recombinant heavy-chain-only antibody (VHH), and other antibody fragments that maintain the binding specificity of the antibody.

“Fc receptors,” abbreviated “FcR,” are classified based on the type of antibody that they recognize. For example, those that bind the most common class of antibody, IgG, are called Fc-gamma receptors (FcγR), those that bind IgA are called Fc-alpha receptors (FcαR), and those that bind IgE are called Fc-epsilon receptors (FcεR). The classes of FcRs are also distinguished by the cells that express them (macrophages, granulocytes, natural killer cells, T and B cells) and the signaling properties of each receptor. Fc-gamma receptors (FcγR) includes several members, FcγRT (CD64), FcγRIIA (CD32), FcγRIIB (CD32), FcγRIIIA (CD16a), and FcγRIIIB (CD16b), which differ in their antibody affinities due to their different molecular structure.

CD16, an FcγR receptor, has been identified to have two isoforms: Fc receptors FcγRIIIa (CD16a) and FcγRIIIb (CD16b). CD16a is a transmembrane protein expressed by NK cells, which binds monomeric IgG to activate NK cells and facilitate antibody-dependent cell-mediated cytotoxicity (ADCC). "High affinity CD16," "non-cleavable CD16," or "high affinity non-cleavable CD16 (hnCD16)," as used herein, refers to a natural or non-natural variant of CD16. The wildtype CD16 has low affinity and is subject to ectodomain shedding, a proteolytic cleavage process that regulates cell surface density of various cell surface molecules on leukocytes upon NK cell activation. F176V and F158V are exemplary CD16 polymorphic variants having high affinity. A CD16 variant having the cleavage site (position 195-198) in the membrane-proximal region (position 189-212) altered or eliminated is not subject to shedding. The cleavage site and the membrane-proximal region are described in detail in International Pub. No. WO 2015/148926, the complete disclosure of which is incorporated herein by reference. The CD16 S197P variant is an engineered non-cleavable version of CD16. A CD16 variant comprising both F158V and S197P has high affinity and is non-cleavable. Another exemplary high affinity and non-cleavable CD16 (hnCD16) variant is an engineered CD16 comprising an ectodomain originated from one or more of the 3 exons of the CD64 ectodomain.

"Chimeric Fc Receptor," abbreviated as "CFcR", refers to engineered Fc receptors having their native transmembrane and/or intracellular signaling domains modified, or replaced, with non-native transmembrane and/or intracellular signaling domains. In some embodiments of the chimeric Fc receptor, in addition to having one of, or both, transmembrane and signaling domains being non-native, one or more stimulatory domains can be introduced to the intracellular portion of the engineered Fc receptor to enhance cell activation, expansion and function upon triggering of the receptor. Unlike a chimeric antigen receptor (CAR), which contains an antigen binding domain to target an antigen, the chimeric Fc receptor binds to an Fc fragment, or the Fc region of an antibody, or the Fc region comprised in an engager, or a ligand, or a binding molecule and activates the cell function with or without bringing the targeted cell close in vicinity. For example, a Fcγ receptor (FcγR) can be engineered to comprise selected transmembrane, stimulatory, and/or signaling domains in the intracellular region that respond to the binding of IgG at the extracellular domain, thereby generating a CFcR. In one example, a CFcR is produced by engineering CD16, a Fcγ receptor, by replacing its transmembrane domain and/or intracellular domain. To further improve the binding affinity of the CD16-based CFcR, the extracellular domain of CD64 or the high-affinity variants of CD16 (F176V, for example) can be incorporated. In some embodiments of the CFcR where high affinity CD16 extracellular domain is involved, the proteolytic cleavage site comprising a serine at position 197 is eliminated or is replaced such that the extracellular domain of the receptor is non-cleavable, i.e., not subject to shedding, thereby obtaining a hnCD16-based CFcR.

I. Cells and Compositions Useful for Adoptive Cell Therapies with Enhanced Properties Provided herein is a strategy to systematically engineer the regulatory circuitry of a clonal iPSC without impacting the differentiation potency of the iPSC and cell development biology of the iPSC and its derivative cells, while enhancing the therapeutic properties of the derivative cells differentiated from the iPSC. In some embodiments, the iPSC-derived cells are functionally improved and suitable for adoptive cell therapies following a combination of selective modalities being introduced to the cells at the level of iPSC through genomic engineering. It was previously unclear whether altered iPSCs comprising one or more provided genetic edits still have the capacity to enter cell development, and/or to mature and generate functional differentiated cells while retaining modulated activities. Unanticipated failures during directed cell differentiation from iPSCs have been attributed to aspects including, but not limited to, development stage specific gene expression or lack thereof, requirements for HLA complex presentation, protein shedding of introduced surface expressing modalities, and the need for reconfiguration of differentiation protocols enabling phenotypic and/or functional changes in the cell. As demonstrated, the selected genomic modifications as provided herein do not negatively impact iPSC differentiation potency, and the functional effector cells derived from the engineered iPSC have enhanced and/or acquired therapeutic properties attributable to the individual or combined genomic modifications retained in the effector cells following the iPSC differentiation.

1. Cell Surface CFR (Chimeric Fusion Receptor)

The designs of the CFRs provided herein enable an effector cell to initiate an appropriate signal transduction cascade through CFR binding with a selected agonist for enhanced therapeutic properties of the effector cell expressing the CFR. Such enhanced effector cell therapeutic properties include, but are not limited to, increased activation and cytoxicity, acquired dual targeting capability, prolonged persistency, improved trafficking and tumor penetration, enhanced ability in priming, activating or recruiting bystander immune cells to tumor sites, enhanced ability to resist immunosuppression, improved ability in rescuing tumor antigen escape, and/or controlled cell signaling feedback, metabolism and apoptosis.

Accordingly, in various aspects, the invention provides a CFR that comprises an ectodomain, a transmembrane domain, and an endodomain, wherein the ectodomain, the transmembrane domain and the endodomain do not comprise any endoplasmic reticulum (ER) retention signals or endocytosis signals. The ectodomain of the CFR is for initiating signal transduction upon binding to an engager; the transmembrane domain is for membrane anchoring of the CFR; and the endodomain comprises at least one signaling domain that regulates (i.e., activates or deactivates) a signaling pathway of choice for enhancing cell therapeutic properties including, but not limited to, tumor killing, persistence, mobility, differentiation, TME counteracting, and/or controlled apoptosis. The elimination of ER retention signals from the CFR permits CFR cell surface presentation by itself when expressed, and the elimination of endocytosis signals from the CFR reduces CFR internalization and surface downregulation. It is important to either select domain components that have neither ER retention nor endocytosis signals, or remove ER retention or endocytosis signals from selected components of the CFR using molecular engineering tools. In addition, the domains of the CFRs as provided by some embodiments herein are modular, meaning for a given endodomain of a CFR, the ectodomain of the CFR is switchable depending on the binding specificity of a selected agonist, such as an antibody, a BiTE, a TriKE, or any other type of engager, to be used with said CFR; and for a given ectodomain and a specificity matching agonist, the endodomain is switchable depending on the desired signaling pathway to be activated. Additionally, the transmembrane domain in accordance with some embodiments is switchable for a given ectodomain and/or a given endodomain, so long as the transmembrane domain does not comprise any endoplasmic reticulum (ER) retention signals or endocytosis signals.

In some embodiments, the ectodomain of a CFR described herein comprises a full or partial length of the extracellular portion of a protein that is involved in cell-cell signaling or interactions. In some embodiments, the ectodomain of the CFR comprises a full or partial length of the extracellular portion of CD3ε, CD3γ, CD3δ, CD28, CD5, CD16, CD64, CD32, CD33, CD89, NKG2C, NKG2D, or any functional variants, or combinations and chimerics thereof. In some embodiments, the ectodomain of the CFR is recognized by at least an agonist, for example, an antibody or an engager (e.g., BiTE, BiKE or TriKE), that comprises a binding domain specific to an epitope comprised in the ectodomain of said CFR. In some embodiments, the antibody or engager to be used with a CFR expressing cell binds to at least one extracellular epitope of said CFR, wherein the CFR comprises a full or partial length of the extracellular portion of CD3ε, CD3γ, CD3δ, CD28, CD5, CD16, CD64, CD32, CD33, CD89, NKG2C, NKG2D, or any functional variants or combined/chimeric forms thereof. In some embodiments, the engager recognizes at least one tumor antigen comprising B7H3, BCMA, CD10, CD19, CD20, CD22, CD24, CD30, CD33, CD34, CD38, CD44, CD79a, CD79b, CD123, CD138, CD179b, CEA, CLEC12A, CS-1, DLL3, EGFR, EGFRvIII, EPCAM, FLT-3, FOLR1, FOLR3, GD2, gpA33, HER2, HM1.24, LGR5, MSLN, MCSP, MICA/B, PSMA, PAMA, P-cadherin, or ROR1. In particular embodiments of the CFR ectodomain, both ER retention and endocytosis signals are absent, or are removed or eliminated, from the CFR ectodomain using genetic engineering methods.

In some embodiments, the ectodomain of the CFR comprises a full or partial length of the extracellular portion of CD3ε, CD3γ, CD3δ or any functional variants or combined/chimeric forms thereof, to utilize a CD3-based agonist. Non-limiting exemplary CD3-based agonists, including but not limited to antibodies or engagers, comprise CD3×CD19, CD3×CD20, CD3×CD33, blinatumomab, catumaxomab, ertumaxomab, R06958688, AFM11, MT110/AMG 110, MT111/AMG211/MEDI-565, AMG330, MT112/BAY2010112, MOR209/ES414, MGD006/S80880, MGD007, and/or FBTA05. In some embodiments, the ectodomain of the CFR comprises a full or partial length of the extracellular portion of NKG2C, or any functional variants thereof, to utilize an NKG2C-based agonist. Non-limiting exemplary NKG2C-based agonists, including but not limited to antibodies or engagers, comprise NKG2C-IL15-CD33, NKG2C-IL15-CD19, and/or NKG2C-IL15-CD20 tri-specific engagers. In some other embodiments, the ectodomain of the CFR comprises a full or partial length of the extracellular portion of CD28 or any functional variants thereof, to utilize a CD28-based agonist. Non-limiting exemplary CD28-based agonists, including but not limited to antibodies or engagers, comprise at least one of 15E8, CD28.2, CD28.6, YTH913.12, 37.51, 9D7 (TGN1412), 5.11A1, ANC28.1/5D10, and/or 37407.

In some embodiments, the ectodomain of the CFR comprises a full or partial length of the extracellular portion of CD16, CD64, or any functional variants or combined/chimeric forms thereof, to utilize a CD16- or CD64-based agonist. Non-limiting exemplary CD16- or CD64-based agonists, including but not limited to antibodies or engagers, comprise IgG antibodies, or CD16- or CD64-based engagers. When the Fc portion of an IgG antibody binds the CD16- or CD64-based CFRs, it activates antibody dependent cell mediated cytotoxicity (ADCC) in the CFR-expressing cells along with other enhanced therapeutic properties that are imparted by the signaling domains comprised in the endodomains of the CFR. Non-limiting exemplary CD16- or CD64-based agonists, including but not limited to antibodies or engagers, comprise at least one of CD16×CD30, CD64×CD30, CD16×BCMA, CD64×BCMA, CD16-IL-EPCAM or CD64-IL-EPCAM, CD16-IL-CD33 or CD64-IL-CD33, wherein "IL" comprised in a TriKE comprises all or a portion of at least one cytokine comprising IL2, IL4, IL6, IL7, IL9, IL10, IL11, IL12, IL15, IL18, IL21, or any functional variants or combined/chimeric forms thereof.

In general, a transmembrane domain is a three-dimensional protein structure which is thermodynamically stable in a membrane such as the phospholipid bilayer of a biological membrane (e.g., a membrane of a cell or cell vesicle). Thus, in some embodiments, the transmembrane domain of a CFR of the present invention comprises a single alpha helix, a stable complex of several transmembrane alpha helices, a transmembrane beta barrel, a beta-helix of gramicidin A, or any combination thereof. In various embodiments, the transmembrane domain of the CFR comprises all or a portion of a "transmembrane protein" or "membrane protein" that is within the membrane. As used herein, a "transmembrane protein" or "membrane protein" is a protein located at and/or within a membrane. Examples of transmembrane proteins that are suitable for providing a transmembrane domain comprised in a CFR of the invention include, but are not limited to, a receptor, a ligand, an immunoglobulin, a glycophorin, or a combination thereof. In some embodiments, the transmembrane domain comprised in the CFR comprises all or a portion of a transmembrane domain of CD3ε, CD3γ, CD3δ, CD3ζ, CD4, CD8, CD8a, CD8b, CD27, CD28, CD40, CD84, CD137, CD166, FcεRIγ, 4-1BB, OX40, ICOS, ICAM-1, CTLA-4, PD-1, LAG-3, 2B4, BTLA, CD16, IL7, IL12, IL15, KIR2DL4, KIR2DS1, NKp30, NKp44, NKp46, NKG2C, NK G2D, a T cell receptor (such as TCRα and/or TCRβ), a nicotinic acetylcholine receptor, a GABA receptor, or a combination thereof. In some embodiments, the transmembrane domain comprises all or a portion of a transmembrane domain of IgG, IgA, IgM, IgE, IgD, or a combination thereof. In some embodiments, the transmembrane domain comprises all or a portion of a transmembrane domain of glycophorin A, glycophorin D or a combination thereof. In particular embodiments of the CFR transmembrane domain, both ER retention and endocytosis signals are absent or are removed using genetic engineering. In various embodiments, both ER retention and endocytosis signals are absent or are removed or eliminated from the CFR transmembrane domain using genetic engineering methods. In some embodiments, the transmembrane domain comprises all or a portion of a transmembrane domain of CD3ε, CD28, CD27, CD8, ICOS, or CD4.

In some embodiments, the endodomain of a CFR described herein comprises at least one signaling domain that activates an intracellular signaling pathway of choice. In various embodiments of the CFR endodomain, both ER retention and endocytosis signals are absent or are removed or eliminated therefrom using genetic engineering methods. In some embodiments, the endodomain comprises at least a cytoxicity domain. In some other embodiments, the endodomain may optionally comprise, in addition to a cytoxicity domain, one or more of a co-stimulatory domain, a persistency signaling domain, a death-inducing signaling domain, a tumor cell control signaling domain, or any combinations thereof. In some embodiments, the cytoxicity domain of the CFR comprises at least a full length or a portion of a polypeptide of CD3ζ, 2B4, DAP10, DAP12, DNAM1, CD (4-1BB), IL21, IL7, IL12, IL15, NKp30, NKp44, NKp46, NKG2C, or NKG2D. In one embodiment, the cytoxicity domain of a CFR comprises an amino acid sequence that has at least about 85%, about 90%, about 95%, about 96%, about 97%, about 98%, or about 99% identity to at least one ITAM (immunoreceptor tyrosine-based activation motif) of CD3ζ. In one embodiment, the cytoxicity domain of the CFR comprises a modified CD3ζ, represented by an amino acid sequence having at least about 85%, about 90%, about 95%, about 96%, about 97%, about 98%, or about 99% identity to SEQ ID NO: 35.

In some embodiments, the CFR comprises an endodomain further comprising a co-stimulatory domain in addition to a cytotoxicity signaling domain. Co-stimulatory domains suitable for use in the CFR include, but are not limited to, a full length or at least a portion of a polypeptide of CD2, CD27, CD28, CD40L, 4-1BB, OX40, ICOS, PD-1, LAG-3, 2B4, BTLA, DAP10, DAP12, CTLA-4, or NKG2D, or any combination thereof. In some embodiments of the CFR, the co-stimulatory domain thereof comprises a full length or at least a portion of a polypeptide of CD28, 4-1BB, CD27, CD40L, ICOS, CD2, or combinations thereof. In some embodiments, the CFR comprises an endodomain comprising a co-stimulatory domain of CD28 and a cytoxicity domain of CD3 (also referred to as "28ζ"). In some embodiments, the –CD28-CD3ζ portion of an endodomain of the CFR is represented by an amino acid sequence having at least about 85%, about 90%, about 95%, about 96%, about 97%, about 98%, or about 99% identity to SEQ ID NO: 13.

In some embodiments, the CFR comprises an endodomain further comprising a persistency signaling domain in addition to a cytotoxicity signaling domain and/or a co-stimulatory domain. Persistency signaling domains suitable for use in the CFR include, but are not limited to, all or a part of an endodomain of a cytokine receptor such as, IL2R, IL7R, IL15R, IL18R, IL12R, IL23R, or combinations thereof. In addition, an endodomain of a receptor tyrosine kinase (RTK) such as EGFR provides tumor cell control, or a tumor necrosis factor receptor (TNFR) such as FAS provides controlled cell death.

FIG. 1 includes some exemplary CFRs for illustration purposes. Each of the exemplary CFRs respectively comprises at least one extracellular portion of a CD3 subunit-CD3ε, CD3δ, or CD3γ, or CD28, represented respectively by an amino acid sequence of at least about 90%, about 95%, about 96%, about 97%, about 98%, or about 99% identity to SEQ ID NO: 25, SEQ ID NO: 26, SEQ ID NO: 27, and SEQ ID NO: 46; a transmembrane domain of CD28, CD8, or CD4, represented respectively by an amino acid sequence of at least about 90%, about 95%, about 96%, about 97%, about 98%, or about 99% identity to SEQ ID NO: 47, SEQ ID NO: 48, and SEQ ID NO: 49; and an endodomain of CD3ε, CD3γ, CD3δ, or CD28, with ER retention motifs and/or endocytosis motifs in ecto-, transmembrane, and/or endodomains eliminated. For example, the introduction of an R183S mutation to the CD3c wildtype endodomain sequence (SEQ ID NO: 50) eliminates an ER retention motif, resulting in a CD3c endodomain variant represented by an amino acid sequence of at least about 90%, about 95%, about 96%, about 97%, about 98%, or about 99% identity to SEQ ID NO: 51. The introduction of L142A and R169A mutations to the CD3δ wildtype endodomain sequence (SEQ ID NO: 52) eliminates an endocytosis motif and an ER retension motif from the WT sequence, resulting in a CD3δ endodomain variant represented by an amino acid sequence of at least about 90%, about 95%, about 96%, about 97%, about 98%, or about 99% identity to SEQ ID NO: 53. Further, the introduction of L131A and R158A mutations to the CD3γ wildtype endodomain sequence (SEQ ID NO: 54) eliminates ER retension motifs from the WT sequence, resulting in a CD3γ endodomain variant represented by an amino acid sequence of at least about 90%, about 95%, about 96%, about 97%, about 98%, or about 99% identity to SEQ ID NO: 55. In some embodiments, the CD28 wildtype endodomain does not have either ER retension or endocytosis motifs, and is represented by an amino acid sequence of at least about 90%, about 95%, about 96%, about 97%, about 98%, or about 99% identity to SEQ ID NO: 56. Various embodiments of a CFR as provided herein further comprise a signal peptide at the N-terminal of the CFR ectodomain. Non-limiting exemplary signal peptides include those represented by an amino acid sequence of at least about 90%, about 95%, about 96%, about 97%, about 98%, or about 99% identity to SEQ ID NO: 28, SEQ ID NO: 29, SEQ ID NO: 30, or SEQ ID NO: 57.

(ecto-CD28)

SEQ ID NO: 46

NKILVKQSPMLVAYDNAVNLSCKYSYNLFSREFRASLHKGLDSAVEVC

VVYGNYSQQLQVYSKTGFNCDGKLGNESVTFYLQNLYVNQTDIYFCKI

EVMYPPPYLDNEKSNGTIIHVKGKHLCPSPLFPGPSKP (TM-CD28)

SEQ ID NO: 47

FWVLVVVGGVLACYSLLVTVAFIIFWV (TM-CD8)

SEQ ID NO: 48

IYIWAPLAGTCGVLLLSLVIT (TM-CD4)

SEQ ID NO: 49

MALIVLGGVAGLLLFIGLGIFF (endo-CD3ϵ WT)

SEQ ID NO: 50

KNRKAKAKPVTRGAGAGGRQRGQNKERPPPVPNPDYEPIRKGQRDLYS

GLNQRRI (endo-CD3$\epsilon_{mut}$)

SEQ ID NO: 51

KNRKAKAKPVTRGAGAGGRQRGQNKERPPPVPNPDYEPIRKGQRDLYS

GLNQ*S* RI (endo-CD3δ WT)

SEQ ID NO: 52

GHETGRLSGAADTQALLRNDQVYQPLRDRDDAQYSHLGGNWARNK (endo-CD3$\delta_{mut}$)

SEQ ID NO: 53

GHETGRLSGAADTQA*A* LRNDQVYQPLRDRDDAQYSHLGGNWA*A* NK (endo-CD3γ WT)

SEQ ID NO: 54

GQDGVRQSRASDKQTLLPNDQLYQPLKDREDDQYSHLQGNQLRRN

-continued (endo-CD3$\gamma_{mut}$)

SEQ ID NO: 55

GQDGVRQSRASDKQTA LPNDQLYQPLKDREDDQYSHLQGNQLA RN (endo-CD28)

SEQ ID NO: 56

RSKRSRLLHSDYMNMTPRRPGPTRKHYQPYAPPRDFAAYRS

SEQ ID NO: 57

MLRLLLALNLFPSIQVT

In some exemplary designs, the CFR comprises an ectodomain of one CD3 subunit, in some other designs the CFR comprises a single chain heterodimeric ectodomain that comprises the ectodomain of CD3c linked with that of CD3δ or CD3γ (SEQ ID NO: 58 or SEQ ID NO: 59, respectively). The linker type and length in the single chain heterodimeric ectodomain may vary.

SEQ ID NO: 58

DGNEEMGGITQTPYKVSISGTTVILTCPQYPGSEILWQHNDKNIGGDE

DDKNIGSDEDHLSLKEFSELEQSGYYVCYPRGSKPEDANFYLYLRARV

CENCMEMD*GSADDAKKDAAKKDDAKKDDAKKDGS*FKIPIEELEDRVFV

NCNTSITWVEGTVGTLLSDITRLDLGKRILDPRGIYRCNGTDIYKDKE

STVQVHYRMCQSCVELDPATVA (3ϵ-*linker*-3δ; linker sequence and length may vary)

SEQ ID NO: 59

DGNEEMGGITQTPYKVSISGTTVILTCPQYPGSEILWQHNDKNIGGDE

DDKNIGSDEDHLSLKEFSELEQSGYYVCYPRGSKPEDANFYLYLRARV

CENCMEMD*GSADDAKKDAAKKDDAKKDDAKKDGS*QSIKGNHLVKVYDY

QEDGSVLLTCDAEAKNITWFKDGKMIGFLTEDKKKWNLGSNAKDPRGM

YQCKGSQNKSKPLQVYYRMCQNCIELNAATIS (3ϵ-*linker*-3γ; linker sequence and length may vary)

The cell surface expressed CFR (including CD3-based CFR, also called a cs-CD3, as further described below) in various constructions as described herein can function as a cell surface triggering receptor for binding with molecules having selected binding specificity, which molecules include antibodies, engagers, and/or CARs (chimerical antigen receptors). The cells comprising polynucleotides encoding one or more CFRs of the present invention may be any type of cells, including human cells and non-human cells, pluripotent cells or non-pluripotent cells, immune cells or immune regulatory cells, APC (antigen presenting cells) or feeder cells, cells from primary sources (e.g., PMBC), or from cultured or engineered cells (e.g., cell lines, cells, and/or derivative cells differentiated from iPSCs). In some embodiments, the cells comprising polynucleotides encoding one or more CFRs comprise primary or derivative CD34 cells, hematopoietic stem and progenitor cells, hematopoietic multipotent progenitor cells, T cell progenitors, NK cell progenitors, T lineage cells, NKT lineage cells, NK lineage cells, or B lineage cells. In some embodiments, the derivative cells comprising polynucleotides encoding one or more CFRs are effector cells obtained from differentiating an iPSC comprising polynucleotides encoding the one or more CFRs. In some embodiments, the derivative effector cells comprising polynucleotides encoding one or more CFRs are obtained by engineering the derivative effector cells to incorporate the one or more CFRs after generating the derivative effector cells from an iPSC.

As provided further, the cell, or a population thereof, comprising polynucleotides encoding one or more CFRs may further comprise one or more of: TCR knockout; CD16 knock-in; a CAR; a partial or full length peptide of a cell surface expressed exogenous cytokine and/or a receptor thereof; B2M knockout or knockdown (e.g., to yield an HLA-I deficiency); CIITA knockout or knockdown (e.g., to yield an HLA-II deficiency); introduction of HLA-G or non-cleavable HLA-G; CD38 knockout, and additional engineered modalities described herein. Further provided in this application is a master cell bank comprising single cell sorted and expanded clonal engineered iPSCs having at least one phenotype as provided herein, including but not limited to, CFR, TCR$^{neg}$, CD16, CAR, CD38 negative, an exogenous cytokine or a fusion variant thereof, B2M$^{-/-}$, CIITA$^{-/-}$, HLA-G, and any combinations thereof, wherein the cell bank provides a platform for additional iPSC engineering and a renewable source for manufacturing off-the-shelf, engineered, homogeneous effector cells, which are well-defined and uniform in composition, and can be mass produced at significant scale in a cost-effective manner.

2. Designs to Achieve CD3 Reconstitution/Surface Presentation

Alpha-beta T cell receptors (TCRαβ) are antigen specific receptors essential to the immune response and are present on the cell surface of αβ T lymphocytes. Binding of TCRαβ to peptide-major histocompatibility complex (pMHC) initiates TCR-CD3 intracellular activation, recruitment of numerous signaling molecules, and branching and integrating signaling pathways, leading to mobilization of transcription factors that are critical for gene expression and T cell growth and function acquisition. Disrupting the constant region of TCR alpha or TCR beta (TRAC or TRBC), either through direct editing of a T cell or through genomic iPSC editing and differentiation as a source for obtaining a modified derivative T lineage cell, is one of the approaches to produce a TCR$^{neg}$ T cell. TCR$^{neg}$ T cells do not require HLA matching, have reduced alloreactivity, and are able to prevent GvHD (Graft versus Host Disease) when used in allogeneic adoptive cell therapies.

TCR disruption, however, also results in the elimination of the CD3 signaling complex from the T cell surface despite the endogenous CD3 subunit gene expression in the cell. The lack of cell surface CD3 may alter the cells' capacity for expansion and/or survival and reduce the cells' functional potential due to incompatibility with technologies requiring cell surface CD3 recognition and binding, which include, but are not limited to, CD3-based antibody and engager technologies; CD3/CD28 T cell activation bead technology; and CD3-CAR stimulation technology. Further, when TCR$^{neg}$ iPSCs are used for directed T cell differentiation, there may also be undesirable impacts on T cell development biology and T cell function maturation. However, overexpressing CD3 in cells that are TCR negative does not seem to restore the cell surface presentation of CD3 complex and/or CD3 signaling. As for cells that do not express CD3 and/or TCR despite the existence of TCR genes, for example, NK or NK progenitor cells, the acquired surface CD3 expression enables specific signal transduction and cell functions in NK lineage cells via CD3-based antibody, engager and CAR technologies that would not have been naturally compatible with these cells.

The CD3-based CFR design provided above is one of the approaches that can be used to address CD3 reconstitution/ surface presentation in the absence of TCR and surface expressed CD3, and thus, the terms "cell surface presented CD3 (cs-CD3)" or "cell surface CD3 complex, or one or more subunits or subdomains thereof," as used throughout this application would include the CD3-based CFR designs provided herein. Additionally, the following designs, as shown in FIGS. 2A-2C, are also provided as alternative embodiments to obtain cell surface presented CD3 (cs-CD3).

Design 1: Non-Binding Recombinant TCR (Nb-rTCR)

Figure 2A:
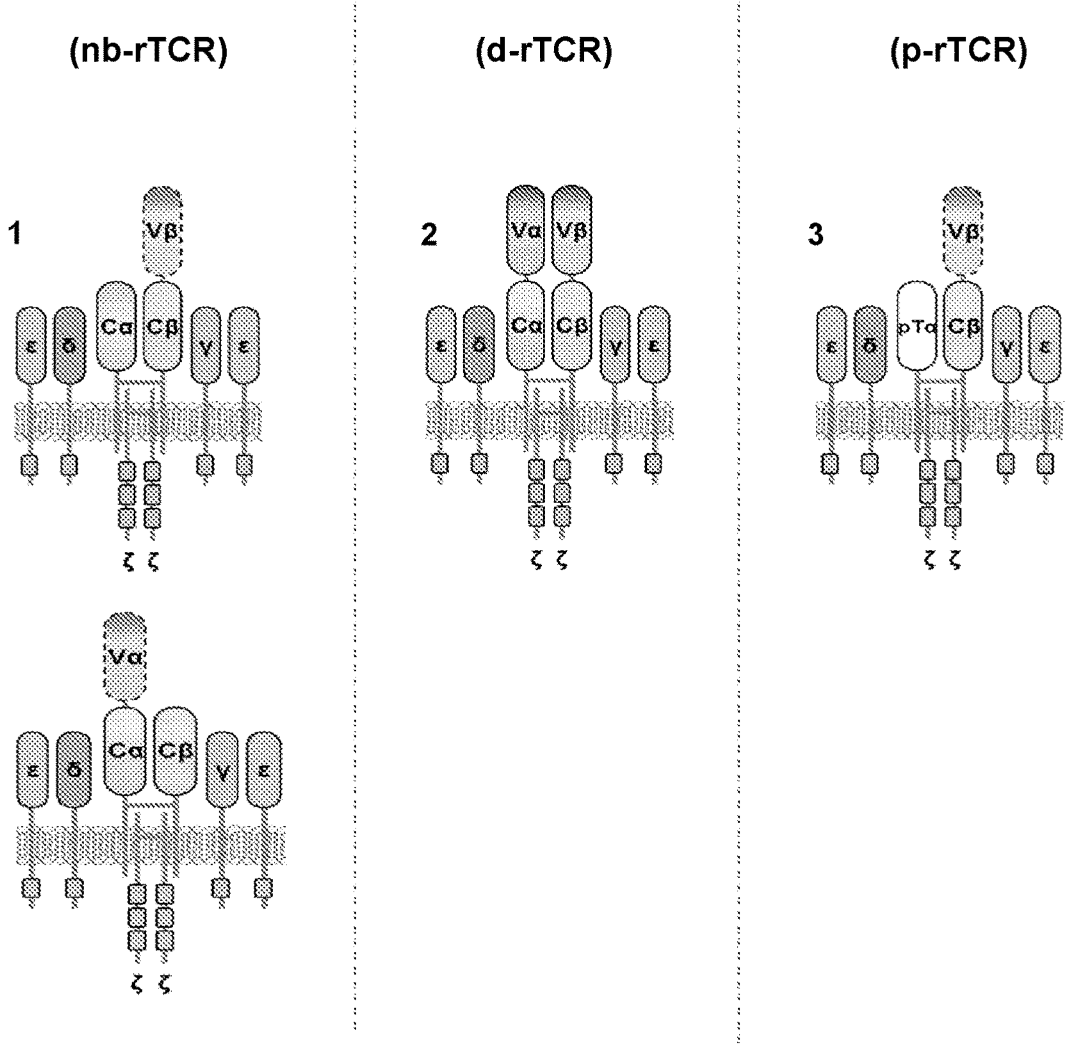
Figure 2B:
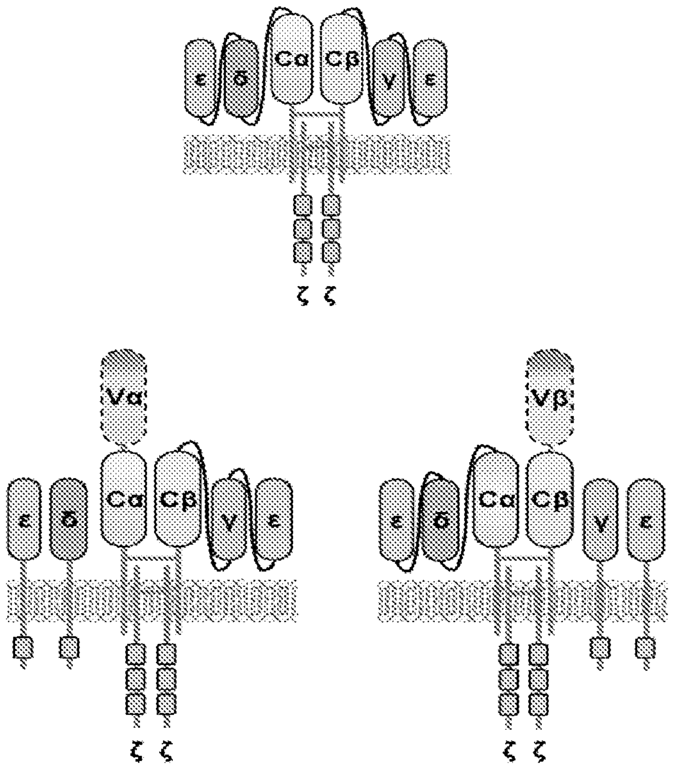
Figure 2B:
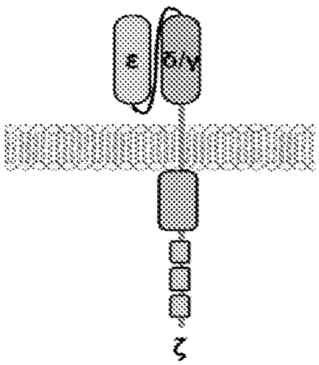

As presented in FIG. 2A, in Design 1, while the endogenous TCRα in a cell is knocked out (TCRα$^{-/-}$) using targeted genomic editing tools, leading to TCR negative (TCR$^{neg}$), the knockout of TCRβ (TCRβ$^{-/-}$) is optional; or vice versa, while the endogenous TCRβ in a cell is knocked out (TCRβ$^{-/-}$) using targeted genomic editing tools, leading to TCR negative (TCR$^{neg}$), the knockout of TCRα (TCRα$^{-/-}$) is optional. In embodiments which comprise TCRα knockout, a polynucleotide encoding a full or partial length of the constant region of TCRα (transgenic TRAC, or tgTRAC) is introduced to the cell subsequently, or is integrated at TRAC upon targeted TRAC knockout, and the expression of the polynucleotide is driven by the endogenous promoter of TCRα, or alternatively, by an exogenous promoter that is operatively linked to the polynucleotide. In some embodiments, the polynucleotide encoding a full or partial length of the constant region of TCRα further comprises an appropriate N-terminal signal peptide coupled with the full or partial length of the constant region of TCRα. In the embodiment where the endogenous TCRβ (TCRβ$^{-/-}$) is knocked out, a polynucleotide encoding a full or partial length of the constant region of TCRβ, (tgTCRβ, or tgTRBC) is introduced to the cell; and the expression of the tgTCRβ or tgTRBC is driven by the endogenous promoter of TCRβ or alternatively by an exogenous promoter. In some embodiments, the polynucleotide encoding a full or partial length of the constant region of TCRβ further comprises an appropriate N-terminal signal peptide coupled with the full or partial length of the constant region of TCRβ. In some embodiments, the exogenous promoter comprises a constitutive, inducible, temporal-, tissue-, or cell type-specific promoter. In some embodiments, the exogenous promoter comprises one of CMV, EF1α, PGK, CAG, and UBC. In one embodiment, the exogenous promoter comprises at least CAG.

In some embodiments, the polynucleotide encoding full or partial TCRα constant region (tgTRAC) comprises a sequence having an identity of at least 50%, 55%, 60%, 65%, 70%, 75%, 80%, 85%, 90%, 95%, 99%, 100%, or any percentage in-between, when compared to the exemplary sequence, SEQ ID NO: 1. In some embodiments, the polynucleotide encoding TCRβ comprising at least a full or partial constant region (tgTRBC) comprises a sequence having an identity of at least 50%, 55%, 60%, 65%, 70%, 75%, 80%, 85%, 90%, 95%, 99%, 100%, or any percentage in-between, when compared to the exemplary sequence, SEQ ID NO: 2 or SEQ ID NO: 3. In some embodiments of the polynucleotide encoding an N-terminal signal peptide and a full or partial length of TCRα or TCRβ constant region, the polynucleotide further comprises a linker peptide in-between the signal peptide and the sequence related to the TCR constant region. In some embodiments of the polynucleotide encoding an N-terminal signal peptide and a full length of TCRα or TCRβ constant region, the polynucleotide further comprises a poly A tail at the C-terminal. In some embodiments of the polynucleotide encoding an N-terminal signal peptide and a partial length of TCRα or TCRβ constant region, the integration of the polynucleotide is at a site within endogenous constant region (for example, an exon) and is in-frame, i.e., in-frame with the remaining endogenous sequence of TCRα or TCRβ constant region downstream of the integration site, such that a full length transgenic/chimeric TRAC or TRBC is formed with a part of its sequence being exogenous/transgenic and another part being endogenous. In some embodiments of Design 1, at least one of the endogenous TCRα and TCRβ is engineered to essentially remove the respective variable region, while presenting to cell surface the respective transgenic constant region when expressed. In some embodiments, only one of the endogenous TCRα and TCRβ is engineered to essentially remove the related variable region while presenting to cell surface a transgenic constant region and a wildtype TCR subunit (TCRα or TCRβ). In some embodiments, both endogenous TCRα and TCRβ are engineered as provided to remove the respective variable region, while presenting to cell surface both transgenic constant region when expressed. Exemplary N-terminal signal peptides include MALPVTALLLPLALLLHA (SEQ ID NO: 4; CD8a sp) or MDFQVQIFSFLLISASVIMSR (SEQ ID NO: 5; IgK sp), or any signal peptide sequence or functional variants thereof known in the art. An exemplary linker peptide includes DYKDDDDK (SEQ ID NO: 6; FLAG), or any linker peptide sequence or functional variants thereof known in the art.

```
(TRAC)
SEQ ID NO: 1:
IQNPDPAVYQLRDSKSSDKSVCLFTDFDSQTNVSQSKDSDVYITDKTV

LDMRSMDFKSNSAVAWSNKSDFACANAFNNSIIPEDTFFPSPESSCDV

KLVEKSFETDTNLNFQNLSVIGFRILLLKVAGFNLLMTLRLWSS

(TRBC1)
SEQ ID NO: 2:
DLNKVFPPEVAVFEPSEAEISHTQKATLVCLATGFFPDHVELSWWVNG

KEVHSGVSTDPQPLKEQPALNDSRYCLSSRLRNHFRCRVSATFWQNPQ

VQFYGLSENDEWTQDRAKPVTQIVSAEAWGRADCGFTSVSYQQGVLSA

TILYEILLGKATLYAVLVSALVLMAMVKRKDF

(TRBC2)
SEQ ID NO: 3
DLKNVFPPKVAVFEPSEAEISHTQKATLVCLATGFYPDHVELSWWVNG

KEVHSGVSTDPQPLKEQPALNDSRYCLSSRLRVSATFWQNPRNHFRCQ

VQFYGLSENDEWTQDRAKPVTQIVSAEAWGRADCGFTSESYQQGVLSA

TILYEILLGKATLYAVLVSALVLMAMVKRKDSRG
```

As demonstrated herein, it is discovered that the transgenic constant region of either TCR subunits, tgTRAC or tgTRBC, while being capable of forming a recombinant TCR complex (rTCR) by associating with the other TCR subunit (endogenous/wildtype or transgenic; if transgenic, with or without its respective variable region) and endogenous CD3 subunits, does not enable peptide-MHC binding for lack of a TCRα or TCRβ variable region that participates in the antigen recognition. The resulting cell regains the canonical TCR/CD3 signaling through the cell surface presented CD3 (cs-CD3) complex but does not have alloreactivity due to endogenous TCR knockout and a rTCR without TCRα variable region. As such, in view of Design 1, provided herein is a cell or a population thereof, wherein the cell is an iPSC, a clonal iPSC, a clonal iPS cell line cell, or a derivative cell obtained from differentiating said iPSC; and the cell comprises: a disruption at at least one of endogenous TCRα and TCRβ constant regions such that the endogenous TCR is knocked out ($TCR^{neg}$), and one or both exogenous polynucleotides encoding the constant region of TCRα (tgTRAC) and/or TCRβ (tgTRBC) that is disrupted; wherein the tgTRAC and/or tgTRBC enables cell surface presentation of endogenous CD3 (cs-CD3) when expressed. The recombinant TCR complex comprising at least one of tgTRAC and tgTRBC does not bind an antigen peptide presented by MEW due to not having both variable regions (Vα and Vβ) of the TCR subunits, and is thus termed as non-binding recombinant TCR (nb-rTCR).

Design 2: Defined Recombinant TCR (d-rTCR)

As presented in FIG. 2A, in Design 2, both endogenous TCRα and endogenous TCRβ are knocked out ($TCR\alpha^{-/-}$ and $TCR\beta^{-/-}$; or $TCR\alpha^{neg}$ $TCR\beta^{neg}$) in a cell using a genomic editing tool, leading to a $TCR^{neg}$ cell. Simultaneously with, or subsequently to, the TCR knockout, a first polynucleotide encoding a TCRα comprising a defined variable region of TCRα and a full or partial constant region (tgTCRα), and a second polynucleotide encoding a TCRβ comprising a defined variable region of TCRβ and a full or partial constant region (tgTCRβ) are introduced to the $TCR^{neg}$ cell. A defined TCRα or TCRβ variable region can be of any given specificity such that its sequence has been, or can be, identified. In some embodiments, one or both of the first and the second polynucleotides is driven by an endogenous promoter of TCRα and TCRβ, respectively. In some other embodiments, one or both of the first and the second polynucleotides is driven by an exogenous promoter. In some embodiments, the second polynucleotide is driven by an endogenous promoter of TCRβ, whereas in some other embodiments, the second polynucleotide is driven by an exogenous promoter. In some embodiments, the exogenous promoter comprises a constitutive, inducible, temporal-, tissue-, or cell type-specific promoter. In some embodiments, the exogenous promoter comprises one of CMV, EF1α, PGK, CAG, or UBC. In one embodiment, the exogenous promoter comprises at least CAG. In some embodiments, the polynucleotide encoding a full or partial length of TCRα constant region and a given defined variable region comprises at least a sequence having an identity of at least 50%, 55%, 60%, 65%, 70%, 75%, 80%, 85%, 90%, 95%, 99%, 100%, or any percentage in-between, when compared to the exemplary sequence, SEQ ID NO: 1. In some embodiments, the polynucleotide encoding a full or partial length of TCRβ constant region and a given defined variable region comprises at least a sequence having an identity of at least 50%, 55%, 60%, 65%, 70%, 75%, 80%, 85%, 90%, 95%, 99%, 100%, or any percentage in-between, when compared to the exemplary sequence, SEQ ID NO: 2 or SEQ ID NO: 3. In some embodiments, the sequence identity is at least 80%. In some embodiments, the sequence identity is at least 90%. In some embodiments, the sequence identity is at least 95%. In some embodiments, the sequence identity is 100%. In some embodiments of the polynucleotide encoding a full length of TCRα or TCRβ constant region, the polynucleotide further comprises a polyA tail at the C' terminal. In some embodiments of the polynucleotide encoding a partial length of TCRα or TCRβ constant region, the integration of the polynucleotide is at a site within the endogenous constant region and is in-frame with the remaining endogenous sequence of TCRα or TCRβ constant region downstream of the integration site, such that a full length transgenic/chimeric TRAC or TRBC is formed with a part of its sequence being exogenous/transgenic and another part being endogenous. Sequences for TCRα or TCRβ variable regions can be found, for example, in the Universal Protein Resource (UniProt) database, and some non-limiting exemplary defined TCRα or TCRβ variable regions are listed in the following Tables A and B, respectively.

TABLE A

| UniProt Sequence Entry No. | Protein Names | Gene Names |
|---|---|---|
| A0A0B4J248 | TCR alpha variable 1-1 | TRAV1-1 |
| A0A0B4J238 | TCR alpha variable 1-2 | TRAV1-2 |
| A0A0B4J234 | TCR alpha variable 2 | TRAV2 |
| A0A0B4J244 | TCR alpha variable 3 | TRAV3 |
| A0A0B4J268 | TCR alpha variable 4 | TRAV4 |
| A0A0B4J249 | TCR alpha variable 5 | TRAV5 |
| A0A075B6T7 | TCR alpha variable 6 | TRAV6 |
| A0A075B6U4 | TCR alpha variable 7 | TRAV7 |
| A0A0A6YYK1 | TCR alpha variable 8-1 | TRAV8-1 |
| A0A0B4J237 | TCR alpha variable 8-2 | TRAV8-2 |
| A0A0A6YYJ7 | TCR alpha variable 8-3 | TRAV8-3 |
| P01737 | TCR alpha variable 8-4 | TRAV8-4 |
| A0A0B4J262 | TCR alpha variable 8-6 | TRAV8-6 |
| A0A075B6U6 | TCR alpha variable 8-7 | TRAV8-7 |
| A0A075B6T8 | TCR alpha variable 9-1 | TRAV9-1 |
| A0A087WT02 | TCR alpha variable 9-2 | TRAV9-2 |
| A0A0B4J240 | TCR alpha variable 10 | TRAV10 |
| A0A0B4J245 | TCR alpha variable 12-1 | TRAV12-1 |
| A0A075B6T6 | TCR alpha variable 12-2 | TRAV12-2 |
| A0A0B4J271 | TCR alpha variable 12-3 | TRAV12-3 |
| A0A0B4J241 | TCR alpha variable 13-1 | TRAV13-1 |
| A0A0B4J235 | TCR alpha variable 13-2 | TRAV13-2 |
| A0A0A6YYC5 | TCR alpha variable 14/delta variable 4 | TRAV14DV4 |
| A0A0A6YYK6 | TCR alpha variable 16 | TRAV16 |
| A0A0B4J275 | TCR alpha variable 17 | TRAV17 |
| A0A075B6X5 | TCR alpha variable 18 | TRAV18 |
| A0A0A6YYK7 | TCR alpha variable 19 | TRAV19 |
| A0A0B4J274 | TCR alpha variable 20 | TRAV20 |
| A0A0B4J279 | TCR alpha variable 21 | TRAV21 |
| A0A0B4J277 | TCR alpha variable 22 | TRAV22 |
| A0A075B6W5 | TCR alpha variable 23/delta variable 6 | TRAV23DV6 |
| A0A0B4J272 | TCR alpha variable 24 | TRAV24 |
| A0A0B4J276 | TCR alpha variable 25 | TRAV25 |

TABLE A-continued

| UniProt Sequence Entry No. | Protein Names | Gene Names |
|---|---|---|
| A0A087WT03 | TCR alpha variable 26-1 | TRAV26-1 |
| A0A0B4J265 | TCR alpha variable 26-2 | TRAV26-2 |
| A0A087WT01 | TCR alpha variable 27 | TRAV27 |
| P04437 | TCR alpha variable 29/delta variable 5 | TRAV29DV5 |
| A0A087WSZ9 | TCR alpha variable 30 | TRAV30 |
| A0A0B4J273 | TCR alpha variable 34 | TRAV34 |
| P0DPF4 | TCR alpha variable 35 | TRAV35 |
| A0A075B6V5 | TCR alpha variable 36/delta variable 7 | TRAV36DV7 |
| A0A0B4J264 | TCR alpha variable 38-1 | TRAV38-1 |
| A0JD32 | TCR alpha variable 38-2/delta variable 8 | TRAV38-2DV8 |
| A0A0B4J263 | TCR alpha variable 39 | TRAV39 |
| A0A0B4J280 | TCR alpha variable 40 | TRAV40 |
| A0A0B4J266 | TCR alpha variable 41 | TRAV41 |

TABLE B

| UniProt Sequence Entry No. | Protein Names | Gene Names |
|---|---|---|
| A0A1B0GX68 | TCR beta variable 2 | TRBV2 |
| A0A576 | TCR beta variable 3-1 | TRBV3-1 |
| A0A577 | TCR beta variable 4-1 | TRBV4-1 |
| A0A539 | TCR beta variable 4-2 | TRBV4-2 |
| A0A589 | TCR beta variable 4-3 | TRBV4-3 |
| A0A578 | TCR beta variable 5-1 | TRBV5-1 |
| A0A0C4DH59 | TCR beta variable 5-4 | TRBV5-4 |
| A0A597 | TCR beta variable 5-5 | TRBV5-5 |
| A0A599 | TCR beta variable 5-6 | TRBV5-6 |
| A0A5A2 | TCR beta variable 5-8 | TRBV5-8 |
| A0A0K0K1D8 | TCR beta variable 6-1 | TRBV6-1 |
| A0A0J9YXY3 | TCR beta variable 6-2 | TRBV6-2 |
| P0DPF7 | TCR beta variable 6-3 | TRBV6-3 |
| A0A1B0GX49 | TCR beta variable 6-4 | TRBV6-4 |
| A0A0K0K1A5 | TCR beta variable 6-5 | TRBV6-5 |
| A0A0A6YYG2 | TCR beta variable 6-6 | TRBV6-6 |
| A0A0A6YYG3 | TCR beta variable 6-8 | TRBV6-8 |

TABLE B-continued

| UniProt Sequence Entry No. | Protein Names | Gene Names |
|---|---|---|
| A0A0J9YX75 | TCR beta variable 6-9 | TRBV6-9 |
| A0A1B0GXF2 | TCR beta variable 7-2 | TRBV7-2 |
| A0A1B0GX95 | TCR beta variable 7-4 | TRBV7-4 |
| A0A1B0GX31 | TCR beta variable 7-6 | TRBV7-6 |
| A0A0K0K1E9 | TCR beta variable 7-7 | TRBV7-7 |
| A0A1B0GX51 | TCR beta variable 7-8 | TRBV7-8 |
| P04435 | TCR beta variable 7-9 | TRBV7-9 |
| A0A0B4J1U6 | TCR beta variable 9 | TRBV9 |
| A0A0K0K1A3 | TCR beta variable 10-1 | TRBV10-1 |
| A0A0K0K1G8 | TCR beta variable 10-2 | TRBV10-2 |
| A0A0K0K1G6 | TCR beta variable 10-3 | TRBV10-3 |
| A0A0K0K1C0 | TCR beta variable 11-1 | TRBV11-1 |
| A0A584 | TCR beta variable 11-2 | TRBV11-2 |
| A0A5A6 | TCR beta variable 11-3 | TRBV11-3 |
| P01733 | TCR beta variable 12-3 | TRBV12-3 |
| A0A0B4J2E0 | TCR beta variable 12-4 | TRBV12-4 |
| A0A1B0GX78 | TCR beta variable 12-5 | TRBV12-5 |
| A0A0A6YYD4 | TCR beta variable 13 | TRBV13 |
| A0A5B0 | TCR beta variable 14 | TRBV14 |
| A0A087WV62 | TCR beta variable 16 | TRBV16 |
| A0A087X0M5 | TCR beta variable 18 | TRBV18 |
| A0A075B6N1 | TCR beta variable 19 | TRBV19 |
| A0A075B6N2 | TCR beta variable 20-1 | TRBV20-1 |
| A0A075B6N3 | TCR beta variable 24-1 | TRBV24-1 |
| A0A075B6N4 | TCR beta variable 25-1 | TRBV25-1 |
| A0A0K0K1C4 | TCR beta variable 27 | TRBV27 |
| A0A5B6 | TCR beta variable 28 | TRBV28 |

Although NKT cells are a subset of T cells that also express an αβ TCR, NKT cells differ from conventional αβ T cells in that NKT cells' TCR is composed of a canonical invariant TCRα chain (Vα24-Jα18 in humans) and TCRβ chain that use limited VP segments (Vβ11 in humans), which is limited in diversity and recognizes a limited number of lipid antigens presented by CD1d. The expression of a canonical invariant TCRα chain (Vα24-Jα18 in humans; or iTCRα) and TCRβ chain that use limited Vβ segments (Vβ11 in humans; or iTCRβ) results in highly conserved TCR and CD1d-dependent antigen presentation. To utilize this property of the TCR of invariant NKT (iTCR or iTCRαβ), in some embodiments of Design 2, a defined TCR comprises either or both of TCRα and TCRβ of invariant NKT cell (iTCRα or iTCRαβ), such that a polynucleotide encoding a full or partial length of TCRα constant region and a given defined variable region comprises at least a sequence having an identity of at least 50%, 55%, 60%, 65%, 70%, 75%, 80%, 85%, 90%, 95%, 99%, 100%, or any percentage in-between, when compared to the exemplary sequence, SEQ ID NO: 44; and a polynucleotide encoding a full or partial length of TCRβ constant region and a given defined variable region comprises at least a sequence having an identity of at least 50%, 55%, 60%, 65%, 70%, 75%, 80%, 85%, 90%, 95%, 99%, 100%, or any percentage in-between, when compared to the exemplary sequence, SEQ ID NO: In some embodiments, the sequence identity is at least 80%. In some embodiments, the sequence identity is at least 90%. In some embodiments, the sequence identity is at least 95%. In some embodiments, the sequence identity is 100%.

SEQ ID NO: 44

```
MKKHLTTFLVILWLYFYRGNGKNQVEQSPQSLIILEGKNCTLQCNYTV

SPFSNLRWYKQDTGRGPVSLTIMTFSENTKSNGRYTATLDADTKQSSL

HITASQLSDSASYICVVSDRGSTLGRLYFGRGTQLTVWPDIQNPDPAV

YQLRDSKSSDKSVCLFTDFDSQTNVSQSKDSDVYITDKTVLDMRSMDF

KSNSAVAWSNKSDFACANAFNNSIIPEDTFFPSPESSCDVKLVEKSFE

TDTNLNFQNLSVIGFRILLLKVAGFNLLMTLRLWSS
```

(iNKT TCR α chain of human Vα24Jα18; the underlined portion is the variable region)

SEQ ID NO: 45

```
MTIRLLCYMGFYFLGAGLMEADIYQTPRYLVIGTGKKITLECSQTMGH

DKMYWYQQDPGMELHLIHYSYGVNSTEKGDLSSESTVSRIRTEHFPLT

LESARPSHTSQYLCASEDLNKVFPPEVAVFEPSEAEISHTQKATLVCL

ATGFFPDHVELSWWVNGKEVHSGVSTDPQPLKEQPALNDSRYCLSSRL

RVSATFWQNPRNHERCQVQFYGLSENDEWTQDRAKPVTQIVSAEAWGR

ADCGFTSVSYQQGVLSATILYEILLGKATLYAVLVSALVLMAMVKRKD

F
```

(iNKT TCR β chain of human Vβ11; the underlined portion is the variable region)

As further demonstrated herein, it is discovered that a transgenic TCRα (tgTCRα) having a constant region and a defined variable region, optionally with a transgenic TCRβ (tgTCRβ) having a constant region and a defined variable region is capable of forming a recombinant TCR complex (rTCR) by associating with the endogenous CD3 subunits including the CD3ζ chain, while having a defined, or no, peptide-WIC binding due to the specificity of the variable region of tgTCRα and tgTCRβ. In addition to genetic engineering of transgenic TCR subunits for defined recombinant TCR, other approaches to take advantage of the TCRα and TCRβ of invariant NKT cells include reprogramming isolated NKT cells to iPSC, and differentiating the iPSC to a derived T cell, which derived T cell, as a result, comprises the TCRα and TCRβ of invariant NKT cells (iTCRα, iTCRβ; and iTCR, the complex), using the reprogramming and differentiating composition and method disclosed herein. The resulting cell, differentiated from genetically engineered iPSCs or iNKT reprogrammed iPSCs, regains the canonical TCR/CD3 signaling through the cell surface presented CD3 (cs-CD3), while having no, or a known and defined WIC binding specificity. As such, in view of Design 2, provided herein is a cell or a population thereof, wherein the cell is an iPSC, a clonal iPSC, a clonal iPS cell line, or a derivative cell obtained from differentiating the iPSC; and the cell comprises: a disruption at each of an endogenous TCRα and an endogenous TCRβ, an exogenous polynucleotide encoding a tgTCRα having a full or partial constant region and a defined variable region, and an exogenous polynucleotide encoding a tgTCRβ having a full or partial constant region and a defined variable region; wherein an endogenous CD3 molecule is present at the cell surface (cs-CD3) when expressed.

Design 3: Recombinant Pre-TCRα with Optional Non-Binding TCRβ (p-rTCR)

Pre-TCRα is a type I transmembrane receptor protein encoded by a developmentally controlled gene in immature thymocytes, an early stage in T cell development. The pre-TCRα covalently associates with TCRβ and with the CD3 subunits to form a pre-TCR complex. Pre-TCRα, among other structural and functional differences, has a relatively longer cytoplasmic tail as compared to TCRα chain. As presented in FIG. 2A, in this Design 3, the TCR negative cell has at least the endogenous TCRα knocked out (TCR$^{neg}$) using a genomic editing tool, with the knockout of the endogenous TCRβ being optional. Simultaneously with or subsequently to the TCR knockout, a first polynucleotide encoding a full or a partial length of pre-TCRα (tgpTCRα) is introduced to the TCR$^{neg}$ cell. In some embodiments where the TCR$^{neg}$ cell further comprises TCRβ knockout, a second polynucleotide encoding a full or partial TCRβ constant region with or without a given defined variable region (tgTCRβ or tgTRBC) is introduced to the TCR$^{neg}$ cell, wherein the cell is not an early stage, immature thymocyte. In some embodiments, the polynucleotide encoding a full length of TCRα or TCRβ constant region, the polynucleotide further comprises a polyA tail at the C' terminal. In some embodiments of the polynucleotide encoding a partial length of TCRα or TCRβ constant region, the integration of the polynucleotide is at a site within an endogenous constant region and is in-frame with the remaining endogenous sequence of TCRα or TCRβ constant region downstream of the integration site, such that a full length transgenic/chimeric TRAC or TRBC is formed with a part of its sequence being exogenous/transgenic and another part being endogenous.

In some embodiments, the first polynucleotide encoding a full or a partial length of pre-TCRα (tgpTCRα) is operatively linked to an endogenous promoter of TCRα upon integration. In some embodiments, the first polynucleotide encoding a full or a partial length of pre-TCRα (tgpTCRα) is driven by an exogenous promoter. In some embodiments, the second polynucleotide encoding a full or partial TCRβ constant region with or without a given defined variable region is operatively linked to an endogenous promoter of TCRβ upon integration. In some embodiments, the second polynucleotide encoding a full or partial TCRβ constant region with or without a given defined variable region is driven by an exogenous promoter. In some embodiments, the exogenous promoter comprises a constitutive, inducible, temporal-, tissue-, or cell type-specific promoter. In some embodiments, the exogenous promoter comprises one of CMV, EF1α, PGK, CAG, or UBC. In one embodiment, the exogenous promoter comprises at least CAG. In some embodiments, the polynucleotide encoding tgpTCRα comprises at least a sequence having an identity of at least 50%, 55%, 60%, 65%, 70%, 75%, 80%, 85%, 90%, 95%, 99%, 100%, or any percentage in-between, when compared to the exemplary sequence, SEQ ID NO: 23. In some embodiments, the sequence identity is at least 80%. In some embodiments, the sequence identity is at least 90%. In some embodiments, the sequence identity is at least 95%. In some embodiments, the sequence identity is 100%. In some embodiments, the polynucleotide encoding tgpTCRα comprises a partial length of SEQ ID NO: 23, which is represented herein as SEQ ID NO: 24. In some embodiments of the polynucleotide encoding tgpTCRα comprising a full or partial length of SEQ ID NO: 23 or any functional variants thereof, the encoded tgpTCRα further comprises a signal peptide known in the art. One non-limiting exemplary signal peptide comprises a peptide represented by SEQ ID NO: 22.

SEQ ID NO: 22

MAGTWLLLLLALGCPALPTGVGG

SEQ ID NO: 23

TPFPSLAPPIMLLVDGKQQMVVVCLVLDVAPPGLDSPIWFSAGNGSAL

DAFTYGPSPATDGTWTNLAHLSLPSEELASWEPLVCHTGPGAEGHSRS

TQPMHLSGEASTARTCPQEPLRGGCGLLRAPERFLLAGTPGGALWLGV

LRLLLFKLLLFDLLLTCSCLCDPAGPLPSPATTTRLRALGSHRLHPAT

ETGGREATSSPRPQPRDRRWGDTPPGRKPGSPVWGEGSYLSSYPTCPA

QAWCSRSALRAPSSSLGAFFAGDLPPPLQAGAA
(tgpTCRα with TM)

SEQ ID NO: 24

TPFPSLAPPIMLLVDGKQQMVVVCLVLDVAPPGLDSPIWFSAGNGSAL

DAFTYGPSPATDGTWTNLAHLSLPSEELASWEPLVCHTGPGAEGHSRS

TQPMHLSGEASTARTCPQEPLRGGCGLLRAPERFLLAGTPGGALWLGV

LRLLLFKLLLFDLLLTCSCLCDPAGPLPSPATTTRLRALGSHRLHPAT

ETGGREATSSPRPQPRDRRWGDTPPGRKPGSPV
(Truncated tgpTCRα with TM)

In some embodiments, the polynucleotide encoding a TCRβ comprising a full or partial constant region and a given defined variable region comprises at least a sequence having an identity of at least 50%, 55%, 60%, 65%, 70%, 75%, 80%, 85%, 90%, 95%, 99%, 100%, or any percentage in-between, when compared to the exemplary sequence, SEQ ID NO: 2 or SEQ ID NO: 3. In some embodiments, the sequence identity is at least 80%. In some embodiments, the sequence identity is at least 90%. In some embodiments, the sequence identity is at least 95%. In some embodiments, the sequence identity is 100%. A defined TCRβ variable region can be of any given specificity such that its sequence has been or can be identified. Non-limiting defined TCRβ variable regions are exemplified in Table B above, and that comprised in SEQ ID NO: 45 (the underlined portion).

It was unknown previously whether an iPSC having a pre-TCRα expression controlled by a promoter (whether an exogenous promoter or an endogenous TCRα promoter) different from its native promoter (i.e., a pre-TCRα promoter) still has the capacity to differentiate into a functional effector T cell. As demonstrated herein, the cell development biology of iPSC comprising a transgenic pre-TCRα (tgpTCRα) controlled by a non-native promoter can be maintained to an extent that the directed differentiation to iPSC-derived T cell can be carried out to generate a functional T cell. This is surprising because normally the expression of an endogenous pre-TCR is developmentally regulated. Further, the T cells derived from tgpTCRα $TCR^{neg}$ iPSCs comprise an expressed surface recombinant pre-TCR complex (rpTCR) by associating with the endogenous CD3 subunits including CD3ζ chain, while having no peptide-MHC binding capability. Without being limited by theory, the transgenic pre-TCR/CD3 complex may have nonetheless driven the iPSC-derived T cell maturation through the canonical CD3 signaling via the cell surface presented CD3 (cs-CD3) complex. In view of the above, embodiments of the present invention also include various methods of upregulating and/or preventing downregulation of endogenous pre-TCRα. The over-expressed pre-TCRα in a cell that is not an early/immature thymocyte would associate with expressed endogenous TCRβ and CD3 subunits to enable CD3 cell surface presentation while having no peptide-MHC binding capability.

As such, in view of Design 3, provided herein is a cell or a population thereof, wherein the cell is an iPSC, a clonal iPSC, a clonal iPS cell line, or a derivative cell obtained from differentiating the iPSC; and the cell comprises: a disruption at least of an endogenous TCRα or TCRβ such that the endogenous TCR is knocked out ($TCR^{neg}$), and at least an exogenous polynucleotide encoding a peptide comprising a full or partial length of pre-TCRα; wherein the expression of the pre-TCRα, in the absence of TCRα, not only results in the reconstitution of cell surface CD3 (cs-CD3) complex in association with the endogenous or transgenic TCRβ in the cells, but also contributes to the directed differentiation of iPSC into functional derivative effector cells, including T cells.

Design 4: Non-Binding Recombinant TCR Anchored CD3 (Nb-rTCR-CD3)

As presented in FIG. 2B, in this Design 4, one or both endogenous TCRα and endogenous TCRβ are knocked out ($TCR^{neg}$; $TCR\alpha^{-/-}$ and/or $TCR\beta^{-/-}$) in a cell using a genomic editing tool. Simultaneously with, or subsequently to, the TCR knockout, exogenous polynucleotides are introduced to said $TCR^{neg}$ cell, which exogenous polynucleotides comprise: a first polynucleotide encoding a recombinant TCRα comprising a TCRα constant region, full or partial length ectodomains of CD3ε and one of CD3δ and CD3γ; and/or a second polynucleotide encoding a recombinant TCRβ comprising a TCRβ constant region, full or partial length of ectodomains of CD3ε and one of CD3δ and CD3γ that is not comprised in the recombinant TCRα; such that one heterodimer between CD3ε and CD3δ encoded by one polynucleotide, and/or another heterodimer between CD3ε and CD3γ encoded by another polynucleotide could form at the cell surface.

In some embodiments, the recombinant TCRα comprises a full or partial TCRα constant region at the C-terminal, fused with full or partial length of CD3ε and CD3δ ectodomains at the N-terminal (tgCD3(ε-δ)-TRAC). In some embodiments, the recombinant TCRα comprises a full or partial TCRα constant region at the C-terminal, fused with full or partial length of ectodomains of CD3ε and CD3γ at the N-terminal (tgCD3(ε-γ)-TRAC). In some embodiments, the recombinant TCRβ comprises a full or partial length TCRβ constant region at the C-terminal, fused with full or partial length of ectodomains of CD3ε and CD3γ at the N-terminal (tgCD3(ε-γ)-TRBC). In some embodiments, the recombinant TCRβ comprises a full or partial length TCRβ constant region at the C-terminal, fused with full or partial length of ectodomains of CD3ε and CD3δ at the N-terminal (tgCD3(ε-δ)-TRBC). In some embodiments of the polynucleotide encoding a full length of TCRα or TCRβ constant region, the polynucleotide further comprises a polyA tail at the C-terminal. In some embodiments of the polynucleotide encoding a partial length of TCRα or TCRβ constant region, the integration of the polynucleotide is at a site within the respective endogenous constant region and is in-frame with the remaining endogenous sequence of TCRα or TCRβ constant region downstream of the integration site, such that a full length transgenic/chimeric TRAC or TRBC is formed with a part of its sequence being exogenous/transgenic and another part being endogenous.

In some other embodiments, where both of the first and the second polynucleotides are introduced to a cell, the recombinant TCRα is encoded by the first polynucleotide comprising tgCD3(ε-δ)-TRAC, and the recombinant TCRβ is encoded by the second polynucleotide comprising tgCD3(ε-γ)-TRBC; or the recombinant TCRα is encoded by the first polynucleotide comprising tgCD3(ε-γ)-TRAC, and the recombinant TCRβ is encoded by the second polynucleotide comprising tgCD3(ε-δ)-TRBC. As such, in said embodiments, one heterodimer between CD3ε and CD3δ encoded by one polynucleotide and another heterodimer between CD3ε and CD3γ encoded by another polynucleotide could form at the cell surface.

In some embodiments, where only one of the first and the second polynucleotides is introduced to a cell, the other TCR subunit is either wildtype/endogenous or is engineered to comprise only a constant region with its endogenous variable region removed with or without being replaced with a defined variable region: for example, tgTRAC or tgTRBC of Design 1 in FIG. 2A (without variable region), or tgTCRα or tgTCRβ of Design 2 in FIG. 2A (with a defined variable region). As such, as shown in Design 4 of FIG. 2B, in one exemplary embodiment where a first polynucleotide comprising tgCD3(ε-δ)-TRAC is introduced to a cell to provide a recombinant TCRα subunit, another polynucleotide comprising tgTRBC or tgTCRβ is also introduced to the cell to provide a recombinant TCRβ subunit; such that in this embodiment, one heterodimer between endogenous CD3ε and endogenous CD3γ, and another heterodimer between CD3ε and CD3δ encoded by the polynucleotide comprising tgCD3(ε-δ)-TRAC could be formed at the cell surface. In yet another exemplary embodiment of Design 4 of FIG. 2B, where a second polynucleotide comprising tgCD3(ε-γ)-TRBC is introduced to a cell to provide a recombinant TCRβ subunit, another polynucleotide comprising tgTRAC or tgTCRα is also introduced to the cell to provide a recombinant TCRα subunit, such that one heterodimer between endogenous CD3ε and endogenous CD3δ, and another heterodimer between CD3ε and CD3γ encoded by the polynucleotide comprising tgCD3(ε-γ)-TRBC could be formed at the cell surface.

In some embodiments, the first polynucleotide is driven by an endogenous promoter of TCRα, whereas in some other embodiments, the first polynucleotide is driven by an exogenous promoter. In some embodiments, the second polynucleotide is driven by an endogenous promoter of TCRβ, whereas in some other embodiments, the second polynucleotide is driven by an exogenous promoter. In some embodiments, the exogenous promoter for either recombinant TCRα or recombinant TCRβ comprises a constitutive, inducible, temporal-, tissue-, or cell type-specific promoter. In some embodiments, the exogenous promoter comprises one of CMV, EF1α, PGK, CAG, or UBC. In one embodiment, the exogenous promoter comprises at least CAG. In some embodiments, the polynucleotide encoding a TCRα constant region comprises at least a sequence having an identity of at least 50%, 55%, 60%, 65%, 70%, 75%, 80%, 85%, 90%, 95%, 99%, 100%, or any percentage in-between, when compared to the exemplary sequence, SEQ ID NO: 1. In some embodiments, the polynucleotide encoding a TCRβ constant region comprises at least a sequence having an identity of at least 50%, 55%, 60%, 65%, 70%, 75%, 80%, 85%, 90%, 95%, 99%, 100%, or any percentage in-between, when compared to the exemplary sequence, SEQ ID NO: 2 or SEQ ID NO: 3. In some embodiments, the polynucleotide encoding a full or partial length of CD3ε ectodomain comprises at least a sequence having an identity of at least 50%, 55%, 60%, 65%, 70%, 75%, 80%, 85%, 90%, 95%, 99%, 100%, or any percentage in-between, when compared to the exemplary sequence, SEQ ID NO: 25. In some embodiments, the polynucleotide encoding a full or partial length of CD3δ ectodomain comprises at least a sequence having an identity of at least 50%, 55%, 60%, 65%, 70%, 75%, 80%, 85%, 90%, 95%, 99%, 100%, or any percentage in-between, when compared to the exemplary sequence, SEQ ID NO: 26. In some embodiments, the polynucleotide encoding a full or partial length of CD3γ ectodomain comprises at least a sequence having an identity of at least 50%, 55%, 60%, 65%, 70%, 75%, 80%, 85%, 90%, 95%, 99%, 100%, or any percentage in-between, when compared to the exemplary sequence, SEQ ID NO: 27. In some embodiments, the sequence identity is at least 80%. In some embodiments, the sequence identity is at least 90%. In some embodiments, the sequence identity is at least 95%. In some embodiments, the sequence identity is 100%. In some embodiments of a polynucleotide encoding a full or partial length of CD3ε, CD3δ, or CD3γ ectodomain, the polynucleotide further comprises nucleic acids encoding a signal peptide. In some embodiments, the signal peptide comprises one of SEQ ID NO: 28, SEQ ID NO: 29, SEQ ID NO: 30, or any other signal peptide known in the art. In some embodiments of a polynucleotide encoding a full or partial length of CD3ε ectodomain, the polynucleotide further comprises nucleic acids encoding a signal peptide of SEQ ID NO: 28. In some embodiments of a polynucleotide encoding a full or partial length of CD3δ ectodomain, the polynucleotide further comprises nucleic acids encoding a signal peptide of SEQ ID NO: 29. In some embodiments of a polynucleotide encoding a full or partial length of CD3γ ectodomain, the polynucleotide further comprises nucleic acids encoding a signal peptide of SEQ ID NO: 30.

(ecto-CD3ε)

SEQ ID NO: 25

DGNEEMGGITQTPYKVSISGTTVILTCPQYPGSEILWQHNDKNIGGDE

DDKNIGSDEDHLSLKEFSELEQSGYYVCYPRGSKPEDANFYLYLRARV

CENCMEMD (ecto-CD3δ)

SEQ ID NO: 26

FKIPIEELEDRVFVNCNTSITWVEGTVGTLLSDITRLDLGKRILDPRG

IYRCNGTDIYKDKESTVQVHYRMCQSCVELDPATVA (ecto-CD3γ)

SEQ ID NO: 27

QSIKGNHLVKVYDYQEDGSVLLTCDAEAKNITWFKDGKMIGFLTEDKK

KWNLGSNAKDPRGMYQCKGSQNKSKPLQVYYRMCQNCIELNAATIS

SEQ ID NO: 28

MQSGTHWRVLGLCLLSVGVWGQ

SEQ ID NO: 29

MEHSTFLSGLVLATLLSQVSP

SEQ ID NO: 30

MEQGKGLAVLILAIILLQGTLA

In some embodiments of a polynucleotide encoding tgCD3(ε-δ)-TRAC fusion protein, the polynucleotide comprises a sequence having an identity of at least 50%, 55%, 60%, 65%, 70%, 75%, 80%, 85%, 90%, 95%, 99%, 100%, or any percentage in-between, when compared to the exemplary sequence, SEQ ID NO: 31, wherein each of the two linker sequences (SEQ ID NO: 33 and SEQ ID NO: 34) comprised in SEQ ID NO: 31 may be replaced with any that is known in the art. In some embodiments of a polynucleotide encoding tgCD3(ε-γ)-TRBC fusion protein, the polynucleotide comprises a sequence having an identity of at least 50%, 55%, 60%, 65%, 70%, 75%, 80%, 85%, 90%, 95%, 99%, 100%, or any percentage in-between, when compared to the exemplary sequence, SEQ ID NO: 32, wherein each of the two linker sequences (SEQ ID NO: 33 and SEQ ID NO: 34) comprised in SEQ ID NO: 32 may be replaced with any that is known in the art. In some embodiments, the sequence identity is at least 80%. In some embodiments, the sequence identity is at least 90%. In some embodiments, the sequence identity is at least 95%. In some embodiments, the sequence identity is 100%. In some embodiments of a recombinant TCRα or TCRβ fusion protein, as provided herein, the fusion protein further comprises a signal peptide known in the art. One non-limiting exemplary signal peptide comprises a peptide represented by SEQ ID NO: 28.

SEQ ID NO: 31

DGNEEMGGITQTPYKVSISGTTVILTCPQYPGSEILWQHNDKNIGGDE

DDKNIGSDEDHLSLKEFSELEQSGYYVCYPRGSKPEDANFYLYLRARV

GSADDAKKDAAKKDDAKKDDAKKDGSFKIPIEELEDRVFVNCNTSITW

VEGTVGTLLSDITRLDLGKRILDPRGIYRCNGTDIYKDKESTVQVHYR

MGGGGSGGGGSGGGGSIQNPDPAVYQLRDSKSSDKSVCLFTDFDSQTN

VSQSKDSDVYITDKTVLDMRSMDFKSNSAVAWSNKSDFACANAFNNSI

IPEDTFFPSPESSCDVKLVEKSFETDTNLNFQNLSVIGFRILLLKVAG

FNLLMTLRLWSS (N'-CD3ϵ-linker-CD3δ-G4S linker-TRAC-C')

SEQ ID NO: 32

DGNEEMGGITQTPYKVSISGTTVILTCPQYPGSEILWQHNDKNIGGDE

DDKNIGSDEDHLSLKEFSELEQSGYYVCYPRGSKPEDANFYLYLRARV

GSADDAKKDAAKKDDAKKDDAKKDGSQSIKGNHLVKVYDYQEDGSVLL

TCDAEAKNITWFKDGKMIGFLTEDKKKWNLGSNAKDPRGMYQCKGSQN

KSKPLQVYYRMGGGGSGGGGSGGGGSDLNKVFPPEVAVFEPSEAEISH

TQKATLVCLATGFFPDHVELSWWVNGKEVHSGVSTDPQPLKEQPALND

SRYCLSSRLRVSATFWQNPRNHFRCQVQFYGLSENDEWTQDRAKPVTQ

IVSAEAWGRADCGFTSVSYQQGVLSATILYEILLGKATLYAVLVSALV

LMAMVKRKDF (N'-CD3ϵ-linker-CD3γ-G4S linker-TRBC-C')

SEQ ID NO: 33

GSADDAKKDAAKKDDAKKDDAKKDGS

SEQ ID NO: 34

GGGGSGGGGSGGGGS

As demonstrated herein, it is discovered that a TCRα or TCRβ constant region fused with ectodomains of CD3ε, and one of CD3δ and CD3γ is capable of associating with a transgenic TCRβ or TCRα constant region with or without fused ectodomains of CD3ε, and one of CD3δ and CD3γ, to form CD3ε/CD3δ and CD3ε/CD3γ heterodimers. The associated transgenic TCRα and TCRβ subunits are capable of further associating with endogenous CD3ζ to support the cell surface expression of CD3 ectodomains (cs-CD3) and signaling transduction through the endogenous CD3, while having no peptide-MHC binding potential. As such, in view of Design 4, provided herein is a cell or a population thereof, wherein the cell is an iPSC, a clonal iPSC, a clonal iPS cell line, or a derivative cell obtained from differentiating said iPSC; and the cell comprises: a disruption at each of an endogenous TCRα constant region and an endogenous TCRβ constant region, and at least one of a first exogenous polynucleotide encoding a tgTCRα comprising a fused full or partial length TCRα constant region, and full or partial length ectodomains of CD3ε and one of CD3δ and CD3γ (tgCD3(ε-δ/γ)-TRAC); and a second exogenous polynucleotide encoding a tgTCRβ comprising a fused full or partial length TCRβ constant region, and full or partial length ectodomains of CD3ε and one of CD3δ and CD3γ (tgCD3(ε-γ/δ)-TRBC); wherein the ectodomains of CD3 subunits are present at the cell surface (cs-CD3) when expressed. In various embodiments, when only said first exogenous polynucleotide is comprised in the cell, the cell further comprises a tgTRBC or tgTCRβ as provided herein; and when only said second exogenous polynucleotide is comprised in the cell, the cell further comprises a tgTRAC or tgTCRα as provided herein.

Design 5: CD3 Chimeric Chain (ccCD3)

As presented in FIG. 2B, in this Design 5, a cell surface presented CD3 (cs-CD3) is in a form of a CD3 chimeric chain (ccCD3), which is constructed to comprise a full or partial length of CD3ε ectodomain, a full or partial length of ectodomains of either CD3γ or CD3δ, and a full or partial length of endodomain of CD3ζ comprising at least one ITAM (immunoreceptor tyrosine-based activation motif). Cells comprising a polynucleotide encoding said CD3 chimeric chain may further comprise a disruption at either or both of endogenous TCRα and TCRβ. When a genomic editing tool is used to generate $TCR^{neg}$ cells by targeted editing of TRAC and/or TRBC, simultaneously with or subsequently to the TCR knockout, at least one polynucleotide encoding said CD3 chimeric chain is introduced to the cell. In some embodiments, the polynucleotide is introduced to TRAC or TRBC, and is respectively driven by an endogenous promoter of TCRα or TCRβ; whereas in some other embodiments, the introduced polynucleotide is driven by an exogenous promoter. In some embodiments, the exogenous promoter comprises a constitutive, inducible, temporal-, tissue-, or cell type-specific promoter. In some embodiments, the exogenous promoter comprises one of CMV, EF1α, PGK, CAG, or UBC. In one embodiment, the exogenous promoter comprises at least CAG.

In some embodiments, the CD3 chimeric chain comprises a full or partial length of CD3ε ectodomain, a full or partial length of ectodomain of CD3γ, and a full or partial length of endodomain of CD3ζ comprising at least one ITAM (tgCD3(ε-γ)-ζ), wherein the CD3 chimeric chain is a fusion protein with either ectodomain at the N-terminal, and wherein the two ectodomains form a heterodimer. In some embodiments, the CD3 chimeric chain comprises a full or partial length of CD3ε ectodomain, a full or partial length of ectodomain of CD3δ, and a full or partial length of endodomain of CD3ζ comprising at least one ITAM (tgCD3(ε-δ)-ζ), wherein the CD3 chimeric chain is a fusion protein with either ectodomain at the N-terminal, and wherein the two ectodomains form a heterodimer. In some embodiments of the CD3 chimeric chain, the endodomain of CD3ζ comprises two ITAMs. In some embodiments of the CD3 chimeric chain, the endodomain of CD3ζ comprises all three ITAMs.

In some embodiments, the polynucleotide encoding a full or partial length of CD3ε ectodomain comprises at least a sequence having an identity of at least 50%, 55%, 60%, 65%, 70%, 75%, 80%, 85%, 90%, 95%, 99%, 100%, or any percentage in-between, when compared to the exemplary sequence, SEQ ID NO: 25. In some embodiments, the polynucleotide encoding a full or partial length of CD3δ ectodomain comprises at least a sequence having an identity of at least 50%, 55%, 60%, 65%, 70%, 75%, 80%, 85%, 90%, 95%, 99%, 100%, or any percentage in-between, when compared to the exemplary sequence, SEQ ID NO: 26. In some embodiments, the polynucleotide encoding a full or partial length of CD3γ ectodomain comprises at least a sequence having an identity of at least 50%, 55%, 60%, 65%, 70%, 75%, 80%, 85%, 90%, 95%, 99%, 100%, or any percentage in-between, when compared to the exemplary sequence, SEQ ID NO: 27. In some embodiments of a polynucleotide encoding a full or partial length of CD3ε, CD3δ, or CD3γ ectodomain, the polynucleotide further comprises nucleic acids encoding a signal peptide. In some embodiments, the signal peptide comprises one of SEQ ID NO: 27, SEQ ID NO: 29, SEQ ID NO: 30, or any other signal peptide known in the art. In some embodiments of a polynucleotide encoding a full or partial length of CD3ε ectodomain, the polynucleotide further comprises nucleic acids encoding a signal peptide of SEQ ID NO: 28. In some embodiments of a polynucleotide encoding a full or partial length of CD3δ ectodomain, the polynucleotide further comprises nucleic acids encoding a signal peptide of SEQ ID NO: 29. In some embodiments of a polynucleotide encoding a full or partial length of CD3γ ectodomain, the polynucleotide further comprises nucleic acids encoding a signal peptide of SEQ ID NO: 30. In some embodiments, the polynucleotide encoding a full or partial length of CD3 endodomain comprises at least a sequence having an identity of at least 50%, 55%, 60%, 65%, 70%, 75%, 80%, 85%, 90%, 95%, 99%, 100%, or any percentage in-between, when compared to the exemplary sequence, SEQ ID NO: 35, which comprises CD3ζ ITAM1, ITAM2, and ITAM3 (SEQ ID NOs: 36-38, respectively). In some embodiments, the sequence identity is at least 80%. In some embodiments, the sequence identity is at least 90%. In some embodiments, the sequence identity is at least 95%. In some embodiments, the sequence identity is 100%.

SEQ ID NO: 35

MKWKALFTAAILQAQLPITEAQSFGLLDPKLCYLLDGILFIYGVILTA

LFLRVKFSRSADAPAYQQGQNQLYNELNLGRREEYDVLDKRRGRDPEM

GGK*PRRKNPQEGLYNELQKDKMAEAYSEIGM*KG*ERRRGKGHDGLYQ*

*GLSTATKDTYDALHMQ*ALPPR (...ITAM1...*ITAM2*...*ITAM3*...)

SEQ ID NO: 36

APAYQQGQNQLYNELNLGRREEYDVLDKR

SEQ ID NO: 37

PRRKNPQEGLYNELQKDKMAEAYSEIGM

SEQ ID NO: 38

ERRRGKGHDGLYQGLSTATKDTYDALHMQ

In some embodiments of the CD3 chimeric chain, the endodomain of CD3ζ comprising at least one, two, or three ITAMs further comprises one or more signaling domains of 2B4, 4-1BB, CD16, CD2, CD28, CD28H, CD3, DAP10, DAP12, DNAM1, FcERIγ IL21R, IL-2Rβ (IL-15Rβ), IL-2Rγ, IL-7R, KIR2DS2, NKG2D, NKp30, NKp44, NKp46, CD3ζ1XX, CS1, or CD8 for signal transduction and/or co-stimulation. In one embodiment of the CD3 chimeric chain, the endodomain of CD3ζ comprising at least one, two, or three ITAMs further comprises at least a signaling domain of CD28 (tgCD3(ε-γ/δ)-28ζ). In some embodiments of the CD3ζ endodomain comprising the signaling domain of CD28, the polynucleotide encoding a full or partial length of 2K endodomain comprises a sequence having an identity of at least 50%, 55%, 60%, 65%, 70%, 75%, 80%, 85%, 90%, 95%, 99%, 100%, or any percentage in-between, when compared to the exemplary sequence, SEQ ID NO: 39, from which any one or two CD3ζ ITAMs may be removed. In some embodiments of the CD3 chimeric chain, the endodomain of CD3ζ comprising at least one, two, or three ITAMs further comprises a signaling domain of 4-1BB (tgCD3(ε-γ/δ-BB)ζ). In some embodiments of the CD3ζ endodomain comprising the signaling domain of 4-1BB, the polynucleotide encoding a full or partial length of BBζ endodomain comprises a sequence having an identity of at least 50%, 55%, 60%, 65%, 70%, 75%, 80%, 85%, 90%, 95%, 99%, 100%, or any percentage in-between, when compared to the exemplary sequence, SEQ ID NO: 40, from which any one or two CD3ζ ITAMs may be removed. In some embodiments of the CD3 chimeric chain, the endodomain of CD3ζ comprising at least one, two, or three ITAMs further comprises a signaling domain of CD28 and a signaling domain of 4-1BB (tgCD3(ε-γ/δ)-(28-BB)ζ). In some embodiments of the CD3ζ endodomain comprising the signaling domain of both CD28 and 4-1BB, the polynucleotide encoding a full or partial length of 28BBζ endodomain comprises a sequence having an identity of at least 50%, 55%, 60%, 65%, 70%, 75%, 80%, 85%, 90%, 95%, 99%, 100%, or any percentage in-between, when compared to the exemplary sequence, SEQ ID NO: 41, from which any one or two CD3ζ ITAMs may be removed. In one embodiment of the polynucleotide encoding tgCD3(ε-γ)-(28/BB)ζ, the encoded polypeptide comprises a sequence having an identity of at least 50%, 55%, 60%, 65%, 70%, 75%, 80%, 85%, 90%, 95%, 99%, 100%, or any percentage in-between, when compared to the exemplary sequence, SEQ ID NO: 42; from which any one or two CD3ζ ITAMs may be removed, from which the linker sequence may be replaced with any other linker sequence known in the art, or from which the CD28 signaling domain may be replaced with, or enhanced by adding, the 4-1BB signaling domain in yet some other embodiment. In one embodiment of tgCD3(ε-δ)-(28/BB)ζ, the encoded polypeptide comprises a sequence having an identity of at least 50%, 55%, 60%, 65%, 70%, 75%, 80%, 85%, 90%, 95%, 99%, 100%, or any percentage in-between, when compared to the exemplary sequence, SEQ ID NO: 43; from which any one or two CD3ζ ITAMs may be removed, from which the linker sequence may be replaced with any other linker sequence known in the art, or from which the CD28 signaling domain may be replaced by, or enhanced via further including, the 4-1BB signaling domain in yet some other embodiments. In some other embodiments of the encoded CD3 chimeric chain tgCD3(ε-γ)-(28/BB)ζ or tgCD3(ε-δ)-(28/BB)ζ, the polypeptide further comprises a signal peptide of SEQ ID NO: 28, or any other signal peptide known in the art. In some embodiments, the sequence identity is at least 80%. In some embodiments, the sequence identity is at least 90%. In some embodiments, the sequence identity is at least 95%. In some embodiments, the sequence identity is 100%.

SEQ ID NO: 39

RSKRSRLLHSDYMNMTPRRPGPTRKHYQPYAPPRDFAAYRSRVKFSRSA

-continued

DAPAYQQGQNQLYNELNLGRREEYDVLDKRRGRDPEMGGK

PRRKNPQEGLYNELQKDKMAEAYSEIGMKG

ERRRGKGHDGLYQGLSTATKDTYDALHMQALPPR
(. . . ITAM1 . . ITAM2 . . ITAM3 . . . )

SEQ ID NO: 40
KRGRKKLLYIFKQPFMRPVQTTQEEDGCSCRFPEEEEGGCELRVKFSRS

ADAPAYQQGQNQLYNELNLGRREEYDVLDKRRGRDPEMGGK

PRRKNPQEGLYNELQKDKMAEAYSEIGMKG

ERRRGKGHDGLYQGLSTATKDTYDALHMQALPPR
(. . . ITAM1 . . ITAM2 . . ITAM3 . . . )

SEQ ID NO: 41
RSKRSRLLHSDYMNMTPRRPGPTRKHYQPYAPPRDFAAYRSKRGRKKLL

YIFKQPFMRPVQTTQEEDGCSCRFPEEEEGGCELRVKFSRSADAPAYQQ

GQNQLYNELNLGRREEYDVLDKRRGRDPEMGGKPRRKNPQEGLY

NELQKDKMAEAYSEIGMKGERRRGKGHDGLYQGLS

TATKDTYDALHMQALPPR
(. . . ITAM1 . . ITAM2 . . ITAM3 . . . )

SEQ ID NO: 42
DGNEEMGGITQTPYKVSISGTTVILTCPQYPGSEILWQHNDKNIGGDED

DKNIGSDEDHLSLKEFSELEQSGYYVCYPRGSKPEDANFYLYLRARVGS

ADDAKKDAAKKDDAKKDDAKKDGSQSIKGNHLVKVYDYQEDGSVLLTCD

AEAKNITWFKDGKMIGFLTEDKKKWNLGSNAKDPRGMYQCKGSQNKSKP

LQVYYRMRAAAIEVMYPPPYLDNEKSNGTIIHVKGK

HLCPSPLFPGPSKPFWVLVVVGGVLACYSLLVTVA

FIIFWVRSKRSRLLHSDYMNMTPRRPGPTRKHYQPYAPPRDFAAYRS

RVKFSRSADAPAYQQGQNQLYNELNLGRREEYDVLDKRRGRDPEMGGKP

RRKNPQEGLYNELQKDKMAEAYSEIGMKGERRRGKGHDGLYQ

GLSTATKDTYDALHMQALPPR
(CD3ε-linker-CD3γ-CD28-CD3ζ
(. . . ITAM1 . . . ITAM2 . . ITAM3 . . . ))

SEQ ID NO: 43
DGNEEMGGITQTPYKVSISGTTVILTCPQYPGSEILWQHNDKNIGGDED

DKNIGSDEDHLSLKEFSELEQSGYYVCYPRGSKPEDANFYLYLRARVGS

ADDAKKDAAKKDDAKKDDAKKDGSFKIPIEELEDRVFVNCNTSITWVEG

TVGTLLSDITRLDLGKRILDPRGIYRCNGTDIYKDKESTVQVHYRMRAA

AIEVMYPPPYLDNEKSNGTIIHVKGKHLCPSPLFP

GPSKPFWVLVVVGGVLACYSLLVTVAFIIFWVRSKR

SRLLHSDYMNMTPRRPGPTRKHYQPYAPPRDFAAYRS

RVKFSRSADAPAYQQGQNQLYNELNLGRREEYDVLDKRRGRDPEMGGKP

RRKNPQEGLYNELQKDKMAEAYSEIGMKG ERRRGKGHDGLYQGL

STATKDTYDALHMQ ALPPR
(CD3ε-linker-CD3δ-CD28-CD3ζ
(. . . ITAM1 . . . ITAM2 . . ITAM3 . . . ))

As demonstrated herein, it is discovered that a CD3 chimeric chain as provided herein, wherein the CD3 chimeric chain is a fusion protein comprising a full or partial length of CD3ε ectodomain, at least one of CD3δ and CD3γ full or partial length ectodomain, and a CD3ζ endodomain comprising at least one ITAM and optionally one or more signaling domains, is capable of presenting the chimeric CD3 ectodomain at the cell surface when expressed in a cell that is TCR$^{neg}$. Further, the cell surface expression of CD3 ectodomains enables CD3 binding triggered signaling transduction through fused CD3ζ endodomain while having no peptide-MHC binding potential.

As such, in view of Design 5, provided herein is a cell or a population thereof, wherein the cell is an iPSC, a clonal iPSC, a clonal iPS cell line, or a derivative cell obtained from differentiating the iPSC; and the cell comprises: a disruption of at least one of an endogenous TCRα constant region and an endogenous TCRβ constant region, and at least an exogenous polynucleotide encoding a CD3 chimeric chain fusion protein (ccCD3), wherein the fusion protein comprises a full or partial length of ectodomain of CD3ε, and a full or partial length ectodomain of either one of CD3δ and CD3γ, and a full or partial length of endodomain of CD3ζ having at least one ITAM and optionally one or more signaling domain, wherein the ectodomains of the CD3 chimeric chain are present at the cell surface (cs-CD3) when expressed.

Provided herein also is an iPSC or iPSC-derived cell comprising one or more polynucleotides encoding one or more exogenous proteins to provide a cell surface CD3 complex, or one or more subunits or subdomains thereof (cs-CD3) when expressed, wherein the cell is optionally TCR negative. When the cs-CD3 is expressed, it functions as a CD3 related cell surface triggering receptor. In some embodiments where the CD3 related surface triggering receptor is provided in a TCR$^{neg}$ cell, the receptor is comprised in a complete or partial endogenous CD3 molecule presented at the effector cell surface when expressed, wherein the endogenous CD3 molecule presentation otherwise does not take place in a TCR$^{neg}$ cell even when expressed, and is enabled by its association with a recombinant TCR comprising one or more of a full or partial length of an exogenous TCRα, an exogenous TCRβ, and any variants thereof as provided herein. In some embodiments, the cell surface presentation of a complete or partial endogenous CD3 molecule in a TCR$^{neg}$ cell is enabled by additionally expressing in said cell at least a recombinant TCR comprising a non-binding recombinant TCR (nb-rTCR), a defined recombinant TCR (d-rTCR), and/or a recombinant pre-TCR.

In some embodiments, the TCR$^{neg}$ cell comprising a CD3 related surface triggering receptor comprises a non-binding recombinant TCR (nb-rTCR), wherein the nb-rTCR comprises one or both of a tgTRAC (transgenic TCRα constant region) and a tgTRBC (transgenic TCRβ constant region); as such, the TCR$^{neg}$ iPSC or iPSC-derived cell comprises one or more polynucleotides encoding tgTRAC and/or tgTRBC. In some embodiments of the TCR$^{neg}$ cell comprising a polynucleotide encoding tgTRAC, said polynucleotide is inserted in a TRAC locus, wherein the inserted polynucleotide disrupts expression of endogenous TRAC thereby leading to endogenous TCR knockout, and optionally wherein the inserted polynucleotide is driven by an endogenous promoter of TRAC or a heterologous promoter. In some embodiments of the TCR$^{neg}$ cell comprising a polynucleotide encoding tgTRBC, said polynucleotide is inserted in a TRBC locus, wherein the inserted polynucleotide disrupts expression of endogenous TRBC thereby leading to endogenous TCR knockout, and optionally wherein the inserted polynucleotide is driven by an endogenous promoter of TRBC or a heterologous promoter.

In some embodiments, the TCR$^{neg}$ cell comprising a CD3 related surface triggering receptor comprises a defined recombinant TCR (d-rTCR), wherein the d-rTCR comprises a tgTCRα (transgenic TCRα) and a tgTCRβ (transgenic TCRβ), wherein each of the tgTCRα and the tgTCRβ comprises a respective defined variable region in addition to a respective constant region (i.e., TRAC and TRBC); as such, the TCR$^{neg}$ iPSC or iPSC-derived cell comprises one or more polynucleotides encoding tgTCRα and/or tgTCRβ. In some embodiments, the defined variable region is originated from TCRα and TCRβ of a T cell having known TCR specificity. In some embodiments, the defined variable region is originated from TCRα and TCRβ of an invariant NKT cell. In some embodiments of the TCR$^{neg}$ cell comprising a polynucleotide encoding tgTCRα, said polynucleotide is inserted in a TRAC locus, wherein the inserted polynucleotide disrupts expression of endogenous TRAC thereby leading to endogenous TCR knockout, and optionally wherein the inserted polynucleotide is driven by an endogenous promoter of TRAC or a heterologous promoter. In some embodiments of the TCR$^{neg}$ cell comprising a polynucleotide encoding tgTCRβ, said polynucleotide is inserted in a TRBC locus, wherein the inserted polynucleotide disrupts expression of endogenous TRBC thereby leading to endogenous TCR knockout, and optionally wherein the inserted polynucleotide is driven by an endogenous promoter of TRBC or a heterologous promoter.

In some embodiments, the TCR$^{neg}$ cell comprising a CD3 related surface triggering receptor comprises a recombinant pre-TCR (p-rTCR), wherein the p-rTCR comprises a tgpTCRα (transgenic pre-TCRα), and optionally a tgTRBC or a tgTCRβ, wherein the tgTCRβ comprises a defined variable region; as such, the TCR$^{neg}$ iPSC or iPSC-derived cell comprises at least a polynucleotide encoding tgpTCRα. In some embodiments of the TCR$^{neg}$ cell comprising a polynucleotide encoding tgpTCRα, said polynucleotide is inserted in a TRAC locus, wherein the inserted polynucleotide disrupts expression of endogenous TRAC thereby leading to endogenous TCR knockout, and optionally wherein the inserted polynucleotide is driven by an endogenous promoter of TRAC or a heterologous promoter. In some embodiments of the TCR$^{neg}$ cell comprising a polynucleotide encoding tgTRBC or tgTCRβ in addition to tgpTCRα, said tgTRBC or tgTCRβ encoding polynucleotide is inserted in a TRBC locus, wherein the inserted polynucleotide disrupts expression of endogenous TRBC thereby leading to endogenous TCR knockout, and optionally wherein the inserted tgTRBC or tgTCRβ encoding polynucleotide is driven by an endogenous promoter of TRBC or a heterologous promoter.

In some embodiments of the CD3 related surface triggering receptor in a TCR$^{neg}$ cell, the receptor is comprised in a complete or partial CD3 molecule comprising at least one exogenous subunit or subdomain from one or more of CD3ε, CD3δ, and CD3γ. In one embodiment, the CD3 related surface triggering receptor for engager recognition in a TCR$^{neg}$ cell is comprised in a partial CD3 molecule comprising at least a full or partial length ectodomain of CD3ε. In one embodiment, the CD3 related surface triggering receptor for engager recognition in a TCR$^{neg}$ cell is comprised in a partial CD3 molecule comprising at least a full or partial length ectodomain of CD3ε, and additionally a full or partial length ectodomain of CD3γ or CD3δ. In one embodiment, said CD3 molecule comprises at least a full or partial length of an ectodomain of CD3ε, CD3γ and/or CD3δ, wherein the full or partial length of the ectodomain(s) is fused with a constant region of TCRα or TCRβ, and wherein the partial fusion proteins each comprising TRAC or TRBC are capable of forming a heterodimer with endogenous CD3ζ. As such, in one embodiment of the TCR$^{neg}$ iPSC or iPSC-derived cell having a CD3 related surface triggering receptor, the cell comprises at least one of: (i) a transgenic fusion protein comprising full or partial length of ectodomains of CD3ε and CD3δ, and a TCRα constant region (tgCD3(ε-δ)-TRAC); (ii) a transgenic fusion protein comprising full or partial length of ectodomains of CD3ε and CD3γ, and a TCRβ constant region (tgCD3(ε-γ)-TRBC); (iii) a transgenic fusion protein comprising full or partial length of ectodomains of CD3ε and CD3γ, and a TCRα constant region (tgCD3(ε-γ)-TRAC); and/or (iv) a transgenic fusion protein comprising full or partial length of ectodomains of CD3ε and CD3δ, and a TCRβ constant region (tgCD3(ε-δ)-TRBC). In some embodiments of the TCR$^{neg}$ cell having a CD3 related surface triggering receptor, the cell comprises a heterodimer comprising a transgenic fusion protein comprising a TCRα constant region fused with a full or partial length of ectodomain of at least CD3ε and a transgenic fusion protein comprising a TCRβ constant region fused with a full or partial length of ectodomain of at least CD3ε.

In addition to the various designs of FIGS. 2A-2C, directed to the cell surface CD3 complex, or one or more subunits or subdomains thereof (cs-CD3) in a TCR$^{neg}$ cell, a CD3-based CFR as described herein can also function as a CD3 related cell surface triggering receptor for binding to molecules including, but not limited to, CD3 specific antibodies, CD3-CARs, and/or CD3 targeted engagers, which are further described below. As provided further, the cell, or a population thereof comprising a polynucleotide encoding a CFR and TCR$^{neg}$ may further comprise one or more of: cs-CD3; CD16 or a variant knock-in; a CAR; an exogenous cytokine or a fusion variant thereof; B2M knockout or knockdown (e.g., to yield an HLA-deficiency); CIITA knockout or knockdown (e.g., to yield an HLA-II deficiency); introduction of HLA-G or non-cleavable HLA-G; CD38 knockout; and additional engineered modalities described herein. Further provided herein is a master cell bank comprising single cell sorted and expanded clonal engineered iPSCs having at least one phenotype as provided herein, including but not limited to, CFR, TCR$^{neg}$, CD16, CAR, CD38 negative, an exogenous cytokine or a fusion variant thereof, B2M$^{-/-}$, CIITA$^{-/-}$, HLA-G, and any combinations thereof.

3. CD16 Knock-In

CD16 has been identified as two isoforms: Fc receptors FcγRIIIa (CD16a; NM_000569.6) and FcγRIIIb (CD16b; NM_000570.4). CD16a is a transmembrane protein expressed by NK cells, which binds monomeric IgG attached to target cells to activate NK cells and facilitate antibody-dependent cell-mediated cytotoxicity (ADCC). CD16b is exclusively expressed by human neutrophils. "High affinity CD16," "non-cleavable CD16," or "high affinity non-cleavable CD16," as used herein, refers to various CD16 variants. The wildtype CD16 has low affinity and is subject to down regulation including ectodomain shedding, a proteolytic cleavage process that regulates the cell surface density of various cell surface molecules on leukocytes upon NK cell activation. F176V (also called F158V in some publications) is an exemplary CD16 polymorphic allele/variant having high affinity; whereas S197P variant is an example of a genetically engineered non-cleavable version of CD16. An engineered CD16 variant comprising both F176V and S197P has high affinity and is non-cleavable, which was described in greater detail in International Pub. No. WO2015/148926, the complete disclosure of which is incorporated herein by reference. In addition, a chimeric CD16 receptor with the ectodomain of CD16 essentially replaced with at least a portion of CD64 ectodomain can also achieve the desired high affinity and non-cleavable features of a CD16 receptor capable of carrying out ADCC. In some embodiments, the replacement ectodomain of a chimeric CD16 comprises one or more of EC1, EC2, and EC3 exons of CD64 (UniPRotKB_P12314 or its isoform or polymorphic variant).

As such, various embodiments of an exogenous CD16 introduced to a cell include functional CD16 variants and chimeric receptors thereof. In some embodiments, the functional CD16 variant is a high-affinity non-cleavable CD16 receptor (hnCD16). An hnCD16, in some embodiments, comprises both F176V and S197P; and in some embodiments, comprises F176V and with the cleavage region eliminated. In some other embodiments, a hnCD16 comprises a sequence having an identity of at least 50%, 55%, 60%, 65%, 70%, 75%, 80%, 85%, 90%, 95%, 99%, 100%, or any percentage in-between, when compared to any of the exemplary sequences, SEQ ID NOs: 7, 8 and 9, each comprising at least a portion of the CD64 ectodomain. In some embodiments, the sequence identity is at least 80%. In some embodiments, the sequence identity is at least 90%. In some embodiments, the sequence identity is at least 95%. In some embodiments, the sequence identity is 100%. SEQ ID NOs: 7, 8 and 9 are encoded respectively by, for example, SEQ ID NOs: 10-12. As used herein and throughout the application, the percent identity between two sequences is a function of the number of identical positions shared by the sequences (i.e., % identity=#of identical positions/total #of positions×100), taking into account the number of gaps, and the length of each gap, which need to be introduced for optimal alignment of the two sequences. The comparison of sequences and determination of percent identity between two sequences can be accomplished using a mathematical algorithm recognized in the art.

SEQ ID NO: 7:
MWFLTTLLLWVPVDGQVDTTKAVITLQPPWVSVFQEETVTLHCEVLHLP
GSSSTQWFLNGTATQTSTPSYRITSASVNDSGEYRCQRGLSGRSDPIQL
EIHRGWLLLQVSSRVFTEGEPLALRCHAWKDKLVYNVLYYRNGKAFKFF
HWNSNLTILKTNISHNGTYHCSGMGKHRYTSAGISVTVKELFPAPVLNA
SVTSPLLEGNLVTLSCETKLLLQRPGLQLYFSFYMGSKTLRGRNTSSEY
QILTARREDSGLYWCEAATEDGNVLKRSPELELQVLGLQLPTPVWFHYQ
*VSFCLVMVLLFAVDTGLYFSVKTNIRSSTRDWKDHKFKWRKDPQDK*
(340 a.a. CD64 domain-based construction; *CD16TM*; *CD16ICD*)

SEQ ID NO: 8
MWFLTTLLLWVPVDGQVDTTKAVITLQPPWVSVFQEETVTLHCEVLHLP
GSSSTQWFLNGTATQTSTPSYRITSASVNDSGEYRCQRGLSGRSDPIQL
EIHRGWLLLQVSSRVFTEGEPLALRCHAWKDKLVYNVLYYRNGKAFKFF
HWNSNLTILKTNISHNGTYHCSGMGKHRYTSAGISVTVKELFPAPVLNA
SVTSPLLEGNLVTLSCETKLLLQRPGLQLYFSFYMGSKTLRGRNTSSEY
QILTARREDSGLYWCEAATEDGNVLKRSPELELQVLGLFFPPGYQ*VSFC*
*LVMVLLFAVDTGLYFSVKTNIRSSTRDWKDHKFKWRKDPQDK*
(336 a.a. CD64 exon-based construction; *CD16TM*; *CD16ICD*)

-continued

SEQ ID NO: 9
MWFLTTLLLWVPVDGQVDTTKAVITLQPPWVSVFQEETVTLHCEVLHLP
GSSSTQWFLNGTATQTSTPSYRITSASVNDSGEYRCQRGLSGRSDPIQL
EIHRGWLLLQVSSRVFTEGEPLALRCHAWKDKLVYNVLYYRNGKAFKFF
HWNSNLTILKTNISHNGTYHCSGMGKHRYTSAGISVTVKELFPAPVLNA
SVTSPLLEGNLVTLSCETKLLLQRPGLQLYFSFYMGSKTLRGRNTSSEY
QILTARREDSGLYWCEAATEDGNVLKRSPELELQVLGFFPPGYQ*VSFCL*
*VMVLLFAVDTGLYFSVKTNIRSSTRDWKDHKFKWRKDPQDK*
(335 a.a. CD64 exon-based construction; *CD16TM*; *CD16ICD*)

SEQ ID NO: 10
cttggagaca acatgtggtt cttgacaact ctgctccttt
gggttccagt tgatgggcaa gtggacacca caaaggcagt
gatcactttg cagcctccat gggtcagcgt gttccaagag
gaaaccgtaa ccttgcattg tgaggtgctc catctgcctg
ggagcagctc tacacagtgg tttctcaatg gcacagccac
tcagacctcg acccccagct acagaatcac ctctgccagt
gtcaatgaca gtggtgaata caggtgccag agaggtctct
cagggcgaag tgaccccata cagctggaaa tccacagagg
ctggctacta ctgcaggtct ccagcagagt cttcacggaa
ggagaacctc tggccttgag gtgtcatgcg tggaaggata
agctggtgta caatgtgctt tactatcgaa atggcaaagc
ctttaagttt ttccactgga attctaacct caccattctg
aaaaccaaca taagtcacaa tggcacctac cattgctcag
gcatgggaaa gcatcgctac acatcagcag gaatatctgt
cactgtgaaa gagctatttc cagctccagt gctgaatgca
tctgtgacat ccccactcct ggaggggaat ctggtcaccc
tgagctgtga aacaaagttg ctcttgcaga ggcctggttt
gcagctttac ttctccttct acatgggcag caagaccctg
cgaggcagga acacatcctc tgaataccaa atactaactg
ctagaagaga agactctggg ttatactggt gcgaggctgc
ccagttacca actcctgtct ggtttcatta ccaagtctct
gagcttcaag tgcttggcct cctttttgca gtggacacag
gactatattt ctctgtgaag ttctgcttgg tgatggtact
aagagactgg aaggaccata aatttaaatg gagaaaggac
acatcagcag gaatatctgt cactgtgaaa gagctatttc
cagctccagt gctgaatgca cctcaagaca aa SEQ ID NO: 11
cttggagaca acatgtggtt cttgacaact ctgctccttt
gggttccagt tgatgggcaa gtggacacca caaaggcagt
gatcactttg cagcctccat gggtcagcgt gttccaagag
gaaaccgtaa ccttgcattg tgaggtgctc catctgcctg
ggagcagctc tacacagtgg tttctcaatg gcacagccac -continued

```
tcagacctcg acccccagct acagaatcac ctctgccagt

gtcaatgaca gtggtgaata caggtgccag agaggtctct

cagggcgaag tgaccccata cagctggaaa tccacagagg

ctggctacta ctgcaggtct ccagcagagt cttcacggaa

ggagaacctc tggccttgag gtgtcatgcg tggaaggata

agctggtgta caatgtgctt tactatcgaa atggcaaagc

ctttaagttt ttccactgga attctaacct caccattctg

aaaaccaaca taagtcacaa tggcacctac cattgctcag

gcatgggaaa gcatcgctac acatcagcag gaatatctgt

cactgtgaaa gagctatttc cagctccagt gctgaatgca

tctgtgacat ccccactcct ggaggggaat ctggtcaccc

tgagctgtga aacaaagttg ctcttgcaga ggcctggttt

gcagctttac ttctccttct acatgggcag caagaccctg

cgaggcagga acacatcctc tgaataccaa atactaactg

ctagaagaga agactctggg ttatactggt gcgaggctgc

cacagaggat ggaaatgtcc ttaagcgcag ccctgagttg

gagcttcaag tgcttggttt gttctttcca cctgggtacc

aagtctcttt ctgcttggtg atggtactcc tttttgcagt

ggacacagga ctatatttct ctgtgaagac aaacattcga

agctcaacaa gagactggaa ggaccataaa tttaaatgga

gaaaggaccc tcaagacaaa
```

SEQ ID NO: 12

```
atgtggttct tgacaactct gctcctttgg gttccagttg

atgggcaagt ggacaccaca aaggcagtga tcactttgca

gcctccatgg gtcagcgtgt tccaagagga aaccgtaacc

ttgcactgtg aggtgctcca tctgcctggg agcagctcta

cacagtggtt tctcaatggc acagccactc agacctcgac

ccccagctac agaatcacct ctgccagtgt caatgacagt

ggtgaataca ggtgccagag aggtctctca gggcgaagtg

accccataca gctggaaatc cacagaggct ggctactact

gcaggtctcc agcagagtct tcacggaagg agaacctctg

gccttgaggt gtcatgcgtg gaaggataag ctggtgtaca

atgtgcttta ctatcgaaat ggcaaagcct ttaagttttt

ccactggaac tctaacctca ccattctgaa aaccaacata

agtcacaatg gcacctacca ttgctcaggc atgggaaagc

atcgctacac atcagcagga atatctgtca ctgtgaaaga

gctatttcca gctccagtgc tgaatgcatc tgtgacatcc

ccactcctgg aggggaatct ggtcaccctg agctgtgaaa

caaagttgct cttgcagagg cctggtttgc agctttactt

ctccttctac atgggcagca agaccctgcg aggcaggaac

acatcctctg aataccaaat actaactgct agaagagaag
```

-continued

```
actctgggtt atactggtgc gaggctgcca cagaggatgg

aaatgtcctt aagcgcagcc ctgagttgga gcttcaagtg

cttggcttct ttccacctgg gtaccaagtc tctttctgct

tggtgatggt actccttttt gcagtggaca caggactata

tttctctgtg aagacaaaca ttcgaagctc aacaagagac

tggaaggacc ataaatttaa atggagaaag gaccctcaag

acaaa
```

Accordingly, provided herein are effector cells or iPSCs genetically engineered to comprise, among other editing as contemplated and described herein, an exogenous CD16 or a variant thereof, wherein the effector cells are cells from primary sources or derived from iPSC differentiation, or wherein the genetically engineered iPSCs are capable of differentiating into derived effector cells comprising the exogenous CD16 introduced to the iPSCs. In some embodiments, the exogenous CD16 is a high-affinity non-cleavable CD16 receptor (hnCD16). In some embodiments, the exogenous CD16 comprises at least a portion of the CD64 ectodomain. In some embodiments, the exogenous CD16 is in a form of a CD16-based chimeric Fc receptor (CFcR) that comprises a transmembrane domain, a stimulatory domain and/or a signaling domain that is not derived from CD16.

In some embodiments, the primary-sourced or derived effector cells comprising the exogenous CD16 or a variant thereof are NK lineage cells. In some embodiments, the primary-sourced or derived effector cells comprising the exogenous CD16 or a variant thereof are T lineage cells. In some embodiments, the exogenous CD16 comprises hnCD16. In some embodiments, the hnCD16 comprises a full or a partial length extracellular domain of CD64. In some embodiments, exogenous CD16 or functional variants thereof comprised in iPSC or effector cells has high affinity in binding to a ligand that triggers downstream signaling upon such binding. Non-limiting examples of ligands binding to the exogenous CD16 or functional variants thereof include not only ADCC antibodies or fragments thereof, but also bi-, tri-, or multi-specific engagers or binders that recognize the CD16 or CD64 extracellular binding domains of said exogenous CD16. Examples of bi-, tri-, or multi-specific engagers or binders are further described below in this application. As such, at least one of the aspects of the present application provides a derivative effector cell or a cell population thereof preloaded with one or more pre-selected ADCC antibodies through an exogenous CD16 expressed on the effector cell, in an amount sufficient for therapeutic use in a treatment of a condition, a disease, or an infection as further detailed in this application, wherein said exogenous CD16 comprises an extracellular binding domain of CD64, or of a CD16 having F176V and S197P.

In some other embodiments, an exogenous CD16 comprises a CD16-, or variants thereof, based CFcR. A chimeric Fc receptor (CFcR) is produced to comprise a non-native transmembrane domain, a non-native stimulatory domain and/or a non-native signaling domain by modifying or replacing the native CD16 transmembrane- and/or the intracellular-domain. The term “non-native” used herein means that the transmembrane, stimulatory or signaling domain are derived from a different receptor other than the receptor which provides the extracellular domain. In the illustration here, the CFcR based on CD16 or variants thereof does not have a transmembrane, stimulatory or signaling domain that is derived from CD16. In some embodiments, the exogenous CD16-based CFcR comprises a non-native transmembrane domain derived from CD3δ, CD3ε, CD3γ, CD3ζ, CD4, CD8, CD8a, CD8b, CD27, CD28, CD40, CD84, CD166, 4-1BB, OX40, ICOS, ICAM-1, CTLA-4, PD-1, LAG-3, 2B4, BTLA, CD16, IL7, IL12, IL15, KIR2DL4, KIR2DS1, NKp30, NKp44, NKp46, NKG2C, NKG2D, or T cell receptor polypeptide. In some embodiments, the exogenous CD16-based CFcR comprises a non-native stimulatory/inhibitory domain derived from CD27, CD28, 4-1BB, OX40, ICOS, PD-1, LAG-3, 2B4, BTLA, DAP10, DAP12, CTLA-4, or NKG2D polypeptide. In some embodiments, the exogenous CD16-based CFcR comprises a non-native signaling domain derived from CD3δ, 2B4, DAP10, DAP12, DNAM1, CD137 (4-1BB), IL21, NKp30, NKp44, NKp46, NKG2C, or NKG2D polypeptide. In one embodiment of CD16-based CFcR, the provided chimeric Fc receptor comprises a transmembrane domain and a signaling domain both derived from one of IL7, IL12, IL15, NKp30, NKp44, NKp46, NKG2C, or NKG2D polypeptide. One particular exemplary embodiment of the CD16-based chimeric Fc receptor comprises a transmembrane domain of NKG2D, a stimulatory domain of 2B4, and a signaling domain of CD3ζ; wherein the extracellular domain of the CFcR is derived from a full length or partial sequence of the extracellular domain of CD64 or CD16, and wherein the extracellular domain of CD16 comprises F176V and S197P. Another exemplary embodiment of the CD16-based chimeric Fc receptor comprises a transmembrane domain and a signaling domain of CD3; wherein the extracellular domain of the CFcR is derived from a full length or partial sequence of the extracellular domain of CD64 or CD16, and wherein the extracellular domain of CD16 comprises F176V and S197P.

The various embodiments of CD16-based chimeric Fc receptor as described above are capable of binding, with high affinity, to the Fc region of an antibody or fragment thereof; or to a bi-, tri-, or multi-specific engager or binder. Upon binding, the stimulatory and/or signaling domains of the chimeric receptor enable the activation and cytokine secretion of the effector cells, and the killing of the tumor cells targeted by the antibody, or said bi-, tri-, or multi-specific engager or binder having a tumor antigen binding component as well as the Fc region. Without being limited by theory, through the non-native transmembrane, stimulatory and/or signaling domains, or through an engager binding to the ectodomain, of the CD16-based chimeric Fc receptor, the CFcR could contribute to effector cells' killing ability while increasing the effector cells' proliferation and/or expansion potential. The antibody and the engager can bring tumor cells expressing the antigen and the effector cells expressing the CFcR into a close proximity, which also contributes to the enhanced killing of the tumor cells. Exemplary tumor antigens for bi-, tri-, multi-specific engagers or binders include, but are not limited to, B7H3, BCMA, CD10, CD19, CD20, CD22, CD24, CD30, CD33, CD34, CD38, CD44, CD79a, CD79b, CD123, CD138, CD179b, CEA, CLEC12A, CS-1, DLL3, EGFR, EGFRvIII, EPCAM, FLT-3, FOLR1, FOLR3, GD2, gpA33, HER2, HM1.24, LGR5, MSLN, MCSP, MICA/B, PSMA, PAMA, P-cadherin, and ROR1. Some non-limiting exemplary bi-, tri-, multi-specific engagers or binders suitable for engaging effector cells expressing the CD16-based CFcR in attacking tumor cells include CD16 (or CD64)-CD30, CD16 (or CD64)-BCMA, CD16 (or CD64)-IL15-EPCAM, and CD16 (or CD64)-IL15-CD33.

Unlike the endogenous CD16 expressed by primary NK cells which gets cleaved from the cellular surface following NK cell activation, the various non-cleavable versions of CD16 in derivative NK cells avoid CD16 shedding and maintain constant expression. In derivative NK cells, non-cleavable CD16 increases expression of TNFα and CD107a, indicative of improved cell functionality. Non-cleavable CD16 also enhances the antibody-dependent cell-mediated cytotoxicity (ADCC), and the engagement of bi-, tri-, or multi-specific engagers. ADCC is a mechanism of NK cell mediated lysis through the binding of CD16 to antibody-coated target cells. The additional high affinity characteristics of the introduced hnCD16 in a derived NK cell also enables in vitro loading of ADCC antibody to the NK cell through hnCD16 before administering the cell to a subject in need of a cell therapy. As provided herein, the hnCD16 may comprise F176V and S197P in some embodiments, or may comprise a full or partial length ectodomain originated from CD64, as exemplified by SEQ ID NOs: 7, 8 or 9, or may further comprise at least one of non-native transmembrane domain, stimulatory domain and signaling domain. As disclosed, the present application also provides a derivative NK cell or a cell population thereof, preloaded with one or more pre-selected ADCC antibodies in an amount sufficient for therapeutic use in a treatment of a condition, a disease, or an infection as further detailed in this application.

Unlike primary NK cells, mature T cells from a primary source (i.e., natural/native sources such as peripheral blood, umbilical cord blood, or other donor tissues) do not express CD16. It was unexpected that iPSC comprising an expressed exogenous non-cleavable CD16 did not impair the T cell developmental biology and was able to differentiate into functional derivative T lineage cells that not only express the exogenous CD16, but also are capable of carrying out function through an acquired ADCC mechanism. This acquired ADCC in the derivative T lineage cell can additionally be used as an approach for dual targeting and/or to rescue antigen escape often occurred with CAR-T cell therapy, where the tumor relapses with reduced or lost CAR-T targeted antigen expression or expression of a mutated antigen to avoid recognition by the CAR (chimerical antigen receptor). When said derivative T lineage cell comprises acquired ADCC through exogenous CD16, including functional variants and CD16 based CFcR, expression, and when an antibody targets a different tumor antigen from the one targeted by the CAR, the antibody can be used to rescue CAR-T antigen escape and reduce or prevent relapse or recurrence of the targeted tumor often seen in CAR-T treatment. Such a strategy to reduce and/or prevent antigen escape while achieving dual targeting is equally applicable to NK cells expressing one or more CARs. Various CARs that can be used in this antigen escape reduction and prevention strategy is further delineated below.

As such, the present invention provides a derivative T lineage cell comprising an exogenous CD16. In some embodiments, the CD16 comprised in the derivative T lineage cell is an hnCD16 that comprises the CD16 ectodomain comprising F176V and S197P. In some other embodiments, the hnCD16 comprised in the derivative T lineage cell comprises a full or partial length ectodomain originated from CD64, as exemplified by SEQ ID NOs: 7, 8 or 9; or may further comprise at least one of non-native transmembrane domain, stimulatory domain and signaling domain. As explained herein, such derivative T lineage cells have an acquired mechanism to target tumors with a monoclonal antibody meditated by ADCC to enhance the therapeutic effect of the antibody. As disclosed, the present application also provides a derivative T lineage cell, or a cell population thereof, preloaded with one or more pre-selected ADCC antibody in an amount sufficient for therapeutic use in a treatment of a condition, a disease, or an infection as further detailed below.

Additionally provided in this application is a master cell bank comprising single cell sorted and expanded clonal engineered iPSCs having at least one phenotype as provided herein, including but not limited to, an exogenous CD16, wherein the cell bank provides a platform for additional iPSC engineering and a renewable source for manufacturing off-the-shelf, engineered, homogeneous cell therapy products, including but not limited to derivative NK and T cells, which are well-defined and uniform in composition, and can be mass produced at significant scale in a cost-effective manner.

4. Chimerical Antigen Receptor (CAR) Expression

Applicable to the genetically engineered iPSC and derivative effector cell thereof may be any CAR design known in the art. CAR is a fusion protein generally including an ectodomain that comprises an antigen recognition region, a transmembrane domain, and an endodomain. In some embodiments, the ectodomain can further include a signal peptide or leader sequence and/or a spacer. In some embodiments, the endodomain can further comprise a signaling peptide that activates the effector cell expressing the CAR. In some embodiments, the antigen recognition domain can specifically bind an antigen. In some embodiments, the antigen recognition domain can specifically bind an antigen associated with a disease or pathogen. In some embodiments, the disease-associated antigen is a tumor antigen, wherein the tumor may be a liquid or a solid tumor. In some embodiments, the CAR is suitable to activate either T or NK lineage cells expressing said CAR. In some embodiments, the CAR is NK cell specific for comprising NK-specific signaling components. In certain embodiments, said T cells are derived from a CAR expressing iPSCs, and the derivative T lineage cells may comprise T helper cells, cytotoxic T cells, memory T cells, regulatory T cells, natural killer T cells, αβ T cells, γδ T cells, or a combination thereof. In certain embodiments, said NK cells are derived from CAR expressing iPSCs.

In certain embodiments, said antigen recognition region comprises a murine antibody, a human antibody, a humanized antibody, a camel Ig, a shark heavy-chain-only antibody (VNAR), Ig NAR, a chimeric antibody, a recombinant antibody, or an antibody fragment thereof. Non-limiting examples of antibody fragments include Fab, Fab', F(ab')2, F(ab')3, Fv, single chain antigen binding fragment (scFv), $(scFv)_2$, disulfide stabilized Fv (dsFv), minibody, diabody, triabody, tetrabody, single-domain antigen binding fragments (sdAb, Nanobody), recombinant heavy-chain-only antibody (VHH), and other antibody fragments that maintain the binding specificity of the whole antibody. Non-limiting examples of antigens that may be targeted by a CAR include ADGRE2, carbonic anhydrase IX (CAIX), CCR1, CCR4, carcinoembryonic antigen (CEA), CD3, CD5, CD7, CD8, CD10, CD19, CD20, CD22, CD30, CD33, CD34, CD38, CD41, CD44, CD44V6, CD49f, CD56, CD70, CD74, CD99, CD123, CD133, CD138, CD269 (BCMA), CDS, CLEC12A, an antigen of a cytomegalovirus (CMV) infected cell (e.g., a cell surface antigen), epithelial glycoprotein-2 (EGP-2), epithelial glycoprotein-40 (EGP-40), epithelial cell adhesion molecule (EpCAM), EGFRvIII, receptor tyrosine-protein kinases erb-B2,3,4, EGFIR, EGFR-VIII, ERBB folate-binding protein (FBP), fetal acetylcholine receptor (AChR), folate receptor-α, Ganglioside G2 (GD2), Ganglioside G3 (GD3), human Epidermal Growth Factor Receptor 2 (HER2), human telomerase reverse transcriptase (hTERT), ICAM-1, Integrin B7, Interleukin-13 receptor subunit alpha-2 (IL-13Rα2), κ-light chain, kinase insert domain receptor (KDR), Lewis A (CA19.9), Lewis Y (LeY), L1 cell adhesion molecule (L1-CAM), LILRB2, melanoma antigen family A 1 (MAGE-A1), MICA/B, Mucin 1 (Muc-1), Mucin 16 (Muc-16), Mesothelin (MSLN), NKCSI, NKG2D ligands, c-Met, cancer-testis antigen NY-ESO-1, oncofetal antigen (h5T4), PRAME, prostate stem cell antigen (PSCA), PRAME prostate-specific membrane antigen (PSMA), tumor-associated glycoprotein 72 (TAG-72), TIM-3, TRBC1, TRBC2, vascular endothelial growth factor R2 (VEGF-R2), Wilms tumor protein (WT-1), and various pathogen antigen known in the art. Non-limiting examples of pathogens include viruses, bacteria, fungi, parasites and protozoa capable of causing diseases.

In some embodiments, the transmembrane domain of a CAR comprises a full length or at least a portion of the native or modified transmembrane region of CD3D, CD3E, CD3G, CD3, CD4, CD8, CD8a, CD8b, CD27, CD28, CD40, CD84, CD166, 4-1BB, OX40, ICOS, ICAM-1, CTLA-4, PD-1, LAG-3, 2B4, BTLA, CD16, IL7, IL12, IL15, KIR2DL4, KIR2DS1, NKp30, NKp44, NKp46, NKG2C, NKG2D, or T cell receptor polypeptide.

In some embodiments, the signaling peptide of the endodomain (or intracellular domain) comprises a full length or at least a portion of a polypeptide of CD3ζ, 2B4, DAP10, DAP12, DNAM1, CD137 (4-1BB), IL21, IL7, IL12, IL15, NKp30, NKp44, NKp46, NKG2C, or NKG2D. In one embodiment, the signaling peptide of a CAR comprises an amino acid sequence that has at least about 85%, about 90%, about 95%, about 96%, about 97%, about 98%, or about 99% identity to at least one ITAM (immunoreceptor tyrosine-based activation motif) of CD3.

In certain embodiments, said endodomain further comprises at least one co-stimulatory signaling region. Said co-stimulatory signaling region can comprise a full length or at least a portion of a polypeptide of CD27, CD28, 4-1BB, OX40, ICOS, PD-1, LAG-3, 2B4, BTLA, DAP10, DAP12, CTLA-4, or NKG2D, or any combination thereof.

In one embodiment, the CAR applicable to the cells provided herein comprises a co-stimulatory domain derived from CD28, and a signaling domain comprising the native or modified ITAM1 of CD3, represented by an amino acid sequence having at least about 85%, about 90%, about 95%, about 96%, about 97%, about 98%, or about 99% identity to SEQ ID NO: 13. In a further embodiment, the CAR comprising a co-stimulatory domain derived from CD28, and a native or modified ITAM1 of CD3ζ also comprises a hinge domain and trans-membrane domain derived from CD28, wherein an scFv may be connected to the trans-membrane domain through the hinge, and the CAR comprises an amino acid sequence of at least about 85%, about 90%, about 95%, about 96%, about 97%, about 98%, or about 99% identity to SEQ ID NO: 14. In some embodiments, the sequence identity is at least 80%. In some embodiments, the sequence identity is at least 90%. In some embodiments, the sequence identity is at least 95%. In some embodiments, the sequence identity is 100%.

SEQ ID NO: 13

RSKRSRLLHSDYMNMTPRRPGPTRKHYQPYAPPRDFAAYRSRVKFSRSA

-continued

```
DAPAYQQGQNQLYNELNLGRREEYDVLDKRRGRDPEMGGKPRRKNPQEG

LFNELQKDKMAEAFSEIGMKGERRRGKGHDGLFQGLSTATKDTFDALHM

QALPPR
(153 a.a. CD28 co-stim + CD3ζITAM)
```

SEQ ID NO: 14

```
IEVMYPPPYLDNEKSNGTIIHVKGKHLCPSPLFPGPSKPFWVLVVVGGV

LACYSLLVTVAFIIFWVRSKRSRLLHSDYMNMTPRRPGPTRKHYQPYAP

PRDFAAYRSRVKFSRSADAPAYQQGQNQLYNELNLGRREEYDVLDKRRG

RDPEMGGKPRRKNPQEGLFNELQKDKMAEAFSEIGMKGERRRGKGHDGL

FQGLSTATKDTFDALHMQALPPR
(219 a.a. CD28 hinge + CD28 TM + CD28 co-stim +
CD3ζITAM)
```

In another embodiment, the CAR applicable to the cells provided herein comprises a transmembrane domain derived from NKG2D, a co-stimulatory domain derived from 2B4, and a signaling domain comprising the native or modified CD3, represented by an amino acid sequence of at least about 85%, about 90%, about 95%, about 96%, about 97%, about 98%, or about 99% identity to SEQ ID NO: 15. Said CAR comprising a transmembrane domain derived from NKG2D, a co-stimulatory domain derived from 2B4, and a signaling domain comprising the native or modified CD3ζ may further comprise a CD8 hinge, wherein the amino acid sequence of such a structure is of at least about 85%, about 90%, about 95%, about 96%, about 97%, about 98%, or about 99% identity to SEQ ID NO: 16. In some embodiments, the sequence identity is at least 80%. In some embodiments, the sequence identity is at least 90%. In some embodiments, the sequence identity is at least 95%. In some embodiments, the sequence identity is 100%.

SEQ ID NO: 15

```
SNLFVASWIAVMIIFRIGMAVAIFCCFFFPSWRRKRKEKQSETSPKEFL

TIYEDVKDLKTRRNHEQEQTFPGGGSTIYSMIQSQSSAPTSQEPAYTLY

SLIQPSRKSGSRKRNHSPSFNSTIYEVIGKSQPKAQNPARLSRKELENF

DVYSRVKFSRSADAPAYKQGQNQLYNELNLGRREEYDVLDKRRGRDPEM

GGKPRRKNPQEGLYNELQKDKMAEAYSEIGMKGERRRGKGHDGLYQGLS

TATKDTYDALHMQALPPR
(263 a.a NKG2D TM + 2B4 + CD3ζ)
```

SEQ ID NO: 16

```
TTTPAPRPPTPAPTIASQPLSLRPEACRPAAGGAVHTRGLDFACDSNLF

VASWIAVMIIFRIGMAVAIFCCFFFPSWRRKRKEKQSETSPKEFLTIYE

DVKDLKTRRNHEQEQTFPGGGSTIYSMIQSQSSAPTSQEPAYTLYSLIQ

PSRKSGSRKRNHSPSFNSTIYEVIGKSQPKAQNPARLSRKELENFDVYS

RVKFSRSADAPAYKQGQNQLYNELNLGRREEYDVLDKRRGRDPEMGGKP

RRKNPQEGLYNELQKDKMAEAYSEIGMKGERRRGKGHDGLYQGLSTATK

DTYDALHMQALPPR
(308 a.a CD8 hinge + NKG2D TM + 2B4 + CD3ζ)
```

Non-limiting CAR strategies further include heterodimeric, conditionally activated CAR through dimerization of a pair of intracellular domain (see for example, U.S. Pat. No. 9,587,020); split CAR, where homologous recombination of antigen binding, hinge, and endodomains to generate a CAR (see for example, U.S. Pub. No. 2017/0183407); multi-chain CAR that allows non-covalent link between two transmembrane domains connected to an antigen binding domain and a signaling domain, respectively (see for example, U.S. Pub. No. 2014/0134142); CARs having bispecific antigen binding domain (see for example, U.S. Pat. No. 9,447,194), or having a pair of antigen binding domains recognizing same or different antigens or epitopes (see for example, U.S. Pat. No. 8,409,577), or a tandem CAR (see for example, Hegde et al., *J Clin Invest.* 2016; 126(8):3036-3052); inducible CAR (see for example, U.S. Pub. Nos. 2016/0046700, 2016/0058857, and 2017/0166877); switchable CAR (see for example, U.S. Pub. No. 2014/0219975); and any other designs known in the art.

As such, aspects of the present invention provide derivative cells obtained from differentiating genomically engineered iPSCs, wherein both the iPSCs and the derivative cells comprise one or more CARs along with additional modified modalities. Additionally provided in this application is a master cell bank comprising single cell sorted and expanded clonal engineered iPSCs having at least a CFR, a CAR and one or both of TCR$^{neg}$, and an exogenous CD16, wherein the cell bank provides a platform for additional iPSC engineering and a renewable source for manufacturing off-the-shelf, engineered, homogeneous cell therapy products.

In a further embodiment, the iPSC and its derivative effector cells comprising a CFR and a CAR have the CAR inserted in a TCR constant region, leading to TCR knockout, and placing CAR expression under the control of the endogenous TCR promoter. Additional insertion sites include, but are not limited to, AAVS1, CCR5, ROSA26, collagen, HTRP, H11, GAPDH, RUNX1, B2M, TAP1, TAP2, tapasin, NLRC5, CIITA, RFXANK, RFX5, RFXAP, NKG2A, NKG2D, CD38, CD58, CD54, CD56, CIS, CBL-B, SOCS2, PD1, CTLA4, LAG3, TIM3, and TIGIT. In some embodiments, a TCR$^{neg}$/CAR/CFR T cell derived from engineered iPSCs further comprises an exogenous CD16 having an ectodomain native to CD16 (F176V and/or S197P) or derived from CD64, and native or non-native transmembrane, stimulatory and signaling domains. In another embodiment, the iPSC and its derivative NK cells comprise a CFR and a CAR, where the CAR is inserted in the NKG2A locus or NKG2D locus, leading to NKG2A or NKG2D knockout, thereby placing CAR expression under the control of the endogenous NKG2A or NKG2D promoter.

5. Exogenously Introduced Cytokine and/or Cytokine Signaling

By avoiding systemic high-dose administration of clinically relevant cytokines, the risk of dose-limiting toxicities due to such a practice is reduced while cytokine mediated cell autonomy is being established. To achieve lymphocyte autonomy without the need to additionally administer soluble cytokines, a partial or full length peptide of one or more of IL2, IL4, IL6, IL7, IL9, IL10, IL11, IL12, IL15, IL18, IL21, and/or their respective receptors may be introduced to the cell to enable cytokine signaling with or without the expression of the cytokine itself, thereby maintaining or improving cell growth, proliferation, expansion, and/or effector function with reduced risk of cytokine toxicities. In some embodiments, the introduced cytokine and/or its respective native or modified receptor for cytokine signaling are expressed on the cell surface. In some embodiments, the cytokine signaling is constitutively activated. In some embodiments, the activation of the cytokine signaling is inducible. In some embodiments, the activation of the cytokine signaling is transient and/or temporal.

Figure 3:
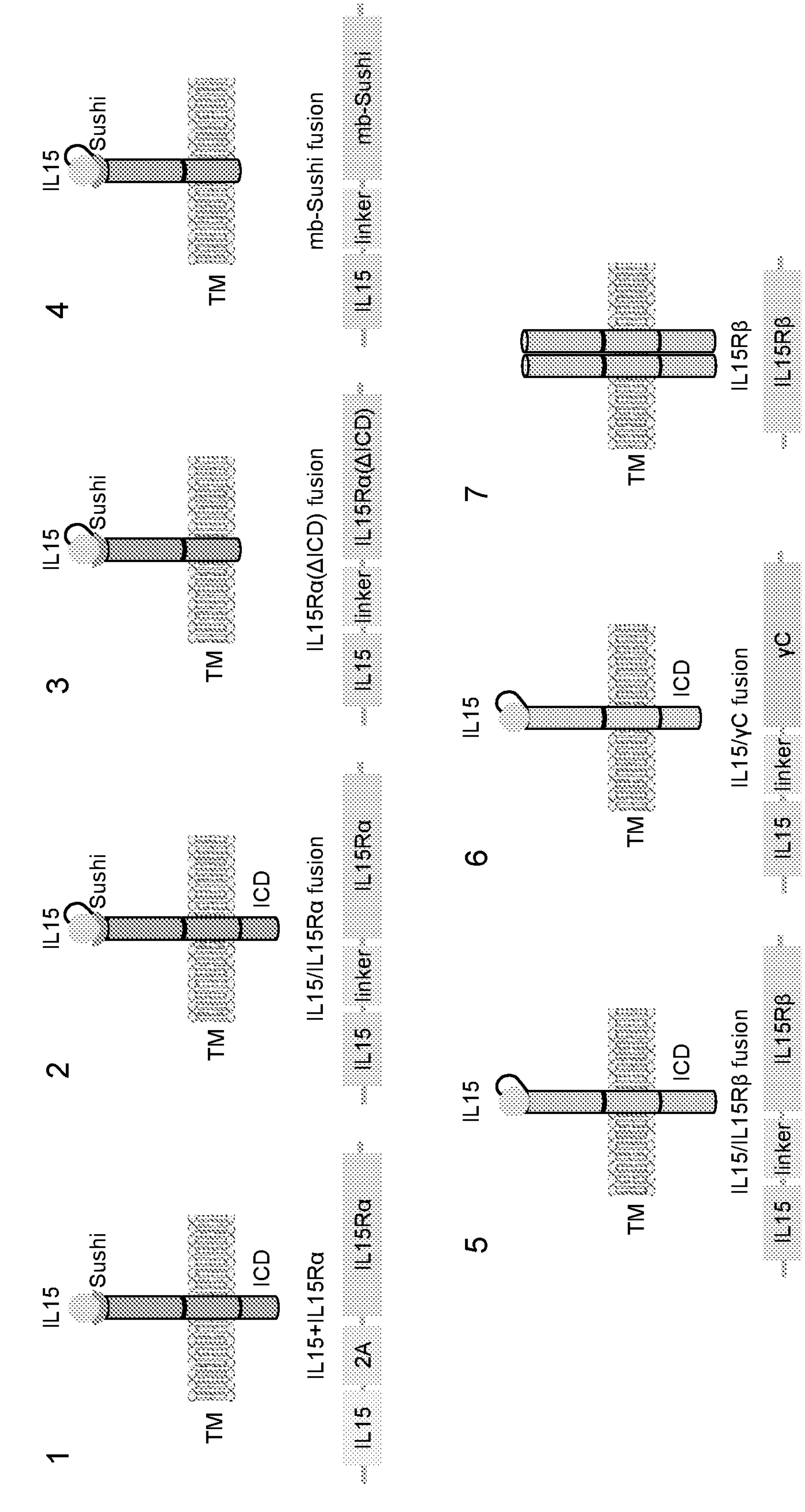
FIG. 3 is a graphic representation of several exemplary construct designs for cell surface expressed cytokine in iPSC derived cells. IL15 is used as an illustrative example, which can be replaced with other desirable cytokines.

FIG. 3 presents several construct designs for IL2, IL4, IL6, IL7, IL9, IL10, IL11, IL12, IL15, IL18, or IL21, using IL15 as an illustrative example. The transmembrane (TM) domain of any of the designs in FIG. 3 can be native to the IL15 receptor or may be modified or replaced with transmembrane domain of any other membrane bound proteins.

As shown in FIG. 3, Design 1 provides that IL15 and IL15Rα are co-expressed by using a self-cleaving peptide, mimicking trans-presentation of IL15, without eliminating cis-presentation of IL15.

As shown in Design 2 of FIG. 3, IL15Rα is fused to IL15 at the C-terminus through a linker, mimicking trans-presentation without eliminating cis-presentation of IL15 as well as ensuring IL15 membrane-bound.

As shown in Design 3 of FIG. 3, IL15Rα with truncated intracellular domain is fused to IL15 at the C-terminus through a linker, mimicking trans-presentation of IL15, maintaining IL15 membrane-bound, and additionally eliminating cis-presentation and/or any other potential signal transduction pathways mediated by a normal IL15R through its intracellular domain. The intracellular domain of IL15Rα has been deemed as critical for the receptor to express in the IL15 responding cells, and for the responding cells to expand and function. Such a truncated construct comprises an amino acid sequence of at least 75%, 80%, 85%, 90%, 95% or 99% identity to SEQ ID NO: 17, which may be encoded by an exemplary nucleic acid sequence represented by SEQ ID NO: 18. In one embodiment of the truncated IL15/IL15Rα, the construct does not comprise the last 4 amino acid residues "KSRQ" of SEQ ID NO: 17, and comprises an amino acid sequence of at least 75%, 80%, 85%, 90%, 95% or 99% identity to SEQ ID NO: 21. In some embodiments, the sequence identity is at least 80%. In some embodiments, the sequence identity is at least 90%. In some embodiments, the sequence identity is at least 95%. In some embodiments, the sequence identity is 100%.

SEQ ID NO: 17

```
MDWTWILFLVAAATRVHSGIHVFILGCFSAGLPKTEANWVNVISDLKKI

EDLIQSMHIDATLYTESDVHPSCKVTAMKCFLLELQVISLESGDASIHD

TVENLIILANNSLSSNGNVTESGCKECEELEEKNIKEFLQSFVHIVQMF

INTSSGGGSGGGGSGGGGSGGGGSGGGSLQITCPPPMSVEHADIWVKSY

SLYSRERYICNSGFKRKAGTSSLTECVLNKAINVAHWTTPSLKCIRDPA

LVHQRPAPPSTVTTAGVTPQPESLSPSGKEPAASSPSSNNTAATTAAIV

PGSQLMPSKSPSTGTTEISSHESSHGTPSQTTAKNWELTASASHQPPGV

YPQGHSDTTVAISTSTVLLCGLSAVSLLACYLKSRQ
(379 a.a.; signal and linker peptides are
underlined)
```

SEQ ID NO: 18

```
ATGGACTGGACCTGGATTCTGTTCCTGGTCGCGGCTGCAACGCGAGTCC

ATAGCGGTATCCATGTTTTTATTCTTGGGTGTTTTTCTGCTGGGCTGCC

TAAGACCGAGGCCAACTGGGTAAATGTCATCAGTGACCTCAAGAAAATA

GAAGACCTTATACAAAGCATGCACATTGATGCTACTCTCTACACTGAGT

CAGATGTACATCCCTCATGCAAAGTGACGGCCATGAAATGTTTCCTCCT

CGAACTTCAAGTCATATCTCTGGAAAGTGGCGACGCGTCCATCCACGAC

ACGGTCGAAAACCTGATAATACTCGCTAATAATAGTCTCTCTTCAAATG

GTAACGTAACCGAGTCAGGTTGCAAAGAGTGCGAAGAGTTGGAAGAAAA
```

-continued

```
AAACATAAAGGAGTTCCTGCAAAGTTTCGTGCACATTGTGCAGATGTTC

ATTAATACCTCTAGCGGCGGAGGATCAGGTGGCGGTGGAAGCGGAGGTG

GAGGCTCCGGTGGAGGAGGTAGTGGCGGAGGTTCTCTTCAAATAACTTG

TCCTCCACCGATGTCCGTAGAACATGCGGATATTTGGGTAAAATCCTAT

AGCTTGTACAGCCGAGAGCGGTATATCTGCAACAGCGGCTTCAAGCGGA

AGGCCGGCACAAGCAGCCTGACCGAGTGCGTGCTGAACAAGGCCACCAA

CGTGGCCCACTGGACCACCCCTAGCCTGAAGTGCATCAGAGATCCCGCC

CTGGTGCATCAGCGGCCTGCCCCTCCAAGCACAGTGACAACAGCTGGCG

TGACCCCCCAGCCTGAGAGCCTGAGCCCTTCTGGAAAAGAGCCTGCCGC

CAGCAGCCCCAGCAGCAACAATACTGCCGCCACCACAGCCGCCATCGTG

CCTGGATCTCAGCTGATGCCCAGCAAGAGCCCTAGCACCGGCACCACCG

AGATCAGCAGCCACGAGTCTAGCCACGGCACCCCATCTCAGACCACCGC

CAAGAACTGGGAGCTGACAGCCAGCGCCTCTCACCAGCCTCCAGGCGTG

TACCCTCAGGGCCACAGCGATACCACAGTGGCCATCAGCACCTCCACCG

TGCTGCTGTGTGGACTGAGCGCCGTGTCACTGCTGGCCTGCTACCTGAA

GTCCAGACAGTGA
(1140 n.a.)
```

SEQ ID NO: 21

```
MDWTWILFLVAAATRVHSGIHVFILGCFSAGLPKTEANWVNVISDLKKI

EDLIQSMHIDATLYTESDVHPSCKVTAMKCFLLELQVISLESGDASIHD

TVENLIILANNSLSSNGNVTESGCKECEELEEKNIKEFLQSFVHIVQMF

INTSSGGGSGGGGSGGGGSGGGGSGGGSLQITCPPPMSVEHADIWVKSY

SLYSRERYICNSGFKRKAGTSSLTECVLNKATNVAHWTTPSLKCIRDPA

LVHQRPAPPSTVTTAGVTPQPESLSPSGKEPAASSPSSNNTAATTAAIV

PGSQLMPSKSPSTGTTEISSHESSHGTPSQTTAKNWELTASASHQPPGV

YPQGHSDTTVAISTSTVLLCGLSAVSLLACYL
(375 a.a.; signal and linker peptides are
underlined)
```

One having ordinary skill in the art would appreciate that the signal peptide and the linker sequences above are illustrative and in no way limit their variations suitable for use as a signal peptide or linker. There are many suitable signal peptide or linker sequences known and available to those in the art. It will be understood that the signal peptide and/or linker sequences may be substituted for another sequence without altering the activity of the functional peptide led by the signal peptide or linked by the linker.

Since the Design 3 construct was shown to be functional in promoting effector cell survival and expansion, Design 4 of FIG. 3 demonstrates that the cytoplasmic domain of IL15Rα can be omitted without negatively impacting the autonomous feature of the effector cell equipped with IL15 in such a design. Thus, Design 4 is a construct providing another working alternative of Design 3, from which essentially the entire IL15Rα is removed except for the Sushi domain fused with IL15 at one end and a transmembrane domain on the other (mb-Sushi), optionally with a linker between the Sushi domain and the trans-membrane domain. The fused IL15/mb-Sushi is expressed at the cell surface through the transmembrane domain of any membrane bound protein. With a construct such as Design 4, unnecessary signaling through IL15Rα, including cis-presentation, is eliminated when only the desirable trans-presentation of IL15 is retained. In some embodiments, the component comprising IL15 fused with the Sushi domain comprises an amino acid sequence of at least 75%, 80%, 85%, 90%, 95% or 99% identity to SEQ ID NO: 19, which may be encoded by an exemplary nucleic acid sequence represented by SEQ ID NO: 20. In some embodiments, the sequence identity is at least 80%. In some embodiments, the sequence identity is at least 90%. In some embodiments, the sequence identity is at least 95%. In some embodiments, the sequence identity is 100%.

```
                                  SEQ ID NO: 19
MDWTWILFLVAAATRVHSGIHVFILGCFSAGLPKTEANWVNVISDLKKI

EDLIQSMHIDATLYTESDVHPSCKVTAMKCFLLELQVISLESGDASIHD

TVENLIILANNSLSSNGNVTESGCKECEELEEKNIKEFLQSFVHIVQMF

INTSSGGGSGGGGSGGGGSGGGGSGGGSLQITCPPPMSVEHADIWVKSY

SLYSRERYICNSGFKRKAGTSSLTECVLNKATNVAHWTTPSLKCIR
(242 a.a.; signal and linker peptides are
underlined)

                                  SEQ ID NO: 20
ATGGACTGGACCTGGATTCTGTTCCTGGTCGCGGCTGCAACGCGAGTCC

ATAGCGGTATCCATGTTTTTATTCTTGGGTGTTTTTCTGCTGGGCTGCC

TAAGACCGAGGCCAACTGGGTAAATGTCATCAGTGACCTCAAGAAAATA

GAAGACCTTATACAAAGCATGCACATTGATGCTACTCTCTACACTGAGT

CAGATGTACATCCCTCATGCAAAGTGACGGCCATGAAATGTTTCCTCCT

CGAACTTCAAGTCATATCTCTGGAAAGTGGCGACGCGTCCATCCACGAC

ACGGTCGAAAACCTGATAATACTCGCTAATAATAGTCTCTCTTCAAATG

GTAACGTAACCGAGTCAGGTTGCAAAGAGTGCGAAGAGTTGGAAGAAAA

AAACATAAAGGAGTTCCTGCAAAGTTTCGTGCACATTGTGCAGATGTTC

ATTAATACCTCTAGCGGCGGAGGATCAGGTGGCGGTGGAAGCGGAGGTG

GAGGCTCCGGTGGAGGAGGTAGTGGCGGAGGTTCTCTTCAAATAACTTG

TCCTCCACCGATGTCCGTAGAACATGCGGATATTTGGGTAAAATCCTAT

AGCTTGTACAGCCGAGAGCGGTATATCTGCAACAGCGGCTTCAAGCGGA

AGGCCGGCACAAGCAGCCTGACCGAGTGCGTGCTGAACAAGGCCACCAA

CGTGGCCCACTGGACCACCCCTAGCCTGAAGTGCATCAGA
(726 n.a.)
```

One having ordinary skill in the art would appreciate that the signal peptide and the linker sequences above are illustrative and in no way limit their variations suitable for use as a signal peptide or linker. There are many suitable signal peptide or linker sequences known and available to those in the art. It will be understood that the signal peptide and/or linker sequences may be substituted for another sequence without altering the activity of the functional peptide led by the signal peptide or linked by the linker.

As shown in Design 5 of FIG. 3, a native or modified IL15Rβ is fused to IL15 at the C-terminus through a linker, enabling constitutive signaling and maintaining IL15 membrane-bound and trans-representation.

As shown in Design 6 of FIG. 3, a native or modified common receptor γC is fused to IL15 at the C-terminus through a linker for constitutive signaling and membrane bound trans-presentation of the cytokine. The common receptor γC is also called the common gamma chain or CD132, which is also known as IL2 receptor subunit gamma or IL2RG. γC is a cytokine receptor sub-unit that is common to the receptor complexes for many interleukin receptors, including, but not limited to, IL2, IL4, IL7, IL9, IL15 and IL21 receptor.

As shown in Design 7 of FIG. 3, engineered IL15Rβ that forms a homodimer in the absence of IL15 is useful for producing constitutive signaling of the cytokine.

In some embodiments, one or more of cytokines IL2, IL4, IL6, IL7, IL9, IL10, IL11, IL12, IL15, IL18 and IL21, and/or receptors thereof, may be introduced to iPSC using one or more of the designs shown in FIG. 3, and to its derivative cells upon iPSC differentiation. In some embodiments, IL2 or IL15 cell surface expression and signaling is through the construct illustrated in any one of Designs 1-7 of FIG. 3. In some embodiments, IL4, IL7, IL9, or IL21 cell surface expression and signaling is through the construct illustrated in Designs 5, 6, or 7 of FIG. 3, by using either a common receptor or a cytokine specific receptor. In some embodiments, IL7 surface expression and signaling is through the construct illustrated in Design 5, 6, or 7 of FIG. 3, by using either a common receptor or a cytokine specific receptor, such as an IL4 receptor. The transmembrane (TM) domain of any of the designs in FIG. 3 can be native to the respective cytokine receptor or may be modified or replaced with the transmembrane domain of any other membrane bound proteins.

In addition to an induced pluripotent stem cell (iPSC), a clonal iPSC, a clonal iPS cell line, or iPSC-derived cells, comprising at least one engineered modality as disclosed herein are provided. Also provided is a master cell bank comprising single cell sorted and expanded clonal engineered iPSCs having at least an exogenously introduced cytokine and/or cytokine receptor signaling as described in this section, wherein the cell bank provides a platform for additional iPSC engineering and a renewable source for manufacturing off-the-shelf, engineered, homogeneous cell therapy products, which are well-defined and uniform in composition, and can be mass produced at significant scale in a cost-effective manner. In iPSCs and derivative cells therefrom comprising both CAR and exogenous cytokine and/or cytokine receptor signaling, the CAR and IL may be expressed in separate constructs, or may be co-expressed in a bi-cistronic construct comprising both CAR and IL. In some further embodiments, IL15 in a form represented by any of the construct designs in FIG. 3 can be linked to either the 5' or the 3' end of a CAR expression construct through a self-cleaving 2A coding sequence, illustrated as, for example, CAR-2A-IL15 or IL15-2A-CAR. As such, the IL15 and CAR may be in a single open reading frame (ORF). In one embodiment, the CAR-2A-IL15 or IL15-2A-CAR construct comprises IL15, as shown in Design 3 of FIG. 3. In another embodiment, the CAR-2A-IL15 or IL15-2A-CAR construct comprises IL15, as shown in Design 4 of FIG. 3. In yet another embodiment, the CAR-2A-IL15 or IL15-2A-CAR construct comprises IL15, as shown in Design 7 of FIG. 3. When CAR-2A-IL15 or IL15-2A-CAR is expressed, the self-cleaving 2A peptide allows the expressed CAR and IL15 to dissociate, and the dissociated IL15 can then be presented at the cell surface. The CAR-2A-IL15 or IL15-2A-CAR bi-cistronic design allows for coordinated CAR and IL15 expression both in timing and quantity, and under the same control mechanism that may be chosen to incorporate, for example, an inducible promoter for the expression of the single ORF. Self-cleaving peptides are found in members of the Picornaviridae virus family, including aphthoviruses such as foot-and-mouth disease virus (FMDV), equine rhinitis A virus (ERAV), Thosea asigna virus (TaV) and porcine tescho virus-1 (PTV-I) (Donnelly, M L, et al, J. Gen. Virol, 82, 1027-101 (2001); Ryan, M D, et al., J. Gen. Virol., 72, 2727-2732 (2001)), and cardioviruses such as Theilovirus (e.g., Theiler's murine encephalomyelitis) and encephalomyocarditis viruses. The 2A peptides derived from FMDV, ERAV, PTV-I, and TaV are sometimes also referred to as "F2A", "E2A", "P2A", and "T2A", respectively.

The bi-cistronic CAR-2A-IL15 or IL15-2A-CAR embodiment as disclosed herein for IL15 is also contemplated for expression of any other cytokine provided herein, for example, IL2, IL4, IL6, IL7, IL9, IL10, IL11, IL12, IL18, and IL21. In some embodiments, IL2 cell surface expression and signaling is through the construct illustrated in any of the Designs 1-7 of FIG. 3. In some other embodiments, IL4, IL7, IL9, or IL21 cell surface expression and signaling is through the construct illustrated in Designs 5, 6, or 7 of FIG. 3, either using a common receptor and/or a cytokine specific receptor.

In iPSCs and derivative cells therefrom comprising both CAR and exogenous cytokine and/or cytokine receptor signaling, including but not limited to IL15, the iPSCs and derivative cells may further comprise CFR, $TCR^{neg}$, and/or exogenous CD16.

6. HLA-I- and HLA-II-Deficiency

Multiple HLA class I and class II proteins must be matched for histocompatibility in allogeneic recipients to avoid allogeneic rejection problems. Provided herein is an iPSC cell line and its derivative cells differentiated therefrom with eliminated or substantially reduced expression of both HLA class I and HLA class II proteins. HLA class I deficiency can be achieved by functional deletion of any region of the HLA class I locus (chromosome 6p21), or deletion or reducing the expression level of HLA class-I associated genes including, but not limited to, beta-2 microglobulin (B2M) gene, TAP1 gene, TAP2 gene and Tapasin. For example, the B2M gene encodes a common subunit essential for cell surface expression of all HLA class I heterodimers. B2M negative cells are HLA-I deficient. HLA class II deficiency can be achieved by functional deletion or reduction of HLA-II associated genes including, but not limited to, RFXANK, CIITA, RFX5 and RFXAP. CIITA is a transcriptional coactivator, functioning through activation of the transcription factor RFX5 required for class II protein expression. CIITA negative cells are HLA-II deficient. Provided herein is an iPSC line and its derivative cells with both HLA-I and HLA-II deficiency, for example lacking both B2M and CIITA expression, wherein the obtained derivative effector cells enable allogeneic cell therapies by eliminating the need for MHC (major histocompatibility complex) matching, and avoid recognition and killing by host (allogeneic) T cells.

For some cell types, a lack of HLA class I expression leads to lysis by NK cells. To overcome this "missing self" response, HLA-G may be optionally knocked in to avoid NK cell recognition and killing of the HLA-I deficient effector cells derived from an engineered iPSC. In one embodiment, the HLA-I deficient iPSC and its derivative cells further comprise HLA-G knock-in. In some embodiments, the provided HLA-I deficient iPSC and its derivative cells further comprise one or both of CD58 knockout and CD54 knockout. CD58 (or LFA-3) and CD54 (or ICAM-1) are adhesion proteins initiating signal-dependent cell interactions, and facilitating cell, including immune cell, migration. It was shown that CD58 knockout has a higher efficiency in reducing allogeneic NK cell activation than CD54 knockout; while double knockout of both CD58 and CD54 has the most enhanced reduction of NK cell activation. In some observations, the CD58 and CD54 double knockout is even more effective than HLA-G overexpression for HLA-I deficient cells in overcoming the "missing-self" effect.

As provided above, in some embodiments, the HLA-I and HLA-II deficient iPSC and its derivative cells have an exogenous polynucleotide encoding HLA-G. In some embodiments, the HLA-I and HLA-II deficient iPSC and its derivative cells are CD58 null. In some other embodiments, the HLA-I and HLA-II deficient iPSC and its derivative cells are CD54 null. In yet some other embodiments, the HLA-I and HLA-II deficient iPSC and its derivative cells are CD58 null and CD54 null.

7. CD38 Knockout

The cell surface molecule CD38 is highly upregulated in multiple hematologic malignancies derived from both lymphoid and myeloid lineages, including multiple myeloma and a CD20 negative B-cell malignancy, which makes it an attractive target for antibody therapeutics to deplete cancer cells. Antibody mediated cancer cell depletion is usually attributable to a combination of direct cell apoptosis induction and activation of immune effector mechanisms such as ADCC (antibody-dependent cell-mediated cytotoxicity). In addition to ADCC, the immune effector mechanisms in concert with the therapeutic antibody may also include antibody-dependent cell-mediated phagocytosis (ADCP) and/or complement-dependent cytotoxicity (CDC).

Other than being highly expressed on malignant cells, CD38 is also expressed on plasma cells as well as on NK cells, and activated T and B cells. During hematopoiesis, CD38 is expressed on $CD34^+$ stem cells and lineage-committed progenitors of lymphoid, erythroid, and myeloid, and during the final stages of maturation which continues through the plasma cell stage. As a type II transmembrane glycoprotein, CD38 carries out cell functions as both a receptor and a multifunctional enzyme involved in the production of nucleotide-metabolites. As an enzyme, CD38 catalyzes the synthesis and hydrolysis of the reaction from $NAD^+$ to ADP-ribose, thereby producing secondary messengers CADPR and NAADP which stimulate release of calcium from the endoplasmic reticulum and lysosomes, critical for the process of cell adhesion, which process is calcium dependent. As a receptor, CD38 recognizes CD31 and regulates cytokine release and cytotoxicity in activated NK cells. CD38 is also reported to associate with cell surface proteins in lipid rafts, to regulate cytoplasmic $Ca^{2+}$ flux, and to mediate signal transduction in lymphoid and myeloid cells.

In malignancy treatment, systemic use of CD38 antigen binding receptor transduced T cells have been shown to lyse the $CD38^+$ fractions of $CD34^+$ hematopoietic progenitor cells, monocytes, NK cells, T cells and B cells, leading to incomplete treatment responses and reduced or eliminated efficacy because of the impaired recipient immune effector cell function. In addition, in multiple myeloma patients treated with daratumumab, a CD38 specific antibody, NK cell reduction in both bone marrow and peripheral blood was observed, although other immune cell types, such as T cells and B cells, were unaffected despite their CD38 expression (Casneuf et al., Blood Advances. 2017; 1(23):2105-2114). Without being limited by theories, the present application provides a strategy to leverage the full potential of CD38 targeted cancer treatment by overcoming CD38 specific antibody and/or CD38 antigen binding domain induced effector cell depletion or reduction through fratricide. In addition, since CD38 is upregulated on activated lymphocytes such as T or B cells, by suppressing activation of these recipient lymphocytes using a CD38 specific antibody such as daratumumab in the recipient of allogeneic effector cells, the allorejection against these effector cells would be reduced and/or prevented, thereby increasing effector cell survival and persistency. As such, the present application also provides a strategy to enhance effector cell persistency and/or survival through reducing or preventing allorejection by using a CD38 specific antibody, a secreted CD38 specific engager or a CD38-CAR (chimeric antigen receptor) against activation of recipient T and B cells, i.e., lymphodepletion of activated T and B cells, often prior to adoptive cell transferring. Specifically, the strategies as provided include generating a CD38 knockout iPSC line, a master cell bank comprising single cell sorted and expanded clonal CD38 negative iPSCs, and obtaining CD38 negative (CD38"g) derivative effector cells through directed differentiation of the engineered iPSC line, wherein the derivative effector cells are protected against fratricide and allorejection among other advantages when CD38 targeted therapeutic moieties are employed with the effector cells. In addition, anti-CD38 monoclonal antibody therapy significantly depletes a patient's activated immune system without adversely affecting the patient's hematopoietic stem cell compartment. A CD38 negative derivative cell has the ability to resist CD38 antibody mediated depletion, and may be effectively administered in combination with anti-CD38 or CD38-CAR without the use of toxic conditioning agents and thus reduce and/or replace chemotherapy based lymphodepletion.

In one embodiment as provided herein, the CD38 knockout in an iPSC line is a bi-allelic knockout. As disclosed herein, the provided CD38 negative iPSC line further comprises at least a CFR, and optionally one or more of TCR$^{neg}$, hnCD16, CAR, exogenous cytokine or a fusion variant thereof, and HLA-I and/or HLA-II deficiency; and said iPSC is capable of directed differentiation to produce functional derivative hematopoietic cells including, but not limited to, immune effector cells. In some embodiments, when an anti-CD38 antibody is used to induce ADCC or an anti-CD38 CAR is used for targeted cell killing, the CD38"g iPSC and/or derivative effector cells thereof are not eliminated by the anti-CD38 antibody, the anti-CD38 CAR, or recipient activated T or B cells, thereby increasing the iPSC and its effector cell persistence and/or survival in the presence of, and/or after exposure to, such therapeutic moieties. In some embodiments, the effector cell has increased persistence and/or survival in vivo in the presence of, and/or after exposure to, such therapeutic moieties.

8. Additional Modifications

In some embodiments, the iPSC, and its derivative effector cells comprising CFR and one or more of TCR$^{neg}$, CD16, CAR, IL, HLA-I and/or HLA-II deficiency, and CD38$^{-/-}$ may additionally comprise disruption of at least one of TAP1, TAP2, Tapasin, NLRC5, PD1, LAG3, TIM3, RFXANK, RFX5, RFXAP, RAG1, and any gene in the chromosome 6p21 region; or introduction of at least one of HLA-E, 4-1BBL, CD4, CD8, CD47, CD113, CD131, CD137, CD80, PDL1, $A_{2A}$R, TCR, Fc receptor, an antibody, an engager, and surface triggering receptor for coupling with bi-, multi-specific or universal engagers.

Bi- or multi-specific engagers are fusion proteins consisting of two or more single-chain variable fragments (scFvs), or other functional variants, of different antibodies, with at least one scFv binds to an effector cell surface molecule or surface triggering receptor, and at least another to a tumor cell via a tumor specific surface molecule. In some embodiments, the surface triggering receptor facilitates bi- or multi-specific antibody engagement between the effector cells and a specific target cell (e.g., a tumor cell), independent of the effector cell's natural receptors and cell types. In some other embodiments, one or more exogenous surface triggering receptors may be introduced to the effector cells using the methods and compositions provided herein, i.e., through engineering of an iPSC, optionally generating a master cell bank comprising single cell sorted and expanded clonal engineered iPSCs, and then directing the differentiation of the iPSC to T, NK or any other effector cells comprising the same genotype as the source iPSC.

Using this approach, one may also generate iPSCs comprising a universal surface triggering receptor, and then differentiate such iPSCs into populations of various effector cell types that express the universal surface triggering receptor. In some embodiments, engagers having the same tumor targeting specificity are used to couple with different universal surface triggering receptor. In some embodiments, engagers having different tumor targeting specificity are used to couple with the same universal surface triggering receptor. As such, one or multiple effector cell types can be engaged to kill one specific type of tumor cells in some case, and to kill two or more types of tumors in some other cases. A surface triggering receptor generally comprises a co-stimulatory domain for effector cell activation and an anti-epitope that is specific to the epitope of an engager, or vice versa, the surface triggering receptor comprises an epitope that is recognizable or specific to the anti-epitope of the engager. For example, a bi-specific engager is specific to the epitope of a surface triggering receptor on one end and is specific to a tumor antigen on the other end. Examples of engagers include, but are not limited to, bi-specific T cell engagers (BiTEs), bi-specific killer cell engagers (BiKEs), tri-specific killer cell engagers (TriKEs), multi-specific killer cell engagers, and universal engagers compatible with multiple immune cell types. Non-limiting examples of TriKEs are described in U.S. Pub. No. 2018/0282386, which is incorporated herein by reference.

As provided herein, various forms of CFR as disclosed are applicable, among other functions, as cell surface triggering receptors for engager recognition. In addition, as provided herein, the various forms of cell surface presented CD3 molecules, including the CD3-based CFRs as disclosed are applicable, among other functions, as CD3 related cell surface triggering receptors for engager recognition, which is particularly useful in a cell that is TCR negative such that the expressed CD3 molecule does not present on the cell surface despite the expression.

Other than CFR or cs-CD3, additional effector cell surface molecules, or surface triggering receptors, that can be used for bi- or multi-specific engager recognition, or coupling, or binding, include, but are not limited to, CD28, CD5, CD16, CD64, CD32, CD33, CD89, NKG2C, NKG2D, or any functional variants or chimeric receptor forms thereof as disclosed herein. In some embodiments, the CD16 expressed on the surface of effector cells for engager recognition is a hnCD16, comprising CD16 (containing F176V and optionally S197P) or CD64 extracellular domain, and native or non-native transmembrane, stimulatory and/or signaling domains as described herein. In some embodiments, the CD16 expressed on the surface of effector cells for engager recognition is a CD16-based chimeric Fc receptor (CFcR). In some embodiments, the CD16-based CFcR comprises a transmembrane domain of NKG2D, a stimulatory domain of 2B4, and a signaling domain of CD3ζ; wherein the extracellular domain of the CD16 is derived from a full length or partial sequence of the extracellular domain of CD64 or CD16; and optionally wherein the extracellular domain of CD16 comprises F176V and optionally S197P.

The exemplary tumor cell surface molecules for bi- or multi-specific engager recognition include, but are not limited to, B7H3, BCMA, CD10, CD19, CD20, CD22, CD24, CD30, CD33, CD34, CD38, CD44, CD79a, CD79b, CD123, CD138, CD179b, CEA, CLEC12A, CS-1, DLL3, EGFR, EGFRvIII, EPCAM, FLT-3, FOLR1, FOLR3, GD2, gpA33, HER2, HM1.24, LGR5, MSLN, MCSP, MICA/B, PSMA, PAMA, P-cadherin, and ROR1.

In view of the above, for engaging CD3 on the effector cells, in one embodiment, the bi-specific antibody is CD3-CD19; and in another embodiment, the bi-specific antibody is CD3-CD33. For engaging CD16 on the effector cells, the bi-specific antibody is CD16-CD30 or CD64-CD30. In another embodiment, the bi-specific antibody is CD16-BCMA or CD64-BCMA. In yet another embodiment, the bi-specific antibody further comprises a linker between the effector cell and tumor cell antigen binding domains, for example, a modified IL15 may be used as a linker for effector NK cells to facilitate effector cell expansion (called TriKE, or Tri-specific Killer Engager, in some publications). In one embodiment, the TriKE is CD16-IL15-EPCAM or CD64-IL15-EPCAM. In another embodiment, the TriKE is CD16-IL15-CD33 or CD64-IL15-CD33. In yet another embodiment, the TriKE is NKG2C-IL15-CD33. The IL15 in the TriKE may also originate from other cytokines including, but not limited to, IL2, IL4, IL6, IL7, IL9, IL10, IL11, IL12, IL18, and IL21.

9. Genetically Engineered iPSC Line and iPSC-Derived Cells Provided Herein

In light of the above, the present application provides a cell, or a population thereof, comprising at least a polynucleotide encoding a CFR, wherein the cell is an eukaryotic cell, an animal cell, a human cell, an induced pluripotent stem cell (iPSC), an iPSC-derived effector cell, an immune cell, or a feeder cell. Also provided is a master cell bank comprising single cell sorted and expanded clonal engineered iPSCs having a phenotype as described herein, wherein the cell bank provides a renewable source for manufacturing off-the-shelf, engineered, homogeneous cell therapy products, which are well-defined and uniform in composition, and can be mass produced at significant scale in a cost-effective manner. In some embodiments, the iPSC-derived cells are hematopoietic cells including, but not limited to, mesodermal cells with definitive hemogenic endothelium (HE) potential, definitive HE, CD34 hematopoietic cells, hematopoietic stem and progenitor cells, hematopoietic multipotent progenitors (MPP), T cell progenitors, NK cell progenitors, myeloid cells, neutrophil progenitors, and/or sharing features with T cells, NKT cells, NK cells, B cells, neutrophils, dendritic cells, and macrophages. In some embodiments, the iPSC-derived hematopoietic cells comprise immune effector cells expressing at least a CFR. Further provided herein is a cell comprising a polynucleotide encoding a CFR, and one or more of $TCR^{neg}$; an exogenous CD16; a target specific CAR; HLA-I deficiency and/or HLA-II deficiency; a cytokine signaling complex comprising a cytokine and/or its receptor or variants thereof; and CD38 knockout, wherein the iPSC is capable of directed differentiation to produce functional derivative hematopoietic cells. In some embodiments, the functional derivative hematopoietic cells are immune effector cells. In some embodiments, the functional derivative immune effector cells share features with NK and/or T cells. In some embodiments, the functional derivative immune effector cells sharing features with NK and/or T cells are not NK cells or T cells.

In some embodiments of the cell that comprises at least a polynucleotide encoding a CFR, the cell is $TCR^{neg}$. As used herein, $TCR^{neg}$ is also referred to as TCR negative, $TCR^{-/-}$, "TCR null", or TCR knockout, which comprises cells without endogenous TCR expression either by nature (for example, NK cell or iPSC derived NK cell), by gene expression regulation, or by genomic editing of an iPSC cell (for example, iPSC, iPSC reprogrammed from T cell (TiPSC)) or a T cell to knock out an endogenous TCR or one or more subunits thereof, or by obtaining TCR negative derivative cells differentiated from iPSC having TCR knocked out. As such, the TCR that is knocked out in a cell as disclosed is an endogenous TCR complex. Disrupting the expression of the constant region of either TCRα or TCRβ of TCR in a cell is one of many methods of knocking out the endogenous TCR complex of the cell. $TCR^{neg}$ cells are discovered as not being able to present CD3 complex to the cell surface despite of the expression of all CD3 subunits in the $TCR^{neg}$ cells, which adversely affects cell functions that requires cell surface CD3 recognition, binding and/or signaling. In some embodiments of the $TCR^{neg}$ cells comprising a polynucleotide encoding CFR, the CFR is CD3-based. In some embodiments, the $TCR^{neg}$ cells which comprise a polynucleotide encoding CFR also comprise a cell surface CD3 complex, or one or more subunits or subdomains thereof (cs-CD3) when expressed. In some embodiments of cells having a CFR $TCR^{neg}$ cs-CD3 genotype, the CFR is not CD3-based. In some other embodiments of cells having a CFR $TCR^{neg}$ cs-CD3 genotype, the CFR is CD3-based. In addition to CD3-based CFR, the cell surface CD3 complex, or one or more subunits or subdomains thereof (cs-CD3), as disclosed herein, in a $TCR^{neg}$ cell can function as a CD3-related cell surface triggering receptor for binding with molecules including, not limited to, antibodies or functional variants thereof, and/or engagers as described herein.

Provided herein also is an iPSC or iPSC-derived cell comprising one or more polynucleotides encoding one or more exogenous proteins to provide a cell surface CD3 complex, or one or more subunits or subdomains thereof (cs-CD3) when expressed, wherein the cell is optionally TCR negative. When the cs-CD3 is expressed, it functions as a CD3-related cell surface triggering receptor. In some embodiments of the CD3-related surface triggering receptor as provided in a $TCR^{neg}$ cell, the receptor is comprised in a complete or partial endogenous CD3 molecule presented at the effector cell surface when expressed, wherein the endogenous CD3 molecule presentation otherwise does not take place in a $TCR^{neg}$ cell even when expressed, is enabled by its association with a recombinant TCR comprising one or more of a full or partial length of an exogenous TCRα, an exogenous TCRβ, and any variants thereof as provided in this application. In some embodiments, the cell surface presentation of a complete or partial endogenous CD3 molecule in a $TCR^{neg}$ cell is enabled by additionally expressing in said cell at least a recombinant TCR comprising a non-binding recombinant TCR (nb-rTCR), a defined recombinant TCR (d-rTCR), and/or a recombinant pre-TCR.

In some embodiments, the $TCR^{neg}$ cell comprising a CD3 related surface triggering receptor comprises a non-binding recombinant TCR (nb-rTCR), wherein the nb-rTCR comprises one or both of a tgTRAC (transgenic TCRα constant region) and a tgTRBC (transgenic TCRβ constant region); as such, the $TCR^{neg}$ iPSC or iPSC-derived cell comprises one or more polynucleotides encoding tgTRAC and/or tgTRBC. In some embodiments of the TCR$^{neg}$ cell comprising a polynucleotide encoding tgTRAC, said polynucleotide is inserted in a TRAC locus, wherein the inserted polynucleotide disrupts expression of endogenous TRAC, thereby leading to endogenous TCR knockout, and optionally wherein the inserted polynucleotide is driven by an endogenous promoter of TRAC or a heterologous promoter. In some embodiments of the TCR$^{neg}$ cell comprising a polynucleotide encoding tgTRBC, said polynucleotide is inserted in a TRBC locus, wherein the inserted polynucleotide disrupts expression of endogenous TRBC thereby leading to endogenous TCR knockout, and optionally wherein the inserted polynucleotide is driven by an endogenous promoter of TRBC or a heterologous promoter.

In some embodiments, the TCR$^{neg}$ cell comprising a CD3-related surface triggering receptor comprises a defined recombinant TCR (d-rTCR), wherein the d-rTCR comprises a tgTCRα (transgenic TCRα) and a tgTCRβ (transgenic TCRβ), wherein each of the tgTCRα and the tgTCRβ comprises a respective defined variable region in addition to a respective constant region (i.e., TRAC and TRBC); as such, the TCR$^{neg}$ iPSC or iPSC-derived cell comprises one or more polynucleotides encoding tgTCRα and/or tgTCRβ. In some embodiments, the defined variable region is originated from TCRα and TCRβ of a T cell having known TCR specificity. In some embodiments, the defined variable region is originated from TCRα and TCRβ of invariant NKT cells. In some embodiments of the TCR$^{neg}$ cell comprising a polynucleotide encoding tgTCRα, said polynucleotide is inserted in a TRAC locus, wherein the inserted polynucleotide disrupts expression of endogenous TRAC, thereby leading to endogenous TCR knockout, and optionally wherein the inserted polynucleotide is driven by an endogenous promoter of TRAC or a heterologous promoter. In some embodiments of the TCR$^{neg}$ cell comprising a polynucleotide encoding tgTCRβ, said polynucleotide is inserted in a TRBC locus, wherein the inserted polynucleotide disrupts expression of endogenous TRBC, thereby leading to endogenous TCR knockout, and optionally wherein the inserted polynucleotide is driven by an endogenous promoter of TRBC or a heterologous promoter.

In some embodiments, the TCR$^{neg}$ cell comprising a CD3-related surface triggering receptor comprises a recombinant pre-TCR (p-rTCR), wherein the p-rTCR comprises a tgpTCRα (transgenic pre-TCRα), and optionally a tgTRBC or a tgTCRβ, wherein the tgTCRβ comprises a defined variable region; as such, the TCR$^{neg}$ iPSC or iPSC-derived cell comprises at least a polynucleotide encoding tgpTCRα. In some embodiments of the TCR$^{neg}$ cell comprising a polynucleotide encoding tgpTCRα, said polynucleotide is inserted in a TRAC locus, wherein the inserted polynucleotide disrupts expression of endogenous TRAC, thereby leading to endogenous TCR knockout, and optionally wherein the inserted polynucleotide is driven by an endogenous promoter of TRAC or a heterologous promoter. In some embodiments of the TCR$^{neg}$ cell comprising a polynucleotide encoding tgTRBC or tgTCRβ in addition to tgpTCRα, said tgTRBC or tgTCRβ encoding polynucleotide is inserted in a TRBC locus, wherein the inserted polynucleotide disrupts expression of endogenous TRBC, thereby leading to endogenous TCR knockout, and optionally wherein the inserted tgTRBC or tgTCRβ encoding polynucleotide is driven by an endogenous promoter of TRBC or a heterologous promoter.

In some embodiments of the CD3-related surface triggering receptor in a TCR$^{neg}$ cell, the receptor is comprised in a complete or partial CD3 molecule comprising at least one exogenous subunit or subdomain from one or more of CD3ε, CD3δ, and CD3γ. In one embodiment, the CD3-related surface triggering receptor for engager recognition in a TCR$^{neg}$ cell is comprised in a partial CD3 molecule comprising at least a full or partial length ectodomain of CD3ε. In one embodiment, the CD3 related surface triggering receptor for engager recognition in a TCR$^{neg}$ cell is comprised in a partial CD3 molecule comprising at least a full or partial length ectodomain of CD3ε, and additionally a full or partial length ectodomain of CD3γ or CD3δ. In one embodiment, said CD3 molecule comprises at least a full or partial length of an ectodomain of CD3ε, CD3γ and/or CD3δ, wherein the full or partial length of ectodomain(s) is fused with a constant region of TCRα or TCRβ, and wherein the partial fusion proteins each comprising TRAC or TRBC are capable of forming a heterodimer with endogenous CD3. As such, in one embodiment of the TCR$^{neg}$ iPSC or iPSC-derived cell having a CD3-related surface triggering receptor, the cell comprises at least one of: (i) a transgenic fusion protein comprising full or partial length of ectodomains of CD3ε and CD3δ, and a TCRα constant region (tgCD3(ε-δ)-TRAC); (ii) a transgenic fusion protein comprising full or partial length of ectodomains of CD3ε and CD3γ, and a TCRβ constant region (tgCD3(ε-γ)-TRBC); (iii) a transgenic fusion protein comprising full or partial length of ectodomains of CD3ε and CD3γ, and a TCRα constant region (tgCD3(ε-γ)-TRAC); and/or (iv) a transgenic fusion protein comprising full or partial length of ectodomains of CD3ε and CD3δ, and a TCRβ constant region (tgCD3(ε-δ)-TRBC). In some embodiments of the TCR$^{neg}$ cell having a CD3-related surface triggering receptor, the cell comprises a heterodimer comprising a transgenic fusion protein comprising a TCRα constant region fused with a full or partial length of ectodomain of at least CD3ε and a transgenic fusion protein comprising a TCRβ constant region fused with a full or partial length of ectodomain of at least CD3ε.

In some embodiments of the CD3-related surface triggering receptor in a TCR$^{neg}$ cell, the receptor is comprised in a complete or partial CD3 molecule comprising at least one exogenous subunit or subdomain from one or more of CD3ε, CD3δ, CD3γ, and/or CD3ζ, and optionally one or more signaling domains of 2B4, 4-1BB, CD16, CD2, CD28, CD28H, CD3, DAP10, DAP12, DNAM1, FcERIγ IL21Rβ (IL-15Rβ), IL-2Rγ, IL-7R, KIR2DS2, NKG2D, NKp30, NKp44, NKp46, CD3ζ1XX, CS1, or CD8 for signal transduction and/or co-stimulation, wherein all subunits or subdomains, including the signaling domains are fused to form a chimeric chain. In one embodiment, the CD3-related surface triggering receptor for engager recognition in a TCR$^{neg}$ cell is comprised in a CD3 chimeric chain comprising at least a full or partial length ectodomain of CD3ε; a full or partial length ectodomain of one or both of CD3δ and CD3γ; and a full or partial length endodomain of CD3ζ. In one embodiment, the CD3-related surface triggering receptor for engager recognition in a TCR$^{neg}$ cell is comprised in a CD3 chimeric chain comprising a full or partial length ectodomain of CD3ε; a full or partial length ectodomain of one or both of CD3δ and CD3γ; a full or partial length endodomain of CD3ζ, and further comprises a cytoplasmic signaling domain of one or both of CD28 and 4-1BBL. As such, in one embodiment of the TCR$^{neg}$ iPSC or iPSC-derived cell having a CD3-related surface triggering receptor, the cell comprises at least one of: (i) a transgenic fusion protein comprising full or partial length of ectodomains of CD3ε and CD3γ, and a full or partial length of endodomain of CD3ζ [tgCD3(ε-γ)-ζ]; (ii) a transgenic fusion protein comprising full or partial length of ectodomains of CD3ε and CD3δ, and a full or partial length of endodomain of CD3ζ [tgCD3(ε-δ)-ζ]; (iii) a transgenic fusion protein comprising a full or partial length ectodomain of CD3ε, a transgenic fusion protein comprising a full or partial length ectodomain of CD3γ or CD3δ, a full or partial length endodomain of CD3, and a signaling domain of CD28 [tgCD3(ε-γ/δ)-28ζ]; (iv) a transgenic fusion protein comprising a full or partial length ectodomain of CD3ε, a transgenic fusion protein comprising a full or partial length ectodomain of CD3γ or CD3δ, a full or partial length endodomain of CD3, and a signaling domain of 4-1BB [tgCD3(ε-γ/δ)-BBζ]; and/or (v) a transgenic fusion protein comprising a full or partial length ectodomain of CD3γ or CD3δ, a full or partial length endodomain of CD3, a signaling domain of CD28, and a signaling domain of 4-1BB [tgCD3(ε-γ/δ)-(28-BB)ζ].

Further provided herein is an iPSC comprising a polynucleotide encoding a CFR, and one or more of $TCR^{neg}$; an exogenous CD16; a target specific CAR; HLA-I deficiency and/or HLA-II deficiency; a cytokine signaling complex comprising a cytokine and/or its receptor or variants thereof; and CD38 knockout, wherein the iPSC is capable of directed differentiation to produce functional derivative hematopoietic cells.

In some embodiments, the cell comprising a CFR is $TCR^{neg}$. In some embodiments, the cell comprising a CFR comprises a CAR inserted in a constant region of TCR. In some embodiments, the cell comprising a CFR is $TCR^{neg}$ and comprises a CAR inserted in a constant region of TCR and the expression of the CAR is driven by an endogenous TCR promoter. In some embodiments, the cell comprising a CFR comprises an exogenous cytokine signaling of IL2, IL4, IL6, IL7, IL9, IL10, IL11, IL12, IL15, IL18, IL21, or any combinations thereof. In some embodiments, the exogenous cytokine signaling is cell membrane bound. In some embodiments, the exogenous cytokine signaling comprises an introduced partial or full peptide of a cytokine and/or its respective receptor or mutated or truncated variants thereof. In some embodiments, the cytokine signaling is constitutively activated. In some embodiments, the activation of the cytokine signaling is inducible. In some embodiments, the activation of the cytokine signaling is transient and/or temporal. In some embodiments, the transient/temporal expression of a cell surface cytokine signaling is through a retrovirus, Sendai virus, an adenovirus, an episome, mini-circle, or RNAs including mRNA. In some embodiments, the exogenous cell surface cytokine signaling enables IL7 signaling. In some embodiments, the exogenous cell surface cytokine signaling enables IL10 signaling. In some embodiments, the exogenous cell surface cytokine signaling enables IL15 signaling. In some embodiments, the cell comprising a CFR further comprises an exogenous CD16 or functional variants or chimeric receptors thereof. In some embodiments, the exogenous CD16 comprises an ectodomain comprising F176V and S197P. In some embodiments, the exogenous CD16 comprises a full or a partial length of an ectodomain of CD64. In some other embodiments, the exogenous CD16 comprises a chimeric Fc receptor. The exogenous CD16 enables cell killing through ADCC, thereby providing a dual targeting mechanism to an effector cell expressing, for example, a CAR.

In some embodiments, the cell comprising a CFR further comprises a CD38 knockout. The cell surface molecule CD38 is highly upregulated in multiple hematologic malignancies derived from both lymphoid and myeloid lineages, including multiple myeloma and a CD20 negative B-cell malignancy, which makes it an attractive target for antibody therapeutics to deplete cancer cells. Other than being highly expressed on malignant cells, CD38 is also expressed on plasma cells as well as on NK cells, and activated T and B cells. In some embodiments, effector cells that are $CD38^{-/-}$ can avoid CD38 induced fractricide. In some embodiments, when an anti-CD38 antibody, a CD38 binding CAR, or an CD3 engager comprising anti-CD38 scFV is used to induce the ADCC and/or tumor cell targeting, the $CD38^{-/-}$ iPSC and/or its derivative effector cells can target the CD38 expressing (tumor) cells without causing effector cell elimination, i.e., reduction or depletion of CD38 expressing effector cells, thereby increasing the iPSC and its effector cell persistence and/or survival.

In some embodiments of the cell comprising a polynucleotide encoding a CFR, the cell further comprises a HLA-I deficiency (e.g., B2M knockout) and/or HLA-II deficiency (e.g., a CIITA knockout), and optionally, a polynucleotide encoding HLA-G or HLA-E.

In view of the above, provided herein is an iPSC comprising a polynucleotide encoding a CFR, and optionally one, two, three, or more, or all of: $TCR^{neg}$, exogenous CD16 or a variant, CAR, an exogenous IL, CD38 knockout, and B2M/CIITA knockout; wherein when B2M is knocked out, a polynucleotide encoding HLA-G, or alternatively, one or both of CD58 and CD54 knockout, is optionally introduced, and wherein the iPSC is capable of directed differentiation to produce functional derivative hematopoietic cells.

As such, the present application provides iPSCs and functional derivative hematopoietic cells thereof, which comprise any one of the following genotypes in Table 1. Also provided herein is a master cell bank comprising single cell sorted and expanded clonal engineered iPSCs comprising any one of the following genotypes in Table 1, i.e., a having CFR, and one or more of $TCR^{neg}$, exogenous CD16 or a variant, CAR, an exogenous IL, CD38 knockout, and HLA-I and/or HLA-II deficiency, without adversely impacting the differentiation potential of the iPSC and function of the derived effector cells. Said cell bank provides a platform for additional iPSC engineering, and a renewable source for manufacturing off-the-shelf, engineered, homogeneous cell therapy products.

"IL", as provided in Table 1 stands for one of IL2, IL4, IL6, IL7, IL9, IL10, IL11, IL12, IL15, IL18, and IL21, depending on which specific cytokine/receptor or combination expression is selected. For example, when IL15 is selected, "IL" stands for IL15-related signaling complex, including IL154. Shown as "IL15Rα(ΔICD) fusion" and "IL5/mb-Sushi" in FIG. 3, these embodiments are further collectively abbreviated as IL154 throughout this application. In some embodiments, IL154 is the truncated IL15/IL15Rα fusion protein lacking an intracellular domain and comprising an amino acid sequence of at least 75%, 80%, 85%, 90%, 95% or 99% identity to SEQ ID NOs: 17, 19 or 21. In some embodiments, the truncated IL15/IL15Rα fusion protein lacking an intracellular domain comprises an amino acid sequence of SEQ ID NO: 17. In some embodiments, the truncated IL15/IL15Rα fusion protein lacking an intracellular domain comprises an amino acid sequence of SEQ ID NO: 19. In some embodiments, the truncated IL15/IL15Rα fusion protein lacking an intracellular domain comprises an amino acid sequence of SEQ ID NO: 21. Further, when iPSCs and functional derivative hematopoietic cells thereof have a genotype comprising both CAR and IL, the CAR and IL may optionally be comprised in a bi-cistronic expression cassette comprising a 2A sequence. As comparison, in some other embodiments, CAR and IL are in separate expression cassettes comprised in iPSCs and functional derivative hematopoietic cells thereof

TABLE 1

Applicable Genotypes of the Cells Provided:

| CFR | TCR$^{neg}$ | CD16 | CAR | IL | CD38$^{-/-}$ | B2M$^{-/-}$CIITA$^{-/-}$ | HLA-G or (CD58$^{-/-}$ w/or w/o CD54$^{-/-}$) | Genotype |
|---|---|---|---|---|---|---|---|---|
| ✓ | | | | | | | | 1. CFR |
| ✓ | ✓ | | | | | | | 2. CFR TCR$^{neg}$ |
| ✓ | | ✓ | | | | | | 3. CFR CD16 |
| ✓ | | | ✓ | | | | | 4. CFR CAR |
| ✓ | | | | ✓ | | | | 5. CFR IL |
| ✓ | | | | | ✓ | | | 6. CFR CD38$^{-/-}$ |
| ✓ | | | | | | ✓ | | 7. CFR B2M$^{-/-}$CIITA$^{-/-}$ |
| ✓ | | | | | | ✓ | ✓ | 8. CFR B2M$^{-/-}$CIITA$^{-/-}$ CD58$^{-/-}$ |
| | | | | | | | | 9. CFR B2M$^{-/-}$CIITA$^{-/-}$ CD54$^{-/-}$ |
| | | | | | | | | 10. CFR B2M$^{-/-}$CIITA$^{-/-}$ CD58$^{-/-}$ CD54$^{-/-}$ |
| | | | | | | | | 11. CFR B2M$^{-/-}$CIITA$^{-/-}$ HLA-G |
| ✓ | ✓ | ✓ | | | | | | 12. CFR TCR$^{neg}$ CD16 |
| ✓ | ✓ | | ✓ | | | | | 13. CFR TCR$^{neg}$ CAR |
| ✓ | ✓ | | | ✓ | | | | 14. CFR TCR$^{neg}$ IL |
| ✓ | ✓ | | | | ✓ | | | 15. CFR TCR$^{neg}$ CD38$^{-/-}$ |
| ✓ | ✓ | | | | | ✓ | | 16. CFR TCR$^{neg}$ B2M$^{-/-}$CIITA$^{-/-}$ |
| ✓ | ✓ | | | | | ✓ | ✓ | 17. CFR TCR$^{neg}$ B2M$^{-/-}$CIITA$^{-/-}$ CD58$^{-/-}$ |
| | | | | | | | | 18. CFR TCR$^{neg}$ B2M$^{-/-}$CIITA$^{-/-}$ CD54$^{-/-}$ |
| | | | | | | | | 19. CFR TCR$^{neg}$ B2M$^{-/-}$CIITA$^{-/-}$ CD58$^{-/-}$ CD54$^{-/-}$ |
| | | | | | | | | 20. CFR TCR$^{neg}$ B2M$^{-/-}$CIITA$^{-/-}$ HLA-G |
| ✓ | | ✓ | ✓ | | | | | 21. CFR CD16 CAR |
| ✓ | | ✓ | | ✓ | | | | 22. CFR CD16 IL |
| ✓ | | ✓ | | | ✓ | | | 23. CFR CD16 CD38$^{-/-}$ |
| ✓ | | ✓ | | | | ✓ | | 24. CFR CD16 B2M$^{-/-}$CIITA$^{-/-}$ |
| ✓ | | ✓ | | | | ✓ | ✓ | 25. CFR CD16 B2M$^{-/-}$CIITA$^{-/-}$ CD58$^{-/-}$ |
| | | | | | | | | 26. CFR CD16 B2M$^{-/-}$CIITA$^{-/-}$ CD54$^{-/-}$ |
| | | | | | | | | 27. CFR CD16 B2M$^{-/-}$CIITA$^{-/-}$ CD58$^{-/-}$ CD54$^{-/-}$ |
| | | | | | | | | 28. CFR CD16 B2M$^{-/-}$CIITA$^{-/-}$ HLA-G |
| ✓ | | | ✓ | ✓ | | | | 29. CFR CAR IL |
| ✓ | | | ✓ | | ✓ | | | 30. CFR CAR CD38$^{-/-}$ |
| ✓ | | | ✓ | | | ✓ | | 31. CFR CAR B2M$^{-/-}$CIITA$^{-/-}$ |
| ✓ | | | ✓ | | | ✓ | ✓ | 32. CFR CAR B2M$^{-/-}$CIITA$^{-/-}$ CD58$^{-/-}$ |
| | | | | | | | | 33. CFR CAR B2M$^{-/-}$CIITA$^{-/-}$ CD54$^{-/-}$ |
| | | | | | | | | 34. CFR CAR B2M$^{-/-}$CIITA$^{-/-}$ CD58$^{-/-}$ CD54$^{-/-}$ |
| | | | | | | | | 35. CFR CAR B2M$^{-/-}$CIITA$^{-/-}$ HLA-G |
| ✓ | | | | ✓ | ✓ | | | 36. CFR IL CD38$^{-/-}$ |
| ✓ | | | | ✓ | | ✓ | | 37. CFR IL B2M$^{-/-}$CIITA$^{-/-}$ |
| ✓ | | | | ✓ | | ✓ | ✓ | 38. CFR IL B2M$^{-/-}$CIITA$^{-/-}$ CD58$^{-/-}$ |
| | | | | | | | | 39. CFR IL B2M$^{-/-}$CIITA$^{-/-}$ CD54$^{-/-}$ |
| | | | | | | | | 40. CFR IL B2M$^{-/-}$CIITA$^{-/-}$ CD58$^{-/-}$ CD54$^{-/-}$ |
| | | | | | | | | 41. CFR IL B2M$^{-/-}$CIITA$^{-/-}$ HLA-G |
| ✓ | | | | | ✓ | ✓ | | 42. CFR CD38$^{-/-}$ B2M$^{-/-}$CIITA$^{-/-}$ |
| ✓ | | | | | ✓ | ✓ | ✓ | 43. CFR CD38$^{-/-}$ B2M$^{-/-}$CIITA$^{-/-}$ CD58$^{-/-}$ |
| | | | | | | | | 44. CFR CD38$^{-/-}$ B2M$^{-/-}$CIITA$^{-/-}$ CD54$^{-/-}$ |
| | | | | | | | | 45. CFR CD38$^{-/-}$ B2M$^{-/-}$CIITA$^{-/-}$ CD58$^{-/-}$ CD54$^{-/-}$ |
| | | | | | | | | 46. CFR CD38$^{-/-}$ B2M$^{-/-}$CIITA$^{-/-}$ HLA-G |

TABLE 1-continued

| Applicable Genotypes of the Cells Provided: | | | | | | | | |
|---|---|---|---|---|---|---|---|---|
| CFR | TCR$^{neg}$ | CD16 | CAR | IL | CD38$^{-/-}$ | B2M$^{-/-}$CIITA$^{-/-}$ | HLA-G or (CD58$^{-/-}$ w/or w/o CD54$^{-/-}$) | Genotype |
| ✓ | ✓ | ✓ | ✓ | | | | | 47. CFR TCR$^{neg}$ CD16 CAR |
| ✓ | ✓ | ✓ | | ✓ | | | | 48. CFR TCR$^{neg}$ CD16 IL |
| ✓ | ✓ | ✓ | | | ✓ | | | 49. CFR TCR$^{neg}$ CD16 CD38$^{-/-}$ |
| ✓ | ✓ | ✓ | | | | ✓ | | 50. CFR TCR$^{neg}$ CD16 B2M$^{-/-}$CIITA$^{-/-}$ |
| ✓ | ✓ | ✓ | | | | ✓ | ✓ | 51. CFR TCR$^{neg}$ B2M$^{-/-}$CIITA$^{-/-}$ CD58$^{-/-}$ |
| | | | | | | | | 52. CFR TCR$^{neg}$ B2M$^{-/-}$CIITA$^{-/-}$ CD54$^{-/-}$ |
| | | | | | | | | 53. CFR TCR$^{neg}$ B2M$^{-/-}$CIITA$^{-/-}$ CD58$^{-/-}$ CD54$^{-/-}$ |
| | | | | | | | | 54. CFR TCR$^{neg}$ B2M$^{-/-}$CIITA$^{-/-}$ HLA-G |
| ✓ | ✓ | | ✓ | ✓ | | | | 55. CFR TCR$^{neg}$ CAR IL |
| ✓ | ✓ | | ✓ | | ✓ | | | 56. CFR TCR$^{neg}$ CAR CD38$^{-/-}$ |
| ✓ | ✓ | | ✓ | | | ✓ | | 57. CFR TCR$^{neg}$ CAR B2M$^{-/-}$CIITA$^{-/-}$ |
| ✓ | ✓ | | ✓ | | | ✓ | ✓ | 58. CFR TCR$^{neg}$ CAR B2M$^{-/-}$CIITA$^{-/-}$ CD58$^{-/-}$ |
| | | | | | | | | 59. CFR TCR$^{neg}$ CAR B2M$^{-/-}$CIITA$^{-/-}$ CD54$^{-/-}$ |
| | | | | | | | | 60. CFR TCR$^{neg}$ CAR B2M$^{-/-}$CIITA$^{-/-}$ CD58$^{-/-}$ CD54$^{-/-}$ |
| | | | | | | | | 61. CFR TCR$^{neg}$ CAR B2M$^{-/-}$CIITA$^{-/-}$ HLA-G |
| ✓ | ✓ | | | ✓ | ✓ | | | 62. CFR TCR$^{neg}$ IL CD38$^{-/-}$ |
| ✓ | ✓ | | | ✓ | | ✓ | | 63. CFR TCR$^{neg}$ IL B2M$^{-/-}$CIITA$^{-/-}$ |
| ✓ | ✓ | | | ✓ | | ✓ | ✓ | 64. CFR TCR$^{neg}$ IL B2M$^{-/-}$CIITA$^{-/-}$ CD58$^{-/-}$ |
| | | | | | | | | 65. CFR TCR$^{neg}$ IL B2M$^{-/-}$CIITA$^{-/-}$ CD54$^{-/-}$ |
| | | | | | | | | 66. CFR TCR$^{neg}$ IL B2M$^{-/-}$CIITA$^{-/-}$ CD58$^{-/-}$ CD54$^{-/-}$ |
| | | | | | | | | 67. CFR TCR$^{neg}$ IL B2M$^{-/-}$CIITA$^{-/-}$ HLA-G |
| ✓ | ✓ | | | | ✓ | ✓ | | 68. CFR TCR$^{neg}$ CD38$^{-/-}$ B2M$^{-/-}$CIITA$^{-/-}$ |
| ✓ | ✓ | | | | ✓ | ✓ | ✓ | 69. CFR TCR$^{neg}$ CD38$^{-/-}$ B2M$^{-/-}$CIITA$^{-/-}$ CD58$^{-/-}$ |
| | | | | | | | | 70. CFR TCR$^{neg}$ CD38$^{-/-}$ B2M$^{-/-}$CIITA$^{-/-}$ CD54$^{-/-}$ |
| | | | | | | | | 71. CFR TCR$^{neg}$ CD38$^{-/-}$ B2M$^{-/-}$CIITA$^{-/-}$ CD58$^{-/-}$ CD54$^{-/-}$ |
| | | | | | | | | 72. CFR TCR$^{neg}$ CD38$^{-/-}$ B2M$^{-/-}$CIITA$^{-/-}$ HLA-G |
| ✓ | | ✓ | ✓ | ✓ | | | | 73. CFR CD16 CAR IL |
| ✓ | | ✓ | ✓ | | ✓ | | | 74. CFR CD16 CAR CD38$^{-/-}$ |
| ✓ | | ✓ | ✓ | | | ✓ | | 75. CFR CD16 CAR B2M$^{-/-}$CIITA$^{-/-}$ |
| ✓ | | ✓ | ✓ | | | ✓ | ✓ | 76. CFR CD16 CAR B2M$^{-/-}$CIITA$^{-/-}$ CD58$^{-/-}$ |
| | | | | | | | | 77. CFR CD16 CAR B2M$^{-/-}$CIITA$^{-/-}$ CD54$^{-/-}$ |
| | | | | | | | | 78. CFR CD16 CAR B2M$^{-/-}$CIITA$^{-/-}$ CD58$^{-/-}$CD54$^{-/-}$ |
| | | | | | | | | 79. CFR CD16 CAR B2M$^{-/-}$CIITA$^{-/-}$ HLA-G |
| ✓ | | ✓ | | ✓ | ✓ | | | 80. CFR CD16 IL CD38$^{-/-}$ |
| ✓ | | ✓ | | ✓ | | ✓ | | 81. CFR CD16 IL B2M$^{-/-}$CIITA$^{-/-}$ |
| ✓ | | ✓ | | ✓ | | ✓ | ✓ | 82. CFR B2M$^{-/-}$CIITA$^{-/-}$ CD58$^{-/-}$ |
| | | | | | | | | 83. CFR B2M$^{-/-}$CIITA$^{-/-}$ CD54$^{-/-}$ |
| | | | | | | | | 84. CFR B2M$^{-/-}$CIITA$^{-/-}$ CD58$^{-/-}$ CD54$^{-/-}$ |
| | | | | | | | | 85. CFR B2M$^{-/-}$CIITA$^{-/-}$ HLA-G |
| ✓ | | ✓ | | | ✓ | ✓ | | 86. CFR CD16 CD38$^{-/-}$ B2M$^{-/-}$CIITA$^{-/-}$ |
| ✓ | | ✓ | | | ✓ | ✓ | ✓ | 87. CFR CD16 CD38$^{-/-}$ B2M$^{-/-}$CIITA$^{-/-}$ CD58$^{-/-}$ |
| | | | | | | | | 88. CFR CD16 CD38$^{-/-}$ B2M$^{-/-}$CIITA$^{-/-}$ CD54$^{-/-}$ |
| | | | | | | | | 89. CFR CD16 CD38$^{-/-}$ B2M$^{-/-}$CIITA$^{-/-}$ CD58$^{-/-}$ CD54$^{-/-}$ |
| | | | | | | | | 90. CFR CD16 CD38$^{-/-}$ B2M$^{-/-}$CIITA$^{-/-}$ HLA-G |
| ✓ | | | ✓ | ✓ | ✓ | | | 91. CFR CAR IL CD38$^{-/-}$ |
| ✓ | | | ✓ | ✓ | | ✓ | | 92. CFR CAR IL B2M$^{-/-}$CIITA$^{-/-}$ |
| ✓ | | | ✓ | ✓ | | ✓ | ✓ | 93. CFR CAR IL B2M$^{-/-}$CIITA$^{-/-}$ CD58$^{-/-}$ |
| | | | | | | | | 94. CFR CAR IL B2M$^{-/-}$CIITA$^{-/-}$ CD54$^{-/-}$ |

TABLE 1-continued

| Applicable Genotypes of the Cells Provided: | | | | | | | | |
|---|---|---|---|---|---|---|---|---|
| CFR | TCR$^{neg}$ | CD16 | CAR | IL | CD38$^{-/-}$ | B2M$^{-/-}$CIITA$^{-/-}$ | HLA-G or (CD58$^{-/-}$ w/or w/o CD54$^{-/-}$) | Genotype |
| | | | | | | | | 95. CFR CAR IL B2M$^{-/-}$CIITA$^{-/-}$ CD58$^{-/-}$ CD54$^{-/-}$ |
| | | | | | | | | 96. CFR CAR IL B2M$^{-/-}$CIITA$^{-/-}$ HLA-G |
| ✓ | | | ✓ | | ✓ | ✓ | | 97. CFR CAR CD38$^{-/-}$B2M$^{-/-}$CIITA$^{-/-}$ |
| ✓ | | | ✓ | | ✓ | ✓ | ✓ | 98. CFR CAR CD38$^{-/-}$B2M$^{-/-}$CIITA$^{-/-}$CD58$^{-/-}$ |
| | | | | | | | | 99. CFR CAR CD38$^{-/-}$ B2M$^{-/-}$CIITA$^{-/-}$ CD54$^{-/-}$ |
| | | | | | | | | 100. CFR CAR CD38$^{-/-}$ B2M$^{-/-}$CIITA$^{-/-}$ CD58$^{-/-}$ CD54$^{-/-}$ |
| | | | | | | | | 101. CFR CAR CD38$^{-/-}$ B2M$^{-/-}$CIITA$^{-/-}$ HLA-G |
| ✓ | | | | ✓ | ✓ | ✓ | | 102. CFR IL CD38$^{-/-}$ B2M$^{-/-}$CIITA$^{-/-}$ |
| ✓ | | | | ✓ | ✓ | ✓ | ✓ | 103. CFR IL CD38$^{-/-}$ B2M$^{-/-}$CIITA$^{-/-}$ CD58$^{-/-}$ |
| | | | | | | | | 104. CFR IL CD38$^{-/-}$ B2M$^{-/-}$CIITA$^{-/-}$ CD54$^{-/-}$ |
| | | | | | | | | 105. CFR IL CD38$^{-/-}$ B2M$^{-/-}$CIITA$^{-/-}$ CD58$^{-/-}$ CD54$^{-/-}$ |
| | | | | | | | | 106. CFR IL CD38$^{-/-}$ B2M$^{-/-}$CIITA$^{-/-}$ HLA-G |
| ✓ | ✓ | ✓ | ✓ | ✓ | | | | 107. CFR TCR$^{neg}$ CD16 CAR IL |
| ✓ | ✓ | ✓ | ✓ | | ✓ | | | 108. CFR TCR$^{neg}$ CD16 CAR CD38$^{-/-}$ |
| ✓ | ✓ | ✓ | ✓ | | | ✓ | | 109. CFR TCR$^{neg}$ CD16 CAR B2M$^{-/-}$CIITA$^{-/-}$ |
| ✓ | ✓ | ✓ | ✓ | | | ✓ | ✓ | 110. CFR TCR$^{neg}$ CD16 B2M$^{-/-}$CIITA$^{-/-}$ CD58$^{-/-}$ |
| | | | | | | | | 111. CFR TCR$^{neg}$ CD16 B2M$^{-/-}$CIITA$^{-/-}$ CD54$^{-/-}$ |
| | | | | | | | | 112. CFR TCR$^{neg}$ CD16 B2M$^{-/-}$CIITA$^{-/-}$ CD58$^{-/-}$ CD54$^{-/-}$ |
| | | | | | | | | 113. CFR TCR$^{neg}$ CD16 B2M$^{-/-}$CIITA$^{-/-}$ HLA-G |
| ✓ | | ✓ | ✓ | ✓ | ✓ | | | 114. CFR CD16 CAR IL CD38$^{-/-}$ |
| ✓ | | ✓ | ✓ | ✓ | | ✓ | | 115. CFR CD16 CAR IL B2M$^{-/-}$CIITA$^{-/-}$ |
| ✓ | | ✓ | ✓ | ✓ | | ✓ | ✓ | 116. CFR CD16 CAR IL B2M$^{-/-}$CIITA$^{-/-}$ CD58$^{-/-}$ |
| | | | | | | | | 117. CFR CD16 CAR IL B2M$^{-/-}$CIITA$^{-/-}$ CD54$^{-/-}$ |
| | | | | | | | | 118. CFR CD16 CAR IL B2M$^{-/-}$CIITA$^{-/-}$ CD58$^{-/-}$ CD54$^{-/-}$ |
| | | | | | | | | 119. CFR CD16 CAR IL B2M$^{-/-}$CIITA$^{-/-}$ HLA-G |
| ✓ | | ✓ | | ✓ | ✓ | ✓ | | 120. CFR CD16 IL CD38$^{-/-}$ B2M$^{-/-}$CIITA$^{-/-}$ |
| ✓ | | ✓ | | ✓ | ✓ | ✓ | ✓ | 121. CFR CD16 IL CD38$^{-/-}$ B2M$^{-/-}$CIITA$^{-/-}$ CD58$^{-/-}$ |
| | | | | | | | | 122. CFR CD16 IL CD38$^{-/-}$ B2M$^{-/-}$CIITA$^{-/-}$ CD54$^{-/-}$ |
| | | | | | | | | 123. CFR CD16 IL CD38$^{-/-}$ B2M$^{-/-}$CIITA$^{-/-}$ CD58$^{-/-}$ CD54$^{-/-}$ |
| | | | | | | | | 124. CFR CD16 IL CD38$^{-/-}$ B2M$^{-/-}$CIITA$^{-/-}$ HLA-G |
| ✓ | | | ✓ | ✓ | ✓ | ✓ | | 125. CFR CAR IL CD38$^{-/-}$ B2M$^{-/-}$CIITA$^{-/-}$ |
| ✓ | | | ✓ | ✓ | ✓ | ✓ | ✓ | 126. CFR CAR IL CD38$^{-/-}$ B2M$^{-/-}$CIITA$^{-/-}$ CD58$^{-/-}$ |
| | | | | | | | | 127. CFR CAR IL CD38$^{-/-}$ B2M$^{-/-}$CIITA$^{-/-}$ CD54$^{-/-}$ |
| | | | | | | | | 128. CFR CAR IL CD38$^{-/-}$ B2M$^{-/-}$CIITA$^{-/-}$ CD58$^{-/-}$ CD54$^{-/-}$ |
| | | | | | | | | 129. CFR CAR IL CD38$^{-/-}$ B2M$^{-/-}$CIITA$^{-/-}$ HLA-G |
| ✓ | ✓ | ✓ | ✓ | ✓ | ✓ | | | 130. CFR TCR$^{neg}$ CD16 CAR IL CD38$^{-/-}$ |
| ✓ | ✓ | ✓ | ✓ | ✓ | | ✓ | | 131. CFR TCR$^{neg}$ CD16 CAR IL B2M$^{-/-}$CIITA$^{-/-}$ |
| ✓ | ✓ | ✓ | ✓ | ✓ | | ✓ | ✓ | 132. CFR TCR$^{neg}$ CD16 CAR IL B2M$^{-/-}$CIITA$^{-/-}$ CD58$^{-/-}$ |
| | | | | | | | | 133. CFR TCR$^{neg}$ CD16 CAR IL B2M$^{-/-}$CIITA$^{-/-}$ CD54$^{-/-}$ |
| | | | | | | | | 134. CFR TCR$^{neg}$ CD16 CAR IL B2M$^{-/-}$CIITA$^{-/-}$ CD58$^{-/-}$ CD54$^{-/-}$ |
| | | | | | | | | 135. CFR TCR$^{neg}$ CD16 CAR IL B2M$^{-/-}$CIITA$^{-/-}$ HLA-G |
| ✓ | | ✓ | ✓ | ✓ | ✓ | ✓ | | 136. CFR CD16 CAR IL CD38$^{-/-}$ B2M$^{-/-}$CIITA$^{-/-}$ |
| ✓ | | ✓ | ✓ | ✓ | ✓ | ✓ | ✓ | 137. CFR CD16 CAR IL CD38$^{-/-}$ B2M$^{-/-}$CIITA$^{-/-}$ CD58$^{-/-}$ |
| | | | | | | | | 138. CFR CD16 CAR IL CD38$^{-/-}$ B2M$^{-/-}$CIITA$^{-/-}$ CD54$^{-/-}$ |
| | | | | | | | | 139. CFR CD16 CAR IL CD38$^{-/-}$ B2M$^{-/-}$CIITA$^{-/-}$ CD58$^{-/-}$ CD54$^{-/-}$ |
| | | | | | | | | 140. CFR CD16 CAR IL CD38$^{-/-}$ B2M$^{-/-}$CIITA$^{-/-}$ HLA-G |
| ✓ | ✓ | ✓ | ✓ | ✓ | ✓ | ✓ | | 141. CFR TCR$^{neg}$ CD16 CAR IL CD38$^{-/-}$ B2M$^{-/-}$CIITA$^{-/-}$ |
| ✓ | ✓ | ✓ | ✓ | ✓ | ✓ | ✓ | ✓ | 142. CFR TCR$^{neg}$ CD16 CAR IL CD38$^{-/-}$ B2M$^{-/-}$CIITA$^{-/-}$ CD58$^{-/-}$ |

TABLE 1-continued

| Applicable Genotypes of the Cells Provided: | | | | | | | | |
|---|---|---|---|---|---|---|---|---|
| CFR | $TCR^{neg}$ | CD16 | CAR | IL | $CD38^{-/-}$ | $B2M^{-/-}CIITA^{-/-}$ | HLA-G or ($CD58^{-/-}$ w/or w/o $CD54^{-/-}$) | Genotype |
| | | | | | | | | 143. CFR $TCR^{neg}$ CD16 CAR IL $CD38^{-/-}$ $B2M^{-/-}CIITA^{-/-}$ $CD54^{-/-}$ |
| | | | | | | | | 144. CFR $TCR^{neg}$ CD16 CAR IL $CD38^{-/-}$ $B2M^{-/-}CIITA^{-/-}$ $CD58^{-/-}$ $CD54^{-/-}$ |
| | | | | | | | | 145. CFR $TCR^{neg}$ CD16 CAR IL $CD38^{-/-}$ $B2M^{-/-}CIITA^{-/-}$ HLA-G |

10. Antibodies for Immunotherapy

In some embodiments, in addition to the genomically engineered effector cells as provided herein, additional therapeutic agents comprising an antibody, or an antibody fragment that target an antigen associated with a condition, a disease, or an indication may be used with these effector cells in a combinational therapy. In some embodiments, the antibody is a monoclonal antibody. In some embodiments, the antibody is a humanized antibody, a humanized monoclonal antibody, or a chimeric antibody. In some embodiments, the antibody, or antibody fragment, specifically binds to a viral antigen. In other embodiments, the antibody, or antibody fragment, specifically binds to a tumor antigen. In some embodiments, the tumor or viral specific antigen activates the administered iPSC-derived effector cells to enhance their killing ability. In some embodiments, the antibodies suitable for combinational treatment as an additional therapeutic agent to the administered iPSC-derived effector cells include, but are not limited to, anti-CD20 (rituximab, veltuzumab, ofatumumab, ublituximab, ocaratuzumab, obinutuzumab, ibritumomab, ocrelizumab), anti-CD22 (inotuzumab, moxetumomab, epratuzumab), anti-HER2 (trastuzumab, pertuzumab), anti-CD52 (alemtuzumab), anti-EGFR (cetuximab), anti-GD2 (dinutuximab), anti-PDL1 (avelumab), anti-CD38 (daratumumab, isatuximab, MOR202), anti-CD123 (7G3, CSL362), anti-SLAMF7 (elotuzumab), and their humanized or Fc modified variants or fragments or their functional equivalents and biosimilars. In some embodiments, the antibodies suitable for combinational treatment as an additional therapeutic agent to the administered iPSC-derived effector cells further include bi-specific or multi-specific antibodies that target more than one antigen or epitope on a target cell or recruit effector cells (e.g., T cells, NK cells, or macrophage cells) toward target cells while targeting the target cells. Such bi-specific or multi-specific antibodies function as engagers capable of directing an effector cell (e.g., a T cell, a NK cell, an NKT cell, a B cell, a macrophage, and/or a neutrophil) to a tumor cell and activating the immune effector cell, and have shown great potential to maximize the benefits of antibody therapy. An engager is specific to at least one tumor antigen and is specific to at least one surface triggering receptor of an immune effector cell. Examples of engagers include, but are not limited to, bi-specific T cell engagers (BiTEs), bi-specific killer cell engagers (BiKEs), tri-specific killer cell engagers (TriKEs), or multi-specific killer cell engagers, or universal engagers compatible with multiple immune cell types.

In some embodiments, the iPSC-derived effector cells comprise hematopoietic lineage cells comprising a genotype listed in Table 1. In some embodiments, the iPSC-derived effector cells comprise NK cells comprising a genotype listed in Table 1. In some embodiments, the iPSC-derived effector cells comprise T cells comprising a genotype listed in Table 1. In some embodiments of a combination useful for treating liquid or solid tumors, the combination comprises iPSC-derived NK or T cells comprising at least TCR$^{neg}$ cs-CD3, and a bi-specific or multi-specific antibody that engages cells having cell surface CD3. In some embodiments, the CD3 engager comprises at least a first variable segment that binds to a cs-CD3 and a second variable segment that binds to an antigen comprising at least one of ADGRE2, carbonic anhydrase IX (CAIX), CCR1, CCR4, carcinoembryonic antigen (CEA), CD3, CD5, CD7, CD8, CD10, CD19, CD20, CD22, CD30, CD33, CD34, CD38, CD41, CD44, CD44V6, CD49f, CD56, CD70, CD74, CD99, CD123, CD133, CD138, CDS, CLEC12A, an antigen of a cytomegalovirus (CMV) infected cell, epithelial glycoprotein-2 (EGP-2), epithelial glycoprotein-40 (EGP-40), epithelial cell adhesion molecule (EpCAM), EGFRvIII, receptor tyrosine-protein kinases erb-B2,3,4, EGFIR, EGFR-VIII, ERBB folate-binding protein (FBP), fetal acetylcholine receptor (AChR), folate receptor-α, Ganglioside G2 (GD2), Ganglioside G3 (GD3), human Epidermal Growth Factor Receptor 2 (HER2), human telomerase reverse transcriptase (hTERT), ICAM-1, Integrin B7, Interleukin-13 receptor subunit alpha-2 (IL-13Rα2), κ-light chain, kinase insert domain receptor (KDR), Lewis A (CA19.9), Lewis Y (LeY), L1 cell adhesion molecule (L1-CAM), LILRB2, melanoma antigen family A 1 (MAGE-A1), MICA/B, Mucin 1 (Muc-1), Mucin 16 (Muc-16), Mesothelin (MSLN), NKCSI, NKG2D ligands, c-Met, cancer-testis antigen NY-ESO-1, oncofetal antigen (h5T4), PRAME, prostate stem cell antigen (PSCA), PRAME prostate-specific membrane antigen (PSMA), tumor-associated glycoprotein 72 (TAG-72), TIM-3, TRBC1, TRBC2, vascular endothelial growth factor R2 (VEGF-R2), Wilms tumor protein (WT-1), and/or a pathogen antigen. In some other embodiments of the combination therapy comprising the iPSC-derived cells provided herein and at least one bi-specific or multi-specific antibody that engages cells having cell surface CD3 (i.e., is an engager), said antibody is not produced by, or in, the iPSC-derived cells and is additionally administered before, with, or after the administering of the iPSC-derived cells having a genotype listed in Table 1.

In some embodiments of the CD3 engager, the engager comprises at least a first variable segment that binds to a cs-CD3 and a second variable segment that binds to an antigen comprising at least one of BCMA, CD19, CD20, CD33, CD38, CD52, CD123, CEA, EGFR, EpCAM, GD2, GPA33, HER2, MICA/B, PDL1, and/or PSMA. In yet some other embodiments of the CD3 engager, the engager comprises a second variable segment that binds to an antigen comprising at least one of CD19, CD33, CD123, CEA, EpCAM, GPA33, HER2, and/or PSMA. In still some other embodiments of the CD3 engager, the engager is at least one of: blinatumomab, catumaxomab, ertumaxomab, R06958688, AFM11, MT110/AMG 110, MT111/AMG211/MEDI-565, AMG330, MT112/BAY2010112, MOR209/ES414, MGD006/S80880, MGD007, and/or FBTA05. In one embodiment, the combination comprises a CD3 engager and iPSC-derived NK cells comprising TCR$^{neg}$ cs-CD3 and hnCD16. In one embodiment, the combination comprises a CD3 engager and iPSC-derived NK cells comprising TCR$^{neg}$ cs-CD3 and hnCD16. In some further embodiments, the iPSC-derived NK cells comprised in the combination with a CD3 engager comprise TCR$^{neg}$ cs-CD3, hnCD16, IL15, and a CAR targeting one of CD19, BCMA, CD20, CD22, CD38, CD123, HER2, CD52, EGFR, GD2, and PDL1; wherein the IL15 is co- or separately expressed with the CAR; and IL15 is in any one of the forms presented in construct Designs 1 to 7 of FIG. 3. In some particular embodiments, IL15 is in a form of construct Design 3, 4, or 7 of FIG. 3, when it is co- or separately expressed with the CAR.

11. Checkpoint Inhibitors

Checkpoints are cell molecules, often cell surface molecules, capable of suppressing or downregulating immune responses when not inhibited. It is now clear that tumors co-opt certain immune-checkpoint pathways as a major mechanism of immune resistance, particularly against T cells that are specific for tumor antigens. Checkpoint inhibitors (CIs) are antagonists capable of reducing checkpoint gene expression or gene products, or decreasing activity of checkpoint molecules, thereby blocking inhibitory checkpoints, restoring immune system function. The development of checkpoint inhibitors targeting PD1/PDL1 or CTLA4 has transformed the oncology landscape, with these agents providing long term remissions in multiple indications. However, many tumor subtypes are resistant to checkpoint blockade therapy, and relapse remains a significant concern. Thus, one aspect of the present application provides a therapeutic approach to overcome CI resistance by including genomically engineered functional iPSC-derived cells as provided herein in a combination therapy with CI. In one embodiment of the combination therapy, the iPSC-derived cells are NK cells. In another embodiment of the combination therapy, the iPSC-derived cells are T cells. In addition to exhibiting direct antitumor capacity, the derivative NK cells provided herein have been shown to resist PDL1-PD1 mediated inhibition, and to have the ability to enhance T cell migration, to recruit T cells to the tumor microenvironment, and to augment T cell activation at the tumor site. Therefore, the tumor infiltration of T cells facilitated by the functionally potent genomically engineered derivative NK cells indicate that said NK cells are capable of synergizing with T cell targeted immunotherapies, including the checkpoint inhibitors, to relieve local immunosuppression and to reduce tumor burden.

In one embodiment, the derived $TCR^{neg}$ NK cell for checkpoint inhibitor combination therapy comprises cs-CD3, and optionally one, two, three four, or more of: exogenous CD16, B2M/CIITA knockout, CAR expression, CD38 knockout, and an exogenous cell surface cytokine and/or receptor expression; wherein when B2M is knocked out, a polynucleotide encoding HLA-G or knockout of one or both of CD58 and CD54 is optionally included. In some embodiments, the derivative NK cell comprises any one of the genotypes listed in Table 1. In some embodiments, the above derivative NK cell additionally comprises disruption of at least one of TAP1, TAP2, Tapasin, NLRC5, PD1, LAG3, TIM3, RFXANK, RFX5, RFXAP, RAG1, and any gene in the chromosome 6p21 region; or introduction of at least one of HLA-E, 4-1BBL, CD3, CD4, CD8, CD47, CD113, CD131, CD137, CD80, PDL1, $A_{2A}R$, CAR, Fc receptor, an engager, and surface triggering receptor for coupling with bi-, multi-specific or universal engagers.

In another embodiment, the derived $TCR^{neg}$ T cell for checkpoint inhibitor combination therapy comprises cs-CD3, and optionally one, two, three, four or more of: exogenous CD16, B2M/CIITA knockout, CAR expression, a CD38 knockout, and an exogenous cell surface cytokine and/or receptor expression; wherein when B2M is knocked out, a polynucleotide encoding HLA-G or knockout of one or both of CD58 and CD54 is optionally included. In some embodiments, the derivative effector cell comprises any one of the genotypes listed in Table 1. In some embodiments, the above derivative effector cell additionally comprises disruption of at least one of TAP1, TAP2, Tapasin, NLRC5, PD1, LAG3, TIM3, RFXANK, RFX5, RFXAP, RAG1, and any gene in the chromosome 6p21 region; or introduction of at least one of HLA-E, 4-1BBL, CD3, CD4, CD8, CD47, CD113, CD131, CD137, CD80, PDL1, $A_{2A}R$, CAR, Fc receptor, an engager, and surface triggering receptor for coupling with bi-, multi-specific or universal engagers.

In various embodiments, the derivative effector cell is obtained from differentiating an iPSC clonal line comprising $TCR^{neg}$ cs-CD3, and optionally one, two, three, four or more of: exogenous CD16, B2M/CIITA knockout, CAR expression, CD38 knockout, and an exogenous cell surface cytokine expression; wherein when B2M is knocked out, a polynucleotide encoding HLA-G or knockout of one or both of CD58 and CD54 is optionally introduced. In some embodiments, the above-described iPSC clonal line further comprises disruption of at least one of TAP1, TAP2, Tapasin, NLRC5, PD1, LAG3, TIM3, RFXANK, RFX5, RFXAP, RAG1, and any gene in the chromosome 6p21 region; or introduction of at least one of HLA-E, 4-1BBL, CD3, CD4, CD8, CD47, CD113, CD131, CD137, CD80, PDL1, $A_{2A}R$, CAR, Fc receptor, an engager, and surface triggering receptor for coupling with bi-, multi-specific or universal engagers.

Suitable checkpoint inhibitors for combination therapy with the derivative NK or T cells as provided herein include, but are not limited to, antagonists of PD-1 (Pdcdl, CD279), PDL-1 (CD274), TIM-3 (Havcr2), TIGIT (WUCAM and Vstm3), LAG-3 (Lag3, CD223), CTLA-4 (Ctla4, CD152), 2B4 (CD244), 4-1BB (CD137), 4-1BBL (CD137L), $A_{2A}R$, BATE, BTLA, CD39 (Entpdl), CD47, CD73 (NT5E), CD94, CD96, CD160, CD200, CD200R, CD274, CEACAM1, CSF-1R, Foxpl, GARP, HVEM, IDO, EDO, TDO, LAIR-1, MICA/B, NR4A2, MAFB, OCT-2 (Pou2f2), retinoic acid receptor alpha (Rara), TLR3, VISTA, NKG2A/HLA-E, and inhibitory KIR (for example, 2DL1, 2DL2, 2DL3, 3DL1, and 3DL2).

In some embodiments, the antagonist inhibiting any of the above checkpoint molecules is an antibody. In some embodiments, the checkpoint inhibitory antibodies may be murine antibodies, human antibodies, humanized antibodies, a camel Ig, a shark heavy-chain-only antibody (VNAR), Ig NAR, chimeric antibodies, recombinant antibodies, or antibody fragments thereof. Non-limiting examples of antibody fragments include Fab, Fab', F(ab')2, F(ab')3, Fv, single chain antigen binding fragments (scFv), (scFv)2, disulfide stabilized Fv (dsFv), minibody, diabody, triabody, tetrabody, single-domain antigen binding fragments (sdAb, Nanobody), recombinant heavy-chain-only antibody (VHH), and other antibody fragments that maintain the binding specificity of the whole antibody, which may be more cost-effective to produce, more easily used, or more sensitive than the whole antibody. In some embodiments, the one, or two, or three, or more checkpoint inhibitors comprise at least one of atezolizumab (anti-PDL1 mAb), avelumab (anti-PDL1 mAb), durvalumab (anti-PDL1 mAb), tremelimumab (anti-CTLA4 mAb), ipilimumab (anti-CTLA4 mAb), IPH4102 (anti-KIR), IPH43 (anti-MICA), IPH33 (anti-TLR3), lirilumab (anti-KIR), monalizumab (anti-NKG2A), nivolumab (anti-PD1 mAb), petnbrolizumab (anti-PD1 mAb), and any derivatives, functional equivalents, or biositnilars thereof.

In some embodiments, the antagonist inhibiting any of the above checkpoint molecules is microRNA-based, as many miRNAs are found as regulators that control the expression of immune checkpoints (Dragomir et al., Cancer Biol Med. 2018, 15(2):103-115). In some embodiments, the checkpoint antagonistic miRNAs include, but are not limited to, miR-28, miR-15/16, miR-138, miR-342, miR-20b, miR-21, miR-130b, miR-34a, miR-197, miR-200c, miR-200, miR-17-5p, miR-570, miR-424, miR-155, miR-574-3p, miR-513, and miR-29c.

Some embodiments of the combination therapy with the provided iPSC-derived NK or T cells comprise at least one checkpoint inhibitor to target at least one checkpoint molecule; wherein the iPSC-derived cells have a genotype listed in Table 1. Some other embodiments of the combination therapy with the provided derivative NK or T cells comprise two, three or more checkpoint inhibitors such that two, three, or more checkpoint molecules are targeted. In some embodiments of the combination therapy comprising at least one checkpoint inhibitor and the iPSC-derived cells having a genotype listed in Table 1, said checkpoint inhibitor is an antibody, or a humanized or Fc modified variant or fragment, or a functional equivalent or biosimilar thereof, and said checkpoint inhibitor is produced by the iPSC-derived cells by expressing an exogenous polynucleotide sequence encoding said antibody, or a fragment or variant thereof. In some embodiments, the exogenous polynucleotide sequence encoding the antibody, or a fragment or a variant thereof that inhibits a checkpoint is co-expressed with a CAR, either in separate constructs or in a bi-cistronic construct comprising both the CAR and the sequence encoding the antibody, or the fragment thereof. In some further embodiments, the sequence encoding the antibody or the fragment thereof can be linked to either the 5' or the 3' end of a CAR expression construct through a self-cleaving 2A coding sequence, illustrated as, for example, CAR-2A-CI or CI-2A-CAR. As such, the coding sequences of the checkpoint inhibitor and the CAR may be in a single open reading frame (ORF). When the checkpoint inhibitor is delivered, expressed and secreted as a payload by the derivative effector cells capable of infiltrating the tumor microenvironment (TME), it counteracts the inhibitory checkpoint molecule upon engaging the TME, allowing activation of the effector cells by activating modalities such as CAR or activating receptors. In some embodiments, the checkpoint inhibitor co-expressed with CAR inhibits at least one of the checkpoint molecules: PD-1, PDL-1, TIM-3, TIGIT, LAG-3, CTLA-4, 2B4, 4-1BB, 4-1BBL, $A_{2A}$R, BATE, BTLA, CD39 (Entpdl), CD47, CD73 (NT5E), CD94, CD96, CD160, CD200, CD200R, CD274, CEACAM1, CSF-1R, Foxpl, GARP, HVEM, IDO, EDO, TDO, LAIR-1, MICA/B, NR4A2, MAFB, OCT-2 (Pou2f2), retinoic acid receptor alpha (Rara), TLR3, VISTA, NKG2A/HLA-E, and inhibitory KIR. In some embodiments, the checkpoint inhibitor co-expressed with CAR in a derivative cell having a genotype listed in Table 1 is selected from a group comprising atezolizumab, avelumab, durvalumab, tremelimumab, ipilimumab, IPH4102, IPH43, IPH33, lirilumab, monalizumab, nivolumab, pembrolizumab, and their humanized, or Fc modified variants, fragments and their functional equivalents or biosimilars. In some embodiments, the checkpoint inhibitor co-expressed with CAR is atezolizumab, or its humanized, or Fc modified variants, fragments or their functional equivalents or biosimilars. In some other embodiments, the checkpoint inhibitor co-expressed with CAR is nivolumab, or its humanized, or Fc modified variants, fragments or their functional equivalents or biosimilars. In some other embodiments, the checkpoint inhibitor co-expressed with CAR is pembrolizumab, or its humanized, or Fc modified variants, fragments or their functional equivalents or biosimilars.

In some other embodiments of the combination therapy comprising the iPSC-derived cells provided herein and at least one antibody inhibiting a checkpoint molecule, said antibody is not produced by, or in, the iPSC-derived cells and is additionally administered before, with, or after the administering of the iPSC-derived cells having a genotype listed in Table 1. In some embodiments, the administering of one, two, three or more checkpoint inhibitors in a combination therapy with the provided derivative NK or T cells are simultaneous or sequential. In one embodiment of the combination treatment comprising derived NK cells or T cells having a genotype listed in Table 1, the checkpoint inhibitor included in the treatment is one or more of atezolizumab, avelumab, durvalumab, tremelimumab, ipilimumab, IPH4102, IPH43, IPH33, lirilumab, monalizumab, nivolumab, pembrolizumab, and their humanized or Fc modified variants, fragments and their functional equivalents or biosimilars. In some embodiments of the combination treatment comprising derived NK cells or T cells having a genotype listed in Table 1, the checkpoint inhibitor included in the treatment is atezolizumab, or its humanized or Fc modified variant, fragment and its functional equivalent or biosimilar. In some embodiments of the combination treatment comprising derived NK cells or T cells having a genotype listed in Table 1, the checkpoint inhibitor included in the treatment is nivolumab, or its humanized or Fc modified variant, fragment or its functional equivalent or biosimilar. In some embodiments of the combination treatment comprising derived NK cells or T cells having a genotype listed in Table 1, the checkpoint inhibitor included in the treatment is pembrolizumab, or its humanized or Fc modified variant, fragment or its functional equivalent or biosimilar.

II. Methods for Targeted Genome Editing at Selected Locus in iPSCs

Genome editing, or genomic editing, or genetic editing, as used interchangeably herein, is a type of genetic engineering in which DNA is inserted, deleted, and/or replaced in the genome of a targeted cell. Targeted genome editing (interchangeable with "targeted genomic editing" or "targeted genetic editing") enables insertion, deletion, and/or substitution at pre-selected sites in the genome. When an endogenous sequence is deleted at the insertion site during targeted editing, an endogenous gene comprising the affected sequence may be knocked-out or knocked-down due to the sequence deletion. Therefore, targeted editing may also be used to disrupt endogenous gene expression with precision. Similarly used herein is the term "targeted integration," referring to a process involving insertion of one or more exogenous sequences, with or without deletion of an endogenous sequence at the insertion site. In comparison, randomly integrated genes are subject to position effects and silencing, making their expression unreliable and unpredictable. For example, centromeres and sub-telomeric regions are particularly prone to transgene silencing. Reciprocally, newly integrated genes may affect the surrounding endogenous genes and chromatin, potentially altering cell behavior or favoring cellular transformation. Therefore, inserting exogenous DNA in a pre-selected locus such as a safe harbor locus, or genomic safe harbor (GSH) is important for safety, efficiency, copy number control, and for reliable gene response control.

Targeted editing can be achieved either through a nuclease-independent approach, or through a nuclease-dependent approach. In the nuclease-independent targeted editing approach, homologous recombination is guided by homologous sequences flanking an exogenous polynucleotide to be inserted, through the enzymatic machinery of the host cell.

Alternatively, targeted editing could be achieved with higher frequency through specific introduction of double strand breaks (DSBs) by specific rare-cutting endonucleases. Such nuclease-dependent targeted editing utilizes DNA repair mechanisms including non-homologous end joining (NHEJ), which occurs in response to DSBs. Without a donor vector containing exogenous genetic material, the NHEJ often leads to random insertions or deletions (in/dels) of a small number of endogenous nucleotides. In comparison, when a donor vector containing exogenous genetic material flanked by a pair of homology arms is present, the exogenous genetic material can be introduced into the genome during homology directed repair (HDR) by homologous recombination, resulting in a "targeted integration." In some situations, the targeted integration site is intended to be within a coding region of a selected gene, and thus the targeted integration could disrupt the gene expression, resulting in simultaneous knock-in and knockout (KI/KO) in one single editing step.

Inserting one or more transgenes at a selected position in a gene locus of interest (GOI) to knock out the gene at the same time can be achieved. Gene loci suitable for simultaneous knock-in and knockout (KI/KO) include, but are not limited to, B2M, TAP1, TAP2, tapasin, NLRC5, CIITA, RFXANK, RFX5, RFXAP, TCR α or β constant region (TRAC or TRBC), NKG2A, NKG2D, CD38, CD58, CD54, CD56, CIS, CBL-B, SOCS2, PD1, CTLA4, LAGS, TIM3, and TIGIT. With respective site-specific targeting homology arms for position-selective insertion, it allows the transgene (s) to express either under an endogenous promoter at the site or under an exogenous promoter comprised in the construct. When two or more transgenes are to be inserted at a selected location (e.g., in a CD38 locus), a linker sequence, for example, a 2A linker or IRES, is placed between any two transgenes. The 2A linker encodes a self-cleaving peptide derived from FMDV, ERAV, PTV-I, or TaV (referred to as "F2A", "E2A", "P2A", and "T2A", respectively), allowing for separate proteins to be produced from a single translation. In some embodiments, insulators are included in the construct to reduce the risk of transgene and/or exogenous promoter silencing. The exogenous promoter may be CAG, or other constitutive, inducible, temporal-, tissue-, or cell type-specific promoters including, but not limited to CMV, EF1α, PGK, and UBC.

Available endonucleases capable of introducing specific and targeted DSBs include, but are not limited to, zinc-finger nucleases (ZFN), transcription activator-like effector nucleases (TALEN), RNA-guided CRISPR (Clustered Regular Interspaced Short Palindromic Repeats) systems. Additionally, DICE (dual integrase cassette exchange) system utilizing phiC31 and Bxb1 integrases is also a promising tool for targeted integration.

ZFNs are targeted nucleases comprising a nuclease fused to a zinc finger DNA binding domain. By a "zinc finger DNA binding domain" or "ZFBD" it is meant a polypeptide domain that binds DNA in a sequence-specific manner through one or more zinc fingers. A zinc finger is a domain of about 30 amino acids within the zinc finger binding domain whose structure is stabilized through coordination of a zinc ion. Examples of zinc fingers include, but are not limited to, $C_2H_2$ zinc fingers, $C_3H$ zinc fingers, and $C_4$ zinc fingers. A "designed" zinc finger domain is a domain not occurring in nature whose design/composition results principally from rational criteria, e.g., application of substitution rules and computerized algorithms for processing information in a database storing information of existing ZFP designs and binding data. See, for example, U.S. Pat. Nos. 6,140,081; 6,453,242; and 6,534,261; see also International Pub. Nos. WO98/53058; WO98/53059; WO98/53060; WO02/016536 and WO03/016496, the complete disclosures of which are incorporated herein by reference. A "selected" zinc finger domain is a domain not found in nature whose production results primarily from an empirical process such as phage display, interaction trap or hybrid selection. ZFNs are described in greater detail in U.S. Pat. Nos. 7,888,121 and 7,972,854, the complete disclosures of which are incorporated herein by reference. The most recognized example of a ZFN in the art is a fusion of the FokI nuclease with a zinc finger DNA binding domain.

A TALEN is a targeted nuclease comprising a nuclease fused to a TAL effector DNA binding domain. By "transcription activator-like effector DNA binding domain", "TAL effector DNA binding domain", or "TALE DNA binding domain" it is meant the polypeptide domain of TAL effector proteins that is responsible for binding of the TAL effector protein to DNA. TAL effector proteins are secreted by plant pathogens of the genus *Xanthomonas* during infection. These proteins enter the nucleus of the plant cell, bind effector-specific DNA sequences via their DNA binding domain, and activate gene transcription at these sequences via their transactivation domains. TAL effector DNA binding domain specificity depends on an effector-variable number of imperfect 34 amino acid repeats, which comprise polymorphisms at select repeat positions called repeat variable-diresidues (RVD). TALENs are described in greater detail in U.S. Pub. No. 2011/0145940, which is herein incorporated by reference. The most recognized example of a TALEN in the art is a fusion polypeptide of the FokI nuclease to a TAL effector DNA binding domain.

Another example of a targeted nuclease that finds use in the subject methods is a targeted Spo11 nuclease, a polypeptide comprising a Spo11 polypeptide having nuclease activity fused to a DNA binding domain, e.g., a zinc finger DNA binding domain, a TAL effector DNA binding domain, etc., that has specificity for a DNA sequence of interest.

Additional examples of targeted nucleases suitable for the present invention include, but are not limited to, Bxb1, phiC31, R4, PhiBT1, and Wβ/SPBc/TP901-1, whether used individually or in combination.

Other non-limiting examples of targeted nucleases include naturally occurring and recombinant nucleases; CRISPR related nucleases from families including cas, cpf, cse, csy, csn, csd, cst, csh, csa, csm, and cmr; restriction endonucleases; meganucleases; homing endonucleases, and the like.

As an exemplary example, CRISPR/Cas9 requires two major components: (1) a Cas9 endonuclease and (2) the crRNA-tracrRNA complex. When co-expressed, the two components form a complex that is recruited to a target DNA sequence comprising PAM and a seeding region near PAM. The crRNA and tracrRNA can be combined to form a chimeric guide RNA (gRNA) to guide Cas9 to target selected sequences. These two components can then be delivered to mammalian cells via transfection or transduction. When using the CRISPR/Cpf system, it requires a Cpf endonuclease (Cpf1, MAD7 and many more known in the art) and (2) the gNA, which often does not need tracrRNA, to guide Cpf endonuclease to target selected sequences.

DICE-mediated insertion uses a pair of recombinases, for example, phiC31 and Bxb1, to provide unidirectional integration of an exogenous DNA that is tightly restricted to each enzymes' own small attB and attP recognition sites. Because these target att sites are not naturally present in mammalian genomes, therefore they must be first introduced into the genome at the desired integration site. See, for example, U.S. Pub. No. 2015/0140665, the disclosure of which is incorporated herein by reference.

One aspect of the present invention provides a construct comprising one or more exogenous polynucleotides for targeted genome integration. In one embodiment, the construct further comprises a pair of homologous arms specific to a desired integration site, and the method of targeted integration comprises introducing the construct to cells to enable site specific homologous recombination by the cell host enzymatic machinery. In another embodiment, the method of targeted integration in a cell comprises introducing a construct comprising one or more exogenous polynucleotides to the cell and introducing a ZFN expression cassette comprising a DNA-binding domain specific to a desired integration site to the cell to enable a ZFN-mediated insertion. In yet another embodiment, the method of targeted integration in a cell comprises introducing a construct comprising one or more exogenous polynucleotides to the cell and introducing a TALEN expression cassette comprising a DNA-binding domain specific to a desired integration site to the cell to enable a TALEN-mediated insertion. In another embodiment, the method of targeted integration in a cell comprises introducing a construct comprising one or more exogenous polynucleotides to the cell, introducing a Cas9 expression cassette, and a gRNA comprising a guide sequence specific to a desired integration site to the cell to enable a Cas9-mediated insertion. In still another embodiment, the method of targeted integration in a cell comprises introducing a construct comprising one or more att sites of a pair of DICE recombinases to a desired integration site in the cell, introducing a construct comprising one or more exogenous polynucleotides to the cell, and introducing an expression cassette for DICE recombinases, to enable DICE-mediated targeted integration.

Promising sites for targeted integration include, but are not limited to, safe harbor loci, or genomic safe harbor (GSH), which are intragenic or extragenic regions of the human genome that, theoretically, are able to accommodate predictable expression of newly integrated DNA without adverse effects on the host cell or organism. A useful safe harbor must permit sufficient transgene expression to yield desired levels of the vector-encoded protein or non-coding RNA. A safe harbor also must not predispose cells to malignant transformation nor alter cellular functions. For an integration site to be a potential safe harbor locus, it ideally needs to meet criteria including, but not limited to: absence of disruption of regulatory elements or genes, as judged by sequence annotation; is an intergenic region in a gene dense area, or a location at the convergence between two genes transcribed in opposite directions; keep distance to minimize the possibility of long-range interactions between vector-encoded transcriptional activators and the promoters of adjacent genes, particularly cancer-related and microRNA genes; and has apparently ubiquitous transcriptional activity, as reflected by broad spatial and temporal expressed sequence tag (EST) expression patterns, indicating ubiquitous transcriptional activity. This latter feature is especially important in stem cells, where during differentiation, chromatin remodeling typically leads to silencing of some loci and potential activation of others. Within the region suitable for exogenous insertion, a precise locus chosen for insertion should be devoid of repetitive elements and conserved sequences and to which primers for amplification of homology arms could easily be designed.

Suitable sites for human genome editing, or specifically, targeted integration, include, but are not limited to, the adeno-associated virus site 1 (AAVS1), the chemokine (CC motif) receptor 5 (CCR5) gene locus and the human orthologue of the mouse ROSA26 locus. Additionally, the human orthologue of the mouse H11 locus may also be a suitable site for insertion using the composition and method of targeted integration disclosed herein. Further, collagen and HTRP gene loci may also be used as safe harbor for targeted integration. However, validation of each selected site has been shown to be necessary especially in stem cells for specific integration events, and optimization of insertion strategy including promoter election, exogenous gene sequence and arrangement, and construct design is often needed.

For targeted in/dels, the editing site is often comprised in an endogenous gene whose expression and/or function is intended to be disrupted. In one embodiment, the endogenous gene comprising a targeted in/del is associated with immune response regulation and modulation. In some other embodiments, the endogenous gene comprising a targeted in/del is associated with targeting modality, receptors, signaling molecules, transcription factors, drug target candidates, immune response regulation and modulation, or proteins suppressing engraftment, trafficking, homing, viability, self-renewal, persistence, and/or survival of stem cells and/or progenitor cells, and the derived cells therefrom.

As such, another aspect of the present invention provides a method of targeted integration in a selected locus including genome safe harbor or a preselected locus known or proven to be safe and well-regulated for continuous or temporal gene expression such as the B2M, TAP1, TAP2, Tapasin, TRAC, or CD38 locus as provided herein. In one embodiment, the genome safe harbor for the method of targeted integration comprises one or more desired integration sites comprising AAVS1, CCR5, ROSA26, collagen, HTRP, H11, beta-2 microglobulin, CD38, GAPDH, TCR or RUNX1, or other loci meeting the criteria of a genome safe harbor. In some embodiments, the targeted integration is in one or more gene loci where the knock-down or knockout of the gene as a result of the integration is desired, wherein such gene loci include, but are not limited to, B2M, TAP1, TAP2, tapasin, NLRC5, CIITA, RFXANK, RFX5, RFXAP, TCR α or β constant region (TRAC or TRBC), NKG2A, NKG2D, CD38, CD58, CD54, CD56, CIS, CBL-B, SOCS2, PD1, CTLA4, LAGS, TIM3, and TIGIT.

In one embodiment, the method of targeted integration in a cell comprises introducing a construct comprising one or more exogenous polynucleotides to the cell, and introducing a construct comprising a pair of homologous arm specific to a desired integration site and one or more exogenous sequence, to enable site specific homologous recombination by the cell host enzymatic machinery, wherein the desired integration site comprises AAVS1, CCR5, ROSA26, collagen, HTRP, H11, GAPDH, RUNX1, B2M, TAP1, TAP2, tapasin, NLRC5, CIITA, RFXANK, RFX5, RFXAP, TCR α or β constant region (TRAC or TRBC), NKG2A, NKG2D, CD38, CD58, CD54, CD56, CIS, CBL-B, SOCS2, PD1, CTLA4, LAG3, TIM3, or TIGIT.

In another embodiment, the method of targeted integration in a cell comprises introducing a construct comprising one or more exogenous polynucleotides to the cell, and introducing a ZFN expression cassette comprising a DNA-binding domain specific to a desired integration site to the cell to enable a ZFN-mediated insertion, wherein the desired integration site comprises AAVS1, CCR5, ROSA26, collagen, HTRP, H11, GAPDH, RUNX1, B2M, TAP1, TAP2, tapasin, NLRC5, CIITA, RFXANK, RFX5, RFXAP, TCR α or β constant region (TRAC or TRBC), NKG2A, NKG2D, CD38, CD58, CD54, CD56, CIS, CBL-B, SOCS2, PD1, CTLA4, LAG3, TIM3, or TIGIT. In yet another embodiment, the method of targeted integration in a cell comprises introducing a construct comprising one or more exogenous polynucleotides to the cell, and introducing a TALEN expression cassette comprising a DNA-binding domain specific to a desired integration site to the cell to enable a TALEN-mediated insertion, wherein the desired integration site comprises AAVS1, CCR5, ROSA26, collagen, HTRP, H11, GAPDH, RUNX1, B2M, TAP1, TAP2, tapasin, NLRC5, CIITA, RFXANK, RFX5, RFXAP, TCR α or β constant region (TRAC or TRBC), NKG2A, NKG2D, CD38, CD58, CD54, CD56, CIS, CBL-B, SOCS2, PD1, CTLA4, LAG3, TIM3, or TIGIT. In another embodiment, the method of targeted integration in a cell comprises introducing a construct comprising one or more exogenous polynucleotides to the cell, introducing a Cas9 expression cassette, and a gRNA comprising a guide sequence specific to a desired integration site to the cell to enable a Cas9-mediated insertion, wherein the desired integration site comprises AAVS1, CCR5, ROSA26, collagen, HTRP, H11, GAPDH, RUNX1, B2M, TAP1, TAP2, tapasin, NLRC5, CIITA, RFXANK, RFX5, RFXAP, TCR α or β constant region (TRAC or TRBC), NKG2A, NKG2D, CD38, CD58, CD54, CD56, CIS, CBL-B, SOCS2, PD1, CTLA4, LAG3, TIM3, or TIGIT. In still another embodiment, the method of targeted integration in a cell comprises introducing a construct comprising one or more att sites of a pair of DICE recombinases to a desired integration site in the cell, introducing a construct comprising one or more exogenous polynucleotides to the cell, and introducing an expression cassette for DICE recombinases, to enable DICE-mediated targeted integration, wherein the desired integration site comprises AAVS1, CCR5, ROSA26, collagen, HTRP, H11, GAPDH, RUNX1, B2M, TAP1, TAP2, tapasin, NLRC5, CIITA, RFXANK, RFX5, RFXAP, TCR a or (3 constant region (TRAC or TRBC), NKG2A, NKG2D, CD38, CD58, CD54, CD56, CIS, CBL-B, SOCS2, PD1, CTLA4, LAG3, TIM3, or TIGIT.

Further, as provided herein, the above method for targeted integration in a safe harbor is used to insert any polynucleotide of interest, for example, polynucleotides encoding safety switch proteins, targeting modality, receptors, signaling molecules, transcription factors, pharmaceutically active proteins and peptides, drug target candidates, and proteins promoting engraftment, trafficking, homing, viability, self-renewal, persistence, and/or survival of stem cells and/or progenitor cells. In some other embodiments, the construct comprising one or more exogenous polynucleotides further comprises one or more marker genes. In one embodiment, the exogenous polynucleotide in a construct of the invention is a suicide gene encoding a safety switch protein. Suitable suicide gene systems for induced cell death include, but are not limited to Caspase 9 (or caspase 3 or 7) and AP1903; thymidine kinase (TK) and ganciclovir (GCV); cytosine deaminase (CD) and 5-fluorocytosine (5-FC). Additionally, some suicide gene systems are cell type specific, for example, the genetic modification of T lymphocytes with the B-cell molecule CD20 allows their elimination upon administration of mAb Rituximab. Further, modified EGFR containing epitope recognized by cetuximab can be used to deplete genetically engineered cells when the cells are exposed to cetuximab. As such, one aspect of the invention provides a method of targeted integration of one or more suicide genes encoding safety switch proteins selected from caspase 9 (caspase 3 or 7), thymidine kinase, cytosine deaminase, modified EGFR, and B-cell CD20.

In some embodiments, one or more exogenous polynucleotides integrated by the method herein are driven by operatively linked exogenous promoters comprised in the construct for targeted integration. The promoters may be inducible, or constitutive, and may be temporal-, tissue- or cell type-specific. Suitable constitutive promoters for methods of the invention include, but are not limited to, cytomegalovirus (CMV), elongation factor 1α (EF1α), phosphoglycerate kinase (PGK), hybrid CMV enhancer/chicken β-actin (CAG) and ubiquitin C (UBC) promoters. In one embodiment, the exogenous promoter is CAG.

The exogenous polynucleotides integrated by the method provided herein may be driven by endogenous promoters in the host genome, at the integration site. In one embodiment, the method of the invention is used for targeted integration of one or more exogenous polynucleotides at the AAVS1 locus in the genome of a cell. In one embodiment, at least one integrated polynucleotide is driven by the endogenous AAVS1 promoter. In another embodiment, the method of the invention is used for targeted integration at the ROSA26 locus in the genome of a cell. In one embodiment, at least one integrated polynucleotide is driven by the endogenous ROSA26 promoter. In still another embodiment, the method of the invention is used for targeted integration at the H11 locus in the genome of a cell. In one embodiment, at least one integrated polynucleotide is driven by the endogenous H11 promoter. In another embodiment, the method of the invention is used for targeted integration at collagen locus in the genome of a cell. In one embodiment, at least one integrated polynucleotide is driven by the endogenous collagen promoter. In still another embodiment, the method of the invention is used for targeted integration at HTRP locus in the genome of a cell. In one embodiment, at least one integrated polynucleotide is driven by the endogenous HTRP promoter. Theoretically, only correct insertions at the desired location would enable gene expression of an exogenous gene driven by an endogenous promoter.

In some embodiments, the one or more exogenous polynucleotides comprised in the construct for the methods of targeted integration are driven by one promoter. In some embodiments, the construct comprises one or more linker sequences between two adjacent polynucleotides driven by the same promoter to provide greater physical separation between the moieties and maximize the accessibility to enzymatic machinery. The linker peptide of the linker sequences may consist of amino acids selected to make the physical separation between the moieties (exogenous polynucleotides, and/or the protein or peptide encoded therefrom) more flexible or more rigid depending on the relevant function. The linker sequence may be cleavable by a protease or cleavable chemically to yield separate moieties. Examples of enzymatic cleavage sites in the linker include sites for cleavage by a proteolytic enzyme, such as enterokinase, Factor Xa, trypsin, collagenase, and thrombin. In some embodiments, the protease is one which is produced naturally by the host or it is exogenously introduced. Alternatively, the cleavage site in the linker may be a site capable of being cleaved upon exposure to a selected chemical or condition, e.g., cyanogen bromide, hydroxylamine, or low pH. The optional linker sequence may serve a purpose other than the provision of a cleavage site. The linker sequence should allow effective positioning of the moiety with respect to another adjacent moiety for the moieties to function properly. The linker may also be a simple amino acid sequence of a sufficient length to prevent any steric hindrance between the moieties. In addition, the linker sequence may provide for post-translational modification including, but not limited to, e.g., phosphorylation sites, biotinylation sites, sulfation sites, γ-carboxylation sites, and the like. In some embodiments, the linker sequence is flexible so as not to hold the biologically active peptide in a single undesired conformation. The linker may be predominantly comprised of amino acids with small side chains, such as glycine, alanine, and serine, to provide for flexibility. In some embodiments about 80 or 90 percent or greater of the linker sequence comprises glycine, alanine, or serine residues, particularly glycine and serine residues. In several embodiments, a G4S linker peptide separates the end-processing and endonuclease domains of the fusion protein. In other embodiments, a 2A linker sequence allows for two separate proteins to be produced from a single translation. Suitable linker sequences can be readily identified empirically. Additionally, suitable size and sequences of linker sequences also can be determined by conventional computer modeling techniques. In one embodiment, the linker sequence encodes a self-cleaving peptide. In one embodiment, the self-cleaving peptide is 2A. In some other embodiments, the linker sequence provides an Internal Ribosome Entry Sequence (IRES). In some embodiments, any two consecutive linker sequences are different.

Method of introducing into cells a construct comprising exogenous polynucleotides for targeted integration can be achieved using a method of gene transfer to cells known per se. In one embodiment, the construct comprises backbones of viral vectors such as adenovirus vectors, adeno-associated virus vectors, retrovirus vectors, lentivirus vectors, or Sendai virus vectors. In some embodiments, the plasmid vectors are used for delivering and/or expressing the exogenous polynucleotides to target cells (e.g., pAl-11, pXTl, pRc/CMV, pRc/RSV, pcDNAI/Neo) and the like. In some other embodiments, the episomal vector is used to deliver the exogenous polynucleotide to target cells. In some embodiments, recombinant adeno-associated viruses (rAAVs) can be used for genetic engineering to introduce insertions, deletions or substitutions through homologous recombinations. Unlike lentiviruses, rAAVs do not integrate into the host genome. In addition, episomal rAAV vectors mediate homology-directed gene targeting at much higher rates compared to transfection of conventional targeting plasmids. In some embodiments, an AAV6 or AAV2 vector is used to introduce insertions, deletions or substitutions in a target site in the genome of iPSCs. In some embodiments, the genomically modified iPSCs and its derivative cells obtained using the methods and compositions herein comprise at least one genotype listed in Table 1.

III. Method of Obtaining and Maintaining Genome-Engineered iPSCs

The present invention provides a method of obtaining and maintaining genome-engineered iPSCs comprising one or more targeted editing at one or more desired sites, wherein the targeted editing remains intact and functional in expanded genome-engineered iPSCs or the iPSC-derived non-pluripotent cells at the respective selected editing site. The targeted editing introduces into the genome of the iPSC, and the derivative cells therefrom, insertions, deletions, and/or substitutions, i.e., targeted integration and/or in/dels at selected sites. In comparison to direct engineering of patient-sourced, peripheral blood originated primary effector cells, the many benefits of obtaining genomically engineered iPSC derived through editing and differentiating iPSCs as provided herein include, but are not limited to: unlimited source for engineered effector cells; no need for repeated manipulation of the effector cells especially when multiple engineered modalities are involved; the obtained effector cells are rejuvenated for having elongated telomere and experiencing less exhaustion; the effector cell population is homogeneous in terms of editing site, copy number, and void of allelic variation, random mutations and expression variegation, largely due to the enabled clonal selection in engineered iPSCs as provided herein.

In particular embodiments, the genome-engineered iPSCs comprising one or more targeted editing at one or more selected sites are maintained, passaged and expanded as single cells for an extended period in the cell culture medium shown in Table 2 as Fate Maintenance Medium (FMM), wherein the iPSCs retain the targeted editing and functional modification at the selected site(s). The components of the medium may be present in the medium in amounts within an optimal range shown in Table 2. The iPSCs cultured in FMM have been shown to continue to maintain their undifferentiated, and ground or naïve, profile; genomic stability without the need for culture cleaning or selection; and are readily to give rise to all three somatic lineages, in vitro differentiation via embryoid bodies or monolayer (without formation of embryoid bodies); and in vivo differentiation by teratoma formation. See, for example, International Pub. No. WO2015/134652, the disclosure of which is incorporated herein by reference.

TABLE 2

Exemplary media for iPSC reprogramming and maintenance

| Conventional hESC Medium (Conv.) | Fate Reprogramming Medium (FRM) | Fate Maintenance Medium (FMM) |
|---|---|---|
| DMEM/F12 | DMEM/F12 | DMEM/F12 |
| Knockout Serum Replacement (20%) | Knockout Serum Replacement (20%) | Knockout Serum Replacement (20%) |
| | N2 | |
| | B27 | |
| Glutamine | Glutamine | Glutamine (1x) |
| Non-Essential Amino Acids (1x) | Non-Essential Amino Acids (1x) | Non-Essential Amino Acids (1x) |
| β-mercaptoethanol (100 μM) | β-mercaptoethanol (100 μM) | β-mercaptoethanol (100 μM) |
| bFGF (0.2-50 ng/ml) | bFGF (2-500 ng/ml) | bFGF (2-500 ng/mL) |
| | LIF (0.2-50 ng/ml) | LIF (0.2-50 ng/mL) |
| | Thiazovivin (0.1-25 μM) | Thiazovivin (0.1-25 μM) |
| | PD0325901 (0.005-2 μM) | PD0325901 (0.005-2 μM) |
| | CHIR99021 (0.02-5 μM) | CHIR99021 (0.02-5 μM) |
| | SB431542 (0.04-10 μM) | |
| In combination with MEF feeder cells | Feeder-free, in combination with Matrigel ™ or Vitronectin | |

In some embodiments, the genome-engineered iPSCs comprising one or more targeted integrations and/or in/dels are maintained, passaged and expanded in a medium comprising a MEK inhibitor, a GSK3 inhibitor, and a ROCK inhibitor, and free of, or essentially free of, TGFβ receptor/ALK5 inhibitors, wherein the iPSCs retain the intact and functional targeted editing at the selected sites.

Another aspect of the invention provides a method of generating genome-engineered iPSCs through targeted editing of iPSCs; or through first generating genome-engineered non-pluripotent cells by targeted editing, and then reprogramming the selected/isolated genome-engineered non-pluripotent cells to obtain iPSCs comprising the same targeted editing as the non-pluripotent cells. A further aspect of the invention provides genome-engineering non-pluripotent cells which are concurrently undergoing reprogramming by introducing targeted integration and/or targeted in/dels to the cells, wherein the contacted non-pluripotent cells are under sufficient conditions for reprogramming, and wherein the conditions for reprogramming comprise contacting non-pluripotent cells with one or more reprogramming factors and small molecules. In various embodiments of the method for concurrent genome-engineering and reprogramming, the targeted integrations and/or targeted in/dels may be introduced to the non-pluripotent cells prior to, or essentially concomitantly with, initiating reprogramming by contacting the non-pluripotent cells with one or more reprogramming factors and optionally small molecules.

In some embodiments, to concurrently genome-engineer and reprogram non-pluripotent cells, the targeted integrations and/or in/dels may also be introduced to the non-pluripotent cells after the multi-day process of reprogramming is initiated by contacting the non-pluripotent cells with one or more reprogramming factors and small molecules, and wherein the vectors carrying the constructs are introduced before the reprogramming cells present stable expression of one or more endogenous pluripotent genes including but not limited to SSEA4, Tra181 and CD30.

In some embodiments, the reprogramming is initiated by contacting the non-pluripotent cells with at least one reprogramming factor, and optionally a combination of a TGFβ receptor/ALK inhibitor, a MEK inhibitor, a GSK3 inhibitor and a ROCK inhibitor (FRM; Table 2). In some embodiments, the genome-engineered iPSCs through any methods above are further maintained and expanded using a mixture comprising a combination of a MEK inhibitor, a GSK3 inhibitor and a ROCK inhibitor (FMM; Table 2).

In some embodiments of the method of generating genome-engineered iPSCs, the method comprises: genomic engineering an iPSC by introducing one or more targeted integrations and/or in/dels into iPSCs to obtain genome-engineered iPSCs having at least one genotype listed in Table 1. Alternatively, the method of generating genome-engineered iPSCs comprises: (a) introducing one or more targeted edits into non-pluripotent cells to obtain genome-engineered non-pluripotent cells comprising targeted integrations and/or in/dels at selected sites, and (b) contacting the genome-engineered non-pluripotent cells with one or more reprogramming factors, and optionally a small molecule composition comprising a TGFβ receptor/ALK inhibitor, a MEK inhibitor, a GSK3 inhibitor and/or a ROCK inhibitor, to obtain genome-engineered iPSCs comprising targeted integrations and/or in/dels at selected sites. Alternatively, the method of generating genome-engineered iPSCs comprises: (a) contacting non-pluripotent cells with one or more reprogramming factors, and optionally a small molecule composition comprising a TGFβ receptor/ALK inhibitor, a MEK inhibitor, a GSK3 inhibitor and/or a ROCK inhibitor to initiate the reprogramming of the non-pluripotent cells; (b) introducing one or more targeted integration and/or in/dels into the reprogramming non-pluripotent cells for genome-engineering; and (c) obtaining genome-engineered iPSCs comprising targeted integrations and/or in/dels at selected sites. Any of the above methods may further comprise single cell sorting genome-engineered iPSCs to obtain a clonal iPSC. Through clonal expansion of this genome-engineered iPSC, a master cell bank is generated to comprise single cell sorted and expanded clonal engineered iPSCs having at least one phenotype as provided herein in Table 1. The master cell bank is subsequently cryopreserved, providing a platform for additional iPSC engineering and a renewable source for manufacturing off-the-shelf, engineered, homogeneous cell therapy products, which are well-defined and uniform in composition, and can be mass produced at significant scale in a cost-effective manner.

The reprogramming factors are selected from the group consisting of OCT4, SOX2, NANOG, KLF4, LIN28, C-MYC, ECAT1, UTF1, ESRRB, SV40LT, HESRG, CDH1, TDGF1, DPPA4, DNMT3B, ZIC3, L1TD1, and any combinations thereof as disclosed in International Pub. Nos. WO2015/134652 and WO2017/066634, the disclosures of which are incorporated herein by reference. The one or more reprogramming factors may be in the form of polypeptides. The reprogramming factors may also be in the form of polynucleotides, and thus are introduced to the non-pluripotent cells by vectors such as, a retrovirus, a Sendai virus, an adenovirus, an episome, a plasmid, and a mini-circle. In particular embodiments, the one or more polynucleotides encoding at least one reprogramming factor are introduced by a lentiviral vector. In some embodiments, the one or more polynucleotides are introduced by an episomal vector. In various other embodiments, the one or more polynucleotides are introduced by a Sendai viral vector. In some embodiments, the one or more polynucleotides are introduced by a combination of plasmids. See, for example, International Pub. No. WO2019/075057, the disclosure of which is incorporated herein by reference.

In some embodiments, the non-pluripotent cells are transferred with multiple constructs comprising different exogenous polynucleotides and/or different promoters by multiple vectors for targeted integration at the same or different selected sites. These exogenous polynucleotides may comprise a suicide gene, or a gene encoding targeting modality, receptors, signaling molecules, transcription factors, pharmaceutically active proteins and peptides, drug target candidates, or a gene encoding a protein promoting engraftment, trafficking, homing, viability, self-renewal, persistence, and/or survival of the iPSCs or derivative cells therefrom. In some embodiments, the exogenous polynucleotides encode RNA, including but not limited to siRNA, shRNA, miRNA and antisense nucleic acids. These exogenous polynucleotides may be driven by one or more promoters selected form the group consisting of constitutive promoters, inducible promoters, temporal-specific promoters, and tissue or cell type specific promoters. Accordingly, the polynucleotides are expressible when under conditions that activate the promoter, for example, in the presence of an inducing agent or in a particular differentiated cell type. In some embodiments, the polynucleotides are expressed in iPSCs and/or in cells differentiated from the iPSCs. In one embodiment, one or more suicide gene is driven by a constitutive promoter, for example Caspase-9 driven by CAG. These constructs comprising different exogenous polynucleotides and/or different promoters can be transferred to non-pluripotent cells either simultaneously or consecutively. The non-pluripotent cells subjected to targeted integration of multiple constructs can simultaneously contact the one or more reprogramming factors to initiate the reprogramming process concurrently with the genomic engineering, thereby obtaining genome-engineered iPSCs comprising multiple targeted integrations in the same pool of cells. As such, this robust method enables a concurrent reprogramming and engineering strategy to derive a clonal genomically engineered hiPSC with multiple modalities integrated to one or more selected target sites. In some embodiments, the genomically modified iPSCs and their derivative cells obtained using the methods and composition herein comprise at least one genotype listed in Table 1.

IV. A method of Obtaining Genetically-Engineered Effector Cells by Differentiating Genome-Engineered iPSC A further aspect of the present invention provides a method of in vivo differentiation of genome-engineered iPSC by teratoma formation, wherein the differentiated cells derived in vivo from the genome-engineered iPSCs retain the intact and functional targeted editing including targeted integrations and/or in/dels at the desired site(s). In some embodiments, the differentiated cells derived in vivo from the genome-engineered iPSCs via teratoma comprise one or more inducible suicide genes integrated at one or more desired site comprising AAVS1, CCR5, ROSA26, collagen, HTRP H11, beta-2 microglobulin, CD38, GAPDH, TCR or RUNX1, or other loci meeting the criteria of a genome safe harbor. In some other embodiments, the differentiated cells derived in vivo from the genome-engineered iPSCs via teratoma comprise polynucleotides encoding a targeting modality, or encoding proteins promoting trafficking, homing, viability, self-renewal, persistence, and/or survival of stem cells and/or progenitor cells. In some embodiments, the differentiated cells derived in vivo from the genome-engineered iPSCs via teratoma comprising one or more inducible suicide genes further comprise one or more in/dels in endogenous genes associated with immune response regulation and mediation. In some embodiments, the in/del is comprised in one or more endogenous checkpoint genes. In some embodiments, the in/del is comprised in one or more endogenous T cell receptor genes. In some embodiments, the in/del is comprised in one or more endogenous MHC class I suppressor genes. In some embodiments, the in/del is comprised in one or more endogenous genes associated with the major histocompatibility complex. In some embodiments, the in/del is comprised in one or more endogenous genes including, but not limited to, AAVS1, CCR5, ROSA26, collagen, HTRP, H11, GAPDH, RUNX1, B2M, TAP1, TAP2, tapasin, NLRC5, CIITA, RFXANK, RFX5, RFXAP, TCR α or β constant region (TRAC or TRBC), NKG2A, NKG2D, CD38, CD58, CD54, CD56, CIS, CBL-B, SOCS2, PD1, CTLA4, LAGS, TIM3, or TIGIT. In one embodiment, the genome-engineered iPSC comprising one or more exogenous polynucleotides at selected site(s) further comprises a targeted editing in B2M (beta-2-microglobulin) encoding gene.

In particular embodiments, the genome-engineered iPSCs comprising one or more genetic modifications as provided herein are used to derive hematopoietic cell lineages or any other specific cell types in vitro, wherein the derived non-pluripotent cells retain the functional genetic modifications including targeted editing at the selected site(s). In some embodiments, the genome-engineered iPSCs used to derive hematopoietic cell lineages or any other specific cell types in vitro are master cell bank cells that are cryopreserved and thawed right before their usage. In one embodiment, the genome-engineered iPSC-derived cells include, but are not limited to, mesodermal cells with definitive hemogenic endothelium (HE) potential, definitive HE, CD34 hematopoietic cells, hematopoietic stem and progenitor cells, hematopoietic multipotent progenitors (MPP), T cell progenitors, NK cell progenitors, myeloid cells, neutrophil progenitors, T cells, NKT cells, NK cells, B cells, neutrophils, dendritic cells, and macrophages, wherein these cells derived from the genome-engineered iPSCs retain the functional genetic modifications including targeted editing at the desired site(s).

Applicable differentiation methods and compositions for obtaining iPSC-derived hematopoietic cell lineages include those depicted in, for example, International Pub. No. WO2017/078807, the disclosure of which is incorporated herein by reference. As provided, the methods and compositions for generating hematopoietic cell lineages are through definitive hemogenic endothelium (HE) derived from pluripotent stem cells, including hiPSCs, under serum-free, feeder-free, and/or stromal-free conditions and in a scalable and monolayer culturing platform without the need of EB formation. Cells that may be differentiated according to the provided methods range from pluripotent stem cells, to progenitor cells that are committed to particular terminally differentiated cells and transdifferentiated cells, and to cells of various lineages directly transitioned to hematopoietic fate without going through a pluripotent intermediate. Similarly, the cells that are produced by differentiating stem cells range from multipotent stem or progenitor cells, to terminally differentiated cells, and to all intervening hematopoietic cell lineages.

In some embodiments, the methods for differentiating and expanding cells of the hematopoietic lineage from pluripotent stem cells in monolayer culturing comprise contacting the pluripotent stem cells with a BMP pathway activator, and optionally, bFGF. As provided, the pluripotent stem cell-derived mesodermal cells are obtained and expanded without forming embryoid bodies from pluripotent stem cells. The mesodermal cells are then subjected to contact with a BMP pathway activator, bFGF, and a WNT pathway activator to obtain expanded mesodermal cells having definitive hemogenic endothelium (HE) potential without forming embryoid bodies from the pluripotent stem cells. By subsequent contact with bFGF, and optionally, a ROCK inhibitor, and/or a WNT pathway activator, the mesodermal cells having definitive HE potential are differentiated to definitive HE cells, which are also expanded during differentiation.

In some embodiments, the methods provided herein for obtaining cells of the hematopoietic lineage are superior to EB-mediated pluripotent stem cell differentiation, because EB formation leads to modest to minimal cell expansion, does not allow monolayer culturing which is important for many applications requiring homogeneous expansion, and homogeneous differentiation of the cells in a population, and is laborious and low efficiency.

In some embodiments, the provided monolayer differentiation platform facilitates differentiation towards definitive hemogenic endothelium resulting in the derivation of hematopoietic stem cells and differentiated progeny such as T, B, NKT and NK cells. The monolayer differentiation strategy combines enhanced differentiation efficiency with large-scale expansion enables the delivery of therapeutically relevant number of pluripotent stem cell-derived hematopoietic cells for various therapeutic applications. Further, the monolayer culturing using the methods provided herein leads to functional hematopoietic lineage cells that enable full range of in vitro differentiation, ex vivo modulation, and in vivo long term hematopoietic self-renewal, reconstitution and engraftment. As provided, the iPSC-derived hematopoietic lineage cells include, but are not limited to, definitive hemogenic endothelium, hematopoietic multipotent progenitor cells, hematopoietic stem and progenitor cells, T cell progenitors, NK cell progenitors, T cells, NK cells, NKT cells, B cells, macrophages, and neutrophils.

In some embodiments, the method for directing differentiation of pluripotent stem cells into cells of a definitive hematopoietic lineage comprises: (i) contacting pluripotent stem cells with a composition comprising a BMP activator, and optionally bFGF, to initiate differentiation and expansion of mesodermal cells from the pluripotent stem cells; (ii) contacting the mesodermal cells with a composition comprising a BMP activator, bFGF, and a GSK3 inhibitor, wherein the composition is optionally free of TGFβ receptor/ALK inhibitor, to initiate differentiation and expansion of mesodermal cells having definitive HE potential from the mesodermal cells; (iii) contacting the mesodermal cells having definitive HE potential with a composition comprising a ROCK inhibitor; one or more growth factors and cytokines selected from the group consisting of bFGF, VEGF, SCF, IGF, EPO, IL6, and IL11; and optionally, a Wnt pathway activator, wherein the composition is optionally free of TGFβ receptor/ALK inhibitor, to initiate differentiation and expansion of definitive hemogenic endothelium from pluripotent stem cell-derived mesodermal cells having definitive hemogenic endothelium potential.

In some embodiments, the method further comprises contacting pluripotent stem cells with a composition comprising a MEK inhibitor, a GSK3 inhibitor, and a ROCK inhibitor, wherein the composition is free of TGFβ receptor/ALK inhibitors, to seed and expand the pluripotent stem cells. In some embodiments, the pluripotent stem cells are iPSCs, or naïve iPSCs, or iPSCs comprising one or more genetic imprints; and the one or more genetic imprints comprised in the iPSC are retained in the hematopoietic cells differentiated therefrom. In some embodiments of the method for directing differentiation of pluripotent stem cells into cells of a hematopoietic lineage, the differentiation of the pluripotent stem cells into cells of hematopoietic lineage is void of generation of embryoid bodies and is in a monolayer culturing form.

In some embodiments of the above method, the obtained pluripotent stem cell-derived definitive hemogenic endothelium cells are $CD34^+$. In some embodiments, the obtained definitive hemogenic endothelium cells are $CD34^+CD43^-$. In some embodiments, the definitive hemogenic endothelium cells are $CD34^+CD43^-CXCR4^-CD73^-$. In some embodiments, the definitive hemogenic endothelium cells are $CD34^+CXCR4^-CD73^-$. In some embodiments, the definitive hemogenic endothelium cells are $CD34^+CD43^-CD93^-$. In some embodiments, the definitive hemogenic endothelium cells are $CD34^+CD93^-$.

In some embodiments of the above method, the method further comprises (i) contacting pluripotent stem cell-derived definitive hemogenic endothelium with a composition comprising a ROCK inhibitor; one or more growth factors and cytokines selected from the group consisting of VEGF, bFGF, SCF, Flt3L, TPO, and IL7; and optionally a BMP activator; to initiate the differentiation of the definitive hemogenic endothelium to pre-T cell progenitors; and optionally, (ii) contacting the pre-T cell progenitors with a composition comprising one or more growth factors and cytokines selected from the group consisting of SCF, Flt3L, and IL7, but free of one or more of VEGF, bFGF, TPO, BMP activators and ROCK inhibitors, to initiate the differentiation of the pre-T cell progenitors to T cell progenitors or T cells. In some embodiments of the method, the pluripotent stem cell-derived T cell progenitors are $CD34^+CD45^+CD7^+$. In some embodiments of the method, the pluripotent stem cell-derived T cell progenitors are $CD45^+CD7^+$.

In yet some embodiments of the above method for directing differentiation of pluripotent stem cells into cells of a hematopoietic lineage, the method further comprises: (i) contacting pluripotent stem cell-derived definitive hemogenic endothelium with a composition comprising a ROCK inhibitor; one or more growth factors and cytokines selected from the group consisting of VEGF, bFGF, SCF, Flt3L, TPO, IL3, IL7, and IL15; and optionally, a BMP activator, to initiate differentiation of the definitive hemogenic endothelium to pre-NK cell progenitor; and optionally, (ii) contacting pluripotent stem cells-derived pre-NK cell progenitors with a composition comprising one or more growth factors and cytokines selected from the group consisting of SCF, Flt3L, IL3, IL7, and IL15, wherein the medium is free of one or more of VEGF, bFGF, TPO, BMP activators and ROCK inhibitors, to initiate differentiation of the pre-NK cell progenitors to NK cell progenitors or NK cells. In some embodiments, the pluripotent stem cell-derived NK progenitors are $CD3^-CD45^+CD56^+CD7^+$. In some embodiments, the pluripotent stem cell-derived NK cells are $CD3^-CD45^+CD56^+$, and optionally further defined by $NKp46^+$, $CD57^+$ and $CD16^+$.

Therefore, using the above differentiation methods, one may obtain one or more populations of iPSC-derived hematopoietic cells that are: (i) $CD34^+$ HE cells (iCD34), using one or more culture medium selected from iMPP-A, iTC-A2, iTC-B2, iNK-A2, and iNK-B2; (ii) definitive hemogenic endothelium (iHE), using one or more culture medium selected from iMPP-A, iTC-A2, iTC-B2, iNK-A2, and iNK-B2; (iii) definitive HSCs, using one or more culture medium selected from iMPP-A, iTC-A2, iTC-B2, iNK-A2, and iNK-B2; (iv) multipotent progenitor cells (iMPP), using iMPP-A; (v) T cell progenitors (ipro-T), using one or more culture medium selected from iTC-A2, and iTC-B2; (vi) T cells (iTC), using iTC-B2; (vii) NK cell progenitors (ipro-NK), using one or more culture medium selected from iNK-A2, and iNK-B2; and/or (viii) NK cells (iNK), and iNK-B2. In some embodiments, the medium:

a. iCD34-C comprises a ROCK inhibitor, one or more growth factors and cytokines selected from the group consisting of bFGF, VEGF, SCF, IL6, IL11, IGF, and EPO, and optionally, a Wnt pathway activator; and is free of TGFβ receptor/ALK inhibitor;
b. iMPP-A comprises a BMP activator, a ROCK inhibitor, and one or more growth factors and cytokines selected from the group consisting of TPO, IL3, GMCSF, EPO, bFGF, VEGF, SCF, IL6, Flt3L and IL11;
c. iTC-A2 comprises a ROCK inhibitor; one or more growth factors and cytokines selected from the group consisting of SCF, Flt3L, TPO, and IL7; and optionally, a BMP activator;
d. iTC-B2 comprises one or more growth factors and cytokines selected from the group consisting of SCF, Flt3L, and IL7;
e. iNK-A2 comprises a ROCK inhibitor, and one or more growth factors and cytokines selected from the group consisting of SCF, Flt3L, TPO, IL3, IL7, and IL15; and optionally, a BMP activator, and
f. iNK-B2 comprises one or more growth factors and cytokines selected from the group consisting of SCF, Flt3L, IL7 and IL15.

In some embodiments, the genome-engineered iPSC-derived cells obtained from the above methods comprise one or more inducible suicide gene integrated at one or more desired integration sites comprising AAVS1, CCR5, ROSA26, collagen, HTRP, H11, GAPDH, RUNX1, B2M, TAP1, TAP2, tapasin, NLRC5, CIITA, RFXANK, RFX5, RFXAP, TCR α or β constant region (TRAC or TRBC), NKG2A, NKG2D, CD38, CD58, CD54, CD56, CIS, CBL-B, SOCS2, PD1, CTLA4, LAGS, TIM3, or TIGIT, or other loci meeting the criteria of a genome safe harbor. In some other embodiments, the genome-engineered iPSC-derived cells comprise polynucleotides encoding safety switch proteins, targeting modality, receptors, signaling molecules, transcription factors, pharmaceutically active proteins and peptides, drug target candidates, or proteins promoting trafficking, homing, viability, self-renewal, persistence, and/or survival of stem cells and/or progenitor cells. In some embodiments, the genome-engineered iPSC-derived cells comprising one or more suicide genes further comprise one or more in/dels comprised in one or more endogenous genes associated with immune response regulation and mediation, including, but not limited to, checkpoint genes, endogenous T cell receptor genes, and WIC class I suppressor genes. In one embodiment, the genome-engineered iPSC-derived cells comprising one or more suicide genes further comprise an in/del in B2M gene, wherein the B2M is knocked out.

Additionally, applicable dedifferentiation methods and compositions for obtaining genomic-engineered hematopoietic cells of a first fate to genomic-engineered hematopoietic cells of a second fate include those depicted in, for example, International Pub. No. WO2011/159726, the disclosure of which is incorporated herein by reference. Methods and compositions provided therein allow partially reprogramming a starting non-pluripotent cell to a non-pluripotent intermediate cell by limiting the expression of endogenous Nanog gene during reprogramming; and subjecting the non-pluripotent intermediate cell to conditions for differentiating the intermediate cell into a desired cell type. In some embodiments, the genomically modified iPSCs and their derivative cells obtained using the methods and composition herein comprise at least one genotype listed in Table 1.

V. Therapeutic Use of Derivative Immune Cells with Functional Modalities Differentiated from Genetically Engineered iPSCs The present invention provides, in some embodiments, a composition comprising an isolated population or subpopulation functionally enhanced derivative immune cells that have been differentiated from genomically engineered iPSCs using the methods and compositions as disclosed. In some embodiments, the iPSCs of the composition comprise one or more targeted genetic edits such as those listed in Table 1, which are retainable in the iPSC-derived immune cells, wherein the genetically engineered iPSCs and derivative cells therefrom are suitable for cell-based adoptive therapies. In one embodiment, the isolated population or subpopulation of genetically engineered immune cells of the composition comprises iPSC-derived CD34 cells. In one embodiment, the isolated population or subpopulation of genetically engineered immune cells of the composition comprises iPSC-derived HSC cells. In one embodiment, the isolated population or subpopulation of genetically engineered immune cells of the composition comprises iPSC-derived proT or T cells. In one embodiment, the isolated population or subpopulation of genetically engineered immune cells of the composition comprises iPSC-derived proNK or NK cells. In one embodiment, the isolated population or subpopulation of genetically engineered immune cells of the composition comprises iPSC-derived immune regulatory cells or myeloid derived suppressor cells (MDSCs). In some embodiments of the composition, the iPSC-derived genetically engineered immune cells are further modulated ex vivo for improved therapeutic potential. In one embodiment of the composition, an isolated population or subpopulation of genetically engineered immune cells that have been derived from iPSC comprises an increased number or ratio of naïve T cells, stem cell memory T cells, and/or central memory T cells. In one embodiment of the composition, the isolated population or subpopulation of genetically engineered immune cell that have been derived from iPSCs comprises an increased number or ratio of type I NKT cells. In another embodiment of the composition, the isolated population or subpopulation of genetically engineered immune cells that have been derived from iPSCs comprises an increased number or ratio of adaptive NK cells. In some embodiments of the composition, the isolated population or subpopulation of genetically engineered CD34 cells, HSC cells, T cells, NK cells, or myeloid derived suppressor cells derived from iPSCs are allogeneic. In some other embodiments of the composition, the isolated population or subpopulation of genetically engineered CD34 cells, HSC cells, T cells, NK cells, or MDSC derived from iPSCs are autogenic.

In some embodiments of the composition, the iPSC for differentiation comprises genetic imprints selected to convey desirable therapeutic attributes in effector cells, provided that cell development biology during differentiation is not disrupted, and provided that the genetic imprints are retained and functional in the differentiated hematopoietic cells derived from said iPSC.

In some embodiments of the composition, the genetic imprints of the pluripotent stem cells comprise (i) one or more genetically modified modalities obtained through genomic insertion, deletion or substitution in the genome of the pluripotent cells during or after reprogramming a non-pluripotent cell to iPSC; or (ii) one or more retainable therapeutic attributes of a source specific immune cell that is donor-, disease-, or treatment response-specific, and wherein the pluripotent cells are reprogrammed from the source specific immune cell, wherein the iPSC retain the source therapeutic attributes, which are also comprised in the iPSC-derived hematopoietic lineage cells.

In some embodiments of the composition, the genetically modified modalities comprise one or more of: safety switch proteins, targeting modalities, receptors, signaling molecules, transcription factors, pharmaceutically active proteins and peptides, drug target candidates; or proteins promoting engraftment, trafficking, homing, viability, self-renewal, persistence, immune response regulation and modulation, and/or survival of the iPSCs or derivative cells therefrom. In some embodiments of the composition, the genetically modified iPSC and the derivative cells therefrom comprise a genotype listed in Table 1. In some other embodiments of the composition, the genetically modified iPSC and the derivative cells therefrom comprising a genotype listed in Table 1 further comprise additional genetically modified modalities comprising (1) disruption of one or more of TAP1, TAP2, Tapasin, NLRC5, PD1, LAG3, TIM3, RFXANK, CIITA, RFX5, or RFXAP, RAG1, and any gene in the chromosome 6p21 region; and (2) introduction of HLA-E, 4-1BBL, CD3, CD4, CD8, CD47, CD113, CD131, CD137, CD80, PDL1, $A_{2A}R$, CAR, Fc receptor, or surface triggering receptors for coupling with bi- or multi-specific or universal engagers.

In still some other embodiments of the composition, the hematopoietic lineage cells comprise the therapeutic attributes of the source specific immune cell relating to a combination of at least two of the following: (i) one or more antigen targeting receptor expression; (ii) modified HLA; (iii) resistance to tumor microenvironment; (iv) recruitment of bystander immune cells and immune modulations; (v) improved on-target specificity with reduced off-tumor effect; and (vi) improved homing, persistence, cytotoxicity, or antigen escape rescue.

In some embodiments of the composition, the iPSC-derived hematopoietic cells comprising a genotype listed in Table 1 express at least one cytokine and/or its receptor comprising IL2, IL4, IL6, IL7, IL9, IL10, IL11, IL12, IL15, IL18, or IL21, or any modified protein thereof, and express at least a CAR. In some embodiments, the engineered expression of the cytokine(s) and the CAR(s) is NK cell specific. In some other embodiments of the composition, the engineered expression of the cytokine(s) and the CAR(s) is T cell specific. In one embodiment, the CAR comprises a CD38 binding domain. In some embodiments, the iPSC derivative hematopoietic effector cells are antigen specific. In some embodiments, the antigen specific derivative effector cells target a liquid tumor. In some embodiments, the antigen specific derivative effector cells target a solid tumor. In some embodiments, the antigen specific iPSC derivative hematopoietic effector cells are capable of rescuing tumor antigen escape.

A variety of diseases may be ameliorated by introducing immune cells or compositions according to some embodiments of the invention to a subject suitable for adoptive cell therapy. In some embodiments, the iPSC derivative hematopoietic cells or the compositions as provided are for allogeneic adoptive cell therapies. Additionally, the present invention provides, in some embodiments, therapeutic use of the above immune cells or therapeutic compositions by introducing the cells or compositions to a subject suitable for adoptive cell therapy, wherein the subject has an autoimmune disorder; a hematological malignancy; a solid tumor; or an infection associated with HIV, RSV, EBV, CMV, adenovirus, or BK polyomavirus. Examples of hematological malignancies include, but are not limited to, acute and chronic leukemias (acute myelogenous leukemia (AML), acute lymphoblastic leukemia (ALL), chronic myelogenous leukemia (CIVIL), lymphomas, non-Hodgkin lymphoma (NHL), Hodgkin's disease, multiple myeloma, and myelodysplastic syndromes. Examples of solid cancers include, but are not limited to, cancer of the brain, prostate, breast, lung, colon, uterus, skin, liver, bone, pancreas, ovary, testes, bladder, kidney, head, neck, stomach, cervix, rectum, larynx, and esophagus. Examples of various autoimmune disorders include, but are not limited to, alopecia areata, autoimmune hemolytic anemia, autoimmune hepatitis, dermatomyositis, diabetes (type 1), some forms of juvenile idiopathic arthritis, glomerulonephritis, Graves' disease, Guillain-Barré syndrome, idiopathic thrombocytopenic purpura, myasthenia gravis, some forms of myocarditis, multiple sclerosis, pemphigus/pemphigoid, pernicious anemia, polyarteritis nodosa, polymyositis, primary biliary cirrhosis, psoriasis, rheumatoid arthritis, scleroderma/systemic sclerosis, Sjögren's syndrome, systemic lupus, erythematosus, some forms of thyroiditis, some forms of uveitis, vitiligo, granulomatosis with polyangiitis (Wegener's). Examples of viral infections include, but are not limited to, HIV-(human immunodeficiency virus), HSV- (herpes simplex virus), KSHV- (Kaposi's sarcoma-associated herpesvirus), RSV- (Respiratory Syncytial Virus), EBV- (Epstein-Barr virus), CMV- (cytomegalovirus), VZV (Varicella zoster virus), adenovirus-, a lentivirus-, a BK polyomavirus-associated disorders.

The treatment using the derived hematopoietic lineage cells of embodiments disclosed herein, or compositions provided herein, could be carried out upon symptom, or for relapse prevention. The terms "treating," "treatment," and the like are used herein to generally mean obtaining a desired pharmacologic and/or physiologic effect. The effect may be prophylactic in terms of completely or partially preventing a disease and/or may be therapeutic in terms of a partial or complete cure for a disease and/or adverse effect attributable to the disease. "Treatment" as used herein covers any intervention of a disease in a subject and includes: preventing the disease from occurring in a subject which may be predisposed to the disease but has not yet been diagnosed as having it; inhibiting the disease, i.e., arresting its development; or relieving the disease, i.e., causing regression of the disease. The therapeutic agent or composition may be administered before, during or after the onset of a disease or an injury. The treatment of ongoing disease, where the treatment stabilizes or reduces the undesirable clinical symptoms of the patient, is also of particular interest. In particular embodiments, the subject in need of a treatment has a disease, a condition, and/or an injury that can be contained, ameliorated, and/or improved in at least one associated symptom by a cell therapy. Certain embodiments contemplate that a subject in need of cell therapy, includes, but is not limited to, a candidate for bone marrow or stem cell transplantation, a subject who has received chemotherapy or irradiation therapy, a subject who has or is at risk of having a hyperproliferative disorder or a cancer, e.g., a hyperproliferative disorder or a cancer of hematopoietic system, a subject having or at risk of developing a tumor, e.g., a solid tumor, a subject who has or is at risk of having a viral infection or a disease associated with a viral infection.

When evaluating responsiveness to the treatment comprising the derived hematopoietic lineage cells of embodiments disclosed herein, the response can be measured by criteria comprising at least one of: clinical benefit rate, survival until mortality, pathological complete response, semi-quantitative measures of pathologic response, clinical complete remission, clinical partial remission, clinical stable disease, recurrence-free survival, metastasis free survival, disease free survival, circulating tumor cell decrease, circulating marker response, and RECIST (Response Evaluation Criteria In Solid Tumors) criteria.

The therapeutic compositions comprising derived hematopoietic lineage cells as disclosed herein can be administered in a subject before, during, and/or after other treatments. As such, a method of combinational therapy can involve the administration or preparation of iPSC-derived immune cells before, during, and/or after the use of an additional therapeutic agent. As provided above, the one or more additional therapeutic agents comprise a peptide, a cytokine, a checkpoint inhibitor, an engager, a mitogen, a growth factor, a small RNA, a dsRNA (double stranded RNA), mononuclear blood cells, feeder cells, feeder cell components or replacement factors thereof, a vector comprising one or more polynucleic acids of interest, an antibody, a chemotherapeutic agent or a radioactive moiety, or an immunomodulatory drug (IMiD). The administration of the iPSC-derived immune cells can be separated in time from the administration of an additional therapeutic agent by hours, days, or even weeks. Additionally, or alternatively, the administration can be combined with other biologically active agents or modalities such as, but not limited to, an antineoplastic agent, a non-drug therapy, such as, surgery.

In some embodiments of a combinational cell therapy, the therapeutic combination comprises the iPSC-derived hematopoietic lineage cells provided herein and an additional therapeutic agent that is an antibody, or an antibody fragment. In some embodiments, the antibody is a monoclonal antibody. In some embodiments, the antibody may be a humanized antibody, a humanized monoclonal antibody, or a chimeric antibody. In some embodiments, the antibody, or antibody fragment, specifically binds to a viral antigen. In other embodiments, the antibody, or antibody fragment, specifically binds to a tumor antigen. In some embodiments, the tumor or viral specific antigen activates the administered iPSC-derived hematopoietic lineage cells to enhance their killing ability. In some embodiments, the antibodies suitable for combinational treatment as an additional therapeutic agent to the administered iPSC-derived hematopoietic lineage cells include, but are not limited to, anti-CD20 (e.g., rituximab, veltuzumab, ofatumumab, ublituximab, ocaratuzumab, obinutuzumab, ibritumomab, ocrelizumab), anti-CD22 (inotuzumab, moxetumomab, epratuzumab), anti-HER2 (e.g., trastuzumab, pertuzumab), anti-CD52 (e.g., alemtuzumab), anti-EGFR (e.g., cetuximab), anti-GD2 (e.g., dinutuximab), anti-PDL1 (e.g., avelumab), anti-CD38 (e.g., daratumumab, isatuximab, MOR202), anti-CD123 (e.g., 7G3, CSL362), anti-SLAMF7 (elotuzumab), and their humanized or Fc modified variants or fragments or their functional equivalents or biosimilars. In some embodiments, the present invention provides therapeutic compositions comprising the iPSC-derived hematopoietic lineage cells having a genotype listed in Table 1 and provided herein and an additional therapeutic agent that is an antibody, or an antibody fragment, as described above.

In some embodiments, the additional therapeutic agent comprises one or more checkpoint inhibitors. Checkpoints are referred to cell molecules, often cell surface molecules, capable of suppressing or downregulating immune responses when not inhibited. Checkpoint inhibitors are antagonists capable of reducing checkpoint gene expression or gene products, or deceasing activity of checkpoint molecules. Suitable checkpoint inhibitors for combination therapy with the derivative effector cells, including NK or T cells, as provided herein include, but are not limited to, antagonists of PD-1 (Pdcdl, CD279), PDL-1 (CD274), TIM-3 (Havcr2), TIGIT (WUCAM and Vstm3), LAG-3 (Lag3, CD223), CTLA-4 (Ctla4, CD152), 2B4 (CD244), 4-1BB (CD137), 4-1BBL (CD137L), $A_{2A}$R, BATE, BTLA, CD39 (Entpdl), CD47, CD73 (NT5E), CD94, CD96, CD160, CD200, CD200R, CD274, CEACAM1, CSF-1R, Foxpl, GARP, HVEM, IDO, EDO, TDO, LAIR-1, MICA/B, NR4A2, MAFB, OCT-2 (Pou2f2), retinoic acid receptor alpha (Rara), TLR3, VISTA, NKG2A/HLA-E, and inhibitory KIR (for example, 2DL1, 2DL2, 2DL3, 3DL1, and 3DL2).

Some embodiments of the combination therapy comprising the provided derivative effector cells further comprise at least one inhibitor targeting a checkpoint molecule. Some other embodiments of the combination therapy with the provided derivative effector cells comprise two, three or more inhibitors such that two, three, or more checkpoint molecules are targeted. In some embodiments, the effector cells for combination therapy as described herein are derivative NK lineage cells as provided. In some embodiments, the effector cells for combination therapy as described herein are derivative T lineage cells. In some embodiments, the derivative NK or T lineage cells for combination therapies are functionally enhanced as provided herein. In some embodiments, the two, three or more checkpoint inhibitors may be administered in a combination therapy with, before, or after the administering of the derivative effector cells. In some embodiments, the two or more checkpoint inhibitors are administered at the same time, or one at a time (sequential). In some embodiments, the present invention provides therapeutic compositions comprising the iPSC-derived effector cells having a genotype listed in Table 1 and provided herein and one or more checkpoint inhibitors, as described above.

In some embodiments, the antagonist inhibiting any of the above checkpoint molecules is an antibody. In some embodiments, the checkpoint inhibitory antibodies may be murine antibodies, human antibodies, humanized antibodies, a camel Ig, a shark heavy-chain-only antibody (VNAR), Ig NAR, chimeric antibodies, recombinant antibodies, or antibody fragments thereof. Non-limiting examples of antibody fragments include Fab, Fab', F(ab')2, F(ab')3, Fv, single chain antigen binding fragments (scFv), (scFv)2, disulfide stabilized Fv (dsFv), minibody, diabody, triabody, tetrabody, single-domain antigen binding fragments (sdAb, Nanobody), recombinant heavy-chain-only antibody (VHH), and other antibody fragments that maintain the binding specificity of the whole antibody, which may be more cost-effective to produce, more easily used, or more sensitive than the whole antibody. In some embodiments, the one, or two, or three, or more checkpoint inhibitors comprise at least one of atezolizumab, avelumab, durvalumab, ipilimumab, IPH4102, IPH43, IPH33, lirilumab, monalizumab, nivolumab, pembrolizutnab, and their derivatives or functional equivalents.

The combination therapies comprising the derivative effector cells and one or more check inhibitors are applicable to treatment of liquid and solid cancers, including but not limited to cutaneous T-cell lymphoma, non-Hodgkin lymphoma (NHL), Mycosis fungoides, Pagetoid reticulosis, Sezary syndrome, Granulomatous slack skin, Lymphomatoid papulosis, Pityriasis lichenoides chronica, Pityriasis lichenoides et varioliformis acuta, $CD30^{+}$ cutaneous T-cell lymphoma, Secondary cutaneous $CD30^{+}$ large cell lymphoma, non-mycosis fungoides CD30 cutaneous large T-cell lymphoma, Pleomorphic T-cell lymphoma, Lennert lymphoma, subcutaneous T-cell lymphoma, angiocentric lymphoma, blastic NK-cell lymphoma, B-cell Lymphomas, hodgkins lymphoma (HL), Head and neck tumor; Squamous cell carcinoma, rhabdomyosarcoma, Lewis lung carcinoma (LLC), non-small cell lung cancer, esophageal squamous cell carcinoma, esophageal adenocarcinoma, renal cell carcinoma (RCC), colorectal cancer (CRC), acute myeloid leukemia (AML), breast cancer, gastric cancer, prostatic small cell neuroendocrine carcinoma (SCNC), liver cancer, glioblastoma, liver cancer, oral squamous cell carcinoma, pancreatic cancer, thyroid papillary cancer, intrahepatic cholangiocellular carcinoma, hepatocellular carcinoma, bone cancer, metastasis, and nasopharyngeal carcinoma.

In some embodiments, other than the derivative effector cells as provided herein, a combination for therapeutic use comprises one or more additional therapeutic agents comprising a chemotherapeutic agent or a radioactive moiety. Chemotherapeutic agent refers to cytotoxic antineoplastic agents, that is, chemical agents which preferentially kill neoplastic cells or disrupt the cell cycle of rapidly-proliferating cells, or which are found to eradicate stem cancer cells, and which are used therapeutically to prevent or reduce the growth of neoplastic cells. Chemotherapeutic agents are also sometimes referred to as antineoplastic or cytotoxic drugs or agents, and are well known in the art.

In some embodiments, the chemotherapeutic agent comprises an anthracycline, an alkylating agent, an alkyl sulfonate, an aziridine, an ethylenimine, a methylmelamine, a nitrogen mustard, a nitrosourea, an antibiotic, an antimetabolite, a folic acid analog, a purine analog, a pyrimidine analog, an enzyme, a podophyllotoxin, a platinum-containing agent, an interferon, and an interleukin. Exemplary chemotherapeutic agents include, but are not limited to, alkylating agents (cyclophosphamide, mechlorethamine, mephalin, chlorambucil, heamethylmelamine, thiotepa, busulfan, carmustine, lomustine, semustine), animetabolites (methotrexate, fluorouracil, floxuridine, cytarabine, 6-mercaptopurine, thioguanine, pentostatin), vinca alkaloids (vincristine, vinblastine, vindesine), epipodophyllotoxins (etoposide, etoposide orthoquinone, and teniposide), antibiotics (daunorubicin, doxorubicin, mitoxantrone, bisanthrene, actinomycin D, plicamycin, puromycin, and gramicidine D), paclitaxel, colchicine, cytochalasin B, emetine, maytansine, and amsacrine. Additional agents include aminglutethimide, cisplatin, carboplatin, mitomycin, altretamine, cyclophosphamide, lomustine (CCNU), carmustine (BCNU), irinotecan (CPT-11), alemtuzamab, altretamine, anastrozole, L-asparaginase, azacitidine, bevacizumab, bexarotene, bleomycin, bortezomib, busulfan, calusterone, capecitabine, celecoxib, cetuximab, cladribine, clofurabine, cytarabine, dacarbazine, denileukin diftitox, diethlstilbestrol, docetaxel, dromostanolone, epirubicin, erlotinib, estramustine, etoposide, ethinyl estradiol, exemestane, floxuridine, 5-flourouracil, fludarabine, flutamide, fulvestrant, gefitinib, gemcitabine, goserelin, hydroxyurea, ibritumomab, idarubicin, ifosfamide, imatinib, interferon alpha (2a, 2b), irinotecan, letrozole, leucovorin, leuprolide, levamisole, meclorethamine, megestrol, melphalin, mercaptopurine, methotrexate, methoxsalen, mitomycin C, mitotane, mitoxantrone, nandrolone, nofetumomab, oxaliplatin, paclitaxel, pamidronate, pemetrexed, pegademase, pegasparagase, pentostatin, pipobroman, plicamycin, polifeprosan, porfimer, procarbazine, quinacrine, rituximab, sargramostim, streptozocin, tamoxifen, temozolomide, teniposide, testolactone, thioguanine, thiotepa, topetecan, toremifene, tositumomab, trastuzumab, tretinoin, uracil mustard, valrubicin, vinorelbine, and zoledronate. Other suitable agents are those that are approved for human use, including those that will be approved, as chemotherapeutics or radiotherapeutics, and known in the art. Such agents can be referenced through any of a number of standard physicians' and oncologists' references (e.g., Goodman & Gilman's The Pharmacological Basis of Therapeutics, Ninth Edition, McGraw-Hill, N.Y., 1995) or through the National Cancer Institute website (fda.gov/cder/cancer/druglistfrarne.htm), both as updated from time to time.

Immunomodulatory drugs (IMiDs) such as thalidomide, lenalidomide, and pomalidomide stimulate both NK cells and T cells. As provided herein, IMiDs may be used with the iPSC-derived therapeutic immune cells for cancer treatments.

Other than an isolated population of iPSC-derived hematopoietic lineage cells included in the therapeutic compositions, the compositions suitable for administration to a patient can further include one or more pharmaceutically acceptable carriers (additives) and/or diluents (e.g., pharmaceutically acceptable medium, for example, cell culture medium), or other pharmaceutically acceptable components. Pharmaceutically acceptable carriers and/or diluents are determined in part by the particular composition being administered, as well as by the particular method used to administer the therapeutic composition. Accordingly, there is a wide variety of suitable formulations of therapeutic compositions of the present invention (see, e.g., Remington's Pharmaceutical Sciences, $17^{th}$ ed. 1985, the disclosure of which is hereby incorporated by reference in its entirety).

In one embodiment, the therapeutic composition comprises the iPSC-derived T cells made by the methods and composition disclosed herein. In one embodiment, the therapeutic composition comprises the iPSC-derived NK cells made by the methods and composition disclosed herein. In one embodiment, the therapeutic composition comprises the iPSC-derived $CD34^+$ HE cells made by the methods and composition disclosed herein. In one embodiment, the therapeutic composition comprises the iPSC-derived HSCs made by the methods and composition disclosed herein. In one embodiment, the therapeutic composition comprises the iPSC-derived MDSC made by the methods and composition disclosed herein. A therapeutic composition comprising a population of iPSC-derived hematopoietic lineage cells as disclosed herein can be administered separately by intravenous, intraperitoneal, enteral, or tracheal administration methods or in combination with other suitable compounds to affect the desired treatment goals.

These pharmaceutically acceptable carriers and/or diluents can be present in amounts sufficient to maintain a pH of the therapeutic composition of between about 3 and about 10. As such, the buffering agent can be as much as about 5% on a weight to weight basis of the total composition. Electrolytes such as, but not limited to, sodium chloride and potassium chloride can also be included in the therapeutic composition. In one aspect, the pH of the therapeutic composition is in the range from about 4 to about 10. Alternatively, the pH of the therapeutic composition is in the range from about 5 to about 9, from about 6 to about 9, or from about 6.5 to about 8. In another embodiment, the therapeutic composition includes a buffer having a pH in one of said pH ranges. In another embodiment, the therapeutic composition has a pH of about 7. Alternatively, the therapeutic composition has a pH in a range from about 6.8 to about 7.4. In still another embodiment, the therapeutic composition has a pH of about 7.4.

The invention also provides, in part, the use of a pharmaceutically acceptable cell culture medium in particular compositions and/or cultures of the present invention. Such compositions are suitable for administration to human subjects. Generally speaking, any medium that supports the maintenance, growth, and/or health of the iPSC-derived immune cells in accordance with embodiments of the invention are suitable for use as a pharmaceutical cell culture medium. In particular embodiments, the pharmaceutically acceptable cell culture medium is a serum free, and/or feeder-free medium. In various embodiments, the serum-free medium is animal-free, and can optionally be protein-free. Optionally, the medium can contain biopharmaceutically acceptable recombinant proteins. Animal-free medium refers to medium wherein the components are derived from non-animal sources. Recombinant proteins replace native animal proteins in animal-free medium and the nutrients are obtained from synthetic, plant or microbial sources. Protein-free medium, in contrast, is defined as substantially free of protein. One having ordinary skill in the art would appreciate that the above examples of media are illustrative and in no way limit the formulation of media suitable for use in the present invention and that there are many suitable media known and available to those in the art.

The iPSC-derived hematopoietic lineage cells can have at least 50%, 60%, 70%, 80%, 90%, 95%, 98%, or 99% T cells, NK cells, NKT cells, proT cells, proNK cells, $CD34^+$ HE cells, HSCs, B cells, myeloid-derived suppressor cells (MDSCs), regulatory macrophages, regulatory dendritic cells, or mesenchymal stromal cells. In some embodiments, the isolated pluripotent stem cell derived hematopoietic lineage cells has about 95% to about 100% T cells, NK cells, proT cells, proNK cells, $CD34^+$ HE cells, or myeloid-derived suppressor cells (MDSCs). In some embodiments, the present invention provides therapeutic compositions having purified T cells or NK cells, such as a composition having an isolated population of about 95% T cells, NK cells, proT cells, proNK cells, $CD34^+$ HE cells, or myeloid-derived suppressor cells (MDSCs) to treat a subject in need of the cell therapy.

In one embodiment, the combinational cell therapy, or composition used therefor, comprises a therapeutic protein or peptide that is a CD3 engager and a population of NK cells derived from genomically engineered iPSCs comprising a genotype listed in Table 1, wherein the derived NK cells comprise $TCR^{neg}$ cs-CD3. In another embodiment, the combinational cell therapy, or composition used therefor, comprises a therapeutic protein or peptide that is a CD3 engager and a population of T cells derived from genomically engineered iPSCs comprising a genotype listed in Table 1, wherein the derived T cells comprise $TCR^{neg}$ cs-CD3. In some embodiments, the combinational cell therapy, or composition used therefor, comprises one of blinatumomab, catumaxomab, ertumaxomab, R06958688, AFM11, MT110/AMG 110, MT111/AMG211/MEDI-565, AMG330, MT112/BAY2010112, MOR209/ES414, MGD006/S80880, MGD007, and/or FBTA05, and a population of NK or T cells derived from genomically engineered iPSCs comprising a genotype listed in Table 1, wherein the derived NK or T cells comprise $TCR^{neg}$ cs-CD3, and optionally, hnCD16. In yet some other embodiments, the combinational cell therapy, or composition used therefor, comprises one of blinatumomab, catumaxomab, and ertumaxomab, and a population of NK or T cells derived from genomically engineered iPSCs comprising a genotype listed in Table 1, wherein the derived NK or T cells comprise $TCR^{neg}$ cs-CD3, exogenous CD16 or a variant thereof, and a CAR targeting CD19, BCMA, CD38, CD20, CD22, or CD123. In still some additional embodiments, the combinational cell therapy, or composition used therefor, comprises one of blinatumomab, catumaxomab, and ertumaxomab, and a population of NK or T cells derived from genomically engineered iPSCs comprising a genotype listed in Table 1, wherein the derived NK or T cells comprise $TCR^{neg}$ cs-CD3, exogenous CD16 or a variant thereof, a CAR and one or more exogenous cytokine.

As a person of ordinary skill in the art would understand, both autologous and allogeneic hematopoietic lineage cells derived from iPSC based on the methods and compositions provided herein can be used in cell therapies as described above. For autologous transplantation, the isolated population of derived hematopoietic lineage cells are either complete or partial HLA-match with the patient. In another embodiment, the derived hematopoietic lineage cells are not HLA-matched to the subject, wherein the derived hematopoietic lineage cells are NK cells or T cell with HLA-I and/or HLA-II null.

In some embodiments, the number of derived hematopoietic lineage cells in the therapeutic composition is at least $0.1\times10^5$ cells, at least $1\times10^5$ cells, at least $5\times10^5$ cells, at least $1\times10^6$ cells, at least $5\times10^6$ cells, at least $1\times10^7$ cells, at least $5\times10^7$ cells, at least $1\times10^8$ cells, at least $5\times10^8$ cells, at least $1\times10^9$ cells, or at least $5\times10^9$ cells, per dose. In some embodiments, the number of derived hematopoietic lineage cells in the therapeutic composition is about $0.1\times10^5$ cells to about $1\times10^6$ cells, per dose; about $0.5\times10^6$ cells to about $1\times10^7$ cells, per dose; about $0.5\times10^7$ cells to about $1\times10^8$ cells, per dose; about $0.5\times10^8$ cells to about $1\times10^9$ cells, per dose; about $1\times10^9$ cells to about $5\times10^9$ cells, per dose; about $0.5\times10^9$ cells to about $8\times10^9$ cells, per dose; about $3\times10^9$ cells to about $3\times10^{10}$ cells, per dose, or any range in-between. Generally, $1\times10^8$ cells/dose translates to $1.67\times10^6$ cells/kg for a 60 kg patient.

In one embodiment, the number of derived hematopoietic lineage cells in the therapeutic composition is the number of immune cells in a partial or single cord of blood, or is at least $0.1\times10^5$ cells/kg of bodyweight, at least $0.5\times10^5$ cells/kg of bodyweight, at least $1\times10^5$ cells/kg of bodyweight, at least $5\times10^5$ cells/kg of bodyweight, at least $10\times10^5$ cells/kg of bodyweight, at least $0.75\times10^6$ cells/kg of bodyweight, at least $1.25\times10^6$ cells/kg of bodyweight, at least $1.5\times10^6$ cells/kg of bodyweight, at least $1.75\times10^6$ cells/kg of bodyweight, at least $2\times10^6$ cells/kg of bodyweight, at least $2.5\times10^6$ cells/kg of bodyweight, at least $3\times10^6$ cells/kg of bodyweight, at least $4\times10^6$ cells/kg of bodyweight, at least $5\times10^6$ cells/kg of bodyweight, at least $10\times10^6$ cells/kg of bodyweight, at least $15\times10^6$ cells/kg of bodyweight, at least $20\times10^6$ cells/kg of bodyweight, at least $25\times10^6$ cells/kg of bodyweight, at least $30\times10^6$ cells/kg of bodyweight, $1\times10^8$ cells/kg of bodyweight, $5\times10^8$ cells/kg of bodyweight, or $1\times10^9$ cells/kg of bodyweight.

In one embodiment, a dose of derived hematopoietic lineage cells is delivered to a subject. In one illustrative embodiment, the effective amount of cells provided to a subject is at least $2\times10^6$ cells/kg, at least $3\times10^6$ cells/kg, at least $4\times10^6$ cells/kg, at least $5\times10^6$ cells/kg, at least $6\times10^6$ cells/kg, at least $7\times10^6$ cells/kg, at least $8\times10^6$ cells/kg, at least $9\times10^6$ cells/kg, or at least $10\times10^6$ cells/kg, or more cells/kg, including all intervening doses of cells.

In another illustrative embodiment, the effective amount of cells provided to a subject is about $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, or about $10\times10^6$ cells/kg, or more cells/kg, including all intervening doses of cells.

In another illustrative embodiment, the effective amount of cells provided to a subject is from about $2\times10^6$ cells/kg to about $10\times10^6$ cells/kg, about $3\times10^6$ cells/kg to about $10\times10^6$ cells/kg, about $4\times10^6$ cells/kg to about $10\times10^6$ cells/kg, about $5\times10^6$ cells/kg to about $\mathbf{10\times10}^6$ cells/kg, $2\times10^6$ cells/kg to about $6\times10^6$ cells/kg, $2\times10^6$ cells/kg to about $7\times10^6$ cells/kg, $2\times10^6$ cells/kg to about $8\times10^6$ cells/kg, $3\times10^6$ cells/kg to about $6\times10^6$ cells/kg, $3\times10^6$ cells/kg to about $7\times10^6$ cells/kg, $3\times10^6$ cells/kg to about $8\times10^6$ cells/kg, $4\times10^6$ cells/kg to about $6\times10^6$ cells/kg, $4\times10^6$ cells/kg to about $7\times10^6$ cells/kg, $4\times10^6$ cells/kg to about $8\times10^6$ cells/kg, $5\times10^6$ cells/kg to about $6\times10^6$ cells/kg, $5\times10^6$ cells/kg to about $7\times10^6$ cells/kg, $5\times10^6$ cells/kg to about $8\times10^6$ cells/kg, or $6\times10^6$ cells/kg to about $8\times10^6$ cells/kg, including all intervening doses of cells.

In some embodiments, the therapeutic use of derived hematopoietic lineage cells is a single-dose treatment. In some embodiments, the therapeutic use of derived hematopoietic lineage cells is a multi-dose treatment. In some embodiments, the multi-dose treatment is one dose every day, every 3 days, every 7 days, every 10 days, every 15 days, every 20 days, every days, every 30 days, every 35 days, every 40 days, every 45 days, or every 50 days, or any number of days in-between. In some embodiments, the multi-dose treatment comprises three, four, or five, once weekly doses. In some embodiments of the multi-dose treatment comprising three, four, or five, once weekly doses further comprise an observation period for determining whether additional single or multi doses are needed.

The compositions comprising a population of derived hematopoietic lineage cells of the invention can be sterile, and can be suitable and ready for administration (i.e., can be administered without any further processing) to human patients. A cell-based composition that is ready for administration means that the composition does not require any further processing or manipulation prior to transplant or administration to a subject. In other embodiments, the invention provides an isolated population of derived hematopoietic lineage cells that are expanded and/or modulated prior to administration with one or more agents. For derived hematopoietic lineage cells that are genetically engineered to express recombinant TCR or CAR, the cells can be activated and expanded using methods as described, for example, in U.S. Pat. No. 6,352,694.

In certain embodiments, the primary stimulatory signal and the co-stimulatory signal for the derived hematopoietic lineage cells can be provided by different protocols. For example, the agents providing each signal can be in solution or coupled to a surface. When coupled to a surface, the agents can be coupled to the same surface (i.e., in "cis" formation) or to separate surfaces (i.e., in "trans" formation). Alternatively, one agent can be coupled to a surface and the other agent in solution. In one embodiment, the agent providing the co-stimulatory signal can be bound to a cell surface and the agent providing the primary activation signal is in solution or coupled to a surface. In certain embodiments, both agents can be in solution. In another embodiment, the agents can be in soluble form, and then cross-linked to a surface, such as a cell expressing Fc receptors or an antibody or other binding agent which will bind to the agents such as disclosed in U.S. Pub. Nos. 2004/0101519 and 2006/0034810 for artificial antigen presenting cells (aAPCs) that are contemplated for use in activating and expanding T lymphocytes in embodiments of the present invention.

Some variation in dosage, frequency, and protocol will necessarily occur depending on the condition of the subject being treated. The person responsible for administration will, in any event, determine the appropriate dose, frequency and protocol for the individual subject.

EXAMPLES

The following examples are offered by way of illustration and not by way of limitation.

Example 1—Materials and Methods

To effectively select and test suicide systems under the control of various promoters in combination with different safe harbor loci integration strategies, a proprietary hiPSC platform of the applicant was used, which enables single cell passaging and high-throughput, 96-well plate-based flow cytometry sorting, to allow for the derivation of clonal hiPSCs with single or multiple genetic modulations.

hiPSC Maintenance in Small Molecule Culture: hiPSCs were passaged as single cells once confluency of the culture reached 75%-90%. For single-cell dissociation, hiPSCs were washed once with PBS (Mediatech) and treated with Accutase (Millipore) for 3-5 min at 37° C. followed with pipetting to ensure single-cell dissociation. The single-cell suspension was then mixed in equal volume with conventional medium, centrifuged at 225×g for 4 min, resuspended in FMM, and plated on Matrigel-coated surface. Passages were typically 1:6-1:8, transferred tissue culture plates previously coated with Matrigel for 2-4 hr in 37° C. and fed every 2-3 days with FMM. Cell cultures were maintained in a humidified incubator set at 37° C. and 5% $CO_2$.

Human iPSC engineering with ZFN, CRISPR for targeted editing of modalities of interest: Using ROSA26 targeted insertion as an example, for ZFN mediated genome editing, 2 million iPSCs were transfected with a mixture of 2.5 μg ZFN-L, 2.5 μg ZFN-R and 5 μg donor construct, for AAVS1 targeted insertion. For CRISPR mediated genome editing, 2 million iPSCs were transfected with a mixture of 5 μg ROSA26-gRNA/Cas9 and 5 μg donor construct, for ROSA26 targeted insertion. Transfection was done using Neon transfection system (Life Technologies) using parameters 1500V, 10 ms, 3 pulses. On day 2 or 3 after transfection, transfection efficiency was measured using flow cytometry if the plasmids contain artificial promoter-driver GFP and/or RFP expression cassette. On day 4 after transfection, puromycin was added to the medium at concentration of 0.1 μg/ml for the first 7 days and 0.2 μg/ml after 7 days to select the targeted cells. During the puromycin selection, the cells were passaged onto fresh matrigel-coated wells on day 10. On day 16 or later of puromycin selection, the surviving cells were analyzed by flow cytometry for $GFP^+$ iPS cell percentage.

Bulk sort and clonal sort of genome-edited iPSCs: iPSCs with genomic targeted editing using ZFN or CRISPR-Cas9 were bulk sorted and clonal sorted for $GFP^+SSEA4^+$ $TRA181^+$ iPSCs after 20 days of puromycin selection. Single cell dissociated targeted iPSC pools were resuspended in chilled staining buffer containing Hanks' Balanced Salt Solution (MediaTech), 4% fetal bovine serum (Invitrogen), 1× penicillin/streptomycin (Mediatech) and 10 mM Hepes (Mediatech); made fresh for optimal performance. Conjugated primary antibodies, including SSEA4-PE, TRA181-Alexa Fluor-647 (BD Biosciences), were added to the cell solution and incubated on ice for 15 minutes. All antibodies were used at 7 μL in 100 μL staining buffer per million cells. The solution was washed once in staining buffer, spun down at 225 g for 4 minutes and resuspended in staining buffer containing 10 μM Thiazovivin and maintained on ice for flow cytometry sorting. Flow cytometry sorting was performed on FACS Aria II (BD Biosciences). For bulk sort, $GFP^+SSEA4^+$ $TRA181^+$ cells were gated and sorted into 15 ml canonical tubes filled with 7 ml FMM. For clonal sort, the sorted cells were directly ejected into 96-well plates using the 100 μM nozzle, at concentrations of 3 events per well. Each well was prefilled with 200 μL FMM supplemented with 5 μg/mL fibronectin and 1× penicillin/streptomycin (Mediatech) and previously coated overnight with 5× Matrigel. 5× Matrigel precoating includes adding one aliquot of Matrigel into 5 mL of DMEM/F12, then incubating overnight at 4° C. to allow for proper resuspension and finally adding to 96-well plates at 50 μL per well, followed by overnight incubation at 37° C. The 5× Matrigel is aspirated immediately before the addition of media to each well. Upon completion of the sort, 96-well plates were centrifuged for 1-2 min at 225 g prior to incubation. The plates were left undisturbed for seven days. On the seventh day, 150 μL of medium was removed from each well and replaced with 100 μL FMM. Wells were refed with an additional 100 μL FMM on day 10 post sort. Colony formation was detected as early as day 2 and most colonies were expanded between days 7-10 post sort. In the first passage, wells were washed with PBS and dissociated with 30 μL Accutase for approximately 10 min at 37° C. The need for extended Accutase treatment reflects the compactness of colonies that have sat idle in culture for prolonged duration. After cells are seen to be dissociating, 200 μL of FMM is added to each well and pipetted several times to break up the colony. The dissociated colony is transferred to another well of a 96-well plate previously coated with 5× Matrigel and then centrifuged for 2 min at 225 g prior to incubation. This 1:1 passage is conducted to spread out the early colony prior to expansion. Subsequent passages were done routinely with Accutase treatment for 3-5 min and expansion of 1:4-1:8 upon 75-90% confluency into larger wells previously coated with 1× Matrigel in FMM. Each clonal cell line was analyzed for GFP fluorescence level and TRA1-81 expression level. Clonal lines with near 100% $GFP^+$ and $TRA1\text{-}81^+$ were selected for further PCR screening and analysis, and cryopreserved as a master cell bank. Flow cytometry analysis was performed on Guava EasyCyte 8 HT (Millipore) and analyzed using Flowjo (FlowJo, LLC).

Example 2—The Designs of Expressed CFRs

Bi-allelic disruption of TRAC or TRBC for removal of TCR expression in T cells is an approach to mitigate the risk of GvHD. However, the lack of TCR expression consequently leads to the loss of surface CD3 expression in TCR negative cells. Lacking surface CD3 expression (including NK cells that do not express CD3) limits the potential to differentiate, maturate, and/or expand effector cells (primary or iPSC-derived) under feeder free conditions at manufacturing stage using existing engager strategies, and the potential to activate effector cells with inducible or agonistic ligands including, but not limited to, therapeutic antibodies, BiTEs, or TriKEs at an appropriate cell development stage or in a tumor microenvironment.

Here, a chimeric fusion receptor (CFR) strategy is disclosed to arm an effector cell with at least one CFR to initiate an appropriate signal transduction cascade to enhance effector cell therapeutic attributes including, but not limited to, increased activation and cytoxicity, acquired dual targeting capability, prolonged persistency, improved trafficking and tumor penetration, enhanced ability in activating or recruiting bystander immune cells to tumor sites, enhanced ability to reduce tumor immunosuppression, improved ability in rescuing tumor antigen escape, and/or controlled cell metabolism and apoptosis.

A CFR as provided comprises an ectodomain fused to a transmembrane domain, which is connected to an endodomain, and the CFR does not have ER (endoplasmic reticulum) retention signals or endocytosis signals. The ectodomain of CFR is for initiating signal transduction; the transmembrane domain is for membrane anchoring; and the endodomain provides at least a cytoxicity domain and activates one or more signaling pathways of choice that enhance cell attributes including, but not limited to, persistence, mobility, differentiation, metabolism and/or apoptosis, which lead to long term tumor growth control by the CFR armed effector cells. The endodomain of CFR may comprise, in addition to a cytoxicity domain, optionally one or more of a co-stimulatory domain, a persistency signaling domain, a death-inducing signaling domain, or a signaling pathway domain of choice.

Co-stimulatory domains suitable for a CFR include, but are not limited to, endodomain of CD28, 4-1BB, CD27, CD40L, ICOS, CD2, or combinations thereof. Persistency signaling domains suitable for a CFR include, but are not limited to, endodomain of a cytokine receptor such as, IL2R, IL7R, IL15R, IL18R, IL12R, IL23R, or combinations thereof. Endodomain of a receptor tyrosine kinase (RTK) such as EGFR, or a tumor necrosis factor receptor (TNFR) such as FAS provides additional signaling pathway control when the effector cell is activated through the incorporated CFR. Further, the elimination of ER retention signals is incorporated in a CFR to permit its cell surface presentation by itself when expressed, and the elimination of endocytosis signals in CFR is to reduce its internalization and surface downregulation. It is important to either select domain components that have neither ER retention nor endocytosis signals, or remove ER retention or endocytosis signals from selected components for CFR using molecular engineering tools. In addition, the domains of a CFR as provided are modular, meaning for a given endodomain, the ectodomain of the CFR is switchable depending on the binding specificity of agonistic antibodies, BiTEs, or TriKEs to be used with said CFR; and vice versa, for a given ectodomain and a matching agonist, the endodomain is switchable depending on the desired signaling pathway to be activated.

Figure 4A:
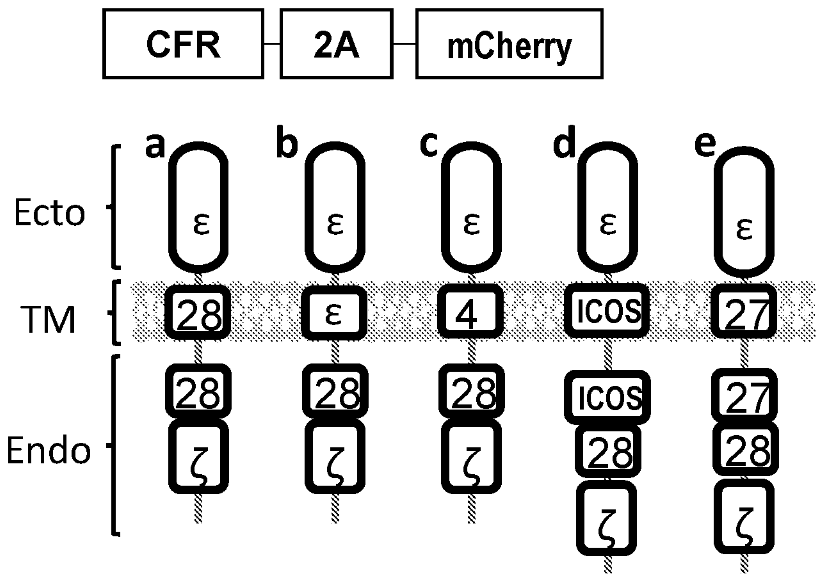
FIGS. 4A-4G show CFR designs with switchable transmembrane domains (FIG. 4A); CFR surface expression on $CAR^-$ (FIG. 4B) and $CAR^+$ (FIG. 4D) Jurkat-NFAT-TRAC KO cells; NFAT reporter activity in CFR expressing $CAR19^-$ (FIG. 4C) and $CAR19^+$ (FIG. 4E) Jurkat-NFAT-TRAC KO cells in the presence of BiTE and target cells; surface expression of CAR on Jurkat-NFAT-TRAC KO $CAR19^+$ cells expressing CFRs with different transmembrane domains (FIG. 4F); and difference of NFAT reporter activity in CFR expressing TRAC KO-$CAR19^+$ or TRAC KO-$CAR19^-$ Jurkat cells in the presence of $Antigen^+$ targets (FIG. 4G).

For proof-of-concept, the choice of the ectodomain in this example takes into consideration of surface molecules that are recognizable by existing agonistic ligands, such as CD3 or CD28 antibodies or BiTEs. As shown in FIG. 1 and FIG. 4A, each of the exemplary CFRs respectively comprises at least one extracellular portion of CD28 or a CD3 subunit (CD3ε, CD3γ or CD3δ); a transmembrane domain of CD28, CD8, CD4, CD27, ICOS, or CD3ε; and an endodomain of CD3ε, CD3γ, CD3δ, CD28, ICSO, CD27, or a combination thereof, with ER retention motifs and/or endocytosis motifs in ecto-, TM-, and/or endo-domains eliminated. For example, CD3ε* comprises an R183S mutation to eliminate an ER retention motif from the endodomain of its WT sequence; CD3δ* comprises L142A and R169A mutations to eliminate an endocytosis motif and an ER retension motif from the endodomain of its WT sequence; and CD3γ* comprises L131A and R158A mutations to eliminate an ER retention motif from the endodomain of its WT sequence. In some exemplary designs, the CFR comprises an ectodomain of one CD3 subunit; in some other designs the CFR comprises a single chain ectodomain that comprises the ectodomain of CD3ε linked with that of CD3δ or CD3γ through a linker (also called spacer). The linker type, length and sequence in the single chain ectodomain may vary.

Sequences for constructs were ordered as gBlocks (IDT, Coralville, IA) and contained a NheI and EcoRI site on the 5' and 3' end, respectively in this example, but restriction enzyme sites may be different in various CFR designs. The gBlock sequences contained two components separated by a 2A element: the construct and a tag is optionally used to determine transduction efficiency including mCherry, Thy 1.1, or Thy 1.2, if desired. NheI and EcoRI were used to cut the gBlock sequences and a lentivector backbone containing an EF1α promotor and Ampicillin resistance gene. The digested DNA was combined and ligated using a Quick Ligation kit (NEB, Ipswich, MA); afterwards the ligated DNA was transformed into DH5α cells and plated onto LB agar plates containing Carbenicillin. An AvrII site was introduced directly after the transmembrane domain to facilitate further cloning of different construct designs using a Q5® Site-Directed Mutagenesis Kit (NEB, Ipswich, MA). For lentiviral production, 293T cells seeded in 10 cm poly-D-lysine coated dishes were cultured for 24 hours prior to transfection. Lentivector and packaging plasmids were transfected with Lipofectamine 3000 (ThermoFisher, Waltham, MA) following the manufacture's guidelines. Virus was harvested 48 and 72 hours after and concentrated through ultra-centrifugation.

Example 3—Surface CFR Expression on TRAC Null Cells

NFAT-luciferase Jurkat reporter cells (Invivogen, San Diego, CA) were thawed, washed, and cultured at 37° C. with 5% $CO_2$ and passaged weekly. For lentiviral transduction of the engineered CFR constructs, the cells were centrifuged and resuspended at $1\times10^6$ cells/mL in media containing 4 μg/mL Polybrene (MilliporeSigma, St. Louis, MO). 1 mL of the cell suspension was placed in a 12-well plate and concentrated virus was added. The cells were then centrifuged for 1 hour and resuspended in fresh medium.

For phenotypic profiling, the transduced cells were harvested and stained with a fixable viability marker and fluorophore-conjugated antibodies: CD3 (SP34 and OKT3), CDS, CD7, CD8, CD45RA, CD62L, CCR7, CD27, CD28, PD1, and TIM3 (BD Biosciences, San Jose, CA; and BioLegend, San Diego, CA). Fluorescent absolute counting beads (Spherotech, Lake Forest, IL) were added just prior to data acquisition. Data acquisition was performed on a BD Fortessa™ X-20 (BD Biosciences) and data were analyzed using FlowJo software (FlowJo, Ashland, OR) and Spotfire (Tibco, Boston, MA).

To test the concept, in one experiment as shown in FIG. 5, Jurkat-TRAC KO cells were transduced with one or two CFRs: (A) 3ε-28-3ε*+3γ-28-3γ*, (B) 3δ-28-3δ*+3δ-28-3δ*, (C) 3ε-28-[-], (D) 3ε-28-3ε*, (E) 3ε-28-28 or (F) 28-28-3ε. Forty-eight hours later, CFR surface expression was analyzed and confirmed by flow cytometry after staining the cells with anti-CD3 antibody clones SP34 and OKT3 for cells transduced with constructs (A)-(E), or anti-CD28 antibody clone CD28.2 for cells transduced with construct (F). CD3 antibody SP34 is specific for CD3ε or functional variants thereof, while OKT3 binding requires heterodimer formation of CD3ε with CD3δ or CD3γ. As observed, CD3 expression in TCR knockout cells is rescued through ER retention and endocytosis motif mutations in CD3 subunit endodomains (compared to FIG. 6B).

Example 4—CFR Signal Transduction Initiated Via Agonistic Antibody Stimulation

To demonstrate the signal transduction ability of CFRs, agnostic antibodies or bi-specific antibodies were used at varying concentrations to initiate intracellular signaling pathways that activate NFAT, which would lead to the production and subsequent detection of luciferase activity. Scheme illustrating principle of NFAT-luciferase reporter assay using antibody stimulation or BiTE crosslinking is shown in FIG. 6A and FIG. 7A, respectively.

Figure 6A:
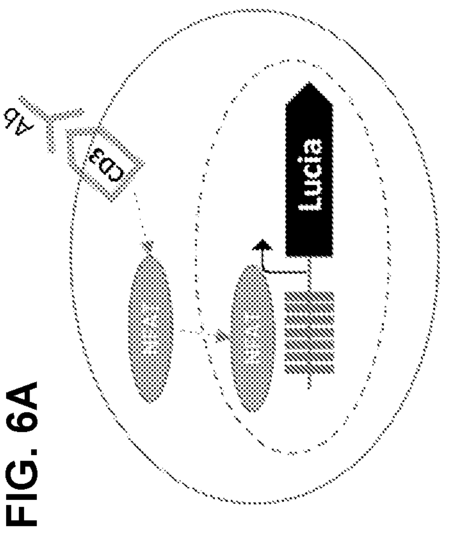
FIGS. 6A-6D show CFR signal transduction initiated via anti-CD3 antibody stimulation.
Figure 6B:
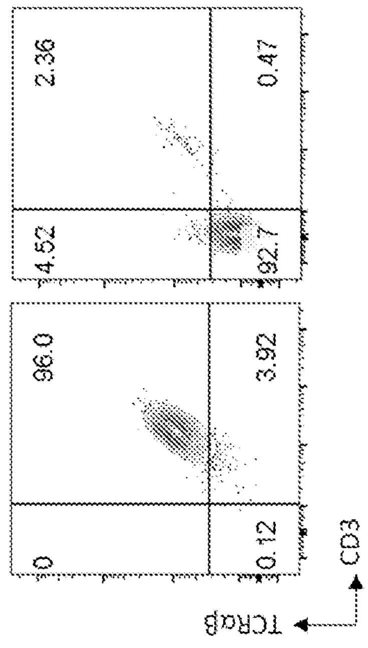
Figure 6C:
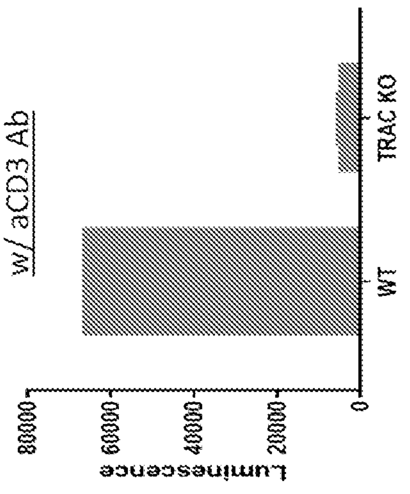
Figure 6D:
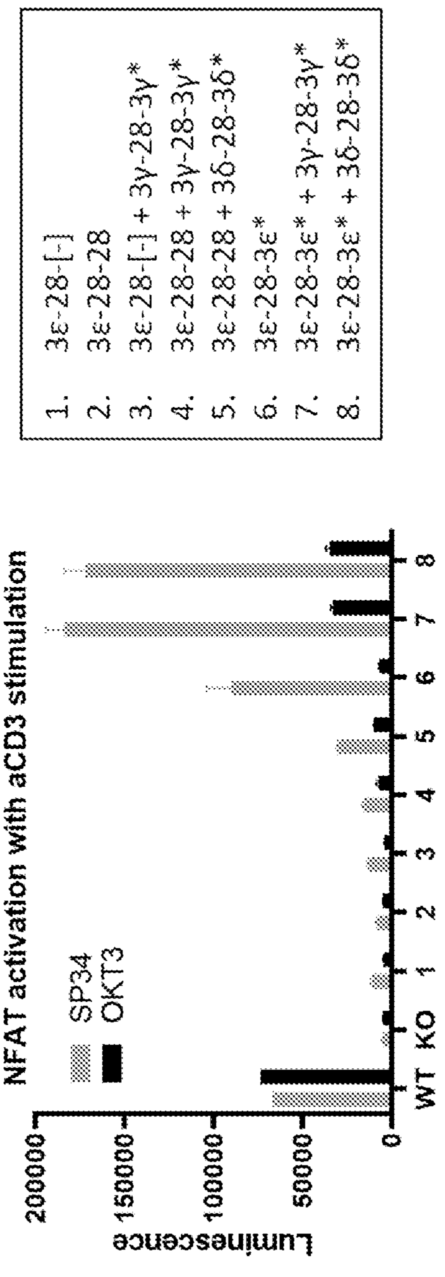
Figure 7A:
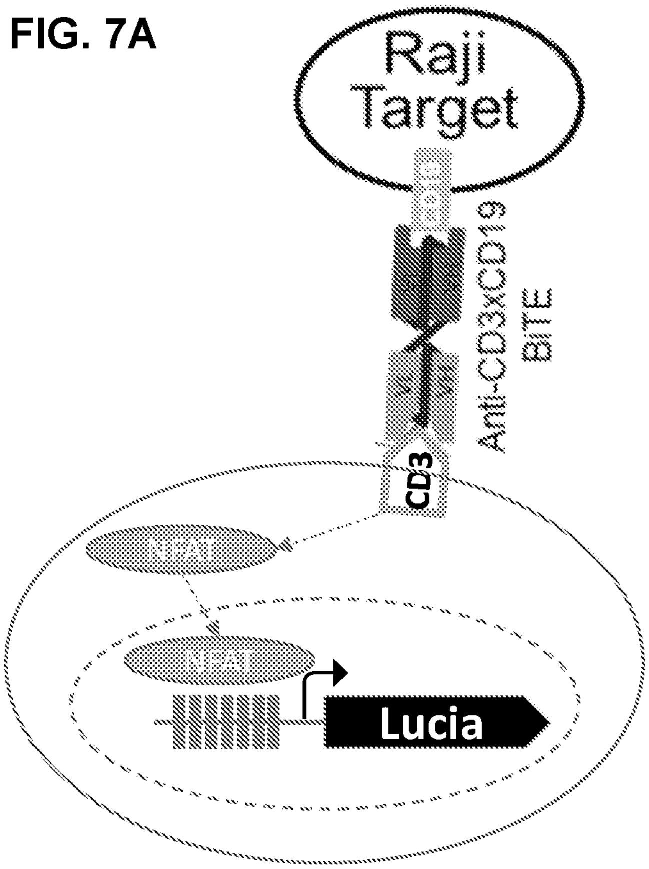
FIGS. 7A-7B show CFR signal transduction initiated by BiTE crosslinking.

For assays illustrated in FIG. 6A, Jurkat T cell line expressing a luciferase reporter driven by NFAT-response element (RE) was used. To detect CFR signal transduction, the transduced cells were plated in a 96 well flat bottom plate with agonistic CD3 antibodies SP34 or OKT3, or agonistic CD28 antibody CD28.2 in either soluble or plate bound format. As shown in FIG. 6B, cell surface CD3 and TCRαβ expression in Jurkat-NFAT WT are present (left plot), which are largely missing in TRAC KO cells (right plot). Upon engaging with anti-CD3 stimulus for 24 hours, endogenous CD3 receptor-mediated signaling induces NFAT translocation to the nucleus and interaction with NFAT RE, resulting in luciferase expression in Jurkat WT cells but not TRAC KO cells (see FIG. 6C). NFAT luciferase activity in various CFR-engineered Jurkat-TRAC KO cells stimulated with either clone SP34 or clone OKT3 antibody for 24 hours is shown in FIG. 6D. As shown, CFRs with modified CD3ε endodomain are able to induce NFAT reporter activity. In addition, constructs 3ε-28-3ε*+3γ-28-3γ*, 3ε-28-3ε *+3δ-28-3δ*, and 3ε-28-3ε* are among the highest performers for CFR signal transduction via anti-CD3 antibody stimulation, indicating synergistic cell activation in cells with co-transduced CFRs.

Figure 7B:
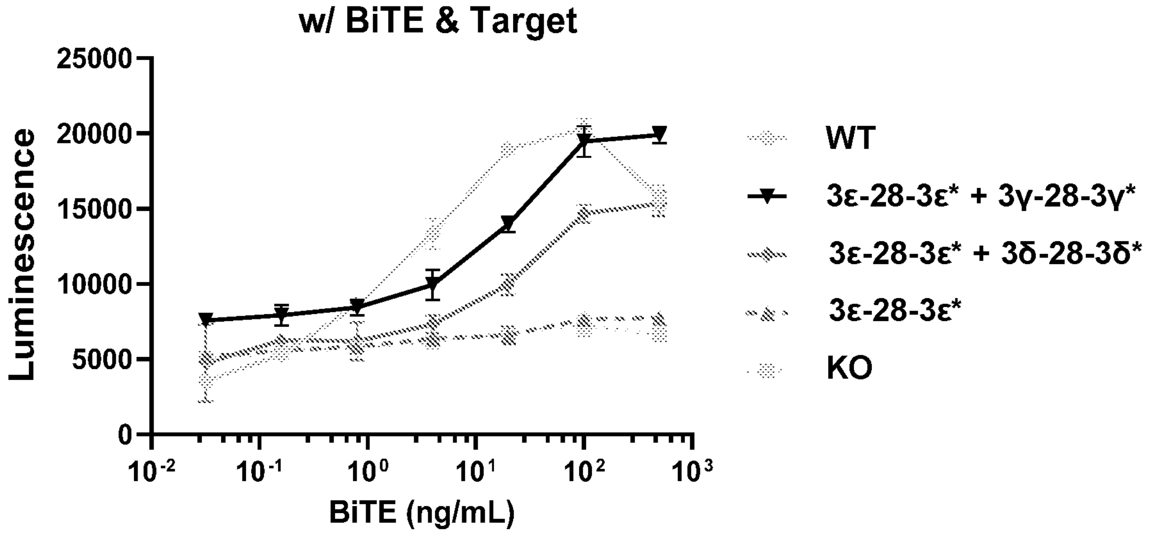

For BiTE experiments, an anti-CD3×CD19 BiTE (Invivogen, San Diego, CA) was selected for proof of concept for binding CD19 on target cells and CD3 on effector cells with the NFAT reporter transgene. NFAT-Luciferase Jurkats (WT or CFR transduced) were co-cultured with Raji cells at an effector to target (E:T) ratio of 3:1 in the presence or absence of the anti-CD3×CD19 BiTE. The cells were incubated overnight at 37° C. with about 5% $CO_2$. Afterwards, the plate was mixed gently, and some of the cell mixture was taken and combined with QUANTI-Luc (Invivogen, San Diego, CA) to detect luciferase activity. The plate was again mixed gently and immediately read on SpectraMax microplate reader (Molecular Devices, San Jose, CA). In the assay demonstrated in FIG. 7A, TRAC-KO reporter cells transduced with CFR(s) of 3ε-28-3ε* alone (dotted dark grey line) or in combination with 3γ-28-3γ* (black line) or 3δ-28-3δ* (dark grey line). Following 24-hour co-culture with target cells and anti-CD3×CD19 BiTE, NFAT activity was measured. As shown in FIG. 7B, WT (light grey line) and TRAC KO (dotted light grey line) NFAT reporter cells were seeded as positive or negative controls, and the transduced cells with CFRs 3ε-28-3ε*+3γ-28-3γ* or 3ε-28-3ε*+3δ-28-3δ* have better BiTE crosslinking initiated signal transduction.

Example 5—CFR Domains are Modular

Figure 8A:
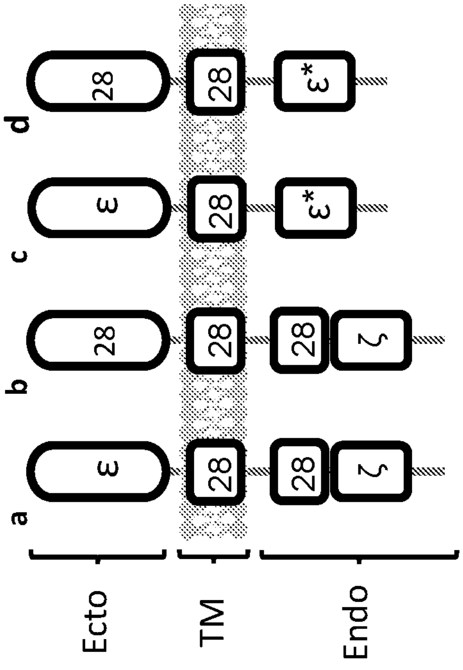
FIGS. 8A-8C show the modular nature of CFR domains.
Figure 8B:
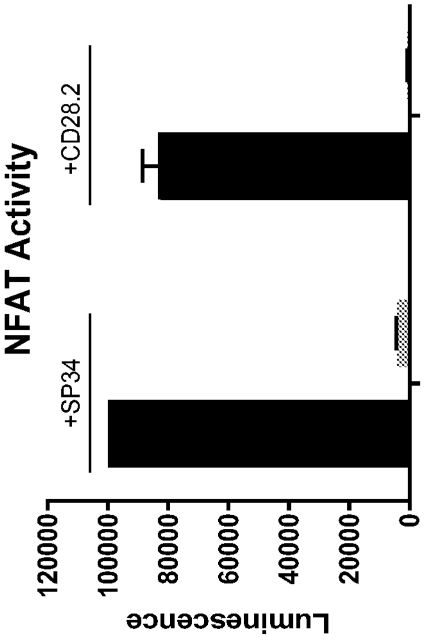
Figure 8C:
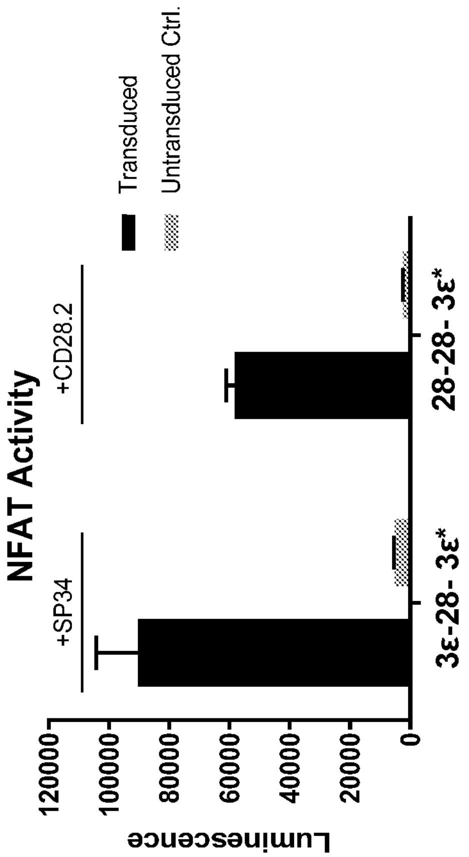

CFR designs as provided comprise modular ecto- and endo-domains. For a given endodomain, the ectodomain of the CFR is switchable depending on the binding specificity of agonistic antibodies, BiTEs, or TriKEs to be used with said CFR; and for a given ectodomain and a matching agonist, the endodomain is switchable depending on the desired signaling pathway to be activated. To illustrate, NFAT reporter activity was measured in CFR-armed Jurkat TRAC KO cells and untransduced controls after 24-hour culture in the presence of agonistic SP34 or CD28.2 antibody. As shown in FIGS. 8A-8C, either CD3ε- or CD28-ectodomain paired with the same CD28ζ endodomain can lead to sufficient signal transduction and elicit appropriate reporter activity. For further illustration, the CD3ε* endodomain is shown to pair with either CD3ε- or CD28-ectodomain to transduce signal and elicit activity (FIG. 8C). On the other hand, for the same exemplary CD3ε ectodomain, any selected endodomain including, but not limited to, CD28ζ endodomain and CD3ε* endodomain can be induced and activated when CD3-based agonist is applied to bind the CD3ε ectodomain of the CFR. For another example, the same CD28 ectodomain, any selected endodomain including, but not limited to, CD28ζ endodomain and CD3ε* endodomain can be induced and activated when CD3-based agonist is used to bind the CD3ε ectodomain of the CFR.

Figure 4B:
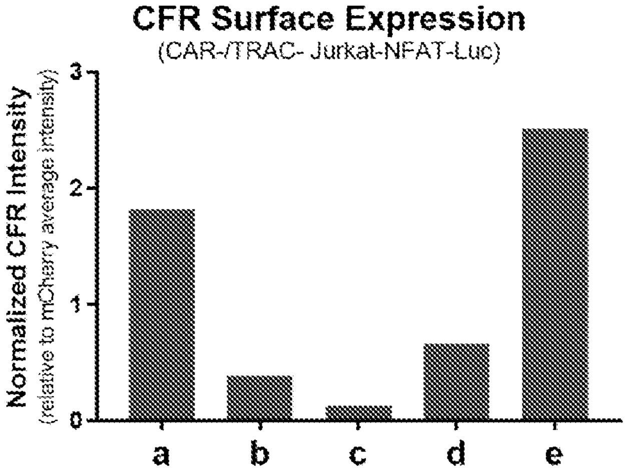
Figure 4C:
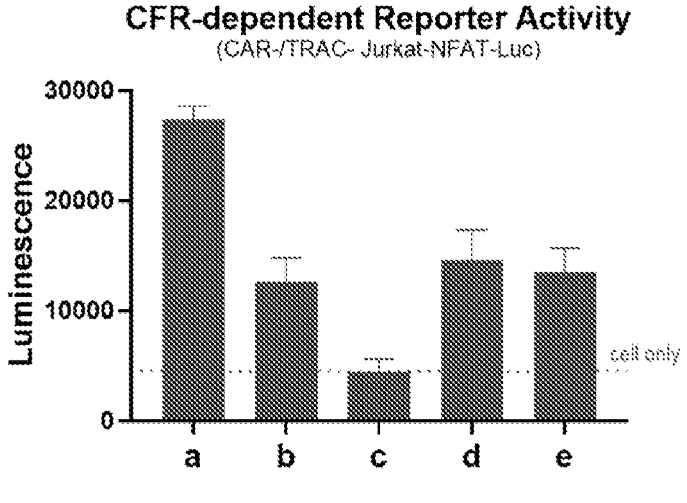
Figure 4D:
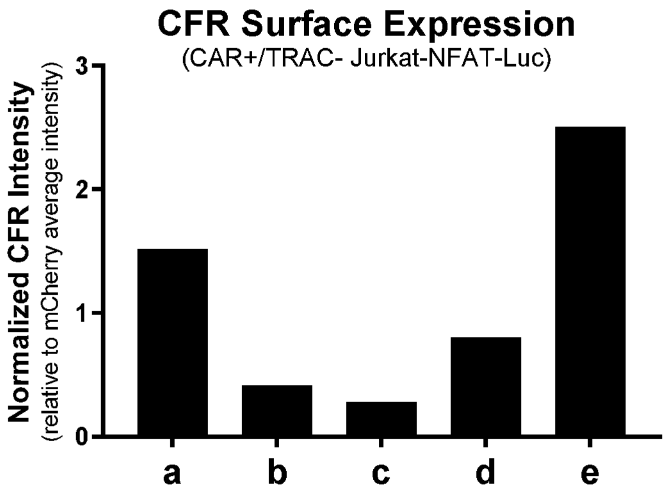
Figure 4E:
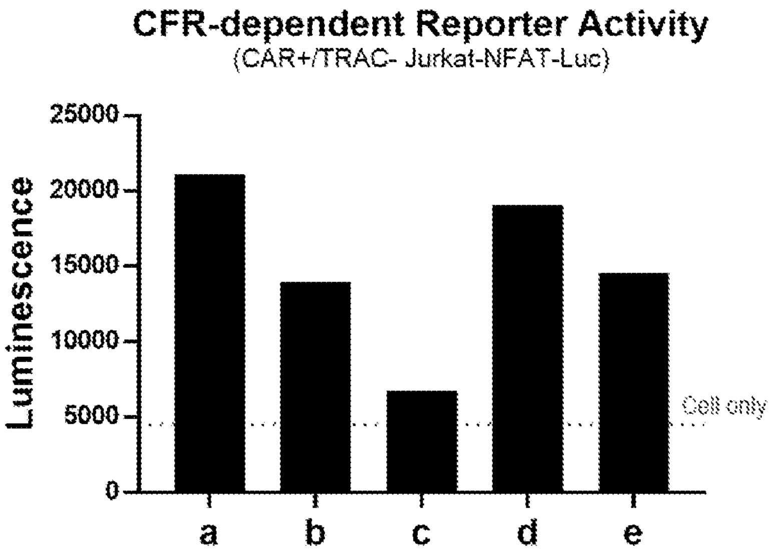
Figure 4F:
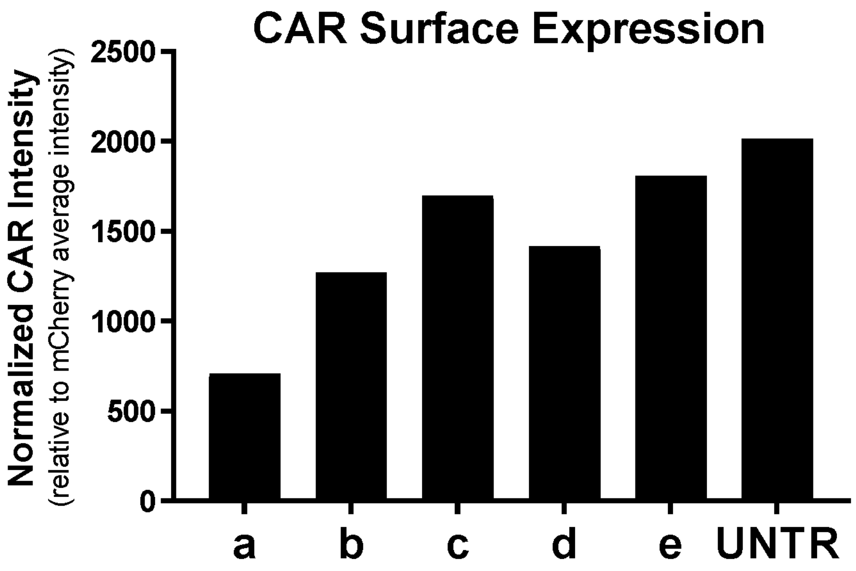
Figure 4G:
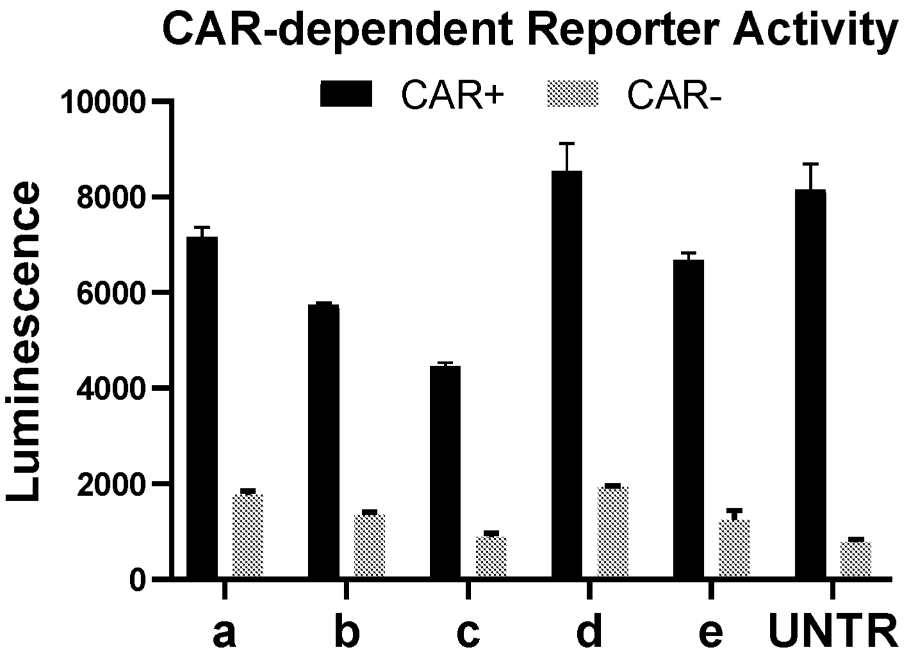
Figure 5A:
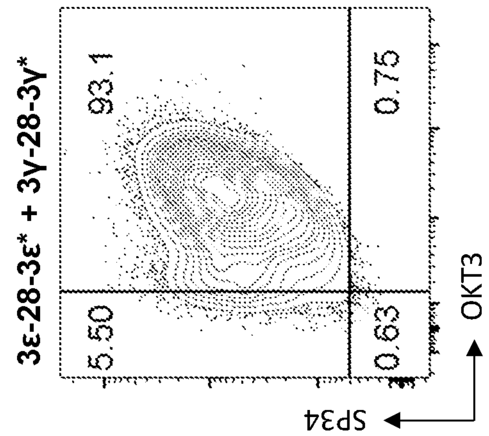
FIGS. 5A-5F show surface expression of CFRs on Jurkat-TRAC KO cells transduced with (FIG. 5A) 3ε-28-3ε*+3γ-28-3γ*, (FIG. 5B) 3ε-28-3ε*+3δ-28-3δ*, (FIG. 5C) 3ε-28-[-], (FIG. 5D) 3ε-28-3ε*, (FIG. 5E) 3ε-28-28 or (FIG. 5F) 28-28-3ε* using anti-CD3 antibody SP34 and OKT3, or anti-CD28 antibody CD28.2.
Figure 5B:
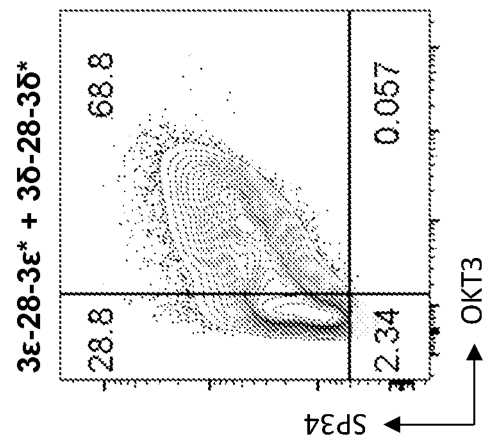
Figure 5C:
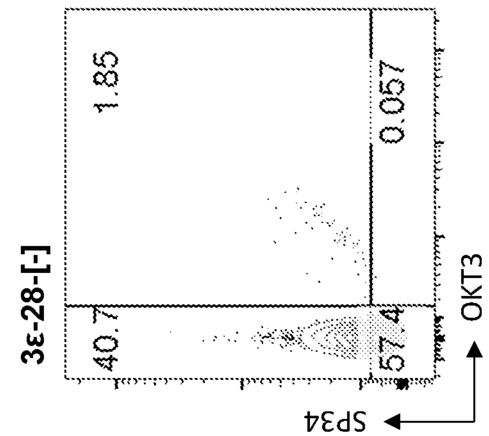
Figure 5D:
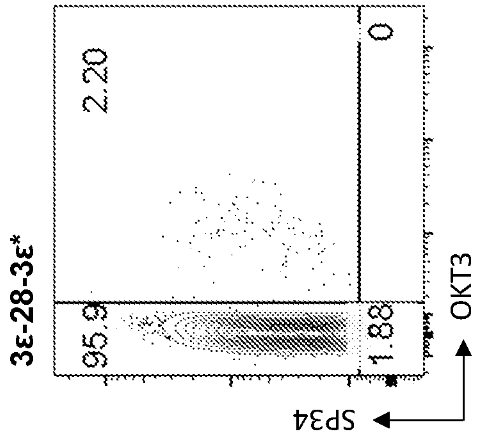
Figure 5E:
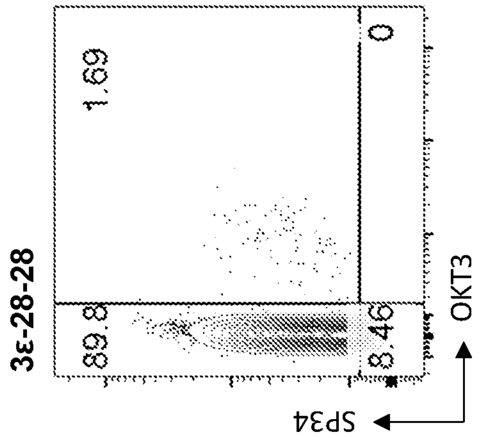
Figure 5F:
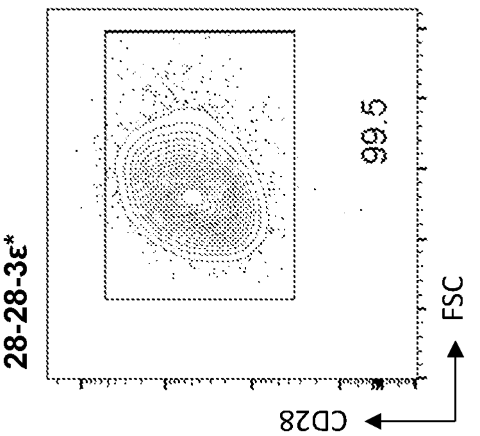

The CFR designs provided herein may also comprise modular transmembrane domains. As shown in FIG. 4A, the CD3ε-ectodomain was fused to the transmembrane domain of CD28, CD3, CD4, ICOS or CD27, and connected to the same CD28ζ endodomain in (a)-(c) or to ICOS-CD28ζ endodomain (d) or to CD27-CD28ζ endodomain (e). Surface expression of each of CFRs (a)-(e) of FIG. 4A on $CAR19^-$ or $CAR19^+$ Jurkat-NFAT-TRAC KO cells are shown in FIGS. 4B and 4D, respectively. The NFAT reporter activity reflecting CFR signaling transduction in $CAR19^-$ or $CAR19^+$ Jurkat-TRAC KO cells in the presence of $EpCAM^+$ targets and a CD3ε×EpCAM BiTE are shown in FIGS. 4C and 4E, respectively. The surface expression of CAR on Jurkat-NFAT-TRAC KO-$CAR19^+$ cells expressing CFRs with different TM domains is demonstrated in FIG. 4F. The difference of NFAT reporter activity in CFR expressing TRAC KO-$CAR19^+$ or TRAC KO-$CAR19^-$ Jurkat cells in the presence of $CD19^+$ target engagement represented the CAR-dependent reporter activity as a reflection of CAR-dependent CFR signaling transduction.

Example 6—CFR-Expressing Effector Cells Show Improved In Vitro and In Vivo Functionalities in the Presence of an Agonist An important function of effector cells, including T or NK cells, is the ability to specifically lyse target cells expressing a cognate antigen. Cytoxicity assays were used to determine if a CFR provides an effector cell an increased ability for target cell lysis. In the assay, derivative T cells (iT) expressing a given CFR were co-cultured with Nalm6-GFP cells at varying effector to target (E:T) ratios in the presence of agonistic antibodies recognizing the ectodomain of the CFR, such as CD3- or CD28-based ectodomain in this example, respectively. The cells were incubated overnight and some of the cell mixture was harvested for flow cytometric analysis. Fluorescent absolute counting beads (Spherotech, Lake Forest, IL) were added just prior to acquisition and were utilized to determine the number of Nalm6 and iT cells present in the cell mixture after the overnight co-culture.

Figure 9A:
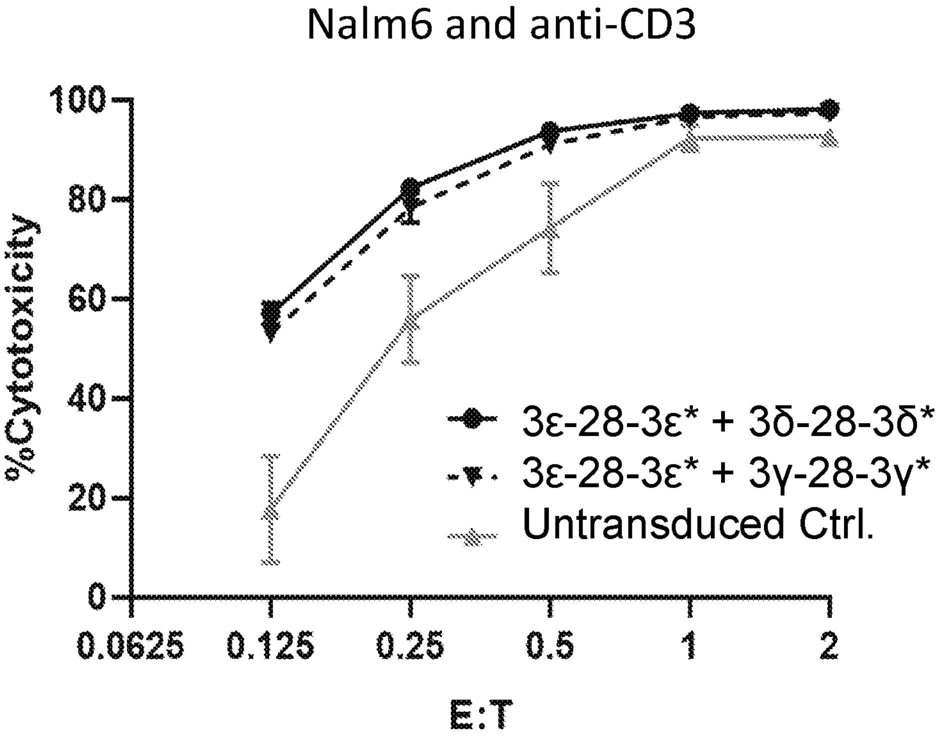
FIGS. 9A-9B show that CFR expressing CAR-iT effectors have improved cytotoxicity with agonistic antibodies using flow-based assay after overnight co-culture with Nalm6 target cells at the indicated E:T ratios.
Figure 9B:
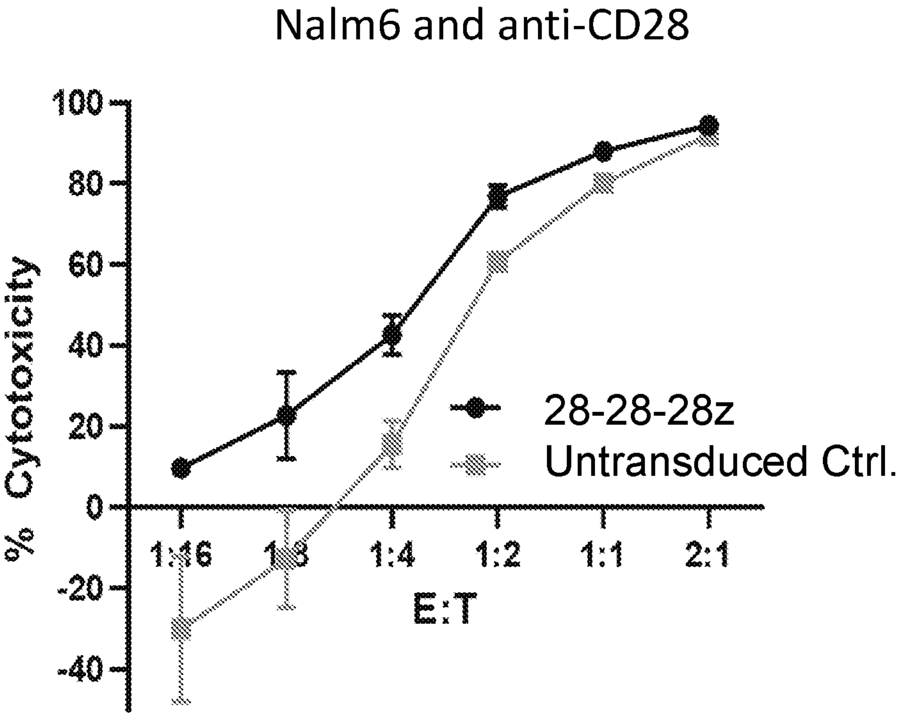

As shown in FIG. 9A, the flow-based assay measured cytotoxicity in CAR-iT cells transduced with CFRs of 3ε-28-3ε* together with 3δ-28-3δ* (black, solid line) or 3γ-28-3γ* (black, dotted line) after overnight co-culture with Nalm6 target cells at the indicated E:T ratios, in the presence of agonistic anti-CD3 antibody. In FIG. 9B, the cytoxicity was measured in CAR-iT cells transduced with CFR of 28-28-28ζ alone (black line) after overnight co-culture with Nalm6 target cells at the indicated E:T ratios in the presence of anti-CD28 antibody. Untransduced CAR-iT cells (gray lines in FIGS. 9A and 9B) are included to show baseline cytotoxicity in each experiment, and the results demonstrated that both CFR-expressing CAR-iT effectors have improved cytotoxicity with agonistic antibodies. Especially at lower E:T ratios, the CFR-expressing CAR-iT effectors have higher killing efficiency.

Figure 10A:
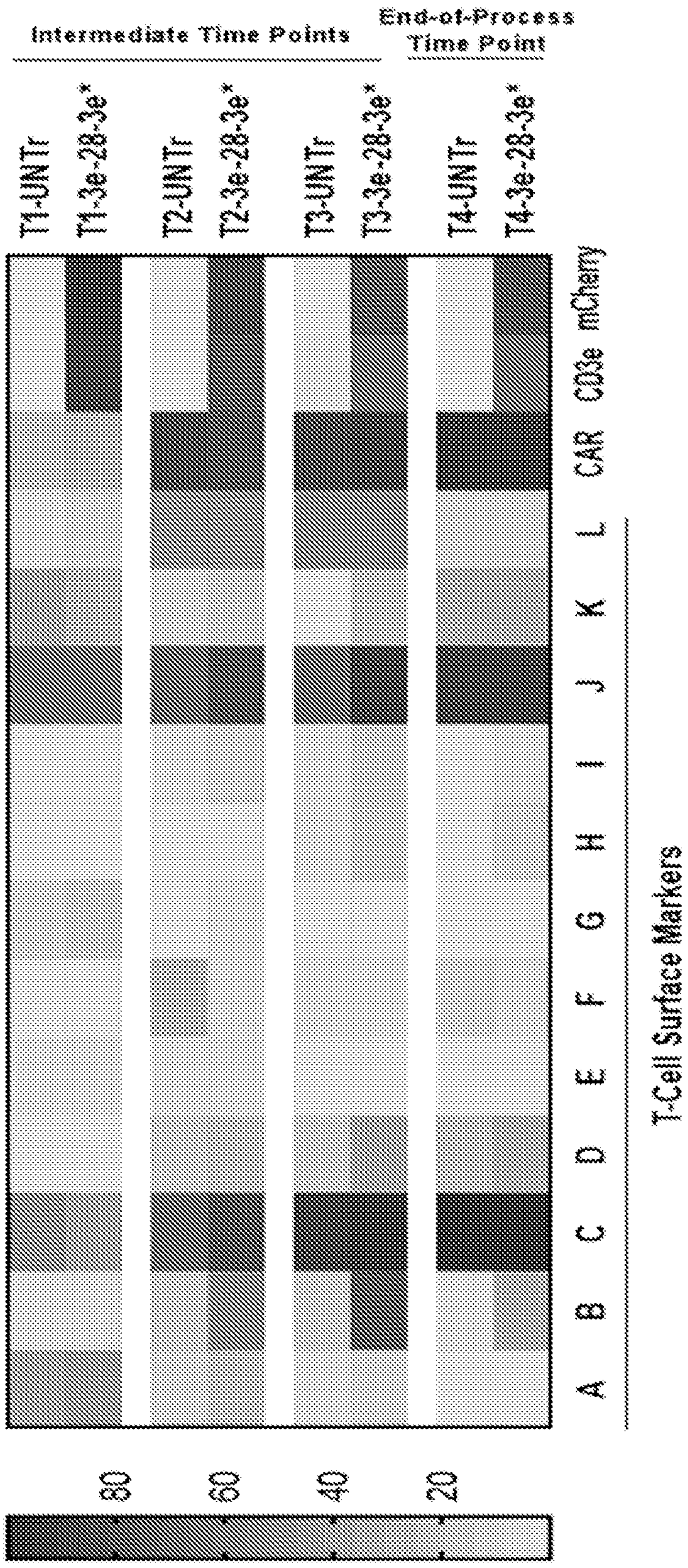
FIGS. 10A-10C show that expressing CFR at the pro-CAR-iT stage does not impair CAR-iT differentiation and function.
Figure 10B:
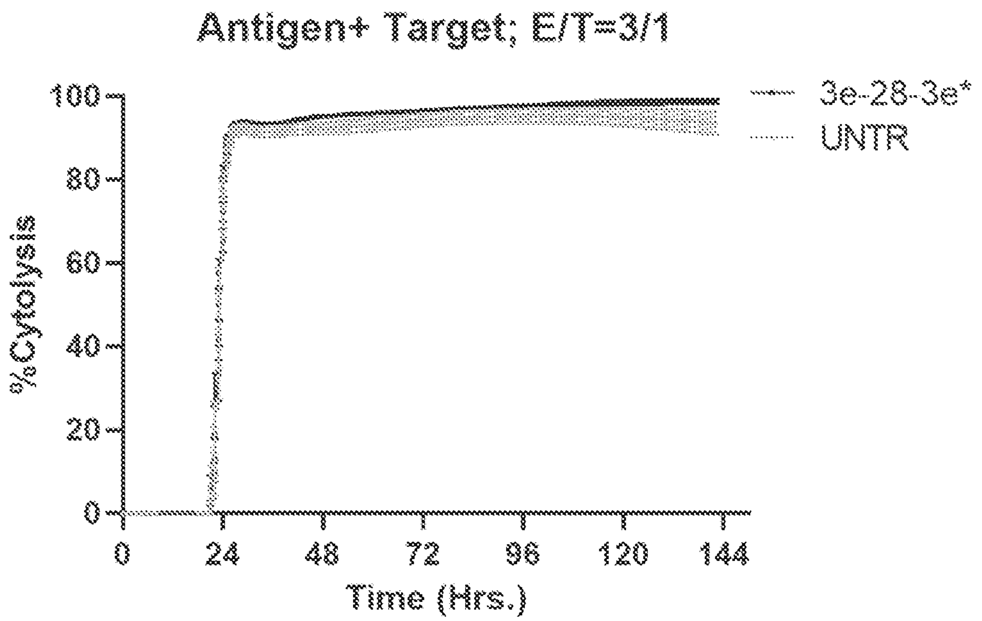
Figure 10C:
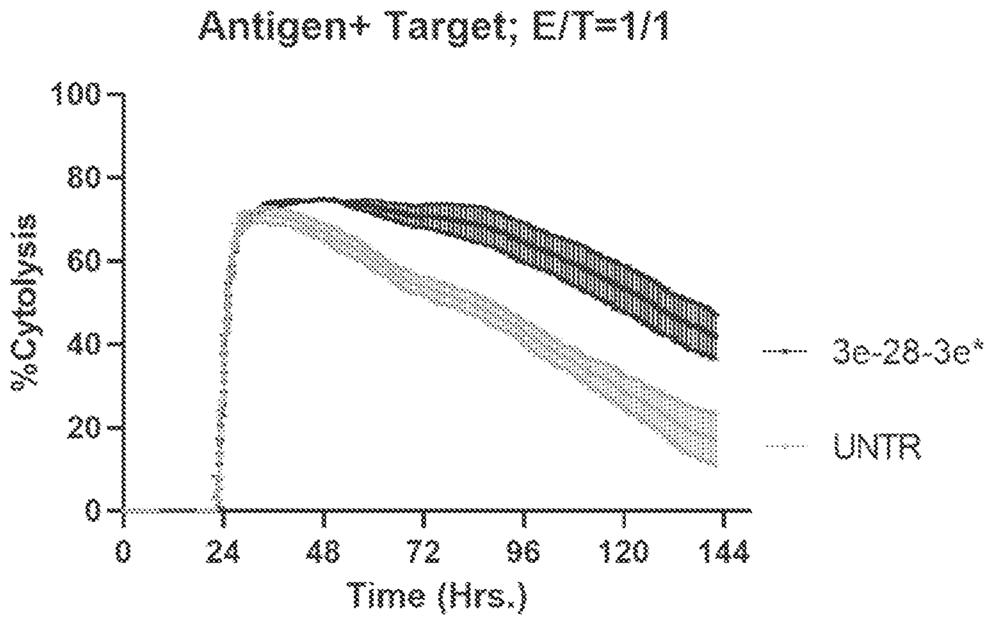

In a separate experiment, the various CFR designs provided herein were transduced with lentivirus at the pro-CAR-iT stage (approximately between differentiation D10 and D20) to determine if CFR expression, using 3ε-28-3ε* as an example, impairs CAR-iT differentiation and function. Phenotyping of $CFR^+$ (CFR transduced) and $CFR^-$ (UNTR; untransduced) CAR-iT cells using T cell surface marker expression along with CAR and CD3ε expression at different time points during differentiation is presented in FIG. 10A, showing that the T cell phenotypes in CFR transduced and untransduced CAR-iT cells are generally consistent during differentiation, and are especially so by the end of the differentiational process (T4). Further, the xCELLigence assay results showed comparable CAR-dependent cytolysis between CFR transduced and untransduced CAR-iT cells at E:T ratios of 3:1 (FIG. 10B) or 1:1 (FIG. 10C) against $Antigen^+$ target cells. Collectively, the data show that the CFR design and expression did not impair effector cell differentiation, phenotype, or the CAR functionality of the iT cells.

Figure 11A:
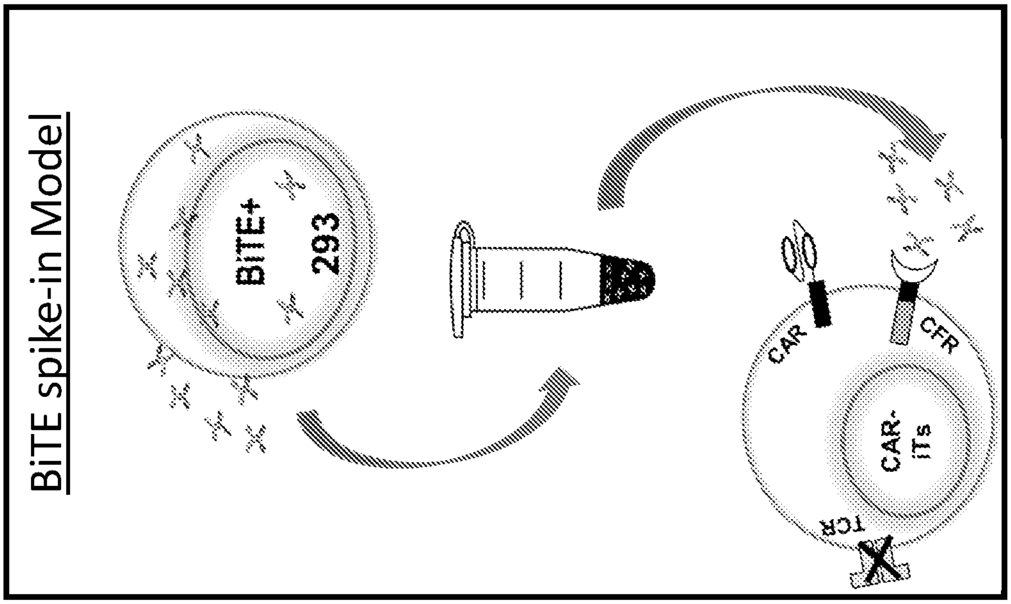
FIGS. 11A-11E show CFR expressing CAR-iTs have improved cytotoxicity against $Antigen^-$ targets in the presence of BiTE supernatant collected from 293 cultures.
Figure 11B:
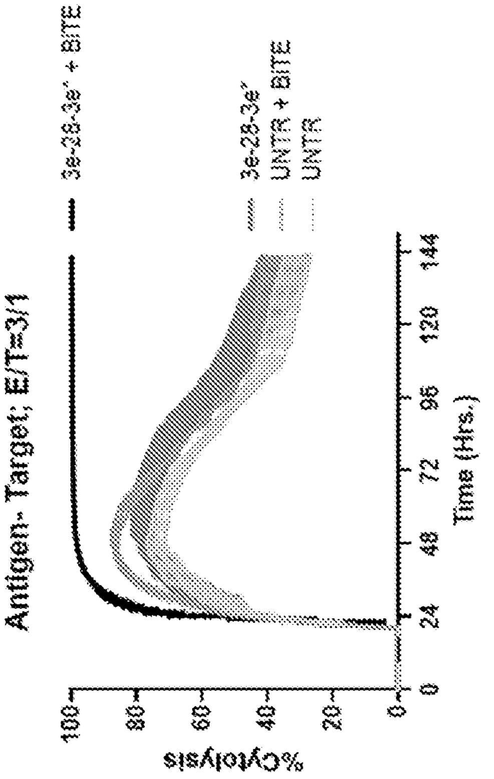
Figure 11C:
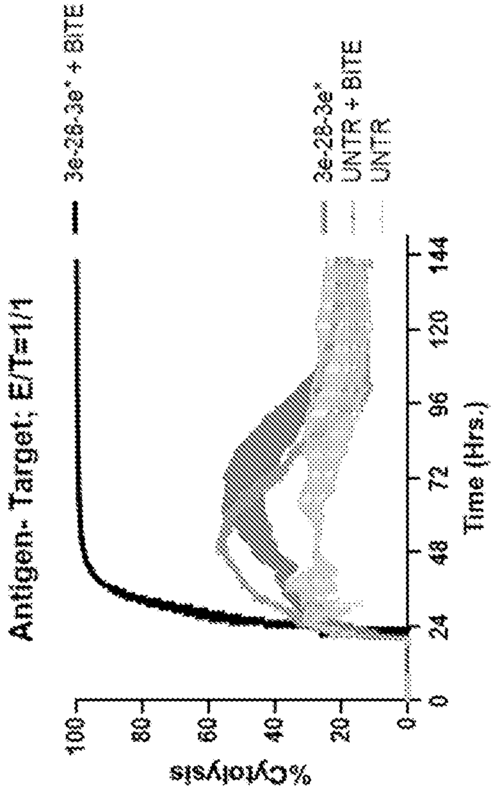
Figure 11D:
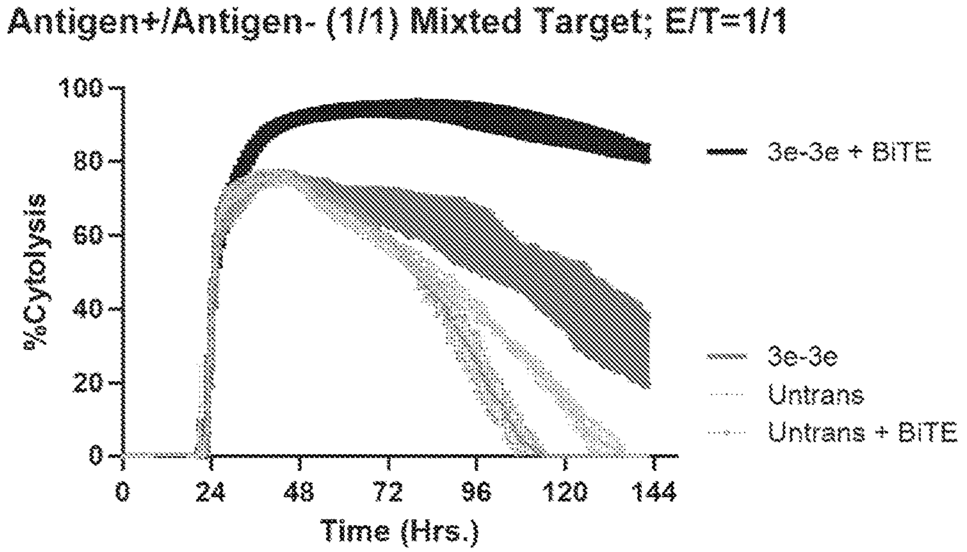
Figure 11E:
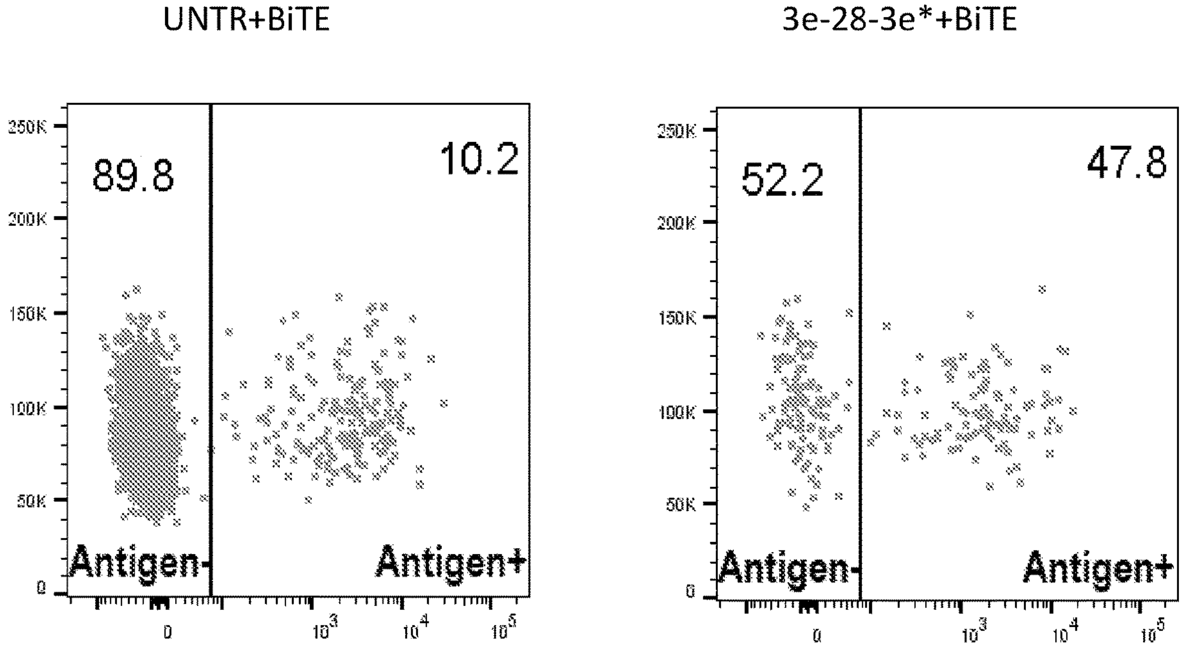

Example 7—CFR Provides a Strategy to Overcome Tumor Antigen Escape and Controlled Cell Apoptosis CFR-expressing CAR-iT effector cells were mixed with engagers (e.g., BiTEs) to show whether cytotoxicity is improved against $Antigen^-$ targets. FIG. 11A shows an exemplary BiTE spike-in model wherein eukaryotic cells for recombinant protein expression can be engineered for BiTE production. In this example, HEK293 cells are used for BiTE production for demonstration. The supernatant of the HEK293 cells was collected and mixed with CFR-expressing CAR-iT effector cells. As shown in FIGS. 11B and 9C, CFR-dependent cytolysis of CAR-iT cells against $Antigen^-$ targets at E:T ratios of 3:1 (FIG. 11B) or 1:1 (FIG. 11C) improves cytolysis and remains nearly constant in CFR transduced (3ε-28-3ε* was used as an exemplary demonstration), and in presence of BiTE as compared to all controls shown in gray (i.e., CFR transduced without BiTE and CFR untransduced with or without BiTE). The CFR-expressing CAR-iT effector cells were also shown to have enhanced cytolysis against $Antigen^+$ and $Antigen^-$ tumor targets in a mixed tumor cell population ($Antigen^+$:$Antigen^-$ 1:1) in the presence of BiTE supernatant at an E:T ratio of 1:1 (FIG. 11D), thereby confirming that the incorporation of BiTE through CFR expression effectively reduces tumor antigen escape under the CAR targeting mechanism. A similar observation was also made in the end-of-assay phenotyping of the mixed $Antigen^+$/$Antigen^-$ target cells after treatment with CFR transduced or non-transduced CAR-iT cells in the presence of a BiTE. As shown in FIG. 11E, left panel, (control), a significantly larger portion of $Antigen^-$ target cells remained in the mixed tumor cell population after being treated with CFR untransduced (UNTR) CAR-iT cells with BiTE. In comparison, after the $Antigen^+$/$Antigen^-$ mixed tumor cell population was co-cultured with CFR-expressing CAR-iT effector cells in the presence of BiTE, nearly an equal portion of $Antigen^+$ and $Antigen^-$ tumor cells with smaller numbers of cells in each portion remained in the mixed tumor cell population, reflecting the effective elimination of $Antigen^-$ tumor cells that escaped the CAR-directed antigen specific tumor targeting (FIG. 11E, right panel).

In a separate experiment, cytotoxicity of CFR expressing effector cells is assessed by co-cultivating iT effector cells derived from CFR transduced iPSC lines with a 50:50 target cell mixture consisting of Nalm6 CD19WT cells labeled with cell proliferation dye eFluor™ 450 and Nalm6-CD19KO cells labeled with cell proliferation dye eFluor™ 670. Mixed target cells are plated in 96 well U bottom plates, and effector cells of various concentrations are added to each well for desired effector to target ratios (E:T) of about 0:1, 1:1, 3.16:1, and 10:1 with or without anti-CD19×CD3 BiTE (Invivogen, San Diego, CA) or anti-CD20×CD3 BiTE (G&P Biosciences, Santa Clara, CA) for about 4 hrs and analyzed subsequently by flow cytometry. The percentage of apoptotic target cells is determined based on the percentage of caspase 3/7+ cells among eFluor™ 450+ Nalm6 CD19WT cells, or the percentage of caspase 3/7+ cells among eFluor™ 670+ Nalm6-CD19KO cells.

It was observed that the BiTE itself (either anti-CD19×CD3 or anti-CD20×CD3) did not trigger enhanced target cell apoptosis, whereas the addition of effector iT cells expressing CD3-based CFR increases tumor cell apoptosis. Thus, CFR expressing iT cells exhibit enhanced specific cytotoxicity in the presence of BiTEs. The improved effector cell functionality is further demonstrated through the decreased EC50 of effector iT cells in the presence of BiTE compared to that of effector iT cells alone in both lines.

Figure 12A:
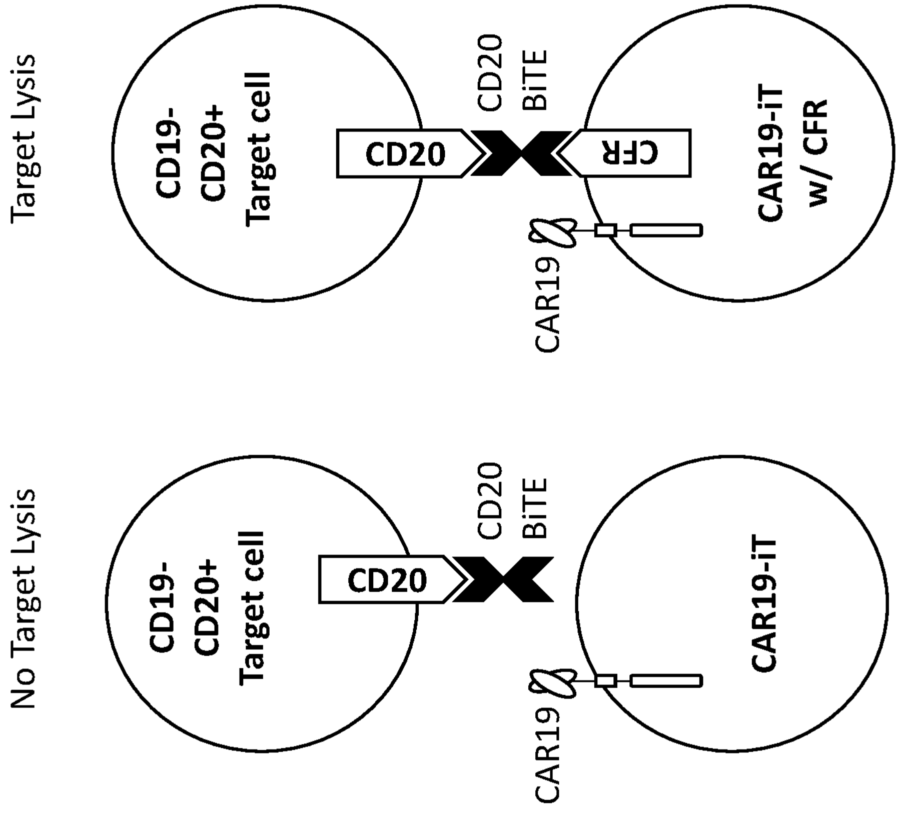
FIGS. 12A-12B illustrate (FIG. 12A): CFR-expressing effector cell and BiTE as strategy for dual targeting and/or against tumor evasion.
Figure 12B:
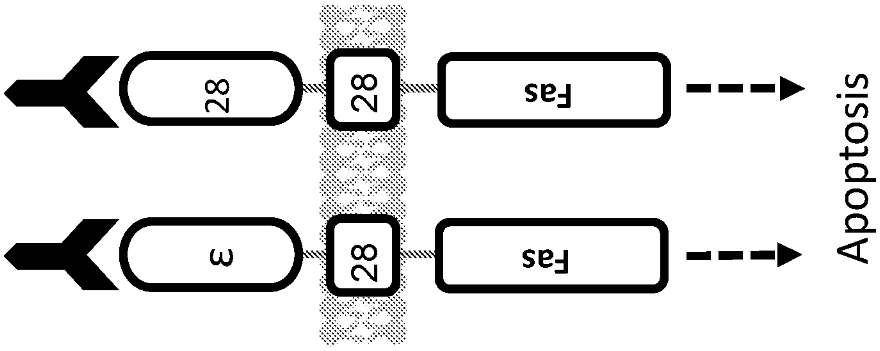

Further, CAR expressing cells armed with CFRs can target primary antigen of the tumor cells through CAR and target a secondary antigen with the presence of an appropriate BiTE or TriKE that binds with the CFR. This dual targeting strategy could also be used to overcome tumor antigen escape when the tumor cells loose or reduce the expression of the primary antigen targeted by CAR. FIGS. 12A and 12B provide an exemplary illustration of the CFR-expressing CD19-CAR-iT cell activation through an agonistic BiTE (for example, an anti-CD20×CD3 BiTE matching a CD3-based CFR and targeting tumor antigen CD20) that binds to a secondary tumor antigen of a target cell which evades CAR-T cell killing through loss of the surface primary antigen.

Example 8—CFR- and BiTE-Expressing Effector Cells Show Target-Dependent Signaling and Activation To get around toxicities associated with systemic administration of BiTEs, it was decided to test whether CFRs could be activated in response to localized BiTE secretion by the same cell. To demonstrate the initiation of CFR signaling transduction via BiTE, CFR- (CD3ε-CD28-CD3ε, also referred to as 3ε-28-3ε*) armed NFAT-Luciferase expressing Jurkats were transduced with lentiviral particles encoding CD3×EpCAM BiTE to generate CFR$^+$ BiTE$^+$ luciferase reporter Jurkats. The cells were then cultured in the presence or absence of EpCAM$^+$ target cells overnight at 37° C. with 5% $CO_2$, after which the function of the CFRs was determined (FIG. 13A).

Afterwards, 20 μL of each sample was mixed with 50 μL of QUANTI®-Luc (Invivogen, San Diego, CA) assay solution in 96-well clear bottom black or white plate, and luciferase activity (FIG. 13B) was read on a SpectraMax® microplate reader (Molecular Devices, San Jose, CA), which demonstrates induction of NFAT activity in the CFR positive cells in the presence of target cells. Analysis of activation markers by flow cytometry showed an increase in the proportion of CD69 and HLA-DR positive cells in the CFR$^+$BiTE$^+$ cells co-cultured with target cells (FIG. 13C). These data demonstrate that cells expressing both a CFR and a matching BiTE (for example, a CD3-based CFR and a BiTE recognizing CD3, or a CD28-based CFR and a BiTE recognizing CD28, etc.) can exhibit target-dependent signaling that leads to effector cell activation.

Figure 14A:
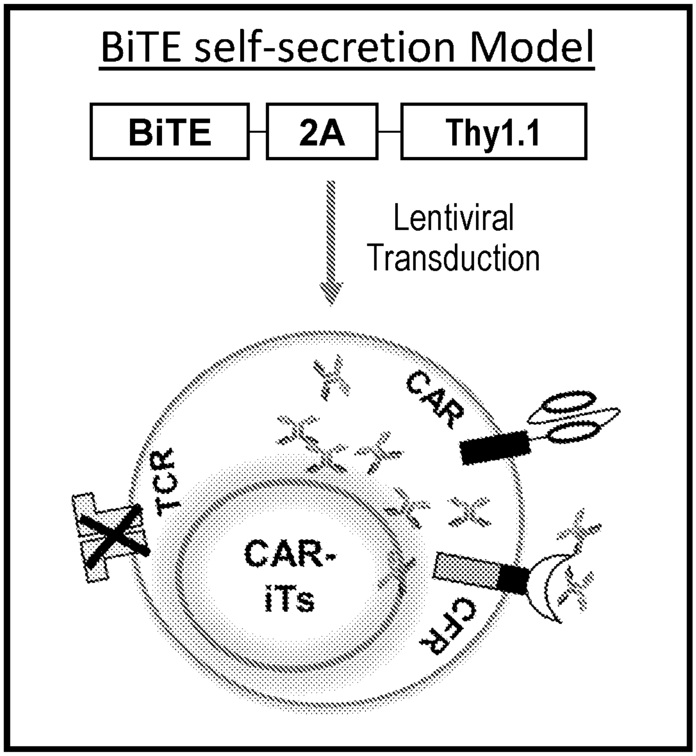
FIGS. 14A-14D show that CFR-expressing/BiTE-producing CAR' iT cells show improved cytotoxicity against $Antigen^-$ targets.
Figure 14B:
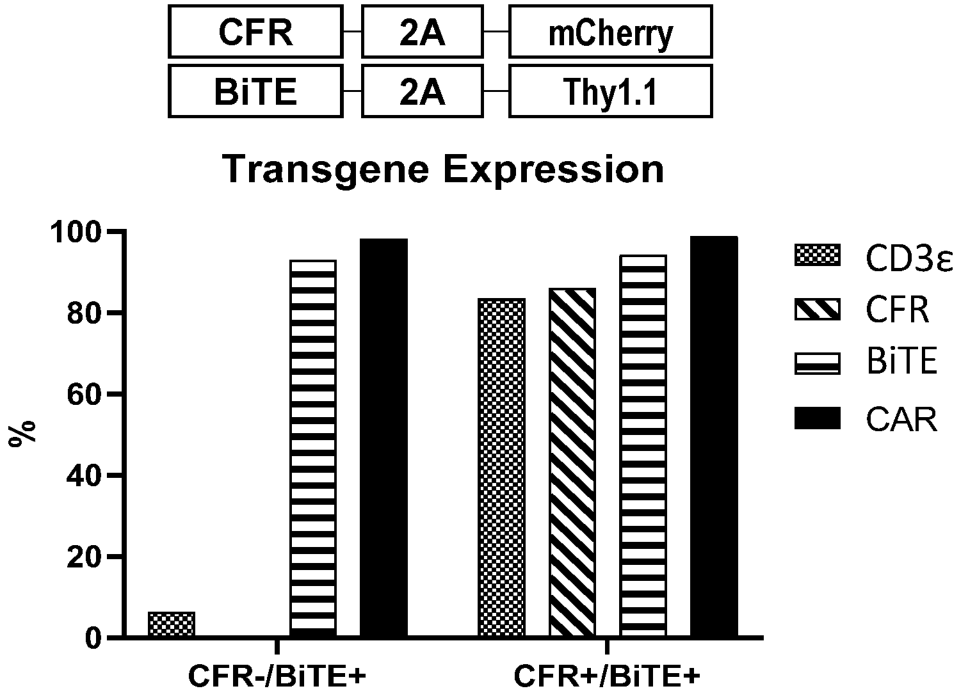
Figure 14C:
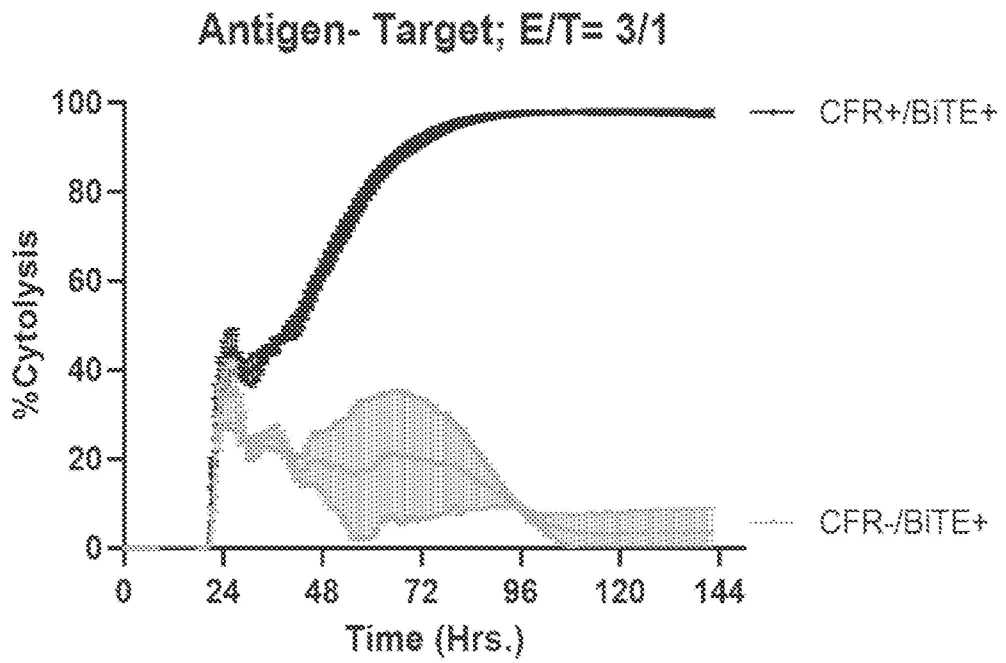
Figure 14D:
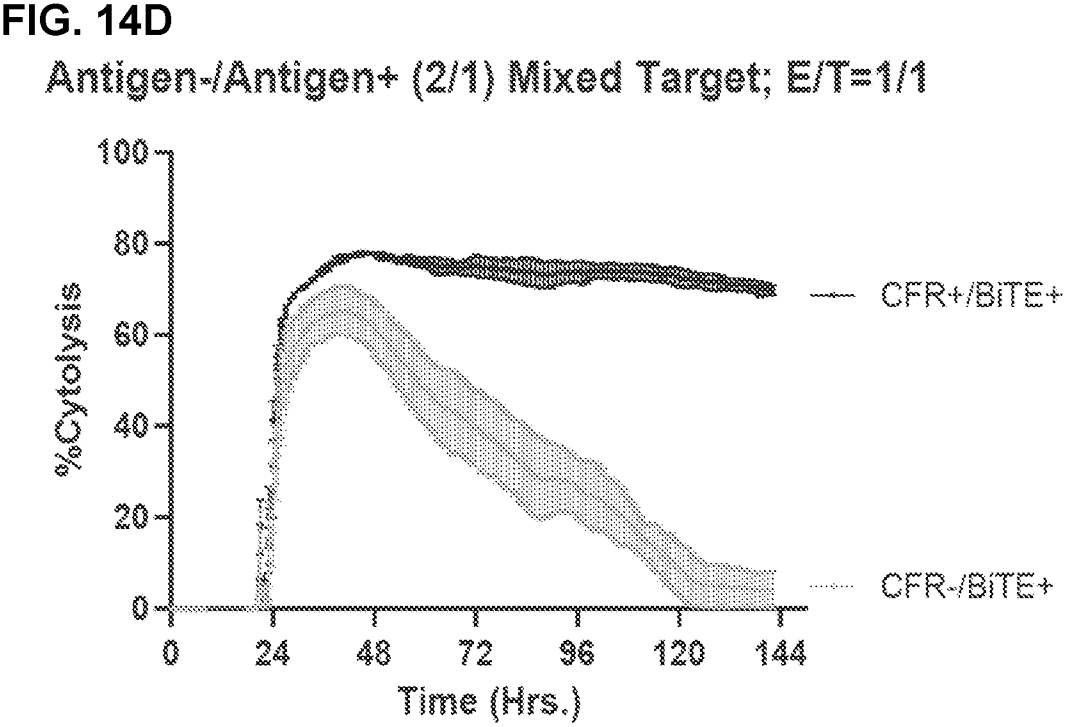

To further explore localized BiTE secretion by the same cell, and also as an alternative to the BiTE spike-in approach to introduce a BiTE to the environment of CFR expressing CAR-iT cells for enhanced tumor killing effect, the CFR expressing CAR-iT cells were engineered to self-express secreted BiTE (see for example, BiTE self-secretion Model in FIG. 14A). To determine if the BiTE self-production affects effector cell functionality after lentiviral transduction of BiTE into CAR-iT cells, the expression of CFR (staining for CD3ε and mCherry in this example), BiTE (staining for Thy1.1 in this example) and CAR in the TRAC knockout iT cells is shown in FIG. 14B, and the expression of surface CD3ε is correlated, or dependent on, the expression the CFR. FIG. 14C shows CFR-dependent BiTE-inducible cytolysis against Antigen$^-$ targets at an E:T ratio of 3:1. As shown in FIG. 14D, CFR$^+$/CAR$^+$ iT cells show enhanced cytolysis against Antigen$^+$/Antigen$^-$ mixed targets at an E:T ratio of 1:1 with self-secreting BiTEs.

Example 9—Stepwise Genomic Engineering of iPSC and iPSC-derived Effector Cells Other than TCR negative and CFR transduction, induced pluripotent stem cells were also serially engineered to comprise exogenous CD16 or a variant thereof, including, but not limited to, high affinity non-cleavable CD16 expression, loss of HLA-I by, for example, knocking out B2M gene, loss of HLA-II, for example, by knocking out CIITA, overexpression of the non-classical HLA molecule HLA-G, and recombinant cytokine signaling complex, for example, through fusion protein construct. After each engineering step, iPSCs were sorted for the desired phenotype prior to the next engineering step. The engineered iPSCs can then be maintained in vitro or for derivative cell generation. It has been demonstrated that these genetically engineered modalities are maintained during hematopoietic differentiation without perturbing the in vitro directed development of the cell into a desired cell fate.

T cell-derived iPSCs in which a CAR construct had been targeted to the TRAC locus, resulting in TCR knock-out (TCRα KO or TCR$^{neg}$), are transduced with lentivirus to constitutively express one or more CD3-based CFRs. The transduced constructs optionally include Thy1.1 as an exemplary reporter for the purpose of assaying for transduction efficiency and enrichment through cell sorting. The resulting iPSC lines are then differentiated, along with wild-type (WT) and TRAC-targeted CAR control lines, to iPSC-derived CD34$^+$ hematopoietic progenitor cells (iCD34) and subsequently to derivative T lineage cells (iT).

iPSCs from the control and transduced lines are then assayed by extracellular flow cytometry for (i) the pluripotency markers SSEA4 and TRA181, and (ii) the construct reporter Thy1.1. The transduction with CFR does not affect iPSC identity as shown by pluripotency markers. The control and transduced iPSCs are then differentiated to iCD34 hematopoietic progenitor cells using the composition and methods described herein and assayed by flow cytometry for CFR and Thy1.1. Lines transduced with CFR maintain Thy1.1 expression, with detectable cell surface CD3 due to the removal of ER retaining and endocytosis motifs. CD3 and TCRαβ are not observed in WT iPSC derived iCD34, suggesting that iTCRα or iTCRαβ transduction does not express or lead to CD3 expression on the cell surface at the iCD34 cell stage.

iCD34 cells are further differentiated into derivative T lineage cells (iT) using the compositions and methods described herein, and assayed by flow cytometry at various timepoints (cell development stages) during the differentiation process for CFR expression. CD3 and TCRαβ expression are absent in the TCR KO line as expected. Additionally, CD3 mean fluorescence intensity (MFI) is similar between the WT and CD3-based CFR transduced lines.

Figure 15:
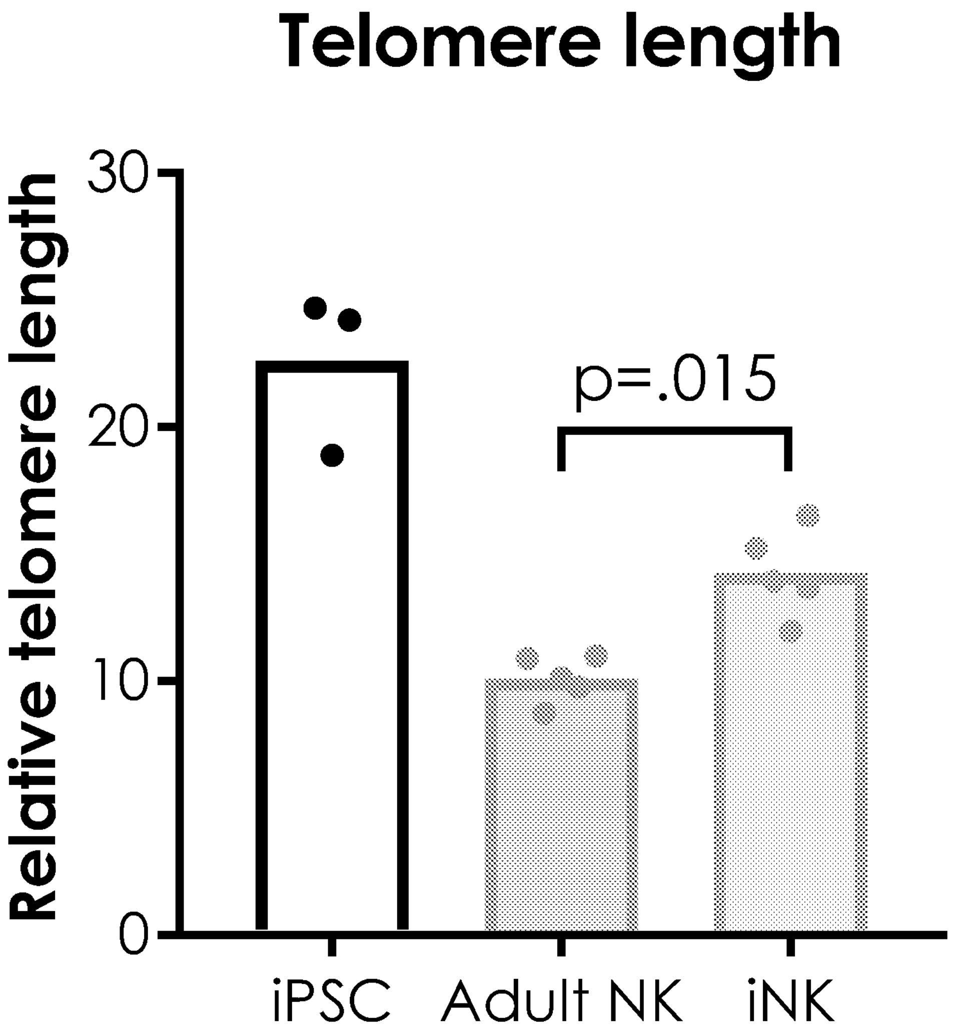
FIG. 15 is a graphic representation of telomere length determined by flow cytometry, and shows mature derivative NK cells from iPSC maintain longer telomeres compared to adult peripheral blood NK cells.

Telomere shortening occurs with cellular aging and is associated with stem cell dysfunction and cellular senescence. As shown in FIG. 15, the mature iNK cells maintain longer telomeres compared to adult peripheral bold NK cells. Telomere length was determined by flow cytometry for iPSC, adult peripheral blood NK cells, and iPSC-derived NK cells using the 1301 T cell leukemia line as a control (100%) with correction for the DNA index of $G_{0/1}$ cells. As further shown in FIG. 15, iPSC-derived NK cells maintain significantly longer telomere length when compared to adult peripheral blood NK cells (p=0.105, ANOVA), representing greater proliferation, survival and persistence potential in the iPSC-derived NK cells. Similar observation was made in iPSC-derived T cells in comparison to primary T cells obtained from peripheral blood.

Example 10—Cytokine Receptor Signaling from CFR Endodomains

Figure 16A:
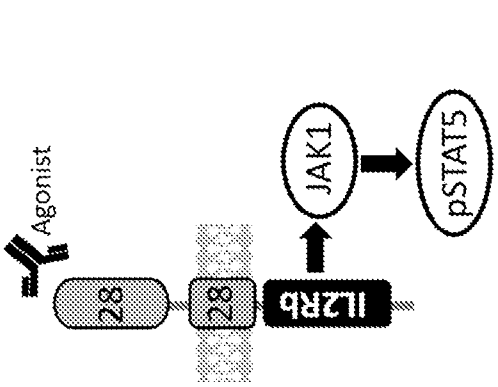
FIGS. 16A-16C show that CFRs with cytokine receptor endodomains can propagate signaling following agonistic antibody binding.

Cytokine receptor signaling can be an important part of proper effector cell activation, and CFRs can be used to provide these signals at the right time. To test whether CFRs with cytokine endodomains are functional, TRAC knockout Jurkat cells, as described above, were lentivirally transduced to express a chimeric fusion receptor comprising a CD28 ecto- and transmembrane-domain fused to an IL-2 receptor beta (IL2Rb) endodomain (FIG. 16A; 28-28-IL2Rb). This chimeric fusion receptor construct allows the use of an agonistic ligand, such as an anti-CD28 antibody or BiTE, to initiate signaling upon binding to the CD28 ectodomain, resulting in activation of Jak1 and phosphorylation of STAT5.

Figure 16B:
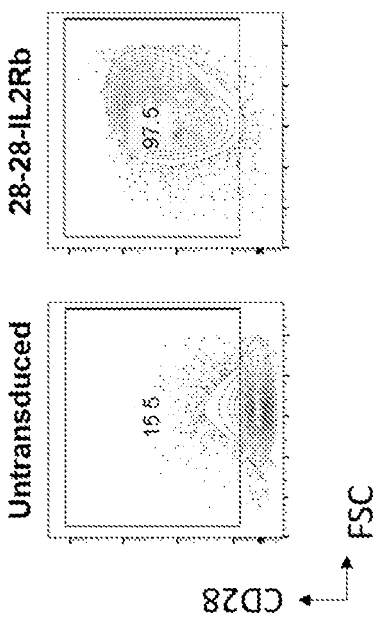

Expression of the CFR was measured by staining the cells with antibody against CD28 and analyzing the cells by flow cytometry. Compared to untransduced TRAC KO Jurkats, which were 15.5% positive for CD28, the CFR-transduced TRAC KO Jurkats were 97.5% positive for surface expression of CD28 (FIG. 16B), indicating successful expression of the CD28 ectodomain CFR transgene. To test for signal transduction from the IL-2 receptor beta endodomain, the untransduced and CFR-transduced (28-28-IL2Rb) Jurkats were cultured for 2 hours in the presence or absence of agonistic anti-CD28 antibody.

Figure 16C:
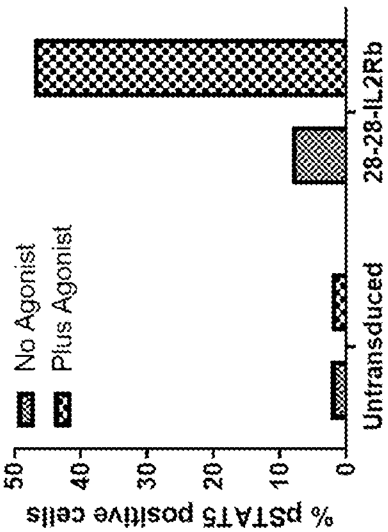

Intracellular staining for phosphorylated STAT5 Y694 (pSTAT5) was performed and the cells were analyzed (FIG. 16C). Briefly, phosphorylated STAT5 in control and CFR-armed cells was analyzed by intracellular flow cytometry in the presence or absence of agonist. The cells were fixed with BD Phosflow® Fix Buffer (BD Biosciences, San Jose, CA), followed by permeabilization by BD Phosflow® Perm Buffer (BD Biosciences, San Jose, CA). Alexa Fluor® 647-conjugated anti-STAT5 (pY694) (BD Biosciences, San Jose, CA) was used for intracellular phosphorylated STAT5 staining.

For phenotypic profiling, cells were harvested and stained with a fixable viability marker (BD Biosciences), followed by surface staining with APC-anti-CD69 and BV711-anti-HLA-DR (BD Biosciences, San Jose) antibodies for 30 mins on ice. Data acquisition was performed on a BD Fortessa™ X-20 (BD Biosciences) and data were analyzed using FlowJo ° software (FlowJo, Ashland, OR) and Spotfire® (Tibco, Boston, MA).

In the absence of agonistic antibody, the CFR-transduced cells had a slightly higher proportion of pSTAT5 positive cells compared to untransduced controls, 8% and 3% respectively. With addition of agonistic anti-CD28, the CFR-transduced cells showed a marked increase in the proportion of pSTAT5 positive cells while there was no change in the untransduced cells. This result demonstrates that cytokine receptor endodomains, such as IL-2 receptor beta, can be used in the context of a chimeric fusion receptor, with signal transduction being induced via agonists, such as agonistic antibodies or BiTEs, and functional equivalents thereof.

One skilled in the art would readily appreciate that the methods, compositions, and products described herein are representative of exemplary embodiments, and not intended as limitations on the scope of the invention. It will be readily apparent to one skilled in the art that varying substitutions and modifications may be made to the present disclosure disclosed herein without departing from the scope and spirit of the invention.

All patents and publications mentioned in the specification are indicative of the levels of those skilled in the art to which the present disclosure pertains. All patents and publications are herein incorporated by reference to the same extent as if each individual publication was specifically and individually indicated as incorporated by reference.

The present disclosure illustratively described herein suitably may be practiced in the absence of any element or elements, limitation or limitations that are not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the present disclosure claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. An isolated cell or an isolated population thereof, wherein the cell comprises a polynucleotide encoding a chimeric fusion receptor (CFR), wherein:

(a) the cell is an eukaryotic cell, an animal cell, a human cell, an immune cell, a feeder cell, an induced pluripotent stem cell (iPSC), a clonal iPSC, or an iPSC-derived effector cell;

(b) the CFR comprises an ectodomain, a transmembrane domain, and an endodomain;

(c) the ectodomain, the transmembrane domain, and the endodomain are fused together in a single polypeptide chain;

(d) the ectodomain comprises a CD3ε ectodomain polypeptide, a CD3γ ectodomain polypeptide, a CD3δ ectodomain polypeptide, or a CD28 ectodomain polypeptide;

(e) the endodomain comprises at least one signaling domain; and (f) the ectodomain, the transmembrane domain and the endodomain do not comprise any endoplasmic reticulum (ER) retention signals or endocytosis signals.

2. The isolated cell or isolated population thereof of claim 1, wherein the effector cell further comprises one or more of:

(i) a CAR having a targeting specificity;

(ii) a CD16 or a variant thereof;

(iii) CD38 knockout;

(iv) a partial or full peptide of a cell surface expressed exogenous cytokine and/or a receptor thereof;

(v) HLA-I deficiency, and optionally HLA-II deficiency;

(vi) introduction of HLA-G or non-cleavable HLA-G, or knockout of one or both of CD58 and CD54;

(vii) at least one of the genotypes listed in Table 1;

(viii) deletion or disruption of at least one of B2M, TAP1, TAP2, Tapasin, NLRC5, CIITA, RFXANK, RFX5, RFXAP, TCR, NKG2A, NKG2D, CD25, CD69, CD44, CD56, CIS, CBL-B, SOCS2, PD1, CTLA4, LAG3, TIM3, and TIGIT; or (ix) introduction of at least one of HLA-E, 4-1BBL, CD3, CD4, CD8, CD16, CD47, CD113, CD131, CD137, CD80, PDL1, $A_{2A}R$, antigen-specific TCR, Fc receptor, an antibody or functional variant or fragment thereof, a checkpoint inhibitor, an engager, and surface triggering receptor for coupling with an agonist.

3. The isolated cell or isolated population thereof of claim 2, wherein the cell has therapeutic properties comprising one or more of:

(i) increased cytotoxicity;

(ii) improved persistency and/or survival;

(iii) enhanced ability in migrating, and/or activating or recruiting bystander immune cells, to tumor sites;

(iv) improved tumor penetration;

(v) enhanced ability to reduce tumor immunosuppression;

(vi) improved ability in rescuing tumor antigen escape;

(vii) controlled apoptosis;

(viii) enhanced or acquired ADCC; and (ix) ability to avoid fratricide, in comparison to its counterpart primary cell obtained from peripheral blood, umbilical cord blood, or any other donor tissues.

4. The isolated cell or isolated population thereof of claim 2, wherein the CD16 or a variant thereof comprises at least one of:

(a) a high affinity non-cleavable CD16 (hnCD16);

(b) F176V and S197P in ectodomain domain of CD16;

(c) a full or partial ectodomain originated from CD64;

(d) a non-native (or non-CD16) transmembrane domain;

(e) a non-native (or non-CD16) intracellular domain;

(f) a non-native (or non-CD16) signaling domain;

(g) a non-native stimulatory domain; and (h) transmembrane, signaling, and stimulatory domains that are not originated from CD16, and are originated from a same or different polypeptide.

5. The isolated cell or isolated population thereof of claim 2, wherein the CAR is:

(i) T cell specific or NK cell specific;

(ii) a bi-specific antigen binding CAR;

(iii) a switchable CAR;

(iv) a dimerized CAR;

(v) a split CAR;

(vi) a multi-chain CAR;

(vii) an inducible CAR;

(viii) co-expressed with a partial or full peptide of a cell surface expressed exogenous cytokine and/or a receptor thereof, optionally in separate constructs or in a bi-cistronic construct;

(ix) co-expressed with a checkpoint inhibitor, optionally in separate constructs or in a bi-cistronic construct;

(x) specific to at least one of CD19, BCMA, CD20, CD22, CD38, CD123, HER2, CD52, EGFR, GD2, MICA/B, MSLN, VEGF-R2, PSMA and PDL1; and/or (xi) specific to any one of ADGRE2, carbonic anhydrase IX (CAIX), CCR1, CCR4, carcinoembryonic antigen (CEA), CD3, CD5, CD7, CD8, CD10, CD20, CD22, CD30, CD33, CD34, CD38, CD41, CD44, CD44V6, CD49f, CD56, CD70, CD74, CD99, CD123, CD133, CD138, CDS, CLEC12A, an antigen of a cytomegalovirus (CMV) infected cell, epithelial glycoprotein-2 (EGP-2), epithelial glycoprotein-40 (EGP-40), epithelial cell adhesion molecule (EpCAM), EGFRvIII, receptor tyrosine-protein kinases erb-B2,3,4, EGFIR, EGFR-VIII, ERBB folate-binding protein (FBP), fetal acetylcholine receptor (AChR), folate receptor-α, Ganglioside G2 (GD2), Ganglioside G3 (GD3), human Epidermal Growth Factor Receptor 2 (HER2), human telomerase reverse transcriptase (hTERT), ICAM-1, Integrin B7, Interleukin-13 receptor subunit alpha-2 (IL-13Rα2), κ-light chain, kinase insert domain receptor (KDR), Lewis A (CA19.9), Lewis Y (LeY), L1 cell adhesion molecule (L1-CAM), LILRB2, melanoma antigen family A 1 (MAGE-A1), MICA/B, Mucin 1

(Muc-1), Mucin 16 (Muc-16), Mesothelin (MSLN), NKCSI, NKG2D ligands, c-Met, cancer-testis antigen NY-ESO-1, oncofetal antigen (h5T4), PRAME, prostate stem cell antigen (PSCA), PRAME prostate-specific membrane antigen (PSMA), tumor-associated glycoprotein 72 (TAG-72), TIM-3, TRBC1, TRBC2, vascular endothelial growth factor R2 (VEGF-R2), Wilms tumor protein (WT-1), and a pathogen antigen; and optionally wherein the CAR of any one of (i) to (xi) is inserted at a TCR locus, and/or is driven by an endogenous promoter of TCR, and/or the TCR is knocked out by the CAR insertion.

6. The isolated cell or isolated population thereof of claim 2, wherein the cell comprises a partial or full peptide of a cell surface expressed exogenous cytokine and/or a receptor thereof, and wherein the exogenous cytokine or receptor thereof:

(a) comprises at least one of IL2, IL4, IL6, IL7, IL9, IL10, IL11, IL12, IL15, IL18, IL21, and its respective receptor(s); or (b) comprises at least one of:

(i) co-expression of IL15 and IL15Rα by using a self-cleaving peptide;

(ii) a fusion protein of IL15 and IL15Rα;

(iii) an IL15/IL15Rα fusion protein with intracellular domain of IL15Rα truncated or eliminated;

(iv) a fusion protein of IL15 and membrane bound Sushi domain of IL15Rα;

(v) a fusion protein of IL15 and IL15Rβ;

(vi) a fusion protein of IL15 and common receptor γC, wherein the common receptor γC is native or modified; and (vii) a homodimer of IL15RB, wherein any one of (i)-(vii) can be co-expressed with a CAR in separate constructs or in a bi-cistronic construct;

and optionally, (c) is transiently expressed.

7. The isolated cell or isolated population thereof of claim 2, wherein the checkpoint inhibitor is an antagonist to one or more checkpoint molecules comprising PD-1, PDL-1, TIM-3, TIGIT, LAG-3, CTLA-4, 2B4, 4-1BB, 4-1BBL, $A_{2A}R$, BATE, BTLA, CD39, CD47, CD73, CD94, CD96, CD160, CD200, CD200R, CD274, CEACAM1, CSF-1R, Foxpl, GARP, HVEM, IDO, EDO, TDO, LAIR-1, MICA/B, NR4A2, MAFB, OCT-2, Rara (retinoic acid receptor alpha), TLR3, VISTA, NKG2A/HLA-E, and inhibitory KIR; or wherein the engager comprises a bi-specific T cell engager (BiTE) or a tri-specific killer cell engager (TriKE).

8. The isolated cell or isolated population thereof of claim 2, wherein the iPSC-derived effector cell is capable of recruiting, and/or migrating T cells to tumor sites, and wherein the iPSC-derived effector cell is capable of reducing tumor immunosuppression in the presence of one or more checkpoint inhibitors.

9. The isolated cell or isolated population thereof of claim 1, wherein the cell comprises:

(i) one or more exogenous polynucleotides integrated in a safe harbor locus or a selected gene locus; or (ii) more than two exogenous polynucleotides integrated in different safe harbor loci or two or more selected gene loci.

10. The isolated cell or isolated population thereof of claim 9, wherein the safe harbor locus comprises at least one of AAVS1, CCR5, ROSA26, collagen, HTRP, H11, GAPDH, or RUNX1; and wherein the selected gene locus is one of B2M, TAP1, TAP2, Tapasin, NLRC5, CIITA, RFXANK, RFX5, RFXAP, TCR, NKG2A, NKG2D, CD38, CD25, CD69, CD44, CD58, CD54, CD56, CIS, CBL-B, SOCS2, PD1, CTLA4, LAG3, TIM3, or TIGIT; and/or wherein the integration of the exogenous polynucleotides knocks out expression of the gene in the locus.

11. The isolated cell or isolated population thereof of claim 10, wherein the TCR locus is a constant region of TCR alpha and/or TCR beta.

12. The isolated cell or isolated population thereof of claim 1, wherein the iPSC-derived effector cell comprises a derivative CD34 cell, a derivative hematopoietic stem and progenitor cell, a derivative hematopoietic multipotent progenitor cell, a derivative T cell progenitor, a derivative NK cell progenitor, a derivative T lineage cell, a derivative NKT lineage cell, a derivative NK lineage cell, a derivative B lineage cell, or a derivative immune effector cell having one or more functional features that are not present in a counterpart primary T, NK, NKT, and/or B cell.

13. A composition comprising the isolated cell or isolated population thereof of claim 1.

14. A composition for therapeutic use, wherein the composition comprises: (i) the isolated cell or isolated population thereof of claim 1, and (ii) one or more therapeutic agents.

15. The composition of claim 14, wherein the therapeutic agents comprise a peptide, a cytokine, a checkpoint inhibitor, an antibody or functional variant or fragment thereof, an engager, a mitogen, a growth factor, a small RNA, a dsRNA (double stranded RNA), mononuclear blood cells, feeder cells, feeder cell components or replacement factors thereof, a vector comprising one or more polynucleic acids of interest, a chemotherapeutic agent or a radioactive moiety, or an immunomodulatory drug (IMiD).

16. The composition of claim 15, wherein:

(a) the checkpoint inhibitor comprises:

(i) one or more antagonist checkpoint molecules comprising PD-1, PDL-1, TIM-3, TIGIT, LAG-3, CTLA-4, 2B4, 4-1BB, 4-1BBL, $A_{2A}R$, BATE, BTLA, CD39, CD47, CD73, CD94, CD96, CD160, CD200, CD200R, CD274, CEACAM1, CSF-1R, Foxpl, GARP, HVEM, IDO, EDO, TDO, LAIR-1, MICA/B, NR4A2, MAFB, OCT-2, Rara (retinoic acid receptor alpha), TLR3, VISTA, NKG2A/HLA-E, or inhibitory KIR;

(ii) one or more of atezolizumab, avelumab, durvalumab, ipilimumab, IPH4102, IPH43, IPH33, lirilumab, monalizumab, nivolumab, pembrolizumab, and their derivatives or functional equivalents; or (iii) at least one of atezolizumab, nivolumab, and pembrolizumab; or (b) the therapeutic agents comprise one or more of venetoclax, azacitidine, and pomalidomide; or (c) the engager comprises a bi-specific T cell engager (BiTE), or a tri-specific killer cell engager (TriKE).

17. The composition of claim 15, wherein:

(a) the antibody, or functional variant or fragment thereof comprises anti-CD20, anti-CD22, anti-HER2, anti-CD52, anti-EGFR, anti-CD123, anti-GD2, anti-PDL1, and/or anti-CD38 antibody;

(b) the antibody, or functional variant or fragment thereof comprises one or more of rituximab, veltuzumab, ofatumumab, ublituximab, ocaratuzumab, obinutuzumab, ibritumomab, ocrelizumab, inotuzumab, moxetumomab, epratuzumab, trastuzumab, pertuzumab, alemtuzumab, cetuximab, dinutuximab, avelumab, daratumumab, isatuximab, MOR202, 7G3, CSL362, elotuzumab, and their humanized or Fc modified variants or fragments and their functional equivalents and biosimilars; or (c) (i) the cell is an iPSC-derived effector cell comprising a CD38 knockout, and (ii) the antibody, or functional variant or fragment thereof comprises daratumumab.

18. The isolated cell or isolated population thereof of claim 1, wherein the ectodomain comprises the CD3ε ectodomain polypeptide.

19. The isolated cell or isolated population thereof of claim 1, wherein the ectodomain comprises the CD3γ ectodomain polypeptide.

20. The isolated cell or isolated population thereof of claim 1, wherein the ectodomain comprises the CD3δ ectodomain polypeptide.

21. The isolated cell or isolated population thereof of claim 1, wherein the ectodomain comprises the CD28 ectodomain polypeptide.

22. A master cell bank (MCB) comprising the clonal iPSC of claim 1.

23. Therapeutic use of the composition of claim 14 by introducing the composition to a subject suitable for adoptive cell therapy, wherein the subject has an autoimmune disorder, a hematological malignancy, a solid tumor, cancer, or a viral infection.

* * * * *